(12) United States Patent
Lardelli Markmiller et al.

(10) Patent No.: US 12,037,588 B2
(45) Date of Patent: Jul. 16, 2024

(54) COMPOSITIONS AND METHODS COMPRISING ENGINEERED SHORT NUCLEAR RNA (snRNA)

(71) Applicant: Locanabio, Inc., San Diego, CA (US)

(72) Inventors: Rea Lardelli Markmiller, San Diego, CA (US); Ranjan Batra, San Diego, CA (US); Rachel A. Adams, San Diego, CA (US); Daniela Roth, San Diego, CA (US); Daniel A. Knowland, San Diego, CA (US)

(73) Assignee: Locanabio, Inc., San Diego, CA (US)

( * ) Notice: Subject to any disclaimer, the term of this patent is extended or adjusted under 35 U.S.C. 154(b) by 0 days.

(21) Appl. No.: 18/447,651

(22) Filed: Aug. 10, 2023

(65) Prior Publication Data

US 2024/0018521 A1 Jan. 18, 2024

Related U.S. Application Data

(63) Continuation of application No. 18/179,110, filed on Mar. 6, 2023.

(60) Provisional application No. 63/379,983, filed on Oct. 18, 2022, provisional application No. 63/316,659, filed on Mar. 4, 2022.

(51) Int. Cl.
  *C12N 15/113* (2010.01)
  *A61P 21/00* (2006.01)
  *A61P 25/28* (2006.01)
  *C12N 15/86* (2006.01)

(52) U.S. Cl.
  CPC .......... *C12N 15/113* (2013.01); *A61P 21/00* (2018.01); *A61P 25/28* (2018.01); *C12N 15/86* (2013.01); *C12N 2310/14* (2013.01); *C12N 2310/531* (2013.01); *C12N 2750/14143* (2013.01)

(58) Field of Classification Search
  None
  See application file for complete search history.

(56) References Cited

U.S. PATENT DOCUMENTS

| | | |
|---|---|---|
| 5,814,500 A | 9/1998 | Dietz et al. |
| 5,994,124 A | 11/1999 | Bozzoni |
| 6,692,910 B2 | 2/2004 | Rowe et al. |
| 6,924,096 B2 | 8/2005 | Dietz et al. |
| 8,343,941 B2 | 1/2013 | Gunderson et al. |
| 8,822,168 B2 | 9/2014 | Dreyfuss et al. |
| 8,907,075 B2 | 12/2014 | Gunderson et al. |
| 9,040,491 B2 | 5/2015 | Dreyfuss et al. |
| 9,074,207 B2 | 7/2015 | Pagani et al. |
| 9,078,823 B2 | 7/2015 | Gunderson et al. |
| 9,080,170 B2 | 7/2015 | Garcia et al. |
| 9,303,258 B2 | 4/2016 | Gallo et al. |
| 9,441,221 B2 | 9/2016 | Gunderson et al. |
| 9,669,109 B1 | 6/2017 | Pagani et al. |
| 9,862,945 B2 | 1/2018 | Flanigan et al. |
| 10,752,898 B2 | 8/2020 | Pietri-Rouxe et al. |
| 11,053,494 B2 | 7/2021 | Flanigan et al. |
| 11,180,755 B2 | 11/2021 | Harper et al. |
| 11,230,707 B2 | 1/2022 | Flanigan et al. |
| 2023/0025574 A1 | 1/2023 | Flanigan et al. |
| 2023/0279397 A1 | 9/2023 | Lardelli Markmiller et al. |
| 2024/0018521 A1 | 1/2024 | Lardelli Markmiller et al. |

FOREIGN PATENT DOCUMENTS

| | | |
|---|---|---|
| EP | 1778297 B1 | 4/2009 |
| EP | 1501931 B1 | 11/2009 |
| EP | 2142672 B1 | 9/2012 |
| EP | 2151497 B1 | 1/2014 |
| EP | 2627339 B1 | 5/2015 |
| EP | 2547768 B1 | 12/2015 |
| EP | 3387130 B1 | 11/2020 |
| WO | WO 98/18811 A1 | 5/1998 |
| WO | WO 02/083908 A1 | 10/2002 |
| WO | WO 03/095647 A2 | 11/2003 |
| WO | WO 2006/021724 A2 | 3/2006 |
| WO | WO 2008/121963 A2 | 10/2008 |
| WO | WO 2011/113889 A1 | 9/2011 |
| WO | WO 2011/154427 A1 | 12/2011 |
| WO | WO 2011/154851 A1 | 12/2011 |
| WO | WO 2012/049665 A1 | 4/2012 |
| WO | WO 2012/138846 A2 | 10/2012 |
| WO | WO 2014/172669 A1 | 10/2014 |
| WO | WO 2016/025339 A2 | 4/2016 |
| WO | WO 2017/098187 A1 | 6/2017 |
| WO | WO 2017/147467 A1 | 8/2017 |
| WO | WO 2020/041634 A1 | 2/2020 |
| WO | WO 2020/185651 A2 | 9/2020 |
| WO | WO 2020/198270 A1 | 10/2020 |
| WO | WO 2020/214763 A1 | 10/2020 |
| WO | WO 2021/014157 A1 | 1/2021 |
| WO | WO 2021/026075 A1 | 2/2021 |
| WO | WO 2021/117729 A1 | 6/2021 |
| WO | WO 2021/216853 A1 | 10/2021 |

(Continued)

OTHER PUBLICATIONS

Alterman, J. F, et al., "A divalent siRNA chemical scaffold for potent and sustained modulation of gene expression throughout the central nervous system," Nat Biotechnol 37, Aug. 2019. 884-894, doi: 10.1038/s41587-019-0205-0.

Anna, A., and Monika, G., "Splicing mutations in human genetic disorders: examples, detection, and confirmation," J Appl Genet 2018, 59, 253-268, doi: 10.1007/s13353-018-0444-7.

Aoki, Y., et al.,"In-frame dystrophin following exon 51-skipping improves muscle pathology and function in the exon 52-deficient mdx mouse," Molecular Therapy, Nov. 2010, vol. 18, No. 11, 1995-2005, doi: 10.1038/mt.2010.186.

(Continued)

*Primary Examiner* — Allison M Fox
*Assistant Examiner* — Kimberly A Aron
(74) *Attorney, Agent, or Firm* — COOLEY LLP; Ivor R. Elrifi; Matthew Pavao

(57) ABSTRACT

SnRNA systems comprising engineered stem loops are disclosed herein.

20 Claims, 26 Drawing Sheets

Specification includes a Sequence Listing.

(56) References Cited

FOREIGN PATENT DOCUMENTS

| WO | WO 2022/067257 A1 | 3/2022 |
|----|-------------------|--------|
| WO | WO 2022/115745 A1 | 6/2022 |
| WO | WO 2022/226334 A1 | 10/2022 |
| WO | WO 2023/168458 A1 | 9/2023 |

OTHER PUBLICATIONS

Aung-Htut, M. T., et al., "Splice modulating antisense oligonucleotides restore some acid-alpha-glucosidase activity in cells derived from patients with late-onset Pompe disease," Sci Rep 2020, 10, 6702, 12 pages, doi: 10.1038/s41598-020-63461-2.

Booth, B. J., et al., "RNA editing: Expanding the potential of RNA therapeutics," Mol Ther, Jun. 2023, vol. 31, No. 6, 1533-1549, doi: 10.1016/j.ymthe.2023.01.005.

Bucholc, K., et al., "Composition and processing activity of a semi-recombinant holo U7 snRNP," Nucleic Acids Research 2020, vol. 48, No. 3, published online Dec. 10, 2019, pp. 1508-1530, doi: 10.1093/nar/gkz1148, including Supplementary Data, 4 pages.

Bulfield et al., "X chromosome-linked muscular dystrophy (mdx) in the mouse," PNAS 81(4):1189-1192 (1984).

Cartegni, L., et al., "ESEfinder: A web resource to identify exonic splicing enhancers," Nucleic Acids Research 2003, vol. 31, No. 13, 3568-3571. doi: 10.1093/nar/gkg616.

Carvill, G. L., et al., "Poison exons in neurodevelopment and disease," Curr Opin Genet Dev 2020, 65: 98-102, doi: 10.1016/j.gde.2020.05.030.

Colella, P., and Mingozzi, F., "Gene Therapy for Pompe Disease: The Time is now," Hum Gene Therapy 2019, vol. 30, No. 10, 1245-1262, doi: 10.1089/hum.2019.109.

Cox, D. B. T. et al., "RNA editing with CRISPR-Cas13," Science, vol. 358, No. 6366, pp. 1019-1027, 9 pages (Nov. 2017).

Crooke, S. T., et al., "RNA-Targeted Therapeutics," Cell Metab 27, Apr. 3, 2018, 714-739, including Update, Cell Metab, vol. 29, Issue 2, Feb. 5, 2019, p. 501.

D'Amario, D., et al., "Dystrophin Cardiomyopathies: Clinical Management, Molecular Pathogenesis and Evolution towards Precision Medicine," J Clin Med 2018, 7, 291,36 pages, doi: 10.3390/jcm7090291.

Dardis, A., et al., "Functional characterization of the common c.-32-13TG mutation of GAA gene: identification of potential therapeutic agents," Nucleic Acids Research 2014, vol. 42, No. 2, 1291-1302, doi: 10.1093/nar/gkt987.

De Angelis, F.G., et al., "Chimeric snRNA molecules carrying antisense sequences against the splice junctions of exon 51 of the dystrophin pre-rnRNA induce exon skipping and restoration of a dystrophinsynthesis in Delta 48-50 DMD cells", Proceedings of the National Academy of Sciences, vol. 99, No. 14, Jul. 9, 2002, pp. 9456-9461, , DOI: 10.1073/PNAS.142302299.

Desjardins, C. A., et al., "Enhanced exon skipping and prolonged dystrophin restoration achieved by TfR1-targeted delivery of antisense oligonucleotide using FORCE conjugation in mdx mice," Nucleic Acids Res 2022, vol. 50, No. 20, 11401-11414, doi: 10.1093/nar/gkac641.

Deverman, BE, Cre-dependent selection yields AAV variants for widespreadgene transfer to the adult brain, Nat. Biotechnol., 34(2):204-209. doi: 10.1038/nbt.3440. PubMed PMID: 26829320 (Epub Feb. 1, 2016).

Duan, D., "Systemic AAV Micro-dystrophin Gene Therapy for Duchenne Muscular Dystrophy," Molecular Therapy, vol. 26, No. 10, Oct. 2018, 2337-2356, doi: 10.1016/j.ymthe.2018.07.011.

Eggers, M., et al., "Muscle-directed gene therapy corrects Pompe disease and uncovers species-specific GAA immunogenicity," EMBO Mol Med 2022, 14: e13968, 15 pages, doi: 10.15252/emmm.202113968.

Engelbeen, S., et al., "Challenges of Assessing Exon 53 Skipping of the Human DMD Transcript with Locked Nucleic Acid-Modified Antisense Oligonucleotides in a Mouse Model for Duchenne Muscular Dystrophy," Nucleic Acid Therapeutics, vol. 33, Nov. 6, 2023, 348-360, doi: 10.1089/nat.2023.0038.

Ezzeddine, N., et al., "A Subset of *Drosophila* Integrator Proteins Is Essential for Efficient U7 snRNA and Spliceosomal snRNA 3'-End Formation", Molecular and Cellular Biology, vol. 31, No. 2, Nov. 15, 2010, pp. 328-341, , DOI: 10.1128/MCB.00943-10.

Filonova, G., and Aartsma-Rus, A., "Next steps for the optimization of exon therapy for Duchenne muscular dystrophy," Expert Opinion on Biological Therapy 2023, 23:2, 133-143, doi: 10.1080/14712598.2023.2169070.

Gadgil, A., et al., "U7 snRNA: A tool for gene therapy", The Journal of Gene Medicine, vol. 23, No. 4, Feb. 23, 2021, , DOI: 10.1002/jgm.3321.

Gorman et al. "Stable alteration of pre-mRNA splicing patterns by modified U7 small nuclear RNAs" Proceedings of the National Academy of Sciences 95:4929:4934 (1998).

Goyenvalle, A., et al., "Engineering Multiple U7snRNA Constructs to Induce Single and Multiexon-skipping for Duchenne Muscular Dystrophy", Molecular Therapy, vol. 20, No. 6, Feb. 21, 2012, pp. 1212-1221, , DOI: 0.1038/MT.2012.26.

Goyenvalle, A., et al., "Enhanced Exon-skipping Induced by U7 snRNA Carrying a Splicing Silencer Sequence:Promising Tool for DMD Therapy," The American Society of Gene Therapy, Jul. 2009, vol. 17, No. 7, 1234-1240.

Goyenvalle, A., et al., Rescue of dystrophic muscle through U7 snRNA-mediated exon skipping, Science 306, Dec. 3, 2004, 1796-1799, doi: 10.1126/science.1104297.

Grieger, J. C. et al., "Production of Recombinant Adeno-associated Virus Vectors Using Suspension HEK293 Cells and Continuous Harvest of Vector From the Culture Media for GMP FIX and FLT1 Clinical Vector," Molecular Therapy, 24(2):287-297 (2016).

Gushchina, L. V., et al., "Lack of Toxicity in Nonhuman Primates Receiving Clinically Relevant Doses of an AAV9.U7snRNA Vector Designed to Induce DMD Exon 2 Skipping," Human Gene Therapy 2021, vol. 32, Nos. 17-18, 882-894, doi: 10.1089/hum.2020.286.

Han, Z., et al., "Antisense oligonucleotides increase Scn1a expression and reduce seizures and SUDEP incidence in a mouse model of Dravet syndrome," Sci Transl Med 12, eaaz6100 (2020), Aug. 26, 2020, 14 pages, doi: 10.1126/scitranslmed.aaz6100.

Havens, M. A., et al., "Targeting RNA splicing for disease therapy," WIREs, vol. 4, May/Jun. 2013, 247-266, doi: 10.1002/wrna.1158.

Hoffman, E.P., et al., "Improved diagnosis of Becker muscular dystrophy by dystrophin testing," Neurology 39, Aug. 1989, pp. 1011-1017, doi: 10.1212/wnl.39.8.1011.

Horowitz, D. S., et al., Mechanisms for selecting 5' splice sites in mammalian pre-mRNA splicing, Trends Genet 1994, vol. 10, No. 3, pp. 100-106.

Imbert, M. et al., "Viral Vector-Mediated Antisense Therapy for Genetic Diseases," Genes 2017, 8, 51, 19 pages, doi: 10.3390/genes8020051.

International Search Report and Written Opinion for PCT Application No. PCT/US2023/063798 dated Aug. 14, 2023, 22 pages.

Invitation to Pay Additional Fees and, Where Applicable, Protest Fee, dated Jun. 23, 2023, for International Application No. PCT/US2023/063798 (15 total pages).

Kolev, N.G., et al., "In vivo assembly of functional U7 snRNP requires RNA backbone flexibility within the Sm-binding site", Nature Structural & Molecular Biology, vol. 13, No. 4, Mar. 19, 2006, pp. 347-353, , DOI: 10.1038/nsmb1075.

Krawczak, M., et al., "Human gene mutation database—a biomedical information and research resource," Human Mutation 15: 45-51 (2000), doi: 10.1002/(SICI)1098-1004(200001) 15:145::AID-HUMU103.0.CO;2-T.

Lesman, D., et al., "U7 snRNA, a Small RNA with a Big Impact in Gene Therapy," Human Gene Therapy 2021, vol. 32, Nos. 21-22, pp. 1317-1329, doi: 10.1089/hum.2021.047.

Lim, K. H., et al., "Using positional distribution to identify splicing elements and predict pre-mRNA processing defects in human genes," Proc Natl Acad Sci USA, Jul. 5, 2011, vol. 108, No. 27, 11093-11098, doi: 10.1073/pnas.1101135108.

Lindow, M., et al., "Assessing unintended hybridization-induced biological effects of oligonucleotides," Nature Biotechnology, vol. 30, No. 10, Oct. 2012, pp. 920-923, doi: 10.1038/nbt.2376.

(56) References Cited

OTHER PUBLICATIONS

Marina, R. J., et al., "Evaluation of Engineered CRISPR-Cas-Mediated Systems for Site-Specific RNA Editing," Cell Reports 33, 108350, Nov. 3, 2020, pp. 1-12:e1-e6, doi: 10.1016/j.celrep.2020.108350.
Martelly, W., et al., "Synergistic roles for human U1 snRNA stem-loops in pre-mRNA splicing", RNA Biology, vol. 18, No. 12, Jun. 9, 2021, pp. 2576-2593, , DOI:10.1080/15476286.2021.1932360.
Marz, M., et al., "U7 snRNAs: A Computational Survey", Genomics Proteomics and Bioinformatics, vol. 5, No. 3, Feb. 8, 2008, pp. 187-195, , DOI: 10.1016/S1672-0229(08)60006-6.
Masat, E.,et al. "Long-term exposure to Myozyme results in a decrease of anti-drug antibodies in late-onset Pompe disease patients," Scientific Reports 6:36182, published Nov. 4, 2016, 13 pages, doi: 10.1038/srep36182.
Mattaj, I. W., et al., "Small nuclear RNAs in messenger RNA and ribosomal RNA processing," FASEB J., vol. 7, Jan. 1993, pp. 47-53.
Mattis, J., et al., "Corticohippocampal circuit dysfunction in a mouse model of Dravet syndrome," eLife 2022, 11.e69293, 30 pages, doi: 10.7554/eLife.69293.
Megan, W., Audentes, T., and Nationwide Children's, H. (2023), AAV9 U7snRNA Gene Therapy to Treat Boys With DMD Exon 2 Duplications, 20 pages.
Nguyen, Q., and Yokota, T., "Antisense oligonucleotides for the treatment of cardiomyopathy in Duchenne muscular dystrophy," Am J Transl Res 2019, 11(3): 1202-1218.
Phelps, S. F., et al., "Expression of full-length and truncated dystrophin mini-genes in transgenic mdx mice," Human Molecular Genetics, 1995, vol. 4, No. 8, 1251-1258, doi: 10.1093/hmg/4.8.1251.
Pillai, R. S., et al., "Unique Sm core structure of U7 snRNPs: assembly by a specialized SMN complex and the role of a new component, Lsm11, in histone RNA processing," Genes & Development 2003, 17:2321-2333, doi: 10.1101/gad.274403.
Poulos, M.G., et al., "Developments in RNA splicing and disease," Cold Spring Harb Perspect Biol 2011, 3: a000778, 16 pages, doi: 10.1101/cshperspect.a000778.
Radukic, M. T., et al., "Nanopore sequencing of native adeno-associated virus (AAV) single-stranded DNA using a transposase-based rapid protocol," NAR Genomics and Bioinformatics, 2020, vol. 2, No. 4, 16 pages, doi: 10.1093/nargab/lqaa074.
Rashnonejad A., et al., "Large-Scale Production of Adeno-Associated Viral Vector Serotype-9 Carrying the Human Survival Motor Neuron Gene," Molecular Biotechnology, Nov. 25, 2015, vol. 58(1), pp. 30-36.
Roberts, T. C., et al., "Advances in oligonucleotide drug delivery," Nature Reviews Drug Discovery, vol. 19, Oct. 2020, pp. 673-694, doi: 10.1038/s41573-020-0075-7.
Sheikh, O., and Yokota, T., "Restoring Protein Expression in Neuromuscular Conditions: A Review Assessing the Current State of Exon Skipping/Inclusion and Gene Therapies for Duchenne Muscular Dystrophy and Spinal Muscular Atrophy," BioDrugs 2021, 35:389-399, doi: 10.1007/s40259-021-00486-7.
Shukla, G. C., et al., "The intramolecular stem-loop structure of U6 snRNA can functionally replace the U6atac snRNA stem-loop", RNA, vol. 7, No. 1, Feb. 2001, pp. 94-105, , DOI:10.1017/S1355838201000218.
Simmons, T. R., et al., "Pre-clinical dose-escalation studies establish a therapeutic range for U7snRNA-mediated DMD exon 2 skipping," Molecular Therapy Methods & Clinical Development, vol. 21, Jun. 2021, pp. 325-340, doi: 10.1016/j.omtm.2021.03.014.

Stefanovic, B., et al., "Assembly, nuclear import and function of U7 snRNPs studied by microinjection of synthetic U7 RNA into Xenopus oocytes," Nucleic Acids Research 1995, vol. 23, No. 16, 3141-3151, doi: 10.1093/nar/23.16.3141.
Steward, C. A., et al., "Re-annotation of 191 developmental and epileptic encephalopathy-associated genes unmasks de novo variants in SCN1A," NPJ Genomic Medicine 2019, 4:31, 11 pages, doi: 10.1038/s41525-019-0106-7.
Sullivan, J., and Wirrell, E. C., "Dravet Syndrome as an Example of Precision Medicine in Epilepsy," Epilepsy Currents 2023, 23(1), pp. 4-7, doi: 10.1177/15357597221106281.
Tanenhaus, A., et al., "Cell-Selective Adeno-Associated Virus-Mediated SCN1A Gene Regulation Therapy Rescues Mortality and Seizure Phenotypes in a Dravet Syndrome Mouse Model and Is Well Tolerated in Nonhuman Primates," Human Gene Therapy 2022, vol. 33, Nos. 11 and 12, pp. 579-597, doi: 10.1089/hum.2022.037.
Thorley, M., et al., "Skeletal muscle characteristics are preserved in hTERT/cdk4 human myogenic cell lines," Skeletal Muscle 2016, 6:43, 12 pages, doi: 10.1186/s13395-016-0115-5.
Tran, N. T., et al., "AAV-Genome Population Sequencing of Vectors Packaging CRISPR Components Reveals Design-Influenced Heterogeneity," Mol Ther Methods Clin Dev, Sep. 2020, vol. 18, pp. 639-651, doi: 10.1016/j.omtm.2020.07.007.
Unnisa, Z., et al., "Gene Therapy Developments for Pompe Disease," Biomedicines 2022, 10, 302, 26 pages, doi: 10.3390/biomedicines10020302.
Vaquero-Garcia, J., et al., "A new view of transcriptome complexity and regulation through the lens of local splicing variations," eLife 2016, 5:e11752, 30 pages, doi: 10.7554/eLife.11752.
Vaquero-Garcia, J., et al., "RNA splicing analysis using heterogeneous and large RNA-seq datasets," Nat Commun 2023, 14:1230, 20 pages, doi: 10.1038/s41467-023-36585-y.
Veltrop, M., et al., "A dystrophic Duchenne mouse model for testing human antisense oligonucleotides," PLoS One, Feb. 21, 2018, 13(2):e0193289, doi: 10.1371/journal.pone.0193289.
Waldrop, M. A., et al., "Clinical Phenotypes of DMD Exon 51 Skip Equivalent Deletions: A Systematic Review," J Neuromuscul Dis 2020, 7, 217-229, doi: 10.3233/JND-200483.
Wein, N., et al., "Absence of Significant Off-Target Splicing Variation with a U7snRNA Vector Targeting DMD Exon 2 Duplications," Hum Gene Ther 2021, vol. 32, Nos. 21-22, pp. 1346-1359, doi: 10.1089/hum.2020.315.
Wein, N., et al., "Translation from a DMD exon 5 IRES results in a functional dystrophin isoform that attenuates dystrophinopathy in humans and mice," Nature Medicine, Sep. 2014, vol. 20, No. 9, pp. 992-1000, including Online Methods & Corrigenda, 6 pages, doi: 10.1038/nm.3628.
Wengert, E. R., et al., "Targeted Augmentation of Nuclear Gene Output (TANGO) of Scn1a rescues parvalbumin interneuron excitability and reduces seizures in a mouse model of Dravet Syndrome," Brain Research 2022, 1775, 147743, 6 pages, doi: 10.1016/j.brainres.2021.147743.
Will, C. L., and Lührmann, R., "Spliceosome structure and function," Cold Spring Harb Perspect Biol 2011, 3:a003707, 23 pages, doi: 10.1101/cshperspect.a003707.
Wu, Y. W., et al., "Incidence of Dravet Syndrome in a US Population," Pediatrics, Nov. 2015, vol. 136, No. 5, e1310-1315, doi: 10.1542/peds.2015-1807.
Xie, J. et al., "Short DNA Hairpins Compromise Recombinant Adeno-Associated Virus Genome Homogeneity," Molecular Therapy, Jun. 2017, vol. 25, No. 6, pp. 1363-1374, doi: 10.1016/j.ymthe.2017.03.028.
Zuberi, S. M., et al., "Genotype-phenotype associations in SCN1A-related epilepsies," Neurology, Feb. 15, 2011, 76, 594-600, doi: 10.1212/WNL.0b013e31820c309b.

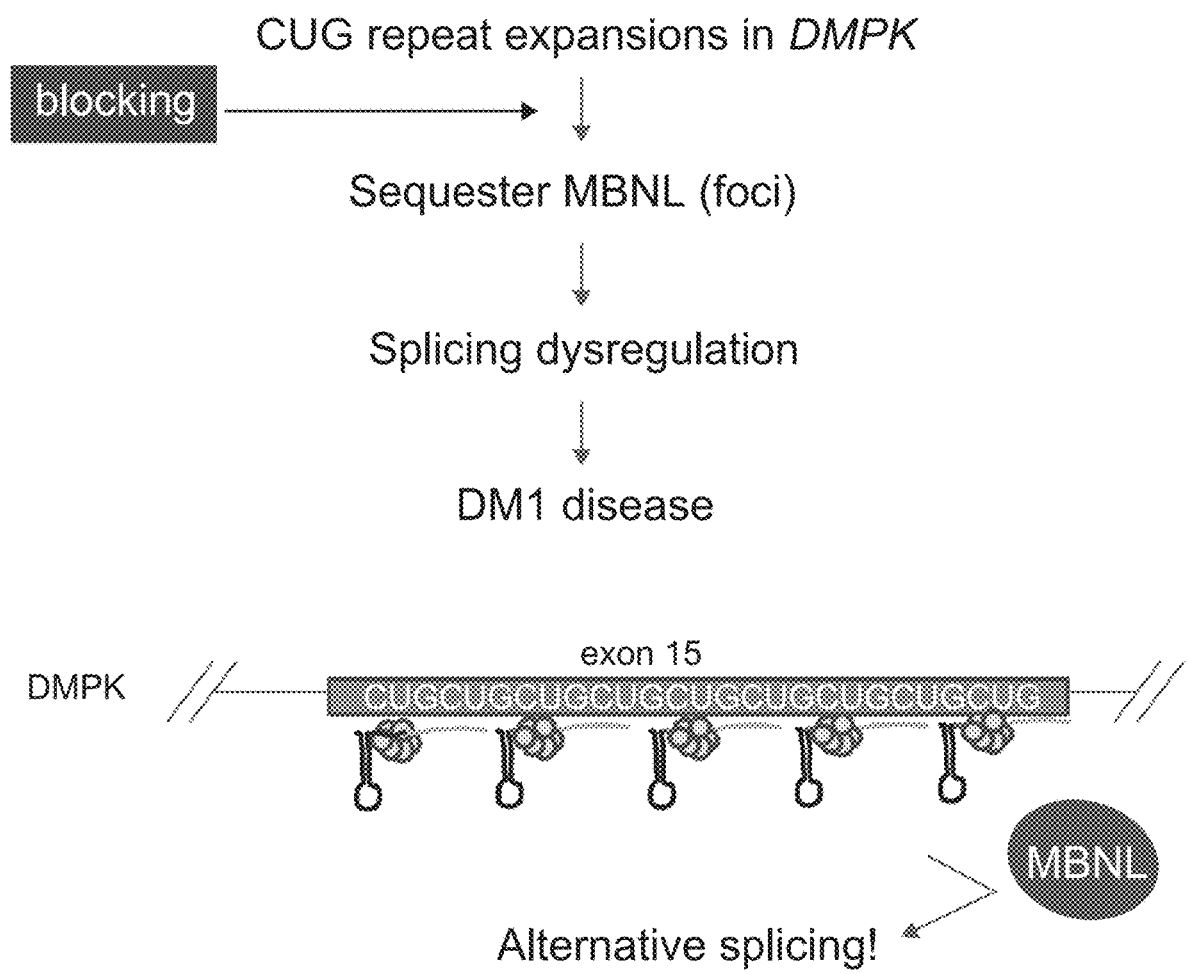

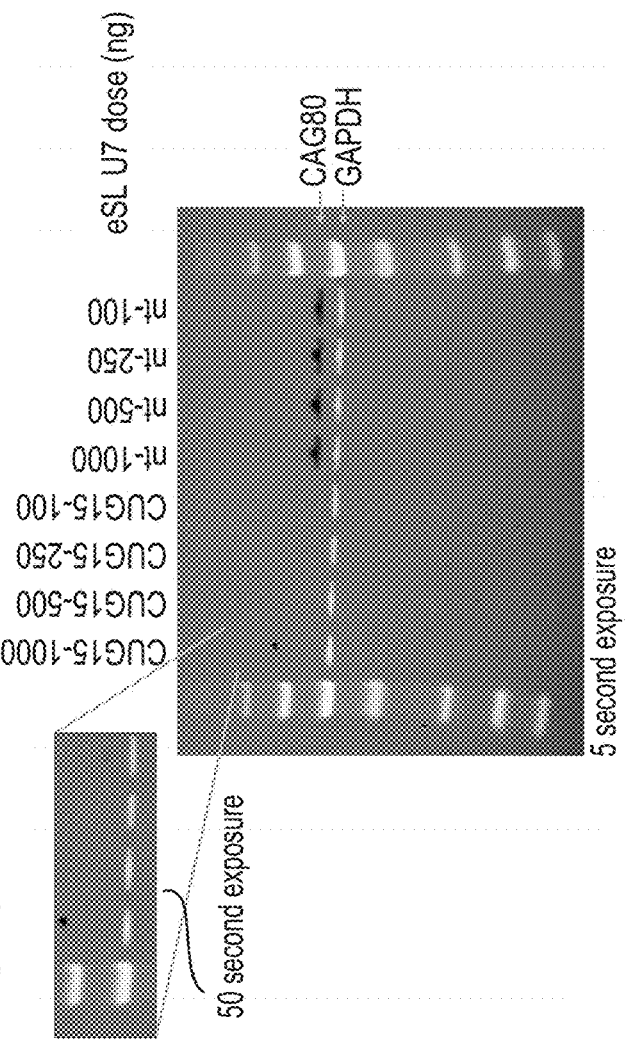
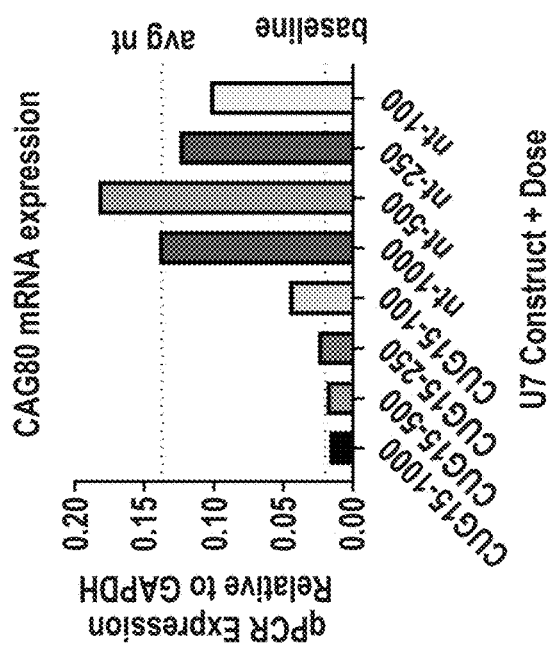
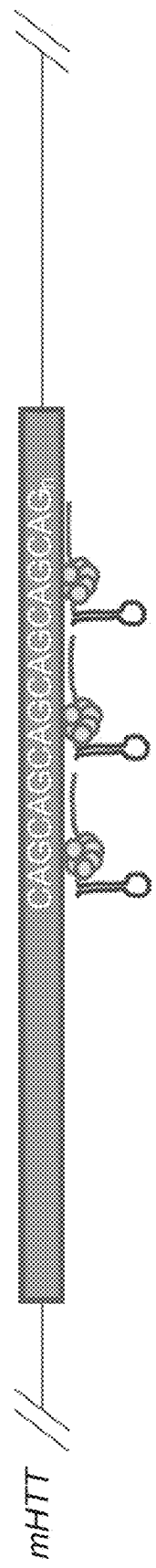
FIG. 3A
FIG. 3B
FIG. 3C

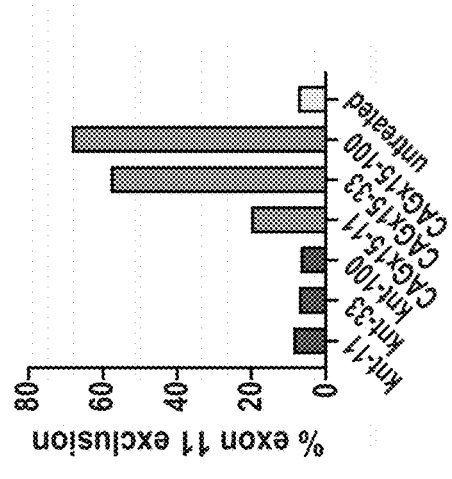
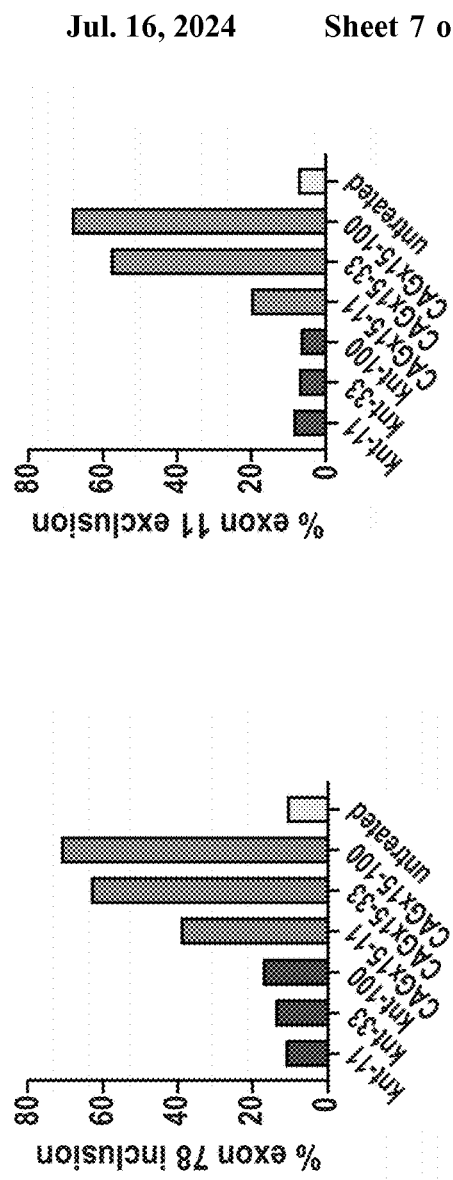
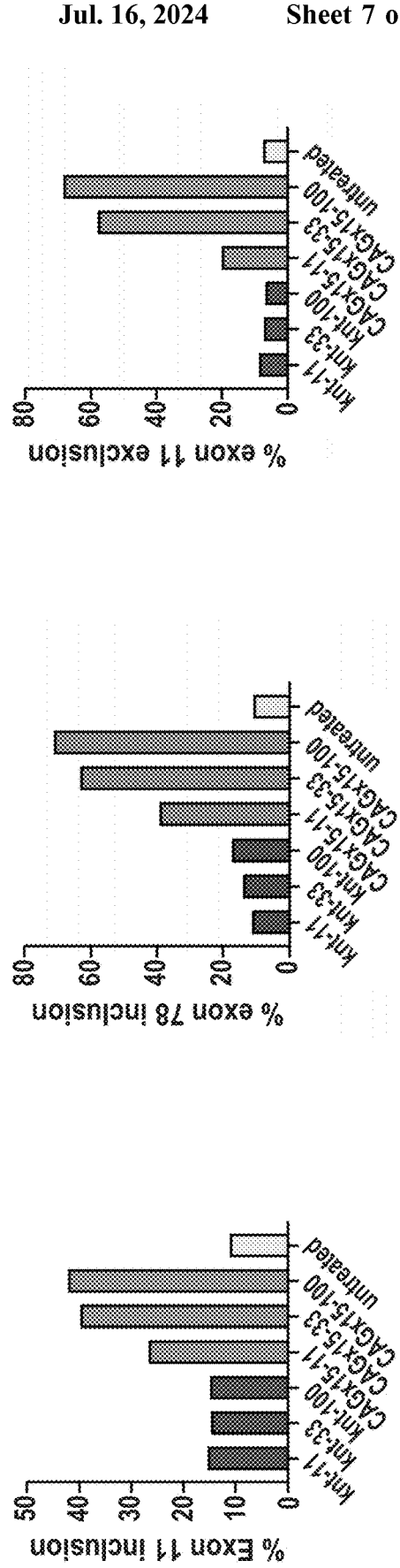
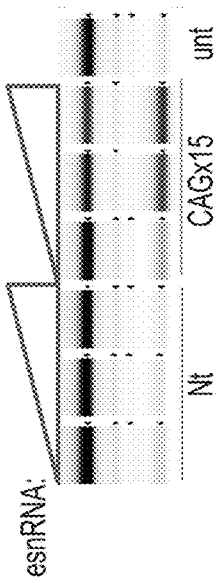
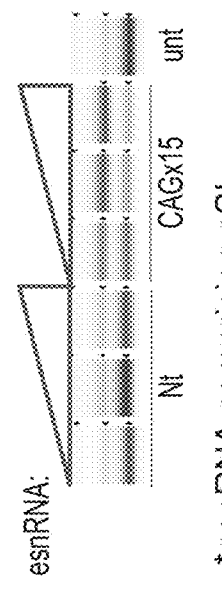
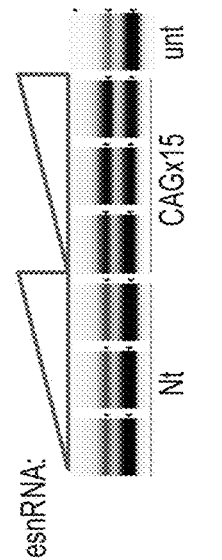
FIG. 5A  FIG. 5B  FIG. 5C
FIG. 5D  FIG. 5E  FIG. 5F

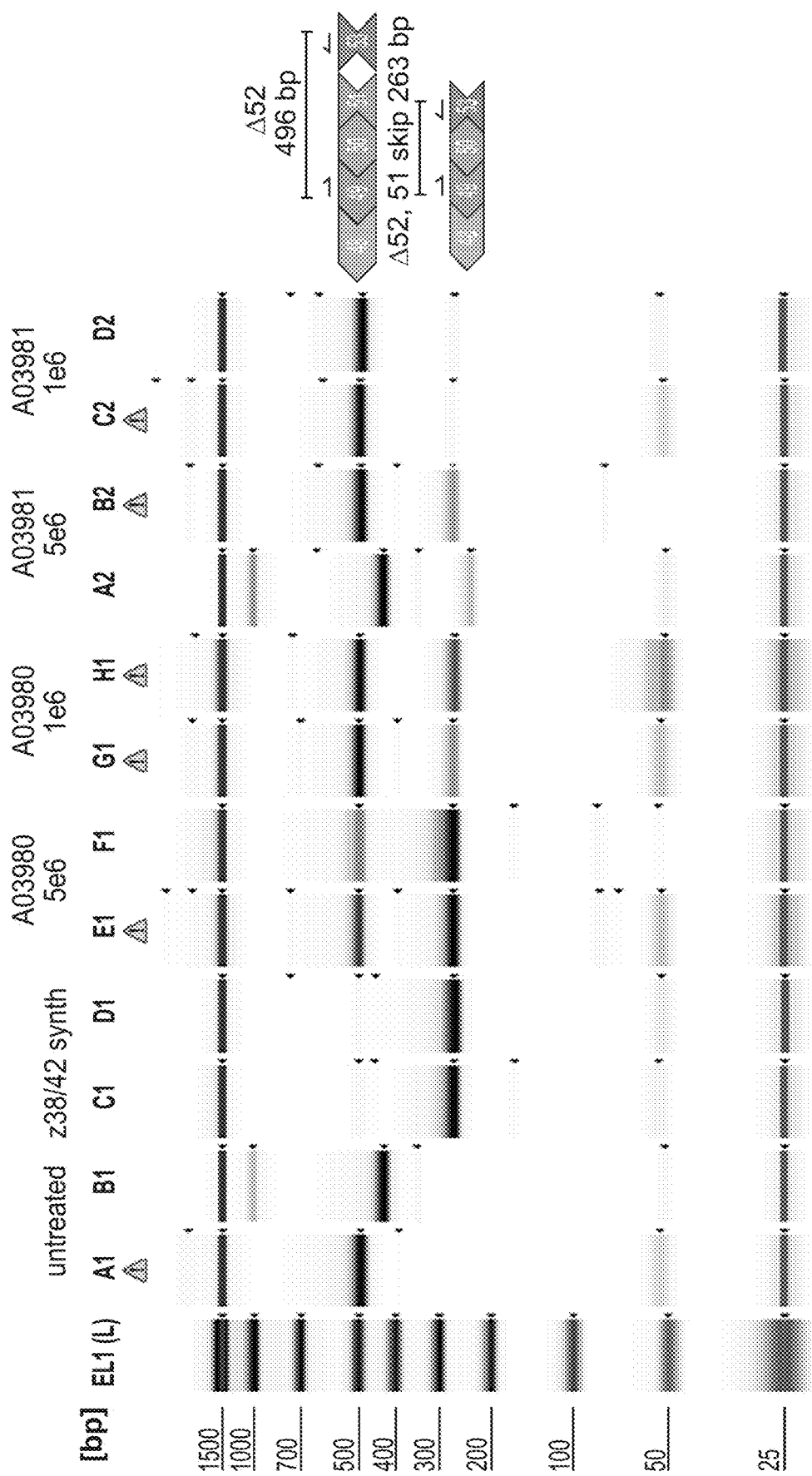

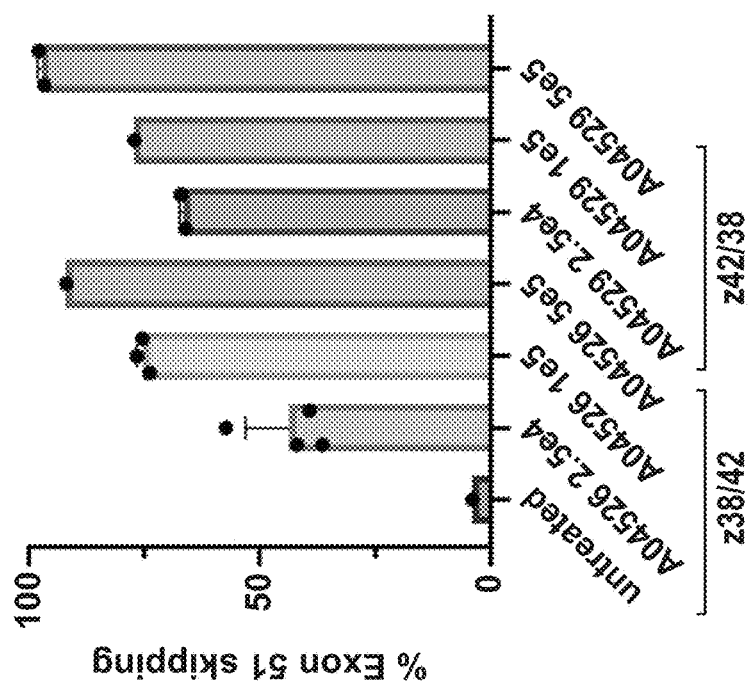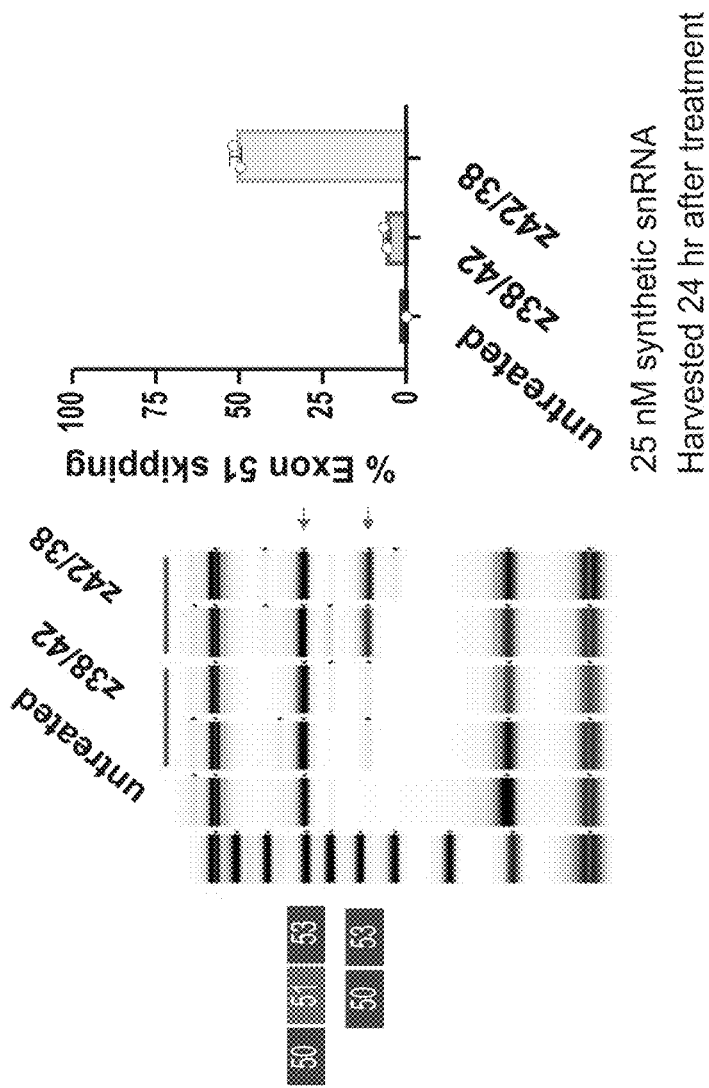
FIG. 15A
FIG. 15B

FIG. 18A
| Vector | MOI | Readouts |
|---|---|---|
| A04390: hU7p_U7CAG15_ hU1p_U7CAG15 snRNA | MOI 1e6, 1e5 | MSD for soluble HTT 2 weeks post-transduction |
FIG. 18B
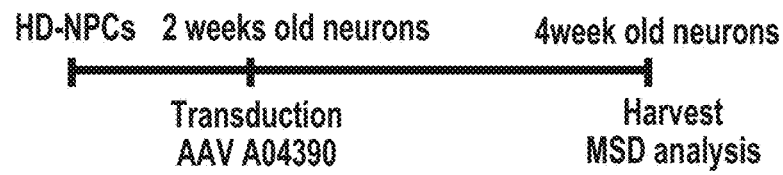
FIG. 18C
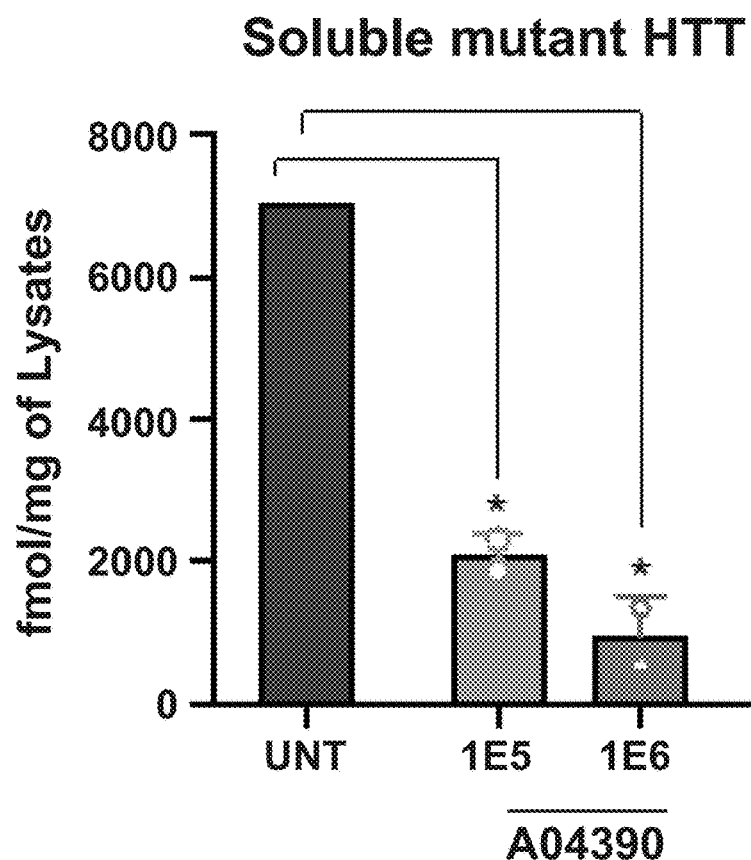

COMPOSITIONS AND METHODS COMPRISING ENGINEERED SHORT NUCLEAR RNA (snRNA)

RELATED APPLICATIONS

This application is a continuation of U.S. application Ser. No. 18/179,110, filed Mar. 6, 2023, which claims priority to, and the benefit of U.S. Provisional Application No. 63/316,659 filed Mar. 4, 2022 and U.S. Provisional Application No. 63/379,983 filed Oct. 18, 2022. The contents of each of these applications are hereby incorporated by reference in their entireties.

REFERENCE TO AN ELECTRONIC SEQUENCE LISTING

The contents of the electronic sequence listing (LOCN_020_C01US_SeqList_ST26.xml; Size: 289,776 bytes; and Date of Creation: Aug. 10, 2023) is herein incorporated by reference in its entirety.

FIELD OF THE DISCLOSURE

The disclosure is directed to molecular biology, gene therapy, and compositions and methods for modifying expression and activity of RNA molecules.

BACKGROUND

There are long-felt but unmet needs in the art for providing effective therapies for correcting dysfunctional messenger RNA.

Small nuclear RNA (snRNA) is one of the smallest types of RNA with an average size of about 150 nucleotides. snRNAs are functional non-coding RNAs. Eucaryotic genomes code for a variety of non-coding RNA such as snRNA, a class of highly abundant RNA, localized in the nucleus with important functions in intron splicing and RNA processing. snRNA, in the pre-mRNA splicing process, are capable of forming ribonucleoprotein particles (snRNPs) along with other proteins. These snRNPs and additional proteins form a large particulate complex (spliceosome) bound to the unspliced pre-mRNA transcripts. In addition to splicing, snRNAs function in nuclear maturation of nascent transcripts, gene expression regulation, as a splice donor in non-canonical systems, and in 3' end processing of replication-dependent histone mRNAs. U7 snRNA can be programmed to bind and modulate mRNA without exogenous protein expression but there still exists a need to develop a highly specific mRNA-targeting therapeutic that minimizes immunogenic risk. Furthermore, the small size of these programmed snRNAs creates an opportunity to develop single vector, highly specific (allele-specific), single target and multi-targeting gene therapy approaches.

Accordingly, the disclosure provides compositions and methods comprising a new therapeutic RNA-targeting platform comprised of engineered snRNAs.

SUMMARY

The disclosure provides gene therapy compositions comprising a new therapeutic RNA-targeting platform comprised of engineered snRNA (esnRNA) comprising an engineered snRNA stem loop (eSL).

Disclosed herein are compositions comprising nucleic acid molecules, and vectors comprising the engineered snRNA (esnRNA).

Disclosed herein is an RNA-targeting nucleic acid molecule comprising an engineered snRNA (esnRNA) system, wherein the esnRNA system comprises an engineered stem loop (eSL).

In one embodiment, the esnRNA comprises a 5' interaction stabilizer domain (5'ISD).

In one embodiment, the esnRNA comprises a targeting sequence (TS) (or spacer) that targets an RNA of interest. In another embodiment, the target RNA of interest is a microsatellite repeat RNA or a non-repeat RNA. In another embodiment, the microsatellite repeat RNA of interest is selected from the group consisting of CUG, CAG, GGGGCC, and CCCCGG. In one embodiment, the esnRNA comprises a targeting sequence (TS) that targets two target RNAs of interest which are GGGGCC and CCCCGG. In another embodiment, the two target RNAs of interest are a microsatellite repeat RNA and a non-repeat RNA. In another embodiment, the non-repeat RNA is a flanking sequence to the microsatellite repeat RNA. In another embodiment, the esnRNA comprises a targeting sequence (TS) that targets two or more RNAs of interest. In another embodiment the esnRNA comprises two or more targeting sequence (TS) that targets two or more RNAs of interest. In another embodiment, the esnRNA comprises a fusion of the two or more TSs.

In one embodiment, the esnRNA comprises an Sm binding domain (SmBD). In one embodiment, the SmBD is selected from the group consisting of U1, U2, U4, and U5 snRNAs. In another embodiment, the SmBD is derived from a pseudo snRNA.

In one embodiment, the esnRNA is operably linked to an snRNA promoter. In another embodiment, the snRNA promoter is a U7 promoter. In another embodiment, the U7 promoter is an endogenous U7 promoter. In another embodiment, the U7 promoter is a human U7 promoter (hU7) or a mouse U7 promoter (mU7). In another embodiment, the U7 promoter is an endogenous human U7 promoter of SEQ ID NO: 43. In one embodiment, the snRNA promoter is a U1 promoter. In another embodiment, the U1 promoter is a human U1 promoter or a mouse U1 promoter. In another embodiment, the snRNA promoter is selected from the group consisting of: a human U7 promoter, a human U1 promoter, a human U2 promoter, a human U4 promoter, a human U5 promoter, a human U6 promoter, a human 7sk promoter, a tRNA(Val) promoter, a mouse U1 promoter, and a mouse U7 promoter. In another embodiment, the vector comprises one or more esnRNAs, or one or more copies of the esnRNA driven by one or more snRNA promoters. In one embodiment, the vector comprises two copies (2×) of the esnRNA. In one embodiment, the vector comprises two snRNA promoters, wherein each promoter drives a copy of the 2× esnRNA. In another embodiment, the two snRNA promoters are the U7 promoter and the U1 promoter. In another embodiment, the two snRNA promoters are selected from the group consisting of: a human U7 promoter, a human U1 promoter, a human U2 promoter, a human U4 promoter, a human U5 promoter, a human U6 promoter, a human 7sk promoter, a tRNA(Val) promoter, a mouse U1 promoter, a mouse U2 promoter, a mouse U5 promoter, a mouse U6 promoter, a mouse U7 promoter, and a mouse H1 promoter. In another embodiment the two snRNA promoters are a mouse U7 promoter and a mouse U1 promoter.

In one embodiment, the esnRNA is operably linked to an snRNA downstream terminator (DT). In another embodiment, the snRNA DT is a U7 DT.

In one embodiment, the esnRNA comprises the eSL, the U7 promoter, the TS, the SmBD, the 5'ISD, and the DT. In another embodiment, the esnRNA comprises the eSL, the U7 promoter, the U1 promoter, the TS, the SmBD, the 5'ISD, and the DT.

In one embodiment, the esnRNA comprises the eSL, the U7 promoter, the TS, the SmBD, the 5'ISD, and the DT. In another embodiment, the esnRNA comprises the eSL, the U7 promoter, the U1 promoter, the TS, the SmBD, the 5'ISD, and the DT.

Also disclosed herein is a vector comprising the esnRNA. In some embodiments, the vector comprises multiple copies of the esnRNA. In some embodiments, the multiple copies of the esnRNA is 2, 3, or 4 copies (2×, 3×, or 4×) of the esnRNA. In some embodiments, the multiple copies of the esnRNA is 4 or more copies (4× or more) of the esnRNA. In some embodiments, each esnRNA of the multiple copies of esnRNA is separated by a nucleic acid buffer sequence derived from human non-coding genomic sequences downstream of an snRNA. In one embodiment, the buffer sequence is derived from human genomic sequences downstream of U7. In one embodiment, the buffer sequence is selected from the group consisting of: buffer 1 (30 bp, 100 bp, or 500 bp), buffer 2 (30 bp, 100 bp, or 500 bp), buffer 3 (30 bp, 100 bp, or 500 bp), and a combination thereof. In one embodiment, the vector is a viral vector or a non-viral vector. In another embodiment, the viral vector is an AAV vector. In another embodiment, the AAV vector is an scAAV vector or a ssAAV vector. In another embodiment, the AAV vector is an AAV9 vector. In another embodiment, the AAV9 vector is an ssAAV9 vector or an scAAV9 vector.

Also disclosed herein is a method of targeting one or more target RNAs of interest and blocking, knocking down, editing, exon-skipping, exon inclusion or splicing the one or more target RNAs, comprising contacting an esnRNA of the disclosure with a cell comprising the one or more target RNAs.

The disclosure provides aa RNA-targeting nucleic acid molecule comprising an engineered snRNA esnRNA, wherein the esnRNA system comprises an engineered stem loop (eSL) comprising one or more nucleic acid sequences selected from SEQ ID NO: 1-SEQ ID NO: 11, SEQ ID NO: 146-SEQ ID NO: 148, SEQ ID NO: 163, or SEQ ID NO: 186-205.

In some embodiments, the esnRNA comprises a targeting sequence (TS) that targets a target RNA of interest.

In some embodiments, the target RNA is a pre-mRNA or mRNA sequence. In some embodiments, the target RNA of interest is a microsatellite repeat RNA. In some embodiments, the microsatellite repeat RNA is selected from the group consisting of CUG, CAG, and GGGGCC+CCCCGG.

In some embodiments, the target RNA is a sequence encoding DMD. In some embodiments, the targeting sequence is selected from SEQ ID NO: 206 or SEQ ID NO: 207. In some embodiments, the targeting sequence comprises one or more nucleic acid sequences set forth in SEQ ID NO: 208-SEQ ID NO: 227.

In some embodiments, the esnRNA comprises two targeting sequences that target two RNAs of interest. In some embodiments, the two TSs are a fusion sequence.

In some embodiments, the esnRNA comprises an Sm binding domain (SmBD) selected from the group consisting of a U1, U2, U4, and U5 SmBD.

In some embodiments, the SmBD comprises a nucleic acid sequence set forth in any one of SEQ ID NO: 31-SEQ ID NO: 38, or SEQ ID NO: 164.

In some embodiments, the esnRNA comprises a 5' interaction stabilizer domain (5'ISD) comprising a nucleotide sequence selected any one of SEQ ID NO: 12-SEQ ID NO: 23.

In some embodiments, the esnRNA comprises a nucleic acid sequence set forth in any one of SEQ ID NO: 65-SEQ ID NO: 119 or SEQ ID NO: 179-SEQ ID NO: 185.

The disclosure provides a vector comprising one or more esnRNA of the disclosure. In some embodiments, the viral vector is an AAV vector. In some embodiments, the esnRNA is operably linked to a promoter.

In some embodiments, the esnRNA is operably linked to a U7 promoter or a U1 promoter.

In some embodiments, the esnRNA is operably linked to a downstream terminator (DT). In some embodiments, the esnRNA is operably linked to a U7 downstream terminator or a U1 downstream terminator.

In some embodiments, the vector comprises at least one, at least two, at least three, at least four, or at least five esnRNA. In some embodiments, the least one, at least two, at least three, at least four, or at least five esnRNA each target the same target RNA sequences.

In some embodiments, the least one, at least two, at least three, at least four, or at least five esnRNA target two or more target RNA sequences In some embodiments, each esnRNA is separated by a buffer sequence. In some embodiments, the buffer sequence comprises a nucleic acid sequence set forth in any one SEQ ID NO: 24-SEQ ID NO: 30.

In some embodiments, the vector comprises a nucleic acid sequence set forth in any one of SEQ ID NO: 123-SEQ ID NO: 143, SEQ ID NO: 168-SEQ ID NO: 178, or SEQ ID NO: 231-SEQ ID NO: 233.

A DMD exon 51 RNA-targeting nucleic acid molecule comprising a spacer sequence set forth in any one of SEQ ID NO: 206-SEQ ID NO: 230.

The disclosure provides a method of treating a disease or disorder in a subject comprising administering an RNA-targeting nucleic acid molecule of the disclosure or an AAV vector of the disclosure.

In some embodiments, the disease or disorder is associated with a toxic repeat RNA sequence. In some embodiments, the toxic repeat RNA sequence is a CAG, CUG, GGCCCC, CCGGG, or GGCCC+CCGGGG RNA repeat.

In some embodiments, the disease or disorder is myotonic dystrophy (DM1) or Huntington's disease (HD).

In some embodiments, the disease or disorder is Duchenne Muscular Dystrophy. In some embodiments, the RNA-targeting nucleic acid molecule or AAV vector targets an RNA sequence encoding dystrophin (DMD).

In some embodiments, the RNA sequence encoding DMD comprises an intronic or exonic sequence. In some embodiments, the exonic sequence comprises exon 51, or a flanking region thereof, of DMD. In some embodiments, the administration is administration is intravenous, intramuscular, subpial, intrathecal, intraparenchymal, intrathecal, intrastriatal, subcutaneous, intradermal, intraperitoneal, intratumoral, intravenous, intraocular, and/or parenteral administration.

BRIEF DESCRIPTION OF THE DRAWINGS

FIG. 1A shows a tape station image of PCR products which increase in abundance for the engineered SL indicating increased stability of an esnRNA disclosed herein. Predicted PCR product size is shown below the image. FIG. 1B illustrates a schematic of the engineered snRNA (esnRNA) comprising the engineered stem loop (eSL) disclosed herein alongside non-engineered stem loops. FIG. 1C shows alternative mechanisms to protect the 5' end of the snRNA which forego the use of an interaction stabilizer domain (ISD). FIG. 1D shows the approximate size of an snRNA cassette.

FIG. 2A-C. FIG. 2A-2B shows FISH quantification and images of CUG RNA Foci of an esnRNA targeting CUG disclosed herein compared to NT (non-targeting) esnRNA. Y axis depicts percentage average foci per cell normalized to NT, and x axis depicts treatment. Cell nuclei was stained with DAPI and CUG RNA foci labeled with a specific labeled probe. FIG. 2C shows a schematic of the esnRNA MOA targeting and blocking CUG repeat expansions releasing MBLN and restoring splicing defects characteristic in DM1 disease.

FIG. 3A-C. FIG. 3A shows qPCR results of a dose-dependent knockdown of CAG80 reporter mRNA to baseline levels. Y axis depicts CAG repeat RNA expression levels relative to reference gene GAPDH, and x axis depicts snRNA treatment CAG targeting (CUG15) or non-targeting (nt) (using different doses 250 ng, 500 ng or 1000 ng). FIG. 3B shows a Western blot for CAG80 reporter poly-Q protein expression. Top lanes show CAG reporter poly-Q expression and bottom lane GAPDH loading control. FIG. 3C shows CAG repeat expansions in mutant HTT in Huntington's disease and the esnRNA MOA blocking the CAG repeats.

FIG. 4A shows a tape station image of the PCR product to detect USH2A exon 13 inclusion (top band) or exclusion (bottom band) after treatment with esnRNA. FIG. 4C shows the quantification of percentage of exon 13 exclusion after esnRNA treatment compared to NT esnRNA control (shown in A). FIG. 4B shows a schematic of the engineered snRNA comprising the eSL compared to the non-engineered snRNAs. FIG. 4D shows a schematic of splicing modulation in Usher's Syndrome and DMD (Duchenne Muscular Dystrophy).

FIG. 5A-F shows PCR results for restoration of splicing isoforms for BIN1, DMD and LBD3 (mispliced in DM1 patient cells) after treatment with esnRNAs to target CUG repeats in DM1patient derived myotubes. Figures A-C show quantitation of the percentage restoration to the healthy splice isoform from the tape station images shown in Figures D-F. Y axis depicts percentage of correction, and x axis depicts treatment (knt, refers to non-targeting negative control; CAG×15 refers to CUG targeting esnRNA; unt refers to untreated).

FIGS. 7A and B show the relative abundance over time of synthetic engineered snRNAs with alternative 5' stabilizing domains. RNA was collected at 24 hr, 48 hr, and 72 hr time points after transfection of synthetic snRNAs with varying stabilizing domains to determine the relative stability of the snRNA.

FIG. 12A-12B shows results for exon 51 skipping after transduction of human delta exon 52 myotubes with snRNA disclosed herein (A03980: 2× z38/42 fusion snRNA cassettes; A03981: 2 snRNA cassettes, one with z42 TS and the other with z38 TS). FIG. 12A shows a tape station image of PCR products representing the exon 51 included and excluded isoforms and a schematic showing expected fragment sizes. FIG. 12B shows the quantification of the band intensities in FIG. 12A semi-quantitative PCR. Y axis depicts percentage of exon 51 skipping and x axis the treatment (either synthetic snRNA or AAV transduced for A03980 of A03981 with different MOIs).

FIG. 13A shows immunofluorescence for desmin or dystrophin in untreated myotubes, myotubes treated with synthetic snRNAs or myotubes treated with MOI of 1e6 or 5e6 of A03980 (2× z38/z42 fusion snRNA cassettes). FIG. 13B shows immunofluorescence for desmin or dystrophin in myotubes transduced with MOI of 1e6 or 5e6 of A03981 (2 snRNA cassettes with z42 TS and z38 TS).

FIG. 15A-D show the activity of exon 51 ESE-targeting fusion snRNAs in human skeletal myotubes with exon 52 deleted and del52hDMD/mdx mice. (A) tape station image and quantification of exon 51 skipping in human skeletal myotubes with DMD exon 52 deleted 24 hours after transfection of a low dose of synthetic snRNAs carrying the fusion antisense sequences z73 (z38/z42) and z187 (z42/z38). At a low dose, transfection of synthetic snRNA z187 induces higher levels of exon 51 skipping than z73. (FIG. 15B) shows quantification of exon 51 skipping in human skeletal myotubes with DMD exon 52 deleted after transduction with AAV9-A04526 (carrying two esnRNA cassettes each expressing z73) and A04569 (carrying two cassettes each expressing z187) for 7 days with MOIs of 2.5e4, 1e5 and 5e5. (FIG. 15C) shows quantification of exon 51 skipping in the humanized exon 52-deleted DMD (del52hDMD/mdx) mouse model. Mice we injected retro-orbitally with 3e12 vector genomes of A04526 and A04569. Following 3 week survival, RNA was extracted from the tibialis anterior muscle (TA), the Gastrocnemius (Gc) and the heart. Semi-quantitative RT-PCR was performed to detect exon 51 included and excluded bands. (FIG. 15D) shows the quantification of dystrophin positive fibers 4 weeks after intramuscular delivery of a 3e11 vg/muscle dose of A04526 or an ESE-targeting Vivo-Morpholino (ViM) to the Gastrocnemius of del52hDMD/mdx mice. hDMD/mdx mice (gray bar) which expresses wildtype human dystrophin serves as a positive control for dystrophin expression. U=untreated.

Figure 16A:
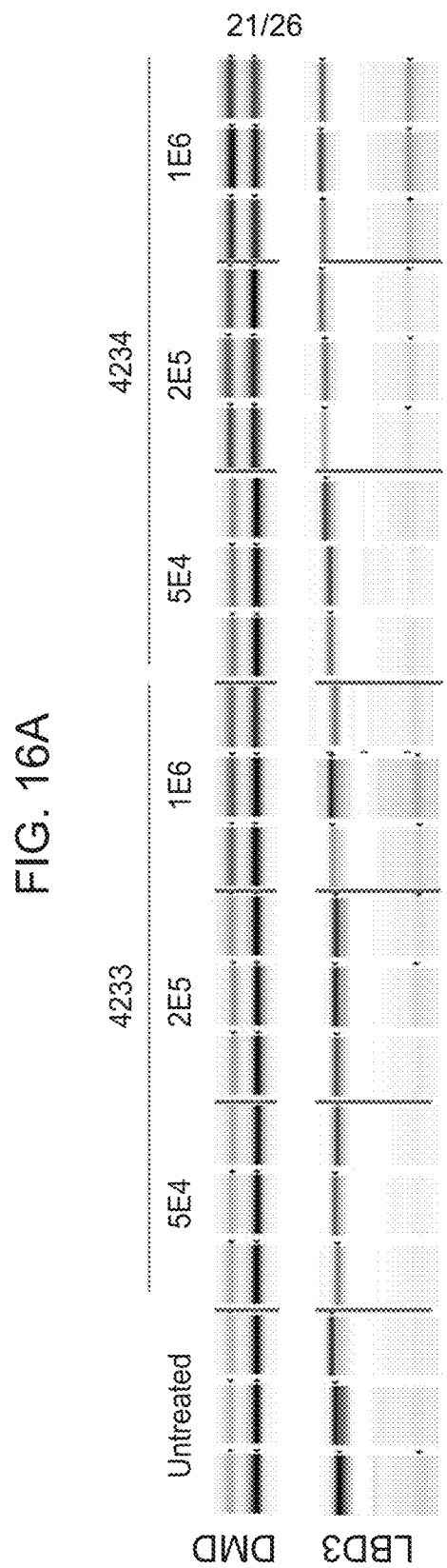
Figure 16B:
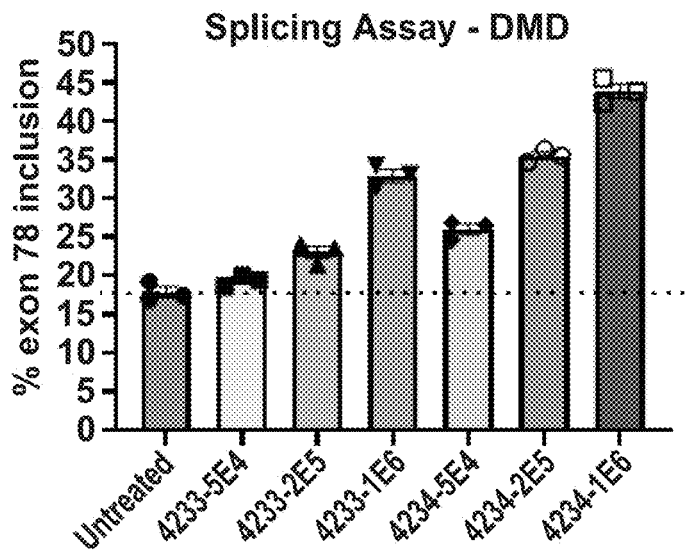
Figure 16C:
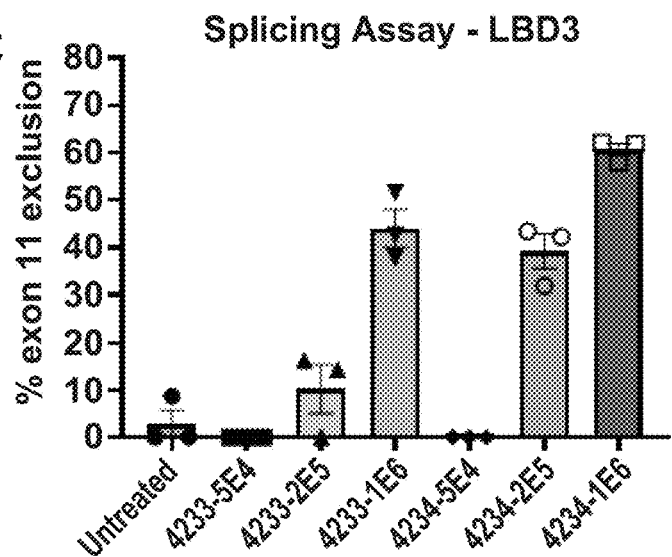
Figure 16D:
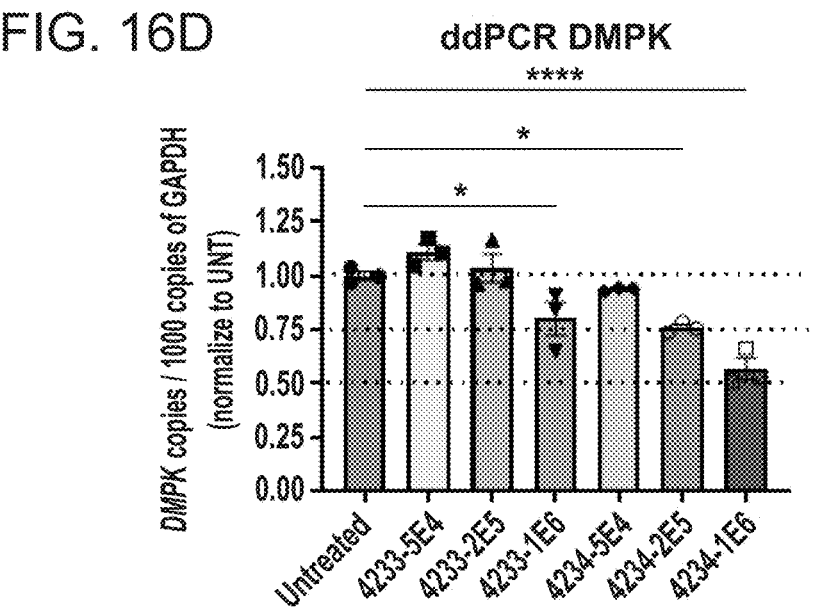

FIG. 16A-D show splicing reversal of DMD and LBD3 splice isoforms and knockdown of DMPK after treatment with snRNA targeting CUG repeats in patient derived myotubes (containing 1700 CUG repeats). DM1 patient fibroblasts were differentiated into myotubes by transduction with myoD Adenovirus vector (for 5 days). Then cells were transduced with multiple MOIs of A04233 and A04234 (scAAV9 dual snRNAs targeting CUG repeats) and harvested 7 days post-transduction. FIG. 16A shows a tape station image of RT-PCR products using specific primers to detect DMD exon 78 inclusion (top band) and LBD3 exon 11 exclusion (bottom band) which are markers of splicing correction seem in normal WT cells. Quantification of DMD exon 78 inclusion (FIG. 16B) and LBD3 exon 11 exclusion (FIG. 16C). The x-axis depicts the treatment (vector and MOI). The y-axis depicts the percentage of splice correction, either exon inclusion for DMD exon 78 or exclusion for LBD3 exon 11. FIG. 16D shows levels of DMPK RNA expression by ddPCR after treatment with snRNAs (AAV9 A04233 and AAV9 A04234) with different MOIs. The x-axis depicts the treatment. The y-axis depicts DMPK copies per 1000 copies of GAPDH reference gene normalized to UNT (untreated cells).

Figure 17A:
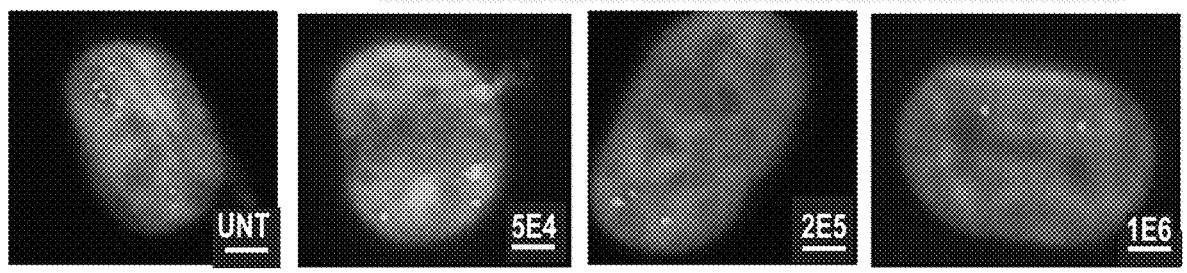
Figure 17A:
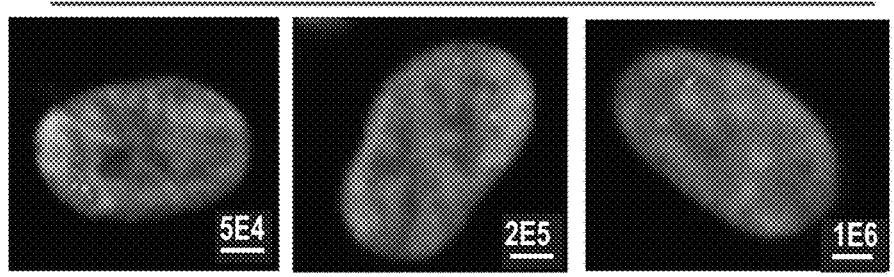
Figure 17B:
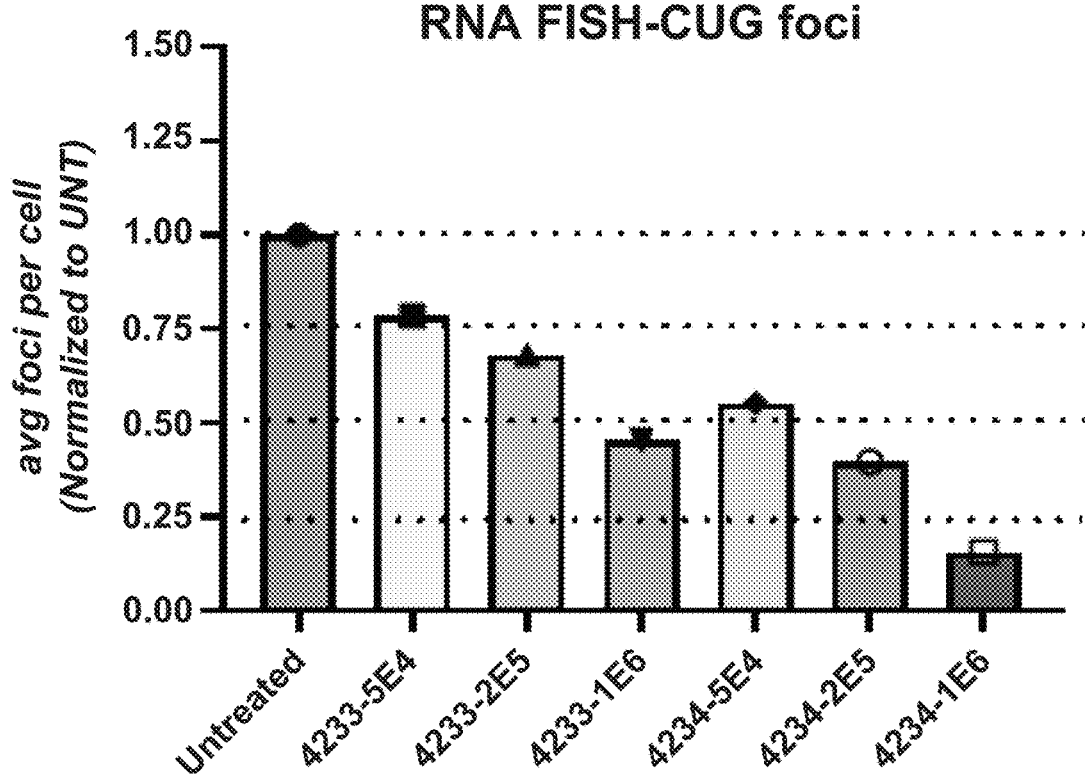

FIG. 17A-B shows images and quantification of nuclear RNA foci from patient-derived myotubes transduced with different MOIs of AAV9 A04233 and AAV9 A04234. DM1 patient fibroblasts were differentiated into myotubes by transduction with myoD Adenovirus vector (for days). Then cells were transduced with multiple MOIs of A04233 and A04234 (scAAV9 dual snRNAs targeting CUG repeats) and harvested 7 days post-transduction for RNA FISH (to detect CUG Foci). FIG. 17A shows images of CUG RNA foci obtained from untreated and treated myotubes with AAV9 snRNA vectors A04233 and A04234. Cell nuclei was stained with DAPI and CUG FISH was performed with a CUG labeled probe. Cells were processed 7 days post-transduction. FIG. 17B shows quantification for the average number of CUG foci per cell. The x-axis depicts the treatment and MOI used. The y-axis depicts average of CUG foci per cell normalized to UNT (untreated cells).

FIG. 18A-C depicts the treatment, timeline and quantification of HTT mutant soluble protein after treatment with AAV-snRNA targeting CAG repeats. FIG. 18A shows the experimental design for the vector used AAV-A04390 (2× hU7/hU1 snRNA targeting CAG repeats), the 2 MOIs and the end point assay to detect mutant (mut) HTT soluble protein. FIG. 18B depicts the timeline for this experiment. HD patient iPSc (containing 66 CAG repeats) were differentiated into cortical neurons for 2 weeks and then transduced with AAV-A04390 snRNA vector for an additional 2 weeks. Then cortical neurons were harvested and mutant soluble HTT protein quantified by Meso scale discovery immunoassay (MSD, shown in FIG. 18C). The y-axis depicts fmol of mutant soluble HTT per mg of protein lysate, and the x-axis the treatment and MOI.

Figure 19B:
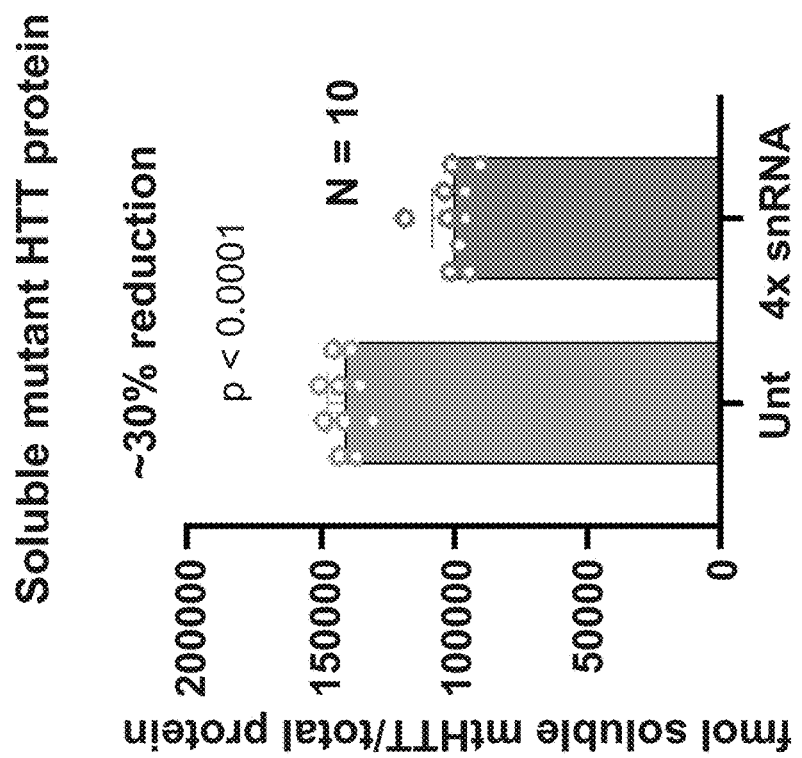
Figure 19A:
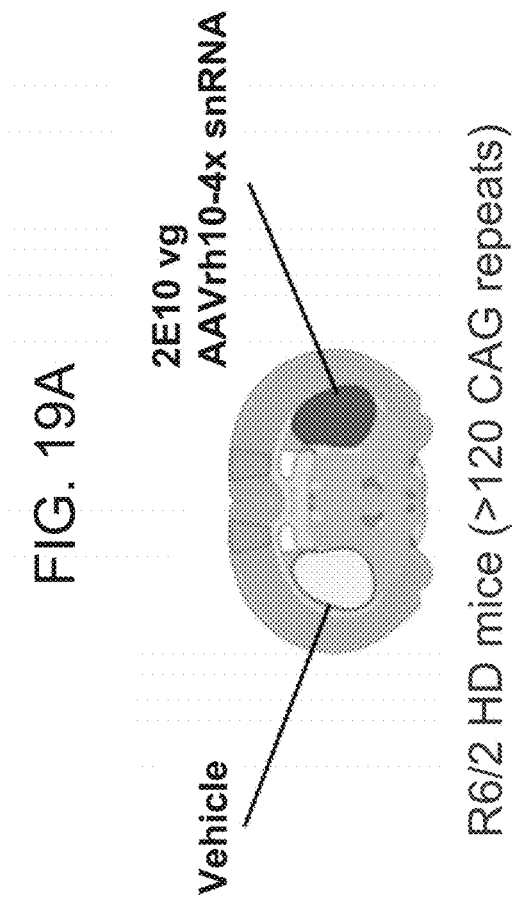

FIG. 19A-B depicts the in vivo study design to target CAG repeats on R6/2 HD mouse model and quantification of mutant HTT soluble protein after treatment with AAV-snRNA targeting CAG repeats (A03081). FIG. 19A diagram shows dosage (2e10 vector genomes) of AAVrh10-snRNA (4×CAG×15 targeting snRNAs vector) administered by intrastriatal injection. Untreated or uninjected contralateral striatal side was used as a control. (FIG. 19B) shows quantification of mutant soluble HTT protein by Meso scale discovery immunoassay (MSD) on untreated and snRNA treated mice (n=10). The y-axis depicts fmol of mutant soluble HTT per mg of total protein lysate, and the x-axis the treatment.

Figure 20B:
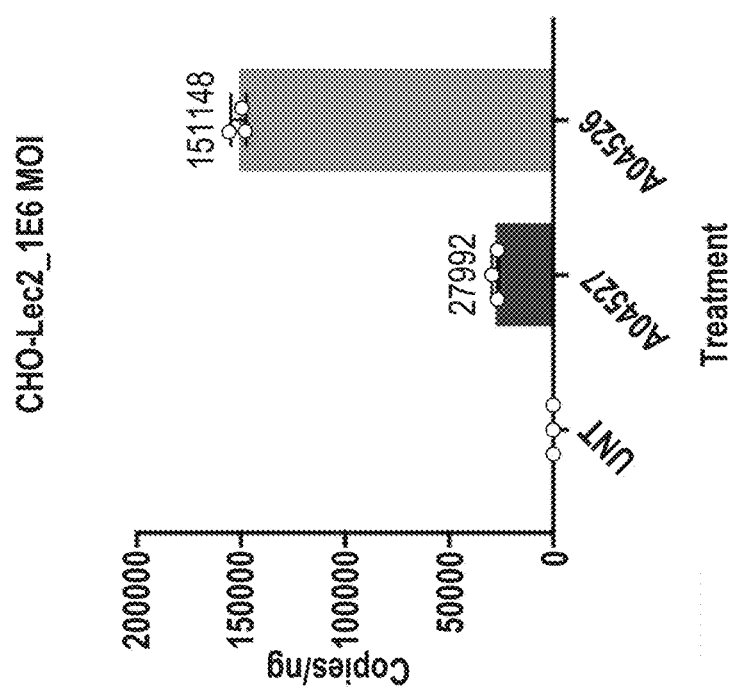
Figure 20A:
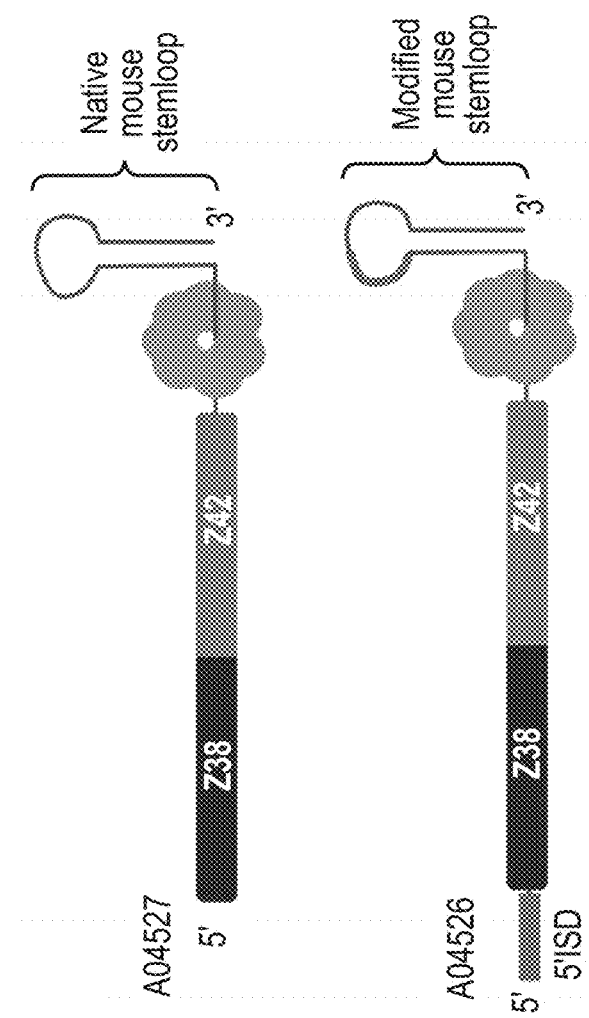

FIG. 20A depicts the differences between the snRNAs expressed from A04527 and A04526 with A04526 expressing engineered snRNAs that have a 5'ISD and engineered mouse SL and A04527 which has no 5'ISD and a mouse native SL. FIG. 20B shows a bar graph of the expression of z38/42 (in snRNA copies/nanogram) 2 days after transduction of CHO-Lec2 cells at an MOI of 1e6 for with AAV9-A04527 or A04526 virus.

DETAILED DESCRIPTION

The disclosure provides gene therapy compositions comprising a new therapeutic RNA-targeting platform comprised of engineered snRNA (esnRNA) comprising an engineered snRNA stem loop (eSL).

Disclosed herein are compositions comprising nucleic acid molecules, and vectors comprising the engineered snRNA (esnRNA).

Small nuclear ribonucleic acids (snRNAs) are essential components of small nuclear ribonucleoprotein complexes (snRNPs) which, when assembled with additional proteins, form the large ribonucleoprotein complex known as the spliceosome, the cell machinery appointed to mediate the entire mRNA maturation process. The spliceosome is responsible for precursor mRNA splicing; the process that removes introns from RNA transcripts before protein production. An individual snRNA is generally about 250 nucleotides or less in size. For example, U1 snRNA is 164 nucleotides in length and is encoded by genes that occur in several copies within the human genome. U1 snRNA represents the ribonucleic component of the nuclear particle U1 snRNP. The U1 snRNA has a stem and loop tridimensional structure and within the 5' region there is a single-stranded sequence, generally about 9 nucleotides in length, capable of binding by complementary base pairing to the splicing donor site on the pre-mRNA molecule. (Horowitz et al., 1994, Trends Genet., 10(3):100-6.) The various spliceosomal snRNAs have been designated as U1, U2, U4, U5, U6, U4ATAC, U6ATAC, U7, U11 and U12, due to the generous amount of uridylic acid they contain. (Mattaj et al., 1993, FASEB J, 15, 7:47-53.)

snRNA systems can be used for treating toxic mutations. For example, antisense oligonucleotides that interfere with splice sites and regulatory elements within an exon containing toxic mutations can induce skipping of specific exons at the pre-RNA level. Such antisense sequences can be packaged in an snRNA sequence delivered using viral vectors carrying a nucleic acid sequence from which the snRNA can be transcribed. U7 snRNA is endogenously involved in histone pre-mRNA 3'-end processing, but can be converted into a versatile tool for splicing modulation by a small change in the binding site for Sm/Lsm proteins. One such therapeutic strategy for treating Duchenne muscular dystrophy has used modified U7 snRNA to convert an out-of-frame mutation into an in-frame mutation, which gives rise to internally deleted toxic RNA, but still functional dystrophin. (Goyenvalle et al., 2009, 17(7): 1234-1240.)

Most U-rich snRNPs are complexes that mediate the splicing of pre-mRNAs. U7 snRNP is an exception. U7 is not involved in splicing but rather is a key factor in the unique 3'-end processing of replication-dependent histone mRNAs. By modifying the U7 snRNA histone binding sequence and the Sm motif, U7 can no longer be involved in processing the histone pre-mRNA and instead targets pre-mRNAs or smRNA for blocking or splicing modulation. In this manner, U7 snRNA can be used as an effective gene therapy platform. A U7 snRNA platform also has the additional advantages of being a compact size, having the capability to accumulate in the nucleus without causing cellular toxicity, and possesses little to no immunoreactivity. (Gadgil et al., 2021, J Gene Med, 23(4): e3321.)

Disclosed herein is a newly engineered and redesigned snRNA platform (or known herein as an esnRNA platform) comprising an 1) engineered stem loop (eSL). Compensatory modifications made to the native stem loop sequence create an engineered stem loop (eSL) which more effectively communicates (folds and anneals) with the snRNA interaction stabilization domain (ISD) which in turn creates a snRNA platform with increased stability. See FIG. 1. U7 snRNAs have been previously shown to be programmable to modulate mRNAs. Disclosed herein are programmed engineered snRNA improvements which are capable of being used as a gene therapy tool. These engineered snRNA systems are shown herein to lead to blocking microsatellite repeat expansions (shown herein for treating myotonic dystrophy (DM1) or Huntington's disease (HD)), exon skipping (for treating DMD) and splicing modulation (shown herein for treating USH2A (Usher Syndrome type 2). In one embodiment, these snRNAs are human snRNAs. In another embodiment, these snRNAs are mouse snRNAs. In another embodiment, the snRNAs are a combination of human and mouse snRNAs. In one embodiment the U7 is a human U7 or a mouse U7. In another embodiment disclosed herein, engineered snRNA comprises varying types of snRNAs (U1-U12, etc.) by combining domains of endogenous snRNAs to fine tune stabilization of the platform and/or to reduce off-target effects. For example, in one embodiment, the engineered snRNA system comprises a combination of human or mouse U7 and human or mouse U1 snRNA components.

Additional elements that can tune the processing and abundance of the RNA can be further engineered into the esnRNAs comprising eSLs. See FIG. 1C. In one embodiment, additional elements that can tune the processing, stability, and abundance of the esnRNA can be further engineered into the esnRNAs at the 5' or 3' ends. In another embodiment, such elements may include but are not limited to stem loops, hairpins, G-C clamps, kissing loops, triplexes, quadruplexes, and protein binding sites.

The esnRNA platform and portions thereof disclosed herein can be used in any therapeutic setting and context so long as a suitable spacer(s) (or TS(s)) is included in the design of the esnRNA therapeutic composition. In certain embodiments, a therapeutic esnRNA composition is used to treat a disease selected from the group consisting of Duchenne Muscular Dystrophy, DM1, and HD. In another embodiment, the esnRNA composition is used to treat DMD caused by exon 51 mutations Engineered Stem Loops The engineered snRNA (esnRNA) system disclosed herein comprises an engineered stem loop (eSL) which includes compensatory modifications to a native snRNA stem loop. These modifications result in increased stability of the esnRNP compared to snRNP comprising an unmodified stem loop. An eSL disclosed herein can be derived from any snRNP such as U1-U12. In one embodiment, the eSL is a human or mouse U7 eSL. In one embodiment, the eSL is a human or mouse eSL. In some embodiments, the eSL is a human and mouse eSL. In some embodiments, the eSL is a non-human eSL selected from the group consisting of mouse, pig, sheep, goat, cow, dog, cat, horse, or a combination thereof. In some embodiments, the eSL is an eSL selected from the group consisting of human, mouse, pig, sheep, goat, cow, dog, cat, horse, or a combination thereof. In some embodiments, the eSL sequence is not a native stem loop sequence. In some embodiments, the nucleic acid sequence of the eSL is at least 65%, 70%, 75%, 80%, 85%, 90%, 95%, 96%, 97%, 98%, 99% or 100% (or any percentage in between) is not a native stem loop sequence.

In some embodiments, a human eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                           (SEQ ID NO: 1))
    ggctttctggctccttaccggaaagcc, (SEQ ID NO: 2)
    ggctttctgggaggttaccggaaagcc, (SEQ ID NO: 3)
    ggctttctggcctccttaccggaaagcc, (SEQ ID NO: 4)
    ggctttctggggaggttaccggaaagcc, (SEQ ID NO: 5)
    ggctttctggctggctaccggaaagcc, (SEQ ID NO: 6)
    ggctttctggcttccccggaaagcc, (SEQ ID NO: 7)
    ggctttctggcttcttcccggaaagcc, (SEQ ID NO: 8)
    ggctttctggcaacttaccggaaagcc, (SEQ ID NO: 9)
    ggctttctggttcggtaccggaaagcc,
```

```
                                         (SEQ ID NO: 10)
ggctttctggaagccttaccggaaagcc, (SEQ ID NO: 11)
ggctttctggcttcttaccggaaagcc,
or (SEQ ID NO: 186)
GGCTTTCTGGCCTCCGCCGGAAAGCCCCT.
```

In some embodiments, a murine eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 163)
ggctttctggctccttaccggaaagccct (SEQ ID NO: 146)
Ggttttctgacctccgtcggaaaaccct, (SEQ ID NO: 147)
ggttttctgacctccttcggtcggaaaacccct, (SEQ ID NO: 148)
Ggttttctgacctccgtcggaaaacc, (SEQ ID NO: 228)
GGTTTTCTGACACTCCGTCGGAAAACCCCT, (SEQ ID NO: 229)
GGTTTTCTGATCTCCATCGGAAAACCCCT,
or (SEQ ID NO: 230)
GGTTTTCCGACCTCCGTCGGAAAACCCCT.
```

In some embodiments, a human or murine eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 190)
GGCTTTCTGGCACTCCACCGGAAAGCCCCT, (SEQ ID NO: 191)
GGCTTTCTGGCACTCCGCCGGAAAGCCCCT,
or (SEQ ID NO: 192)
GGCTTTCTGGCCTCCACCGGAAAGCCCCT.
```

In some embodiments, a dog or cat eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 193)
GGTTTTCCGGTCTCCACCGGAAAGCCCC.
```

In some embodiments, a cow, sheep, or goat eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 194)
GGCTTTCCGGTCTCCACCGGAAAGCCCCT,
or (SEQ ID NO: 195)
GGCTTTCCGGCCTCCGCCGGAAAGCCCCT.
```

In some embodiments, a pig eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 196)
GGTTTTCCGGTCTCCACCGGAAAACCCTT, (SEQ ID NO: 197)
GGTTTTCCGTGCTCCCACGGAAAACCCTT, (SEQ ID NO: 198)
GGTTTTCCGGCCTCCGCCGGAAAACCCTT, (SEQ ID NO: 199)
GGTTTTCCGTGACTCCCACGGAAAACCCTT,
or (SEQ ID NO: 200)
GGTTTTCCGGCACTCCGCCGGAAAACCCTT.
```

In some embodiments, a horse eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 201)
GGTCTTCCGGTCTCCTCCGGAAGGCCCCC,
or (SEQ ID NO: 202)
GGTCTTCCGGCTCCCCGGAAGGCCCCC.
```

In some embodiments, a sheep eSL comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 203)
GGCTTTCCGTGCTCCCACGGAAAGCCCCT, (SEQ ID NO: 204)
GGCTTTCCGTGACTCCCACGGAAAGCCCCT,
or (SEQ ID NO: 205)
GGCTTTCCGGCACTCCGCCGGAAAGCCCCT.
```

In some embodiments, engineered stem loops provide for enhanced stability of an snRNA relative to an snRNA comprising a native stem loop. In some embodiments is a native snRNA stem loop comprises, consists essentially of, or consists of a nucleic acid sequence at least 65%, 70%, 75%, 80%, 85%, 90%, 95%, 96%, 97%, 98%, 99% or 100% (or any percentage in between) identical to one or more of the following nucleotide sequences:

```
                                         (SEQ ID NO: 145)
Ggttttctgacttcggtcggaaaacccct,
```

```
                               (SEQ ID NO: 206)
ggttttctgacttcggtcggaaaacc, (SEQ ID NO: 235)
Ggctttctggctttttaccggaaagcc,
or (SEQ ID NO: 236)
ggctttctggctttttaccggaaagccCCT.
```

5' Interaction Stability Domain

The eSL disclosed herein possesses more effective folding and annealing properties with a 5' interaction stability domain (5'ISD) and this in turn results in increased stability of the esnRNA compared to a non-engineered snRNA. The 5' ISD has nucleotides that are complementary to the nucleotides within the engineered SL, and without wishing to be bound by theory, an interaction between the 5'ISD and eSL is predicted to form secondary structure that protects the 5' end of an snRNA. In some aspects, the 5' ISD anneals and/or hybridizes to an eSL of the disclosure. In some aspects, the 5'ISD is a sequence having complementarity and/or reverse complementarity to a sequence present in an eSL of the disclosure. In some aspects, a disclosed herein can be one of the 5'ISDs selected from the following nucleotide sequences:

```
                               (SEQ ID NO: 12)
ggagt, (SEQ ID NO: 13)
cctct, (SEQ ID NO: 14)
ggaggt, (SEQ ID NO: 15)
cctcct, (SEQ ID NO: 16)
agccag, (SEQ ID NO: 17)
ggaag, (SEQ ID NO: 18)
gaagaag, (SEQ ID NO: 19)
gttg, (SEQ ID NO: 20)
ccgaa, (SEQ ID NO: 21)
taaggag, (SEQ ID NO: 22)
gaag,
or (SEQ ID NO: 23)
ggctt.
```

Targeting Sequences

The esnRNA systems can be programmed to comprise a targeting sequence (TS) (also termed spacer). In some aspects, the targeting sequence is a 5' targeting sequence (5'TS) (also termed spacer) that targets one or more RNAs of interest. In this context, 5' is in reference to the snRNA insert's 5' end and not necessarily to the overall vector configuration comprising the snRNA insert or inserts. And the TS can be located in or near the 5' end of the snRNA. In an alternative embodiment, the targeting sequence(s) (TS) can be located in or near a 3' position in the snRNA construct, thereby generating a 3' targeting sequence (3' TS), particularly if the snRNA construct is not a U7-based snRNA.

Targeting sequences of the disclosure, including 5' TS, and 3'TS can be between about 1 and about 200 nucleotides in length. In some aspects, targeting sequences of the disclosure are between about 10 and about 150 nucleotides in length. In some aspects, targeting sequences of the disclosure are between about 10 and about 100 nucleotides in length. In some aspects, targeting sequences of the disclosure are between about 20 and about 60 nucleotides in length. In some aspects, targeting sequences of the disclosure are at least about 10, 20, 30, 40, 50, 60, or about 70 nucleotides in length.

In one example, U7 snRNA can be programmed by replacing the histone mRNA binding sequence with a sequence complementary to a target of interest. In some aspects, esnRNA systems of the disclosure bind a target mRNA or pre-mRNA sequence of interest. The exemplary esnRNA systems shown herein lead to blocking or knocking down microsatellite repeat expansions (for treating myotonic dystrophy (DM1) or Huntington's disease (HD), hexanucleotide repeat expansion (for treating C9/ALS), splicing modulation (for treating USH2A (Usher Syndrome type 2)), or targeting one or more exon splicing enhancers (ESE) to induce exon skipping (for treating DMD, e.g., DMD exon 51 skipping). In one embodiment, the target RNA of interest is a microsatellite or hexanucleotide repeat RNA or a non-repeat RNA. In another embodiment, the repeat RNA of interest is selected from the group consisting of CUG, CAG, GGGGCC, and CCCCGG. In one embodiment, the esnRNA comprises a targeting sequence (TS) that targets two target RNAs of interest are GGGGCC and CCCCGG. In another embodiment, the two target RNAs of interest are a microsatellite repeat RNA and a non-repeat RNA. In another embodiment, the non-repeat RNA is a flanking sequence to the repeat RNA.

In some embodiments, esnRNA of the disclosure target a pre-mRNA or mRNA sequence encoding the DMD gene. DMD is a gene encoding the protein dystrophin. Mutations in DMD are associated with Duchene muscular dystrophy. In some embodiments, the DMD RNA sequence targeted by esnRNA compositions of the disclosure is an exon 51 DMD RNA sequence.

Target sequences that bind DMD can comprise, consist essentially of, or consist of a nucleic acid sequence at least 65%, 70%, 75%, 80%, 85%, 90%, 95%, 96%, 97%, 98%, 99% or 100% (or any percentage in between) identical to one or more of the following nucleotide sequences set forth in the table which follows:

DMD Exon 51 RNA Targeting Sequences

| UID | Targeting Sequences | SEQ ID NO: |
|---|---|---|
| z38 | TACCTCCAACATCAAGGAAGATGGCA | 206 |
| z42 | GTAACCACAGGTTGTGTCACCAGAGTAACA | 207 |

-continued

| UID | Targeting Sequences | SEQ ID NO: |
|---|---|---|
| | Fusion Sequences | |
| z70 | catacCTTCTGCTTGATGATCATCTCGCACCAGAGTAACAGTCTGAGTAGGAGctaaa | 208 |
| z71 | catacCTTCTGCTTGATGATCATCTCGTGCCGCTGCCCAATGCCATCCTGGAG | 209 |
| z72 | catacCTTCTGCTTGATGATCATCTCGGCCCAATGCCATCCTGGAGTTCctg | 210 |
| z73 (z38/z42) | TACCTCCAACATCAAGGAAGATGGCAGTAACCACAGGTTGTGTCACCAGAGTAACA | 211 |
| z74 | AACATCAAGGAAGATGGCATTTCTAGGTAACCACAGGTTGTGTCACCAGAGTAACA | 212 |
| z75 | AACATCAAGGAAGATGGCATTTCTAGTGCCGCTGCCCAATGCCATCCTGGAG | 213 |
| z76 | TTTTTCTCATACCTTCTGCTTGATGTCTGAGTAGGAGCTAAAATATTTTGGG | 214 |
| Z187 (z42/z38) | GTAACCACAGGTTGTGTCACCAGAGTAACATACCTCCAACATCAAGGAAGATGGCA | 215 |
| z230 | CGAGATGATCATCAAGCAGAAGgtatgCACCAGAGTAACAGTCTGAGTAGGAGctaaa | 216 |
| z231 | CACCAGAGTAACAGTCTGAGTAGGAGctaaaTACCTCCAACATCAAGGAAGATGGCA | 217 |
| z232 | TACCTCCAACATCAAGGAAGATGGCACACCAGAGTAACAGTCTGAGTAGGAGctaaa | 218 |
| z233 | GTCTGAGTAGGAGctaaaatatttgggTACCTCCAACATCAAGGAAGATGGCA | 219 |
| z234 | TACCTCCAACATCAAGGAAGATGGCAGTCTGAGTAGGAGctaaaatatttggg | 220 |
| z235 | GTCTGAGTAGGAGctaaaatatttgggttttttctcatacCTTCTGCTTGAT | 221 |
| z237 | cCTTCTGCTTGATGATCATCTCGGAGTAACAGTCTGAGTAGGAGc | 222 |
| z238 | cCTTCTGCTTGATGATCATCTCGCCAGAGTAACAGTCTGAGTAGGAGc | 223 |
| z239 | cCTTCTGCTTGATGATCATCTCGCAGTCTGAGTAGGAGctaaa | 224 |
| z240 | ctcatacCTTCTGCTTGATGGAGTAACAGTCTGAGTAGGAGc | 225 |
| z241 | ctcatacCTTCTGCTTGATGCCAGAGTAACAGTCTGAGTAGGAGc | 226 |
| z242 | ctcatacCTTCTGCTTGATGCAGTCTGAGTAGGAGctaaa | 227 |

In one embodiment, TSs which are a fusion as in the above table can be a single TS sequence comprised within the fusion sequence.

In another embodiment, the targeting sequences (TSs) that target two or more RNAs of interest. In another embodiment, the TSs which target two or more RNAs of interest are different sequences which target the same pre-mRNA molecule. In one embodiment, the spacers or TSs are a fusion sequence. In another embodiment, the fusion sequence is a spacer targeting DMD exon 51, wherein the fusion sequence is set forth in the table above.

In some embodiments, CUG repeat targeting sequences comprise the nucleic acid (SEQ ID NO: 165)
CAGCAGCAGCAGCAGCAGCAGCAGCAGCAGCAGCAGCAGCAG.

In some embodiments, CAG repeat targeting sequences comprise the nucleic acid sequence:

(SEQ ID NO: 167)
CTGCTGCTGCTGCTGCTGCTGCTGCTGCTGCTGCTGCTGCTG.

Sm Binding Domains

The esnRNA systems disclosed herein utilize an Sm binding domain (SmBD). The Sm protein ring that assembles around the Sm binding domain (SmBD) to form an snRNP includes SmB/B', SmD1, SmD2, SmD3, SmE, SmF, and SmG. The U7 Sm binding site recruits endogenous RNA binding factors and can be replaced with a non-U7 snRNA to make the esnRNA more stable. In one embodiment, the SmBD is selected from the group consisting of U1, U2, U4, and U5 snRNAs. In another embodiment, the SmBD is derived from a pseudo snRNA. In another embodiment, the SmBD is a nucleotide sequence comprising SEQ ID NO: 31 (ATTTTT). In another embodiment, the SmBD comprises a nucleotide sequence selected from the group consisting of SEQ ID NO: 32 (AATTTTTGG), SEQ ID NO: 33 (AATTTGTGG), SEQ ID NO: 34 (AATTTGTGG), SEQ ID NO: 35 (AATTTCTGG), SEQ ID NO: 36 (GAT- TTTTGG), SEQ ID NO: 37 (AATTTTTGA), SEQ ID NO: 38 (AATTTTTTG), SEQ ID NO: 161 (AATTTTTG-GAGCA), and SEQ ID NO: 163 (AATTTTTGGAGTA).

Promoter Sequences

The esnRNA systems disclosed herein comprise an snRNA promoter from any of U1-U12. In one embodiment, the snRNA promoter is a U7 promoter. In another embodiment, the U7 promoter is a human U7 promoter (hU7) or a mouse U7 promoter (mU7). In another embodiment, the U7 promoter is an endogenous human U7 promoter comprising SEQ ID NO: 39:

TACTGCCGAATCCAGGTCTCCGGGCTTAACAACAACGAAGGGGCTGTGAC

TGGCTGCTTTCTCAACCAATCAGCACCGAACTCATTTGCATGGGCTGAGA

ACAAATGTTCGCGAACTCTAGAAATGAATGACTTAAGTAAGTTCCTTAGA

ATATTATTTTTCCTACTGAAAGTTACCACATGCGTCGTTGTTTATACAGT

AATAGGAACAAGAAAAAAGTCACCTAAGCTCACCCTCATCAATTGTGGAG

TTCCTTTATATCCCATCTTCTCTCCAAACACATACGCA.

In one embodiment, the snRNA promoter is a U1 promoter. In another embodiment, the U1 promoter is a human U1 promoter or a mouse U1 promoter.

In another embodiment, an snRNA promoter drives a copy of an snRNA insert. In another embodiment, each copy of an snRNA insert is the same. In another embodiment, different snRNA promoters drive each copy of an snRNA insert. In one embodiment, a 2× snRNA comprises a mouse U7 promoter driving one copy of an snRNA insert and a mouse U1 promoter drives the other copy of an snRNA insert.

In other aspects, the snRNA promoter is a PolII promoter or a PolIII promoter. In other aspects, the snRNA promoter comprises, consists essentially of, or consists of a nucleic acid sequence at least 65%, 70%, 75%, 80%, 85%, 90%, 95%, 96%, 97%, 98%, 99% or 100% (or any percentage in between) identical to a promoter and/or promoter sequence listed in the Exemplary Promoter Table which follows:

| Exemplary Promoter | Promoter Sequence |
|---|---|
| hU1 | AAGGACCAGCTTCTTTGGGAGAGAACAGACGCAGGGGCGGGAGGGA<br>AAAAGGGAGAGGCAGACGTCACTTCCCCTTGGCGGCTCTGGCAGCAG<br>ATTGGTCGGTTGAGTGGCAGAAAGGCAGACGGGGACTGGGCAAGGC<br>ACTGTCGGTGACATCACGGACAGGGCGACTTCTATGTAGATGAGGCA<br>GCGCAGAGGCTGACGTCTTCGCCACTTGCTGCTTCACCACGAAGGAG<br>TTCCCGTGCCCTGGGAGCGGGTTCAGGACCGCTGATCGGAAGTGAGA<br>ATCCCAGCTGTGTGTCAGGGCTGGAAAGGGCTCGGGAGTGCGCGGGG<br>CAAGTGACCGTGTGTGTAAAGAGTGAGGCGTATGAGGCTGTGTCGGG<br>GCAGAGGCacaacgtttc<br>(SEQ ID NO: 40) |
| hU2 | CCACGCCCTCTGTGAAAGGGCGGGGCATGCAAATTCGAAATGAAAGC<br>CCGGGAACGCCGGAAGAAGCACGGGTGTAAGATTTCCCTTTTCAAAG<br>GCAGAGAATAAGAAATCAGCCCGAGAGTGTAAGGGCGTCAATAGCG<br>CTGTGGACGAGACAGAGGGAATGGGGCAAGGAGCGAGGCTGGGGCT<br>CTCACCGCGACTTGAATGTGGATGAGAGTGGGACGGTGACGGCGGGC<br>GCGAAGGCGAGCGC<br>(SEQ ID NO: 41) |
| hU4 | TTCGCAGTCTCTGAATTAAGTCTATTAGCATGTTCCTCCCATAGTGCT<br>TTGCTTCATATCAACAAAAACCTAGCTAAGTGAAATCAGCAACGATA<br>TGCAGAAACCACCTACGCAGGTCACAAACATCTTTCTATGATTGTATA<br>ATTTTCAAGCAAGCAATAAGTGAAGATTTTTCCATAGGCCCTAAACTC<br>ACCTTTGCGAAATAGGAAGCTGGTTTATTGGGAGTGATGAGCAGGGG<br>GCGTAACAAATT<br>(SEQ ID NO: 42) |
| hU5 | GCAGCAAGGCCTCCACTTCACCCCCTAAAGGTTGCCCCAAGAGCACC<br>GTGTGACTGCTAAGGTATTTCCGGAGTCTAAAGACGATTATTCAGGTC<br>TCATTTGCATACCCATAATACACTGCAAACAGTATTTTTTTCGGAAAA<br>ACATTTATATATTGCTTGACATTTTTAAGTATGAGAATTTTGCATGCA<br>GAATTTTTTTGTATAAACTTTCTCAGGTAGTAACCCTTGGGATTAGTA<br>GACACCATCAGTGTACTAGGAATTGCAGTTACCCGAAAATTGAGTTA<br>CAGAAGTAACTGGT<br>(SEQ ID NO: 43) |
| hU6 | Gtttattacagggacagcagagatccagtttggttaattaaggtaccgagggcctatttcccatgattccttcatatttg<br>catatacgatacaaggctgttagagagataattagaattaatttgactgtaaacacaaagatattagtacaaaatacgt<br>gacgtagaaagtaataatttcttgggtagtttgcagttttaaaattatgttttaaaatggactatcatatgcttaccgtaact<br>tgaaagtatttcgatttcttggctttatatatcttgtggaaaggacgaaacacc<br>(SEQ ID NO: 44) |
| h7sk | CTGCAGTATTTAGCATGCCCCACCCATCTGCAAGGCATTCTGGATAGT<br>GTCAAAACAGCCGGAAATCAAGTCCGTTTATCTCAAACTTTAGCATTT<br>TGGGAATAAATGATATTTGCTATGCTGGTTAAATTAGATTTTAGTTAA<br>ATTTCCTGCTGAAGCTCTAGTACGATAAGTAACTTGACCTAAGTGTAA<br>AGTTGAGATTTCCTTCAGGTTTATATAGCTTGTGCGCCGCCTGGGTAC<br>CTC<br>(SEQ ID NO: 45) |

| Exemplary Promoter | Promoter Sequence |
|---|---|
| tRNA(Val) | CAGGACTAGTCTTTTAGGTCAAAAAGAAGAAGCTTTGTAACCGTTGG<br>TTTCCGTAGTGTAGTGGTTATCACGTTCGCCTAACACGCGAAAGGTCC<br>CCGGTTCGAAG<br>(SEQ ID NO: 46) |
| mU1 | TTGTTCCTCTTAGTGTTAATTCACACTAAAGACTGTGCATCCGACTCC<br>TACATTTATGAAAGTAAATGCCTGTTGTTAGAACAAAAAAGGCTACA<br>GAACAAAAAACAAAGCGAAATACCATCTGCTTTAGGTTCAGTGTGGT<br>ATTTTCCCGCTGACAGGGAGGCGGGTTTTTGGGTACAGGAAACGAGT<br>CACTATGGAGGCGGTACTATGTAGATGAGAATTCAGGTGCAAACTGG<br>GAAAAGCAACTGCTTCCAAATATTTGTGATTTTTACAGTGTAGTTTTG<br>GAAAAACTCTTAGCCTACCAATTCTTCTAAGTGTTTTAAAATGTGGGA<br>GCCAGTACACATGAAGTTATAGAGTGTTTTAATGAGGCTTAAATATTT<br>ACCGTAACTATGAAATGCTACGCATATCATGCTGTTCAGGCTCCGTGG<br>CCACGCAACTC<br>(SEQ ID NO: 47) |
| mU7+<br>extra 3' | TaacaacataggagctgtgattggctgttttcagccaatcagcactgActcatttgcatagcctttacaagcggtcac<br>aaactcaagaaacgagcggttttaatagtcttttagaatattgtttatcgaaccgaataaggaactgtgctttgtgattca<br>catatcagtggaggggtgtggaaatggcaccttgatctcaccctcatcgaaagtggagttgatgtcctTccctggct<br>cgctacagacgcacttccgcaa<br>(SEQ ID NO: 48) |
| mU7 | taacaacataggagctgtgattggctgttttcagccaatcagcactgActcatttgcatagcctttacaagcggtcac<br>aaactcaagaaacgagcggttttaatagtcttttagaatattgtttatcgaaccgaataaggaactgtgctttgtgattca<br>catatcagtggaggggtgtggaaatggcaccttgatctcaccctcatcgaaagtggagttgatgtcctTccctggct<br>cgctacagacgcacttccgc (SEQ ID NO: 151) |
| hU7 | TACTGCCGAATCCAGGTCTCCGGGCTTAACAACAACGAAGGGGCTGT<br>GACTGGCTGCTTTCTCAACCAATCAGCACCGAACTCATTTGCATGGGC<br>TGAGAACAAATGTTCGCGAACTCTAGAAATGAATGACTTAAGTAAGT<br>TCCTTAGAATATTATTTTTCCTACTGAAAGTTACCACATGCGTCGTTG<br>TTTATACAGTAATAGGAACAAGAAAAAAGTCACCTAAGCTCACCCTC<br>ATCAATTGTGGAGTTCCTTTATATCCCATCTTCTCTCCAAACACATAC<br>GCA<br>(SEQ ID NO: 39) |
| mU5 | TGCCAACAGCTTTGAAATCCTCTGTGCTCTTGTGCCAATCCCACCCTC<br>AGAACAGGGAGTCTGTCGGTTATGTTTTCGTCCTTTACAGTTCTTCGC<br>CGTCTAATCCATTGGAAACCTCCTTTATTTAAAGGAAACCGTGTCCAA<br>ATTCAGTGTACAGAGGTGCAAACCTCCGCCCCGCTCCTTGTAGGAAG<br>CCCACGGGAACTGGGCCAATCGGACGGCGCTTACTCGGCTCATTTAC<br>ATACCCATAACACACCGCGGCTAATGCAAATATTTTCGTGAAAAGAT<br>CTTCCATTACTCGAAGTTTTAAAACTAAAAACAAAATATTATTTCAAA<br>AGATCATGAAGAAATTTCTGTCGGTAACAGCAGTTTCAATTGATAAA<br>TCACCATCACTTATCTAGGAGGTTCTGTTACTCTAGAAGTGAATTAAG<br>CAGGACAGCTGT (SEQ ID NO: 152) |
| mU2 | Gggcggggcatgcaaataactgctctgtggaactctgggagcaaaaacaaaaaactgcaaccaaaacttctcggc<br>ctccttgaatcttacaggcttttcgtggcgtaaaggtggtgtactcaatgaagaggagagtctgtgttggctgcatgttt<br>gagtcggttggttggtgactgtgaatTAAAGGTGTGGtcggtgttgagtgtatggggcgtgtgggcgtagt<br>tcggt (SEQ ID NO: 153) |
| mU6 | cgacgccgccatctctaggcccgcgccggcccctcgcacagacttgtgggagaagctcggctactcccctgccc<br>cggttaatttgcatataatatttcctagtaactatagaggcttaatgtgcgataaaagacagataatctgttcttttaatac<br>tagctacatttacatgataggcttggattctataagagatacaaatactaaattattattttaaaaaacagcacaaaag<br>gaaactcaccctaactgtaaagtaattgtgtgttttgagactataaatatcccttggagaaaagccttgttt (SEQ ID<br>NO: 154) |
| mH1 | CATgCAAATTACGCGCTgTGCTTTGTGGGAAATCACCCTAAACGTAAA<br>ATTTATTCCTCTTTcGAGCCTTATAGTGGcGGCCGGTCTACACCCTAAA<br>(SEQ ID NO: 155) |

Terminator Sequences

The esnRNA systems disclosed herein comprise an snRNA downstream terminator (DT). Downstream terminators define the end of a transcriptional unit, such as an esnRNA or snRNA. In another embodiment the snRNA DT is a U7 DT comprising:

CCTCTTATGATGTTTGTTGCCAATGATAGATTGTTTTCACTGTGCAAAAA
TTATGGGTAGTTTTGGTGGTCTTGATGCAGTTGTAAGCTTGGAG.
(SEQ ID NO: 49)

In one embodiment, the esnRNA comprises the eSL, one or more promoters, the TS, the SmBD, the 5'ISD, and the DT. In one aspect, promoter and DT combinations are be mixed and matched.

In another embodiment, the DT is selected from the exemplary DTs and/or DT sequences listed in the Exemplary DT Table below:

| Exemplary DT | DT Sequence |
| --- | --- |
| hU1 | ACTTTCTGGAGTTTCAAAAACAGACTGTACGCCAAGGGTCATATCTT TTT (SEQ ID NO: 50) |
| hU2 | CCGGGGATACAACGTGTTTCCTAAAAGTAGAGGGAGGTAAGAGACG GTAG (SEQ ID NO: 51) |
| hU4 | CTGAATTTTCTTGCAGTTGAACAACAGAGGCTTTTTTTGTGTGTGTGG GG (SEQ ID NO: 52) |
| hU5 | ATATGTGGTAATCCAACAATAGAAATTATTTTTAAGTTTGTGTGTTCC TT (SEQ ID NO: 53) |
| hU6 | TTTTTT (SEQ ID NO: 54) |
| h7sk | TTTTTT SEQ ID NO: 55) |
| tRNA(Val) | TTTTTT (SEQ ID NO: 56) |
| mU1 | GTTTACTTGGTTTTAAAAATAGCTTGCACTAGCGATACGGAATATGG TTATTAGGTTTGTTAGGCATCATGTCGTGTCTTACTATAGAAAAATA ACGTAGTGTTCATTTTAGCCTGCCTGTATGTGTTAATTTGTCCTTATT GCGCATTGTTCTTGTTAAGTCTTCTGTAAGGAGTTGCGGGTTTCAAA CTGTCAGTCTGAGAGCA (SEQ ID NO: 57) |
| mU7+ | Cccaatttcactggtctacaatgaaagcaaaacagttctcttccccgctccccggtgtgtgagagggctttgatcc ttctctggtttcctaggaaacgcgtatgtgtac (SEQ ID NO: 58) |
| mU7 | Cccaatttcactggtctacaatgaaagcaaaacagttctcttccccgctccccggtgtgtgagagggctttgatcc ttctctggtttcctaggaaacgcgtatgtg (SEQ ID NO: 156) |
| hU7 | CCTCTTATGATGTTTGTTGCCAATGATAGATTGTTTTCACTGTGCAAA AATTATGGGTAGTTTTGGTGGTCTTGATGCAGTTGTAAGCTTGGAG (SEQ ID NO: 49) |
| hU7 | CTTATGATGTTTGTTGCCAATGATAGATTGTTTTCACTGTGCAAAAAT TATGGGTAGTTTTGGTGGTCTTGATGCAGTTGTAAGCTTGGAG (SEQ ID NO: 234) |
| mU5 | CCACATTTTGTGTTTAAAAATAGAAATATTTAAGTGAGATCAGTTTA AATCTGCTTTATCTAGGGTGTCTAACTGCTTGCATCTTTTTAACTTTT CCTTATTTGTGAGAAGGTCTGTAAAACTTATTATATGTTAGTACACT GTAGCTGTCTTCAGACACTCCAGAAGAGGGATTCAGATCACCTTACA GATGGTTTTGA (SEQ ID NO: 157) |
| mU2 | CCCTCTGGGGAgtaaagttggttttaaagtcagagcatggtgattgtagggcagtccaactttttaaatat gctgtg (SEQ ID NO: 158) |
| mU6 | TTTTTT (SEQ ID NO: XX) |
| mH1 | TTTTTTT (SEQ ID NO: XX) |

In one embodiment, the esnRNA is delivered in an AAV vector.

In some embodiments, the AAV vector comprises multiple copies of the esnRNA. In some embodiments, the multiple copies of the esnRNA are 2, 3, or 4 copies (2×, 3×, or 4×) of the esnRNA. In some embodiments, the multiple copies of the esnRNA are 4 or more copies of the esnRNA.

In some embodiments, each esnRNA of the multiple copies of esnRNA is separated by a nucleic acid buffer sequence derived from human non-coding genomic sequences downstream of an snRNA. In one embodiment, the buffer sequence is derived from human genomic sequences downstream of U7.

In one embodiment, the buffer sequence is selected from the group consisting of the following nucleic acid sequence:

```
buffer 1 (30 bp)
                                    (SEQ ID NO: 24)
CAAACTACAGAGCCAAGTGCTATCCACAGA, buffer 2 (30 bp)
                                    (SEQ ID NO: 25)
GAGCTTTCTGGGTTGCCATCTCAAGCAGAC, buffer 3 (30 bp)
                                    (SEQ ID NO: 26)
TACAAGGCCATCAGCTCATACTCACAATTG,
and a combination thereof
```

In another embodiment, the buffer sequence is selected from the group consisting of the following nucleic acid sequence:

```
buffer 1 (100 bp)
                                    (SEQ ID NO: 27)
CAAACTACAGAGCCAAGTGCTATCCACAGAGAGCTTTCTGGGTTGCCAT

CTCAAGCAGACTACAAGGCCATCAGCTCATACTCACAATTGACTTTGAG

AG, buffer 2 (100 bp)
                                    (SEQ ID NO: 28)
TTGACCACATACGTGCTCTTTCAAAGTTCTGTGTTTGAAGTTATGTTAG

TAACAACTGATGCCCATCCTGCAATGACAAATCCAATTCTCAGTGCAGC

TC,
and a combination thereof.
```

In another embodiment, the buffer sequence is selected from the group consisting of the following nucleic acid sequence:

```
buffer 1 (500 bp)
                                    (SEQ ID NO: 29)
CAAACTACAGAGCCAAGTGCTATCCACAGAGAGCTTTCTGGGTTGCCAT

CTCAAGCAGACTACAAGGCCATCAGCTCATACTCACAATTGACTTTGAG

AGTCATTTTCCAATGCTCCTACACACCCCTTCTTCACAATCCCCAACAA

ATCTGAGGCTGGAACTTGGTACCATAACAATCATTACATTATTTCACCA

GAAGTACACCTTGCCTGGAAGATTGGCATTATAGCATCTTCTAACATTG

TGAAAGTTAGTGACCAATGAGGAGATCCAAGTCAGTTCCAGTTGGATTT

CTCTATACTCTATAATAAATATATATGGTGTCTTCAACAATAGGACTTT

GCCATCCAGTGATGCTAAAAATCAATAACAATGGCAATAACCTGCCCTG

TTTGGAAAGCCTCTGGCTTCCATGACTAACAATTCAAGGCAGGTCTCCT

ATACCTAGTACTGAGATTTTTATTTGATAAACTATATCTTCTGGGAGGA

GAAGC, buffer 2 (500 bp)
                                    (SEQ ID NO: 30)
TTGACCACATACGTGCTCTTTCAAAGTTCTGTGTTTGAAGTTATGTTAG

TAACAACTGATGCCCATCCTGCAATGACAAATCCAATTCTCAGTGCAGC

TCTCTGAAATAGTTTTGCTTTCTCTCTCTAGGTCTGTTCTATACTCCTA

ACTCTCCAGGAGTTTACAAGGAATAAAATCTCTTCCAAATGCTTTCTGT

TGCAACAACTGGACCATACTGAAAGCTGAGGCCCACAATTGCAATCTAG

GTTAGCAGGTAATCATTGTTGGTGAGGTCCTCCCTTTCCCCAGGCTCGT

GTTTGTATTGGGGAGCAGGAAATTTTTGCTAGAGCAGCACTGCCATCTC

TCTACACTCCACCTGATTGGTGGGATGGACCAGAGAAATGGACATTCCC

AACACAGTCCCTCCTTTCACATCTGCTCACCTGCCCACAGGATACTTTC

CACCATGCATACTGGGCTCTGCACCAACCATTCAGCAGTGATGAAGAGG

AAACTTGAAC,
and/or a combination thereof.
```

The 100 bp and 500 bp buffer 1 sequences are derived from a sequence starting 100 bp downstream of the *Mus musculus* U7 pseudogene 8 (Location Chromosome 14: 4,409,359-4,409,421 reverse strand. GRCm39: CM001007.3). The 100 bp and 500 bp buffer 2 sequences are derived from the sequence starting 130 bp downstream of human U7 pseudogene 5 (Chromosome X: 140,451,148-140,451,208 forward strand. GRCh38:CM000685.2). Both 100 bp buffers are the first 100 bp of the corresponding 500 bp buffer. The 30 bp buffers 1, 2, and 3, are sequential 30 bp sequences within "100 bp buffer 1", downstream of the *Mus musculus* U7 pseudogene 8. These downstream sequences were selected due to the lack of any known regulatory sites or genes within or nearby to the sequence (using Gencode/Ensembl), in addition to lack of repetitive sequence, 40-60% GC content for total buffer, 40-60% GC content in the 20 bp region at both ends of the buffer, and minimal sequence complexity.

esnRNA Sequences

Exemplary esnRNA sequences of the disclosure can comprise any combination of esnRNA features described herein. In some aspects, the esnRNA comprises, consists essentially of, or consists of a nucleic acid sequence at least 65%, 70%, 75%, 80%, 85%, 90%, 95%, 96%, 97%, 98%, 99% or 100% (or any percentage in between) identical to an esnRNA listed in the esnRNA Table which follows:

esnRNA Sequences of the Disclosure

| ID | Description | Target Repeat or Gene Symbol | SEQ ID NO: | Sequence |
|---|---|---|---|---|
| | u7 snRNA CUG | CUG | 65 | ggagtCAGCAGCAGCAGCAGCAGCAGCAGCAGC AGCAGCAGCAGCAGAATTTTTGGAGTAggctttctggctc cttaccggaaagcc |
| | u7 snRNA NT | non-targeting | 66 | ggagtTCACCAGAAGCGTACCATACTCACGAAATTTT TGGAGTAggctttctggctccttaccggaaagcc |
| | u7 snRNA CAG | CAG | 67 | ggagtCTGCTGCTGCTGCTGCTGCTGCTGCTGCT GCTGCTGCTGCTGAATTTTTGGAGTAggctttctggctcctta ccggaaagcc |
| | z38/42 csnRNA targeting dystrophin exon 51 | DMD exon 51 | 68 | ggagtTACCTCCAACATCAAGGAAGATGGCAGTAAC CACAGGTTGTGTCACCAGAGTAACAAATTTTTGGA GTAggctttctggctccttaccggaaagcc |
| | z42 esnRNA | DMD exon 51 | 69 | ggagtGTAACCACAGGTTGTGTCACCAGAGTAACAA ATTTTTGGAGTAggctttctggctccttaccggaaagcc |
| | z38 esnRNA | DMD exon 51 | 70 | ggagtTACCTCCAACATCAAGGAAGATGGCAAATTTT TGGAGTAggctttctggctccttaccggaaagcc |
| SR2 20031 | U7CUGx15-U1 Sm site_U7 term opt sl | CUG | 71 | ggagtCAGCAGCAGCAGCAGCAGCAGCAGCAGCAGC AGCAGCAGCAGCAGAATTTGTGGAGTAggctttctggctc cttaccggaaagcc |
| SR2 20032 | U7CUGx15-Sm mut 1_U7 term opt sl | CUG | 72 | ggagtCAGCAGCAGCAGCAGCAGCAGCAGCAGCAGC AGCAGCAGCAGCAGTCGAGTTGGAGTAggctttctggctc cttaccggaaagcc |
| SR2 20033 | U7CAGx15-no Sm_U7 term opt sl | CUG | 73 | ggagtCAGCAGCAGCAGCAGCAGCAGCAGCAGCAGC AGCAGCAGCAGCAGAGTAggctttctggctccttaccggaaagcc |
| SR2 20034 | U7knt-U1 Sm site_U7 term opt sl | non-targeting | 74 | ggagtTCACCAGAAGCGTACCATACTCACGAAATTTG TGGAGTAggctttctggctccttaccggaaagcc |
| SR2 20035 | U7knt-Sm mut 1_U7 term opt sl | non-targeting | 75 | ggagtTCACCAGAAGCGTACCATACTCACGATCGAGT TGGAGTAggctttctggctccttaccggaaagcc |
| SR2 20036 | U7knt-no Sm_U7 term opt sl | non-targeting | 76 | ggagtTCACCAGAAGCGTACCATACTCACGAAGTAgg ctttctggctccttaccggaaagcc |
| SR2 20037 | U7CAGx15-U1 Sm site_U7 term opt sl | CAG | 77 | ggagtCTGCTGCTGCTGCTGCTGCTGCTGCTGCT GCTGCTGCTGCTGAATTTGTGGAGTAggctttctggctcctta ccggaaagcc |
| SR2 20038 | U7CAGx15-Sm mut 1_U7 term opt sl | CAG | 78 | ggagtCTGCTGCTGCTGCTGCTGCTGCTGCTGCT GCTGCTGCTGCTGTCGAGTTGGAGTAggctttctggctcctt accggaaagcc |
| SR2 20039 | U7CAGx15-no Sm_U7 term opt sl | CAG | 79 | ggagtCTGCTGCTGCTGCTGCTGCTGCTGCTGCT GCTGCTGCTGCTGAGTAggctttctggctccttaccggaaagcc |
| SR2 20040 | U7CAGx5-U1 Sm site_U7 term opt sl | CAG | 80 | ggagtCTGCTGCTGCTGCTGAATTTGTGGAGTAggctttct ggctccttaccggaaagcc |
| SR2 20041 | U7CAGx5-Sm mut 1_U7 term opt sl | CAG | 81 | ggagtCTGCTGCTGCTGCTGTCGAGTTGGAGTAggctttct ggctccttaccggaaagcc |
| SR2 20042 | U7CAGx5-no Sm_U7 term opt Sl | CAG | 82 | ggagtCTGCTGCTGCTGCTGAGTAggctttctggctccttaccgga aagcc |
| SR2 20056 | U7-z38-delSm | DMD | 83 | ggagtTACCTCCAACATCAAGGAAGATGGCAggctttctg gctccttaccggaaagcc |
| SR2 20087 | U7 5'SL with ISD; non- | non-targeting | 84 | GTTCCCGAAGTAACCCTTCGGGAACggagtTCACCAG AAGCGTACCATACTCACGAAATTTTTGGAGTAggcttt |

-continued

| ID | Description | Target Repeat or Gene Symbol | SEQ ID NO: | Sequence |
|---|---|---|---|---|
| | targeting NT (not made) | | | ctggctccttaccggaaagcc |
| SR2 20088 | U7 5'SL with no ISD; non-targeting NT (not made) | non-targeting | 85 | GTTCCCGAAGTAACCCTTCGGGAACTCACCAGAAG CGTACCATACTCACGAAATTTTTGGAGTAggctttctggc tccttaccggaaagcc |
| SR2 20089 | U7 5'Kissing SL with no ISD; non-targeting NT (not made) | non-targeting | 86 | GTTCCCGAAGggagtCTTCGGGAACTCACCAGAAGC GTACCATACTCACGAAATTTTTGGAGTAggctttctggctc cttaccggaaagcc |
| SR2 20090 | U7 5'GC clamp with no ISD; non-targeting NT (not made) | non-targeting | 87 | GGGCCCTCACCAGAAGCGTACCATACTCACGAAAT TTTTGGAGTAggctttctggctccttaccggaaagcc |
| SR2 20091 | U7 5'Triple helix with no ISD; non-targeting NT (not made) | non-targeting | 88 | GAGAAGATTCGTCTTCTCTCTCTCTCTTCTTCACCA GAAGCGTACCATACTCACGAAATTTTTGGAGTAggc tttctggctccttaccggaaagcc |
| SR2 20092 | U7 5'SL with ISD; CUGx15 | CUG | 89 | GTTCCCGAAGTAACCCTTCGGGAACggagtCAGCAG CAGCAGCAGCAGCAGCAGCAGCAGCAGCAGCAGCAG AGCAGAATTTTTGGAGTAggctttctggctccttaccggaaagcc |
| SR2 20093 | U7 5'SL with no ISD; CUGx15 | CUG | 90 | GTTCCCGAAGTAACCCTTCGGGAACCAGCAGCAGC AGCAGCAGCAGCAGCAGCAGCAGCAGCAGCAGCA GAATTTTTGGAGTAggctttctggctccttaccggaaagcc |
| SR2 20094 | U7 5'Kissing SL with no ISD; CUGx15 | CUG | 91 | GTTCCCGAAGggagtCTTCGGGAACCAGCAGCAGCA GCAGCAGCAGCAGCAGCAGCAGCAGCAGCAGCAG AATTTTTGGAGTAggctttctggctccttaccggaaagcc |
| SR2 20095 | U7 5'GC clamp with no ISD; CUGx15 | CUG | 92 | GGGCCCCAGCAGCAGCAGCAGCAGCAGCAGCAGC AGCAGCAGCAGCAGAATTTTTGGAGTAggctttct ggctccttaccggaaagcc |
| SR2 20096 | U7 5'Triple helix with no ISD; CUGx15 | CUG | 93 | GAGAAGATTCGTCTTCTCTCTCTCTCTTCTCAGCAG CAGCAGCAGCAGCAGCAGCAGCAGCAGCAGCAGC AGCAGAATTTTTGGAGTAggctttctggctccttaccggaaagcc |
| SR2 20004 | U7-nt | non-targeting | 94 | ggagtTCACCAGAAGCGTACCATACTCACGAAATTTT TGGAGTAggctttctggctccttaccggaaagcc |
| SR2 20097 | U7 alt ISD SEQID 16 non-targeting nt1 | non-targeting | 95 | cctctTCACCAGAAGCGTACCATACTCACGAAATTTT TGGAGTAggctttctgggaggttaccggaaagcc |
| SR2 20098 | U7 alt ISD SEQID17 non-targeting nt1 | non-targeting | 96 | ggaggtTCACCAGAAGCGTACCATACTCACGAAATTT TTGGAGTAggctttctggcctccttaccggaaagcc |
| SR2 20099 | U7 alt ISD SEQID18 non-targeting nt1 | non-targeting | 97 | cctcctTCACCAGAAGCGTACCATACTCACGAAATTTT TGGAGTAggctttctggggaggttaccggaaagcc |
| SR2 20100 | U7 alt ISD SEQID19 non-targeting nt1 | non-targeting | 98 | agccagTCACCAGAAGCGTACCATACTCACGAAATTT TTGGAGTAggctttctggctggctaccggaaagcc |
| SR2 20101 | U7 alt ISD SEQID20 non-targeting nt1 | non-targeting | 99 | ggaagTCACCAGAAGCGTACCATACTCACGAAATTTT TGGAGTAggctttctggcttccccggaaagcc |
| SR2 20102 | U7 alt ISD SEQID21 non-targeting nt1 | non-targeting | 100 | gaagaagTCACCAGAAGCGTACCATACTCACGAAATT TTTGGAGTAggctttctggcttcttcccggaaagcc |
| SR2 20103 | U7 alt ISD SEQID22 non-targeting nt1 | non-targeting | 101 | gttgTCACCAGAAGCGTACCATACTCACGAAATTTTT GGAGTAggctttctggcaacttaccggaaagcc |

-continued

| ID | Description | Target Repeat or Gene Symbol | SEQ ID NO: | Sequence |
|---|---|---|---|---|
| SR2 20104 | U7 alt ISD SEQID23 non-targeting nt1 | non-targeting | 102 | ccgaaTCACCAGAAGCGTACCATACTCACGAAATTTT TGGAGTAggctttctggttcggtaccggaaagcc |
| SR2 20105 | U7 alt ISD SEQID24 non-targeting nt1 | non-targeting | 103 | taaggagTCACCAGAAGCGTACCATACTCACGAAATT TTTGGAGTAggctttctggctccttaccggaaagcc |
| SR2 20106 | U7 alt ISD SEQID25 non-targeting nt1 | non-targeting | 104 | gaagTCACCAGAAGCGTACCATACTCACGAAATTTT TGGAGTAggctttctggcttcttcccggaaagcc |
| SR2 20107 | U7 alt ISD SEQID26 non-targeting nt1 | non-targeting | 105 | ggctttTCACCAGAAGCGTACCATACTCACGAAATTTT TGGAGTAggctttctggaagccttaccggaaagcc |
| SR2 20108 | U7 alt ISD SEQID27 non-targeting nt1 | non-targeting | 106 | gaagTCACCAGAAGCGTACCATACTCACGAAATTTT TGGAGTAggctttctggcttcttaccggaaagcc |
| SR2 20010 | U7-CUGx15 | CUG | 107 | ggagtCAGCAGCAGCAGCAGCAGCAGCAGCAGC AGCAGCAGCAGCAGAATTTTTGGAGTAggctttctggctc cttaccggaaagcc |
| SR2 20109 | U7 alt ISD SEQ ID 16 CUGx15 | CUG | 108 | cctctCAGCAGCAGCAGCAGCAGCAGCAGCAGC AGCAGCAGCAGCAGAATTTTTGGAGTAggctttctgggag gttaccggaaagcc |
| SR2 20110 | U7 alt ISD SEQ ID 17 CUGx15 | CUG | 109 | ggaggtCAGCAGCAGCAGCAGCAGCAGCAGCAGCAG CAGCAGCAGCAGCAGAATTTTTGGAGTAggctttctggcc tccttaccggaaagcc |
| SR2 20111 | U7 alt ISD SEQ ID 18 CUGx15 | CUG | 110 | cctcctCAGCAGCAGCAGCAGCAGCAGCAGCAGCAGC AGCAGCAGCAGCAGAATTTTTGGAGTAggctttctgggga ggttaccggaaagcc |
| SR2 20112 | U7 alt ISD SEQ ID 19 CUGx15 | CUG | 111 | agccagCAGCAGCAGCAGCAGCAGCAGCAGCAGCAG CAGCAGCAGCAGCAGAATTTTTGGAGTAggctttctggct ggctaccggaaagcc |
| SR2 20113 | U7 alt ISD SEQ ID 20 CUGx15 | CUG | 112 | ggaagCAGCAGCAGCAGCAGCAGCAGCAGCAG CAGCAGCAGCAGCAGAATTTTTGGAGTAggctttctggct tccccggaaagcc |
| SR2 20114 | U7 alt ISD SEQ ID 21 CUGx15 | CUG | 113 | gaagaagCAGCAGCAGCAGCAGCAGCAGCAGCAGCA GCAGCAGCAGCAGAATTTTTGGAGTAggctttctgg cttcttcccggaaagcc |
| SR2 20115 | U7 alt ISD SEQ ID 22 CUGx15 | CUG | 114 | gttgCAGCAGCAGCAGCAGCAGCAGCAGCAGCAGCA GCAGCAGCAGCAGAATTTTTGGAGTAggctttctggcaact taccggaaagcc |
| SR2 20116 | U7 alt ISD SEQ ID 23 CUGx15 | CUG | 115 | ccgaaCAGCAGCAGCAGCAGCAGCAGCAGCAGCAGC AGCAGCAGCAGCAGAATTTTTGGAGTAggctttctggttcg gtaccggaaagcc |
| SR2 20117 | U7 alt ISD SEQ ID 24 CUGx15 | CUG | 116 | taaggagCAGCAGCAGCAGCAGCAGCAGCAGCAGCA GCAGCAGCAGCAGAATTTTTGGAGTAggctttctgg ctccttaccggaaagcc |
| SR2 20118 | U7 alt ISD SEQ ID 25 CUGx15 | CUG | 117 | gaagCAGCAGCAGCAGCAGCAGCAGCAGCAGCAGC AGCAGCAGCAGCAGAATTTTTGGAGTAggctttctggcttc ttcccggaaagcc |
| SR2 20119 | U7 alt ISD SEQ ID 26 CUGx15 | CUG | 118 | ggctttCAGCAGCAGCAGCAGCAGCAGCAGCAGCAGC AGCAGCAGCAGCAGAATTTTTGGAGTAggctttctggaag ccttaccggaaagcc |
| SR2 20120 | U7 alt ISD SEQ ID 27 CUGx15 | CUG | 119 | gaagCAGCAGCAGCAGCAGCAGCAGCAGCAGCAGC AGCAGCAGCAGCAGAATTTTTGGAGTAggctttctggcttc ttaccggaaagcc |

-continued

| ID | Description | Target Repeat or Gene Symbol | SEQ ID NO: | Sequence |
|---|---|---|---|---|
| | DMD z42/38 reverse fusion | DMD exon 51 | 179 | ggagtGTAACCACAGGTTGTGTCACCAGAGTAACAT ACCTCCAACATCAAGGAAGATGGCAaATTTTTGGA Gcaggttttctgacctccgtcggaaaacccct |
| | DMD z38/42 forward fusion | DMD exon 51 | 180 | ggagtTACCTCCAACATCAAGGAAGATGGCAGTAAC CACAGGTTGTGTCACCAGAGTAACAaATTTTTGGA Gcaggttttctgacctccgtcggaaaacccct |
| | z42/38 reverse fusion no CCU tail | DMD exon 51 | 181 | ggagtGTAACCACAGGTTGTGTCACCAGAGTAACAT ACCTCCAACATCAAGGAAGATGGCAaATTTTTGGA Gcaggttttctgacctccgtcggaaaacc |
| | z38/42 for fusion no ISD no eSL | DMD exon 51 | 182 | TACCTCCAACATCAAGGAAGATGGCAGTAACCAC AGGTTGTGTCACCAGAGTAACAaATTTTTGGAGcagg ttttctgacttcggtcggaaaacccct |
| | z38/42 forward fusion human loop with ISD and cSL | DMD exon 51 | 183 | ggagtTACCTCCAACATCAAGGAAGATGGCAGTAAC CACAGGTTGTGTCACCAGAGTAACAAATTTTTGGA GTAggctttctggctccttaccggaaagcc |
| | z38/42 forward fusion human loop with ISD and eSL and added CCU tail | DMD exon 51 | 184 | ggagtTACCTCCAACATCAAGGAAGATGGCAGTAAC CACAGGTTGTGTCACCAGAGTAACAAATTTTTGGA GTAggctttctggctccttaccggaaagcccct |
| | Z38/z42 forward fusion long mouse loop with 5' ISD and eSL | DMD exon 51 | 185 | ggagtTACCTCCAACATCAAGGAAGATGGCAGTAAC CACAGGTTGTGTCACCAGAGTAACAaATTTTTGGA GcaGgttttctgacctccttcggtcggaaaacccct |

Vectors

Within the context of a recombinant expression vector, the terminology "operably linked" is intended to mean that the hybrid promoter is linked to an NOI in a manner permitting expression of the nucleotide sequence in, for example, a host cell when the vector is introduced into (or in contact with) the host cell.

In some embodiments of the compositions and methods of the disclosure, a vector comprises the engineered snRNA. In some embodiments, the therapeutic snRNA is in a single or unitary vector.

In some embodiments of the compositions and methods of the disclosure, the RNA-binding snRNA systems are capable of targeting toxic CAG, CUG, GGCCCC, CCGGG, or GGCCC+CCGGGG RNA repeats (or flanking sequences thereof) are in a single vector. In some embodiments of the compositions and methods of the disclosure, the RNA-targeting systems are capable of targeting a non-repeat RNA of interest. In some embodiments of the compositions and methods of the disclosure, the RNA-targeting systems are capable of targeting one or more sequences of DMD. In some aspects, the snRNA systems are capable of targeting multiple (i.e., two or more) RNAs of interest. In some embodiments, the two or more RNAs of interest can be the same pre-mRNA molecule but different sequences within the pre-mRNA molecule.

One type of vector is a "plasmid," which refers to a circular double stranded DNA loop into which additional DNA segments can be inserted, such as by standard molecular cloning techniques. Another type of vector is a viral vector, wherein virally-derived DNA or RNA sequences are present in the vector for packaging into a virus (e.g., retroviruses, replication defective retroviruses, adenoviruses, replication defective adenoviruses, and adeno-associated viruses). Viral vectors also include polynucleotides carried by a virus for transfection into a host cell. In some embodiments, the vector is a lentivirus (such as an integration-deficient lentiviral vector) or adeno-associated viral (AAV) vector. Vectors are capable of autonomous replication in a host cell into which they are introduced such as e.g., bacterial vectors having a bacterial origin of replication and episomal mammalian vectors and other vectors such as, e.g., non-episomal mammalian vectors, are integrated into the genome of a host cell upon introduction into the host cell, and thereby are replicated along with the host genome.

In some embodiments, vectors such as e.g., expression vectors, are capable of directing the expression of genes to which they are operatively-linked. Common expression vectors are often in the form of plasmids. In some embodiments, recombinant expression vectors comprise a nucleic acid provided herein such as e.g., an esnRNA in a form suitable for expression of a protein in a host cell. Recombinant expression vectors include one or more regulatory elements, which may be selected on the basis of the host cells to be used for expression, that is operatively-linked to the nucleic acid sequence to be expressed. Within a recombinant expression vector, "operably linked" is intended to mean that the nucleotide sequence of interest is linked to the regulatory element(s) in a manner that allows for expression of the nucleotide sequence such as e.g., in an in vitro transcription/translation system or in a host cell when the vector is introduced into the host cell. Certain embodiments of a vector depend on factors such as the choice of the host cell to be transformed, and the level of expression desired. A vector can be introduced into host cells to thereby produce transcripts, proteins, or peptides, including fusion proteins or peptides, encoded by nucleic acids as described herein such as, e.g., snRNAs, CRISPR transcripts, proteins, enzymes, mutant forms thereof, fusion proteins thereof, etc.

Viral Vectors

In some embodiments of the compositions and methods of the disclosure, a vector of the disclosure is a viral vector. In some embodiments, the viral vector comprises a sequence isolated or derived from a retrovirus. In some embodiments, the viral vector comprises a sequence isolated or derived from a lentivirus. In some embodiments, the viral vector comprises a sequence isolated or derived from an adenovirus. In some embodiments, the viral vector comprises a sequence isolated or derived from an adeno-associated virus (AAV). In some embodiments, the viral vector is replication incompetent. In some embodiments, the viral vector is isolated or recombinant. In some embodiments, the viral vector is self-complementary.

Adeno-Associated Virus Vectors

An "AAV vector" as used herein refers to a vector comprising, consisting essentially of, or consisting of one or more nucleic acid molecules and one or more AAV inverted terminal repeat sequences (ITRs). In some aspects, the nucleic acid molecule encodes for an esnRNA of the disclosure. Such AAV vectors can be replicated and packaged into infectious viral particles when present in a host cell that provides the functionality of rep and cap gene products, for example, by transfection of the host cell. In some aspects, AAV vectors contain a promoter, at least one nucleic acid that may encode at least one protein or RNA, and/or an enhancer and/or a terminator within the flanking ITRs that is packaged into the infectious AAV particle. The encapsidated nucleic acid portion may be referred to as the AAV vector genome. Plasmids containing AAV vectors may also contain elements for manufacturing purposes, e.g., antibiotic resistance genes, origin of replication sequences etc., but these are not encapsidated and thus do not form part of the AAV particle.

In some aspects, an AAV vector can comprise at least one nucleic acid encoding an esnRNA composition of the disclosure. In some aspects, an AAV vector can comprise at least one regulatory sequence. In some aspects, an AAV vector can comprise at least one AAV inverted terminal (ITR) sequence. In some aspects, an AAV vector can comprise a first ITR sequence and a second ITR sequence. In some aspects, an AAV vector can comprise at least one promoter sequence. In some aspects, an AAV vector can comprise at least one enhancer sequence. In some aspects, an AAV vector can comprise at least one terminator sequence. In some aspects, an AAV vector can comprise at least one polyA sequence. In some aspects, an AAV vector can comprise at least one linker sequence. In some aspects, an AAV vector can comprise at least one buffer sequence. In some aspects, an AAV vector of the disclosure can comprise at least one nuclear localization signal, or nuclear export signal and/or both.

In some aspects, an AAV vector can comprise a first AAV ITR sequence, a promoter sequence, an esnRNA sequence, a terminator sequence and a second AAV ITR sequence. In some aspects, an AAV vector can comprise, in the 5' to 3' direction, a first AAV ITR sequence, a promoter sequence, an esnRNA sequence, a terminator sequence, and a second AAV ITR sequence.

In some aspects, an AAV vector can comprise a first AAV ITR sequence, a first promoter sequence, a first esnRNA sequence, a second promoter sequence, second esnRNA sequence, and a second AAV ITR sequence. In some aspects, an AAV vector can comprise a first AAV ITR sequence, a first promoter sequence, a first esnRNA sequence, a second promoter sequence, a second esnRNA sequence, a third promoter sequence, a third esnRNA sequence, and a second AAV ITR sequence. In some aspects, an AAV vector can comprise a first AAV ITR sequence, a first promoter sequence, a first esnRNA sequence, a second promoter sequence, second esnRNA sequence, and a second AAV ITR sequence. In some aspects, an AAV vector can comprise a first AAV ITR sequence, a first promoter sequence, a first esnRNA sequence, a second promoter sequence, a second esnRNA sequence, a third promoter sequence, a third esnRNA sequence, a fourth promoter sequence, a fourth esnRNA sequence, and a second AAV ITR sequence.

The term "adeno-associated virus" or "AAV" as used herein refers to a member of the class of viruses associated with this name and belonging to the genus Dependoparvovirus, family Parvoviridae. Adeno-associated virus is a single-stranded DNA virus that grows in cells in which certain functions are provided by a co-infecting helper virus. General information and reviews of AAV can be found in, for example, Carter, 1989, Handbook of Parvoviruses, Vol. 1, pp. 169-228, and Berns, 1990, Virology, pp. 1743-1764, Raven Press, (New York). It is fully expected that the same principles described in these reviews will be applicable to additional AAV serotypes characterized after the publication dates of the reviews because it is well known that the various serotypes are quite closely related, both structurally and functionally, even at the genetic level. (See, for example, Blacklowe, 1988, pp. 165-174 of Parvoviruses and Human Disease, J. R. Pattison, ed.; and Rose, Comprehensive Virology 3: 1-61 (1974)). For example, all AAV serotypes apparently exhibit very similar replication properties mediated by homologous rep genes; and all bear three related capsid proteins such as those expressed in AAV2. The degree of relatedness is further suggested by heteroduplex analysis which reveals extensive cross-hybridization between serotypes along the length of the genome; and the presence of analogous self-annealing segments at the termini that correspond to "inverted terminal repeat sequences" (ITRs). The similar infectivity patterns also suggest that the replication functions in each serotype are under similar regulatory control. Multiple serotypes of this virus are known to be suitable for gene delivery; all known serotypes can infect cells from various tissue types.

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is inserted as cloned DNA in plasmids, which makes construction of recombinant genomes feasible. Furthermore, because the signals directing AAV replication and genome encapsidation are contained within the ITRs of the AAV genome, some or all of the internal approximately 4.3 kb of the genome (encoding replication and structural capsid proteins, rep-cap) may be replaced with foreign DNA to generate AAV vectors. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

Recombinant AAV (rAAV) genomes of the invention comprise, consist essentially of, or consist of a nucleic acid molecule encoding at least one esnRNA and one or more AAV ITRs flanking the nucleic acid molecule. Production of pseudotyped rAAV is disclosed in, for example, WO2001083692. Other types of rAAV variants, for example rAAV with capsid mutations, are also contemplated. See, e.g., Marsic et al., Molecular Therapy, 22(11): 1900-1909 (2014). The nucleotide sequences of the genomes of various AAV serotypes are known in the art.

In some embodiments of the compositions and methods of the disclosure, the viral vector comprises a sequence isolated or derived from an adeno-associated virus (AAV). In some embodiments, the viral vector comprises an inverted terminal repeat sequence or a capsid sequence that is isolated or derived from an AAV of serotype AAV1, AAV2, AAV3, AAV4, AAV5, AAV6, AAV7, AAV8, AAV9, AAV10, AAVrh10, AAV11 or AAV12. In some embodiments, the AAV serotype is AAVrh.74. In one embodiment, the AAV vector comprises a modified capsid. In one embodiment the AAV vector is an AAV2-Tyr mutant vector. In one embodiment the AAV vector comprises a capsid with a non-tyrosine amino acid at a position that corresponds to a surface-exposed tyrosine residue in position Tyr252, Tyr272, Tyr275, Tyr281, Tyr508, Tyr612, Tyr704, Tyr720, Tyr730 or Tyr673 of wild-type AAV2. See also WO 2008/124724 incorporated herein in its entirety. In some embodiments, the AAV vector comprises an engineered capsid. AAV vectors comprising engineered capsids include without limitation, AAV2.7m8, AAV9.7m8, AAV2 2tYF, and AAV8 Y733F). In some embodiments, the capsid is a ubiquitination resistant capsid. In another embodiment, the ubiquitination capsid is an AAV2 capsid comprising tyrosine (Y) and serine (S) mutations. In another embodiment, the AAV2 capsid comprises Y, S and threonine (T) mutations. In another embodiment, the AAV2 capsid includes, without limitation, AAV2 capsid mutants such as T455V, T491V, T550V, T659V, Y444+500+730F, and Y444+500+730F+T491V. In some embodiments, the viral vector is replication incompetent. In some embodiments, the viral vector is isolated or recombinant (rAAV). In some embodiments, the viral vector is self-complementary (scAAV). In some embodiments, the viral vector is single-stranded (ssAAV).

AAV ITR Sequences

In some embodiments of the compositions and methods of the disclosure, an AAV inverted terminal repeat sequence can comprise any AAV ITR sequence known in the art. In some aspects, an AAV ITR sequence can comprise or consist of an AAV1 ITR sequence, an AAV2 ITR sequence, an AAV3 ITR sequence, an AAV4 ITR sequence, an AAV5 ITR sequence, an AAV6 ITR sequence, an AAV7 ITR sequence, an AAV8 ITR sequence, an AAV9 ITR sequence, an AAV10 ITR sequence, an AAVrh10 ITR sequence, an AAV11 ITR sequence, an AAV12 ITR sequence, an AAV13 ITR sequence, or an AAVrh74 ITR sequence.

In some aspects, the ITR sequence can comprise a modified AAV ITR sequence.

In some aspects, an AAV ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 59, SEQ ID NO: 60, SEQ ID NO: 61, SEQ ID NO: 162, or SEQ ID NO: 166.

In some aspects, a first AAV ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 59, SEQ ID NO: 60, SEQ ID NO: 61, SEQ ID NO: 162, or SEQ ID NO: 166 and a second AAV ITR sequence can comprise, consist essentially of, or consist of a nucleic acid sequence at least 65%, 70%, 75%, 80%, 85%, 90%, 95%, 96%, 97%, 98%, 99% or 100% (or any percentage in between) identical to SEQ ID NO: 59, SEQ ID NO: 60, SEQ ID NO: 61, SEQ ID NO: 162, or SEQ ID NO: 166.

In some aspects, the first AAV ITR sequence is positioned at the 5' of a AAV vector. In some aspects, the second AAV ITR sequence is positioned at the 3' of a AAV vector.

In some embodiments of the compositions and methods of the disclosure, the viral vector comprises a sequence isolated or derived from an adeno-associated virus (AAV).

In some embodiments of the compositions and methods of the disclosure, a vector of the disclosure is a non-viral vector. In some embodiments, the vector comprises or consists of a nanoparticle, a micelle, a liposome or lipoplex, a polymersome, a polyplex or a dendrimer. In some embodiments, the vector is an expression vector or recombinant expression system. As used herein, the term "recombinant expression system" refers to a genetic construct for the expression of certain genetic material formed by recombination.

esnRNA Vector Constructs

Exemplary esnRNA AAV vectors of the disclosure can comprise one or more esnRNA sequences of the disclosure. In some aspects, the esnRNA AAV vector comprises, consists essentially of, or consists of a nucleic acid sequence at least 65%, 70%, 75%, 80%, 85%, 90%, 95%, 96%, 97%, 98%, 99% or 100% (or any percentage in between) identical to a an esnRNA AAV vector listed in the esnRNA AAV vector Table which follows:

| ID | Description | SEQ ID NO: |
|---|---|---|
| A02962 | ss pAAV-4X U7(15XCUG) (derivative of P00369) targeting CUG repeats | 120 |
| A02963 | ss pAAV-4X U7(NT1) (derivative of P00369) | 121 |
| A02967 | ss pAAV-4X U7(15XCUG) targeting CUG repeats | 122 |
| A03079 | sc pAAV-4X U7(15XCUG) (derivative of P00369) targeting CAG repeats | 123 |
| A03080 | sc pAAV-4X U7(NT1) (derivative of P00369) | 124 |
| A03081 | sc pAAV-4X U7(15XCTG) targeting CUG repeats | 125 |
| A02888 | pAAV_1xU7(15xCUG)_CMV_GFP (no buffer) targeting CUG repeats | 126 |
| A02889 | pAAV_1xU7(NT1)_CMV_GFP (no buffer) | 127 |
| A02925 | pAAV_1xU7(15xCAG)_CMV_GFP (no buffer) targeting CAG repeats | 128 |

| ID | Description | SEQ ID NO: |
|---|---|---|
| A02894 | pAAV_3xU7(15xCUG)_CMV_GFP (100 bp buffer) targeting CUG repeats | 129 |
| A02895 | pAAV_3xU7(NT1)_CMV_GFP (100 bp buffer) | 130 |
| A02968 | pAAV_3xU7(15XCAG)_CMV_GFP (100 bp buffer) targeting CAG repeats | 131 |
| A02896 | pAAV_3xU7(15xCUG)_CMV_GFP (500 bp buffer) | 132 |
| A02897 | PAAV_3xU7(NT1)_CMV_GFP (500 bp buffer) | 133 |
| A02969 | pAAV_3xU7(15xCAG)_CMV_GFP (500 bp buffer) targeting CAG repeats | 134 |
| A03980 | pAAV(ssAAV) U7promoter-esnRNA-z38/42-U7 termination-U1promoter-esnRNAz38/z42-U1 termination | 135 |
| A03981 | pAAV(ssAAV)_U7promoter-esnRNA-z42-U7termination-U1promoter-esnRNA-z38-U1 termination | 136 |
| A04229 | pAAV(scAAV) U7promoter-esnRNAz38/42-U7 termination-U1promoter-esnRNAz38/42-U1 termination-mut ITR | 137 |
| A04184 | pAAV(ssAAV)-U7promoter-z38/42-U7term_U1promoter-z38/42-U1term_buffer combination sequencestuffer | 138 |
| A03681 | pAAV(ssAAV)-U7 promoter-zCUGx15-U7 term_U1 promoter-zCUGx15-U1 term-eCMV-eGFP | 139 |
| A03682 | pAAV(ssAAV)-U1 promoter-zCUGx15-U1 term_U7 promoter-zCUGx15-U7 term-eCMV-eGFP | 140 |
| A03683 | pAAV(ssAAV)-U7 promoter-znt-U7 term_U1 promoter-znt-U1 term-eCMV-eGFP | 141 |
| A03864 | pAAV(ssAAV)-U7 promoter-zCUGx15-U7 term_U1 promoter-zCUGx15-U1 term (minus GFP – derivative of 3681) | 142 |
| A04233 | pAAV(scAAV)-U7promoter-zCUGx15-U7termination-U1promoter-zCUGx15-U1termination (derivative of A03681 no GFP in scAAV) | 143 |
| A04569 | scAAVmU7p-z42/38 rev fus-mU7term_mU1p-z42/38 rev fus-mU1term; mouse loop with5' ISD and eSL | 168 |
| A04526 | scAAVmU7p-z38/42 Forward fus-mU7term_mU1p-z38/42 forward fus-mU1term; mouseloop with5' ISD and eSL | 169 |
| A04771 | scAAVmU7p-z42/38 reverse fus-mU7term_mU1p-z42/38 reverse fus-mU1term; mouseloop with 5' ISD and eSL no CCU tail | 170 |
| A04525 | scAAV-mU7p-z38/42-mU7term_mU7p-z38/42-mU7term; mouse loop no ISD no eSL | 171 |
| A04527 | scAAV-mU7p-z38/42-mU7term_mU1p-z38/42-mU1term; mouse loop no ISD no eSL | 172 |
| A04528 | scAAV-mU7p-z38/42-mU7term_mU1p-z38/42-mU1term; human loop with ISD and eSL | 173 |
| A04529 | scAAV-mU7p-z38/42-mU7term_mU1p-z38/42-mU1term; human loop with ISD and eSL with added CCU tail | 174 |
| A04537 | scAAV-mU7p-z38/42-mU7term_mU1prom- p-z38/42-mU1term; long mouse loop with5' ISD and eSL | 175 |
| A04233 | scAAV- hU7-CUGx15-hU1-CUGx15 (3'mut ITR) | 176 |
| A04234 | scAAV- hU7-CUGx15-hU1-CUGx15 (5' mut ITR) | 177 |
| A04390 | scAAV 5'mITR hU7-CAG15X-hU1-CAGx15 | 178 |
| A04530 | scAAV- mU7p-CUGx15-mU1p-CUGx15; mouseloop with ISD and eSL | 231 |
| A04940 | scAAV- mU7p-CUGx10-mU1p-CUGx10; mouseloop with ISD and eSL no CCU | 232 |
| A04533 | scAAV- mU7p-CAGx15-mU1p-CAGx15; mouseloop with ISD and eSL | 233 |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04569 encoding DMD exon 51 targeting snRNA sequences comprises SEQ ID NO: 168.

A04569: scAAVmU7p-z42/38 rev fus-mU7term_mU1p-z42/38 rev fus-mU1term; Mouse Loop with 5' ISD and eSL

| Plasmid Element | Nucleotide Sequence 5' to 3' |
|---|---|
| 5' ITR | ctgcgcgctcgctcgctcactgaggccgcccgggcaaagcccgggcgtcgggcgacctttggtcgcccggcctcagtgagcgag cgagcgcgcagagagggagtgggtt (SEQ ID NO: 162) |
| Mouse U7 promoter | taacaacataggagctgtgattggctgttttcagccaatcagcactgActcatttgcatagcctttacaagcggtcacaaactca agaaacgagcggttttaatagtctttagaatattgtttatcgaaccgaataaggaactgtgctttgtgattcacatatcagtgg aggggtgtggaaatggcaccttgatctcaccctcatcgaaagtggagttgatgtcctTccctggctcgctacagacgcacttcc gcaa (SEQ ID NO: 48) |

-continued

| Plasmid Element | Nucleotide Sequence 5' to 3' |
|---|---|
| ISD | ggagt (SEQ ID NO: 12) |
| Z42/z38 reverse fusion spacer | GTAACCACAGGTTGTGTCACCAGAGTAACATACCTCCAACATCAAGGAAGATGG CA (SEQ ID NO: 149) |
| SMOPT | aATTTTTGGAGca (SEQ ID NO: 161) |
| Mouse stem loop (eSL) short loop | ggttttctgacctccgtcggaaaacccct (SEQ ID NO: 146) |
| Mouse U7 terminator | cccaatttcactggtctacaatgaaagcaaaacagttctcttccccgctccccggtgtgtgagaggggctttgatccttctctgg tttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTA TGAAAGTAAATGCCTGTTGTTAGAACAAAAAAGGCTACAGAACAAAAAACAAA GCGAAATACCATCTGCTTTAGGTTCAGTGTGGTATTTTCCCGCTGACAGGGAGGC GGGTTTTTGGGTACAGGAAACGAGTCACTATGGAGGCGGTACTATGTAGATGAG AATTCAGGTGCAAACTGGGAAAAGCAACTGCTTCCAAATATTTGTGATTTTTACA GTGTAGTTTTGGAAAAACTCTTAGCCTACCAATTCTTCTAAGTGTTTTAAAATGT GGGAGCCAGTACACATGAAGTTATAGAGTGTTTTAATGAGGCTTAAATATTTACC GTAACTATGAAATGCTACGCATATCATGCTGTTCAGGCTCCGTGGCCACGCAACT C (SEQ ID NO: 47) |
| ISD | ggagt (SEQ ID NO: 12) |
| Z42/z38 reverse fusion spacer | GTAACCACAGGTTGTGTCACCAGAGTAACATACCTCCAACATCAAGGAAGATGG CA (SEQ ID NO: 149) |
| SMOPT | aATTTTTGGAGca (SEQ ID NO: 161) |
| Mouse stem loop (eSL) short loop | ggttttctgacctccgtcggaaaacccct (SEQ ID NO: 146) |
| Mouse U1 terminator | GTTTACTTGGTTTTAAAAATAGCTTGCACTAGCGATACGGAATATGGTTATTAGG TTTGTTAGGCATCATGTCGTGTCTTACTATAGAAAAATAACGTAGTGTTCATTTT AGCCTGCCTGTATGTGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3' ITR | Aggaaccctagtgatggagttggccactccctctctgcgcgctcgctcgctcactgaggccgggcgaccaaaggtcgcccgacg cccgggctttgcccggggggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04526 encoding DMD exon 51 targeting snRNA sequences comprises SEQ ID NO: 169.

A04526: scAAVmU7p-z82/42 Forward fus-mU7term_mU1p-z38/42 forward fus-mU1term; Mouse Loop with 5' ISD and eSL

| Plasmid Element | Nucleotide Sequence 5' to 3' |
|---|---|
| 5' ITR | ctgcgcgctcgctcgctcactgaggccgcccgggcaaagcccgggcgtcgggcgacctttggtcgcccggcctcagtgagcgag cgagcgcgcagagagggagtggggtt (SEQ ID NO: 162) |
| Mouse U7 promoter | taacaacataggagctgtgattggctgttttcagccaatcagcactgActcatttgcatagcctttacaagcggtcacaaactc aagaaacgagcggttttaatagtcttttagaatattgtttatcgaaccgaataaggaactgtgctttgtgattcacatatcagt ggaggggtgtggaaatggcaccttgatctcaccctcatcgaaagtggagttgatgtcctTccctggctcgctacagacgcact tccgcaa (SEQ ID NO: 48) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | aATTTTTGGAGca (SEQ ID NO: 161) |
| Mouse stem loop (eSL) short loop | ggttttctgacctccgtcggaaaacccct (SEQ ID NO: 146) |

| Plasmid Element | Nucleotide Sequence 5' to 3' |
| --- | --- |
| Mouse U7 terminator | cccaatttcactggtctacaatgaaagcaaaacagttctcttccccgctccccggtgtgtgagaggggctttgatccttctctg gtttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTA TGAAAGTAAATGCCTGTTGTTAGAACAAAAAAGGCTACAGAACAAAAAACAAA GCGAAATACCATCTGCTTTAGGTTCAGTGTGGTATTTTCCCGCTGACAGGGAGGC GGGTTTTTGGGTACAGGAAACGAGTCACTATGGAGGCGGTACTATGTAGATGAG AATTCAGGTGCAAACTGGGAAAAGCAACTGCTTCCAAATATTTGTGATTTTTACA GTGTAGTTTTGGAAAAACTCTTAGCCTACCAATTCTTCTAAGTGTTTTAAAATGT GGGAGCCAGTACACATGAAGTTATAGAGTGTTTTAATGAGGCTTAAATATTTACC GTAACTATGAAATGCTACGCATATCATGCTGTTCAGGCTCCGTGGCCACGCAACT C (SEQ ID NO: 47) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | aATTTTTGGAGca (SEQ ID NO: 161) |
| Mouse stem loop (eSL) short loop | ggttttctgacctccgtcggaaaacccct (SEQ ID NO: 146) |
| Mouse U1 terminator | GTTTACTTGGTTTTAAAAATAGCTTGCACTAGCGATACGGAATATGGTTATTAGG TTTGTTAGGCATCATGTCGTGTCTTACTATAGAAAAATAACGTAGTGTTCATTTT AGCCTGCCTGTATGTGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3' ITR | Aggaaccoctagtgatggagttggccactccctctctgcgcgctcgctcgctcactgaggccgggcgaccaaaggtcgcccgacg ccgggctttgcccgggcggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04771 encoding DMD exon 51 targeting snRNA sequences comprises SEQ ID NO: 170.

A04771: scAAVmU7p-z42/38 reverse fus-mU7term_mU1p-z42/38 reverse fus-mU1term; Mouse Loop with 5' ISD and eSL no CCU Tail

| Plasmid Element | Nucleotide Sequence 5' to 3' |
| --- | --- |
| 5' ITR | ctgcgcgctcgctcgctcactgaggccgcccgggcaaagcccgggcgtcgggcgacctttggtcgcccggcctcagtgagcgagc gagcgcgcagagagggagtgggggtt (SEQ ID NO: 162) |
| Mouse U7 promoter | taacaacataggagctgtgattggctgtttttcagccaatcagcactgActcatttgcatagcctttacaagcggtcacaaactca agaaacgagcggttttaatagtctttttagaatatgttttatcgaaccgaataaggaactgtgctttgtgattcacatatcagtgg aggggtgtggaaatggcaccttgatctcaccctcatcgaaagtggagttgatgtcctTccctggctcgctacagacgcacttcc gcaa (SEQ ID NO: 48) |
| ISD | ggagt (SEQ ID NO: 12) |
| Z42/z38 reverse fusion spacer | GTAACCACAGGTTGTGTCACCAGAGTAACATACCTCCAACATCAAGGAAGATGGC A (SEQ ID NO: 149) |
| SMOPT | aATTTTTGGAGca (SEQ ID NO: 161) |
| Mouse stem loop (eSL) short loop no CCU | ggttttctgacctccgtcggaaaacc (SEQ ID NO: 148) |
| Mouse U7 terminator | cccaatttcactggtctacaatgaaagcaaaacagttctcttccccgctccccggtgtgtgagaggggctttgatccttctctg gtttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTAT GAAAGTAAATGCCTGTTGTTAGAACAAAAAAGGCTACAGAACAAAAAACAAAGC GAAATACCATCTGCTTTAGGTTCAGTGTGGTATTTTCCCGCTGACAGGGAGGCGG GTTTTTGGGTACAGGAAACGAGTCACTATGGAGGCGGTACTATGTAGATGAGAAT TCAGGTGCAAACTGGGAAAAGCAACTGCTTCCAAATATTTGTGATTTTTACAGTGT AGTTTTGGAAAAACTCTTAGCCTACCAATTCTTCTAAGTGTTTTAAAATGTGGGAG CCAGTACACATGAAGTTATAGAGTGTTTTAATGAGGCTTAAATATTTACCGTAACT |

| Plasmid Element | Nucleotide Sequence 5' to 3' |
|---|---|
| | ATGAAATGCTACGCATATCATGCTGTTCAGGCTCCGTGGCCACGCAACTC (SEQ ID NO: 47) |
| ISD | ggagt (SEQ ID NO: 12) |
| Z42/z38 reverse fusion spacer | GTAACCACAGGTTGTGTCACCAGAGTAACATACCTCCAACATCAAGGAAGATGGCA (SEQ ID NO: 149) |
| SMOPT | aATTTTTGGAGca (SEQ ID NO: 161) |
| Mouse stem loop (eSL) short loop no CCU | ggttttctgacctccgtcggaaaacc (SEQ ID NO: 148) |
| Mouse U1 terminator | GTTTACTTGGTTTTAAAAATAGCTTGCACTAGCGATACGGAATATGGTTATTAGGTTTGTTAGGCATCATGTCGTGTCTTACTATAGAAAAATAACGTAGTGTTCATTTTAGCCTGCCTGTATGTGTTAATTTGTCCTTATTGCGCATTGTTCTTGTTAAGTCTTCTGTAAGGAGTTGCGGGTTTCAAACTGTCAGTCTGAGAGCA (SEQ ID NO: 57) |
| 3' ITR | Aggaacccctagtgatggagttggccactccctctctgcgcgctcgctcgctcactgaggccgggcgaccaaaggtcgcccgacggggctttgccggggggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U7 promoter sequence, a DMD exon 51 targeting U7 esnRNA sequence, a U7 downstream terminator sequence, and a second ITR sequence. In some aspects, a nucleic acid sequence encoding AAV vector A04525 encoding DMD exon 51 targeting snRNA sequences comprises SEQ ID NO: 171.

A04525: scAAV-mU7p-z38/42-mU7term_mU7p-z38/42-mU7term; Mouse Loop No ISD No eSL

| Plasmid Element | Nucleotide Sequence 5' to 3' |
|---|---|
| 5' ITR | ctgcgcgctcgctcgctcactgaggccgcccgggcaaagcccgggcgtcgggcgacctttggtcgcccggcctcagtgagcgagcgagcgcgcagagagggagtggggtt (SEQ ID NO: 162) |
| Mouse U7 promoter | taacaacataggagctgtgattggctgttttcagccaatcagcactgActcatttgcatagcctttacaagcggtcacaaactcaagaaacgagcggttttaatagtcttttagaatattgtttatcgaaccgaataaggaactgtgctttgtgattcacatatcagtggaggggtgtggaaatggcaccttgatctcaccctcatcgaaagtggagttgatgtcctTccctggctcgctacagacgcacttccgcaa (SEQ ID NO: 48) |
| Z38/z42 forward fusion spacer | TACCTCCAACATCAAGGAAGATGGCAGTAACCACAGGTTGTGTCACCAGAGTAACA (SEQ ID NO: 150) |
| SMOPT | aATTTTTGGAGca (SEQ ID NO: 161) |
| Mouse stem loop (WT) short loop | ggttttctgacttcggtcggaaaacccct (SEQ ID NO: 145) |
| Mouse U7 terminator | cccaatttcactggtctacaatgaaagcaaaacagttctcttcccgctcccggtgtgtgagagggctttgatccttctctggtttcctaggaaacgcgtatgtg (SEQ ID NO: 156) |
| Mouse U7 promoter | taacaacataggagctgtgattggctgttttcagccaatcagcactgActcatttgcatagcctttacaagcggtcacaaactcaagaaacgagcggttttaatagtcttttagaatattgtttatcgaaccgaataaggaactgtgctttgtgattcacatatcagtggaggggtgtggaaatggcaccttgatctcaccctcatcgaaagtggagttgatgtcctTccctggctcgctacagacgcacttccgcaa (SEQ ID NO: 48) |
| Z38/z42 forward fusion spacer | TACCTCCAACATCAAGGAAGATGGCAGTAACCACAGGTTGTGTCACCAGAGTAACA (SEQ ID NO: 150) |
| SMOPT | aATTTTTGGAGca (SEQ ID NO: 161) |
| Mouse stem loop (WT) short loop | ggttttctgacttcggtcggaaaacccct (SEQ ID NO: 145) |
| Mouse U7 terminator | cccaatttcactggtctacaatgaaagcaaaacagttctcttcccgctcccggtgtgtgagagggctttgatccttctctggtttcctaggaaacgcgtatgtg (SEQ ID NO: 156) |
| 3' ITR | Aggaacccctagtgatggagttggccactccctctctgcgcgctcgctcgctcactgaggccgggcgaccaaaggtcgcccgacgcgggctttgccgggcggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04527 encoding DMD exon 51 targeting snRNA sequences comprises SEQ ID NO: 172.

A04527: scAAV-mU7p-z38/42-mU7term_mU1p-z38/42-mU1term; Mouse Loop No ISD No eSL

| Plasmid Element | Nucleotide Sequence 5' to 3' |
| --- | --- |
| 5' ITR | ctgcgcgctcgctcgctcactgaggccgcccgggcaaagcccgggcgtcgggcgacctttggtcgcccggcctcagtgagcgag cgagcgcgcagagagggagtgggggtt (SEQ ID NO: 162) |
| Mouse U7 promoter | taacaacataggagctgtgattggctgttttcagccaatcagcactgActcatttgcatagcctttacaagcggtcacaaactc aagaaacgagcggttttaatagtcttttagaatattgtttatcgaaccgaataaggaactgtgctttgtgattcacatatcag tggaggggtgtggaaatggcaccttgatctcaccctcatcgaaagtggagttgatgtcctTccctggctcgctacagacgcact tccgcaa (SEQ ID NO: 48) |
| Z38/z42 forward fusion spacer | TACCTCCAACATCAAGGAAGATGGCAGTAACCACAGGTTGTGTCACCAGAGTAACA (SEQ ID NO: 150) |
| SMOPT | aATTTTTGGAGca (SEQ ID NO: 161) |
| Mouse stem loop (WT) short loop | ggttttctgacttcggtcggaaaacccct (SEQ ID NO: 145) |
| Mouse U7 terminator | cccaatttcactggtctacaatgaaagcaaaacagttctcttccccgctccccggtgtgtgagaggggctttgatccttctctg gtttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTAT GAAAGTAAATGCCTGTTGTTAGAACAAAAAAGGCTACAGAACAAAAAACAAAGC GAAATACCATCTGCTTTAGGTTCAGTGTGGTATTTTCCCGCTGACAGGGAGGCGG GTTTTTGGGTACAGGAAACGAGTCACTATGGAGGCGGTACTATGTAGATGAGAAT TCAGGTGCAAACTGGGAAAAGCAACTGCTTCCAAATATTTGTGATTTTTACAGTGT AGTTTTGGAAAAACTCTTAGCCTACCAATTCTTCTAAGTGTTTTAAAATGTGGGAG CCAGTACACATGAAGTTATAGAGTGTTTTAATGAGGCTTAAATATTTACCGTAACT ATGAAATGCTACGCATATCATGCTGTTCAGGCTCCGTGGCCACGCAACTC (SEQ ID NO: 47) |
| Z38/z42 forward fusion spacer | TACCTCCAACATCAAGGAAGATGGCAGTAACCACAGGTTGTGTCACCAGAGTAACA (SEQ ID NO: 150) |
| SMOPT | aATTTTTGGAGca (SEQ ID NO: 161) |
| Mouse stem loop (WT) short loop | ggttttctgacttcggtcggaaaacccct (SEQ ID NO: 145) |
| Mouse U1 terminator | GTTTACTTGGTTTTAAAAATAGCTTGCACTAGCGATACGGAATATGGTTATTAGGT TTGTTAGGCATCATGTCGTGTCTTACTATAGAAAAATAACGTAGTGTTCATTTTAG CCTGCCTGTATGTGTTAATTTGTCCTTATTGCGCATTGTTCTTGTTAAGTCTTCTGT AAGGAGTTGCGGGTTTCAAACTGTCAGTCTGAGAGCA (SEQ ID NO: 57) |
| 3' ITR | aggaaccccctagtgatggagttggccactccctctctgcgcgctcgctcgctcactgaggccgggcgaccaaaggtcgcccga cgcccgggctttgcccgggggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04528 encoding DMD exon 51 targeting snRNA sequences comprises SEQ ID NO: 173.

A04528: scAAV-mU7p-z38/42-mU7term_mU1p-z38/42-mU1term; Human Loop with ISD and eSL

| Plasmid Element | Nucleotide Sequence 5' to 3' |
| --- | --- |
| 5' ITR | ctgcgcgctcgctcgctcactgaggccgcccgggcaaagcccgggcgtcgggcgacctttggtcgcccggcctcagtgagcgag cgagcgcgcagagagggagtgggggtt (SEQ ID NO: 162) |
| Mouse U7 promoter | taacaacataggagctgtgattggctgttttcagccaatcagcactgActcatttgcatagcctttacaagcggtcacaaactc aagaaacgagcggttttaatagtcttttagaatattgtttatcgaaccgaataaggaactgtgctttgtgattcacatatcagt |

| Plasmid Element | Nucleotide Sequence 5' to 3' |
|---|---|
| | ggagggtgtggaaatggcaccttgatctcaccctcatcgaaagtggagttgatgtcctTccctggctcgctacagacgcact tccgcaa (SEQ ID NO: 48) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | AATTTTTGGAGTA (SEQ ID NO: 164) |
| Human stem loop (eSL) | ggctttctggctccttaccggaaagcc (SEQ ID NO: 1) |
| Mouse U7 terminator | cccaatttcactggtctacaatgaaagcaaaacagttctcttccccgctccccggtgtgtgagaggggctttgatccttctctg gtttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTA TGAAAGTAAATGCCTGTTGTTAGAACAAAAAAGGCTACAGAACAAAAAACAAA GCGAAATACCATCTGCTTTAGGTTCAGTGTGGTATTTTCCCGCTGACAGGGAGGC GGGTTTTTGGGTACAGGAAACGAGTCACTATGGAGGCGGTACTATGTAGATGAG AATTCAGGTGCAAACTGGGAAAAGCAACTGCTTCCAAATATTTGTGATTTTTACA GTGTAGTTTTGGAAAAACTCTTAGCCTACCAATTCTTCTAAGTGTTTTAAAATGT GGGAGCCAGTACACATGAAGTTATAGAGTGTTTTAATGAGGCTTAAATATTTACC GTAACTATGAAATGCTACGCATATCATGCTGTTCAGGCTCCGTGGCCACGCAACT C (SEQ ID NO: 47) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | AATTTTTGGAGTA (SEQ ID NO: 164) |
| Human stem loop (eSL) | ggctttctggctccttaccggaaagcc (SEQ ID NO: 1) |
| Mouse U1 terminator | GTTTACTTGGTTTTAAAAATAGCTTGCACTAGCGATACGGAATATGGTTATTAGG TTTGTTAGGCATCATGTCGTGTCTTACTATAGAAAAATAACGTAGTGTTCATTTT AGCCTGCCTGTATGTGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3' ITR | aggaaccctagtgatggagttggccactccctctctgcgcgctcgctcgctcactgaggccgggcgaccaaaggtcgcccgac gcccgggctttgcccgggcggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04529 encoding DMD exon 51 targeting snRNA sequences comprises SEQ ID NO: 174.

A04529: scAAV-mU7p-z38/42-mU7term_mU1p-z38/42-mU1term; Human Loop with ISD and eSL with Added CCU Tail

| Plasmid Element | Nucleotide Sequence 5' to 3' |
|---|---|
| 5' ITR | ctgcgcgctcgctcgctcactgaggccgcccgggcaaagcccgggcgtcgggcgacctttggtcgcccggcctcagtgagcgag cgagcgcgcagagagggagtggggtt (SEQ ID NO: 162) |
| Mouse U7 promoter | taacaacataggagctgtgattggctgtttcagccaatcagcactgActcatttgcatagcctttacaagcggtcacaaactc aagaaacgagcggttttaatagtcttttagaatattgtttatcgaaccgaataaggaactgtgctttgtgattcacatatcagt ggagggtgtggaaatggcaccttgatctcaccctcatcgaaagtggagttgatgtcctTccctggctcgctacagacgcac ttccgcaa (SEQ ID NO: 48) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | AATTTTTGGAGTA (SEQ ID NO: 164) |
| Human stem loop (eSL) with CCU tail | ggctttctggctccttaccggaaagccct (SEQ ID NO: 163) |

| Plasmid Element | Nucleotide Sequence 5' to 3' |
|---|---|
| Mouse U7 terminator | cccaatttcactggtctacaatgaaagcaaaacagttctcttccccgctccccggtgtgtgagaggggctttgatccttctct ggtttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTA TGAAAGTAAATGCCTGTTGTTAGAACAAAAAAGGCTACAGAACAAAAAACAAA GCGAAATACCATCTGCTTTAGGTTCAGTGTGGTATTTTCCCGCTGACAGGGAGGC GGGTTTTTGGGTACAGGAAACGAGTCACTATGGAGGCGGTACTATGTAGATGAG AATTCAGGTGCAAACTGGGAAAAGCAACTGCTTCCAAATATTTGTGATTTTTACA GTGTAGTTTTGGAAAAACTCTTAGCCTACCAATTCTTCTAAGTGTTTTAAAATGT GGGAGCCAGTACACATGAAGTTATAGAGTGTTTTAATGAGGCTTAAATATTTACC GTAACTATGAAATGCTACGCATATCATGCTGTTCAGGCTCCGTGGCCACGCAACT C (SEQ ID NO: 47) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | AATTTTTGGAGTA (SEQ ID NO: 164) |
| Human stem loop (eSL) with CCU tail | ggctttctggctccttaccggaaagcccct (SEQ ID NO: 163) |
| Mouse U1 terminator | GTTTACTTGGTTTTAAAAATAGCTTGCACTAGCGATACGGAATATGGTTATTAGG TTTGTTAGGCATCATGTCGTGTCTTACTATAGAAAAATAACGTAGTGTTCATTTT AGCCTGCCTGTATGTGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3' ITR | aggaaccctagtgatggagttggccactccctctctgcgcgctcgctcgctcactgaggccgggcgaccaaaggtcgcccga cgcccgggctttgcccgggggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04537 encoding DMD exon 51 targeting snRNA sequences comprises SEQ ID NO: 175.

A04537: scAAV-mU7p-z38/42-mU7term_mU1prom-p-z38/42-mU1term; Long Mouse Loop with 5' ISD and eSL

| Plasmid Element | Nucleotide Sequence 5' to 3' |
|---|---|
| 5' ITR | ctgcgcgctcgctcgctcactgaggccgcccgggcaaagcccgggcgtcgggcgacctttggtcgcccggcctcagtgagcgag cgagcgcgcagagagggagtggggtt (SEQ ID NO: 162) |
| Mouse U7 promoter | taacaacataggagctgtgattggctgtttcagccaatcagcactgActcatttgcatagcctttacaagcggtcacaaactc aagaaacgagcggttttaatagtcttttagaatattgtttatcgaaccgaataaggaactgtgctttgtgattcacatatcagt ggaggggtgtggaaatggcaccttgatctcaccctcatcgaaagtggagttgatgtcctTccctggctcgctacagacgcact tccgcaa (SEQ ID NO: 48) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA CA (SEQ ID NO: 150) |
| SMOPT | aATTTTTGGAGca (SEQ ID NO: 161) |
| mouse stem loop (eSL) with CCU tail (long extended loop) | Ggttttctgacctccttcggtcggaaaaccccct (SEQ ID NO: 147) |
| Mouse U7 terminator | Cccaatttcactggtctacaatgaaagcaaaacagttctcttccccgctccccggtgtgtgagaggggctttgatccttctctg gtttcctaggaaacgcgtatgtg (SEQ ID NO: 156) |
| Mouse U1 promoter | TTGTTCCTCTTAGTGTTAATTCACACTAAAGACTGTGCATCCGACTCCTACATTTA TGAAAGTAAATGCCTGTTGTTAGAACAAAAAAGGCTACAGAACAAAAAACAAA GCGAAATACCATCTGCTTTAGGTTCAGTGTGGTATTTTCCCGCTGACAGGGAGGC GGGTTTTTGGGTACAGGAAACGAGTCACTATGGAGGCGGTACTATGTAGATGAG AATTCAGGTGCAAACTGGGAAAAGCAACTGCTTCCAAATATTTGTGATTTTTACA GTGTAGTTTTGGAAAAACTCTTAGCCTACCAATTCTTCTAAGTGTTTTAAAATGT GGGAGCCAGTACACATGAAGTTATAGAGTGTTTTAATGAGGCTTAAATATTTACC |

| Plasmid Element | Nucleotide Sequence 5' to 3' |
|---|---|
| | GTAACTATGAAATGCTACGCATATCATGCTGTTCAGGCTCCGTGGCCACGCAACT<br>C (SEQ ID NO: 47) |
| ISD | ggagt (SEQ ID NO: 12) |
| Z38/z42 forward fusion spacer | TACCTCCAACATCAAGGAAGATGGCAGTAACCACAGGTTGTGTCACCAGAGTAA<br>CA (SEQ ID NO: 150) |
| SMOPT | aATTTTTGGAGca (SEQ ID NO: 161) |
| mouse stem loop (eSL) with CCU tail (long extended loop) | ggttttctgacctccttcggtcggaaaacccct (SEQ ID NO: 147) |
| Mouse U1 terminator | GTTTACTTGGTTTTAAAAATAGCTTGCACTAGCGATACGGAATATGGTTATTAGG<br>TTTGTTAGGCATCATGTCGTGTCTTACTATAGAAAAATAACGTAGTGTTCATTTT<br>AGCCTGCCTGTATGTGTTAATTTGTCCTTATTGCGCATTGTTCTTGTTAAGTCTTC<br>TGTAAGGAGTTGCGGGTTTCAAACTGTCAGTCTGAGAGCA (SEQ ID NO: 57) |
| 3' ITR | aggaaccctagtgatggagttggccactccctctctgcgcgctcgctcgctcactgaggccgggcgaccaaaggtcgcccga<br>cgcccgggctttgcccgggggcctcagtgagcgagcgagcgcgcagctgcctgcagg (SEQ ID NO: 60) |

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a U1 promoter sequence, a CUG repeat targeting U7 esnRNA sequence, a U1 downstream terminator sequence, and a second ITR sequence. In some aspects, a nucleic acid sequence encoding AAV vector A04233 encoding CUG repeat targeting snRNA sequences comprises SEQ ID NO: 176.

A04233: scAAV-hU7-CUG×15-hU1-CUG×15 (3'mut ITR)

| Plasmid Element | Nucleotide Sequence 5' to 3' |
|---|---|
| 5' ITR | cctgcaggcagctgcgcgctcgctcgctcactgaggccgcccgggcgtcgggcgacctttggtcgccc<br>ggcctcagtgagcgagcgagcgcgcagagagggagtggccaactccatcactagggggttcct<br>(SEQ ID NO: 59) |
| human U7 promoter | TACTGCCGAATCCAGGTCTCCGGGCTTAACAACAACGAAGGGGCTGTGACTGGC<br>TGCTTTCTCAACCAATCAGCACCGAACTCATTTGCATGGGCTGAGAACAAATGTT<br>CGCGAACTCTAGAAATGAATGACTTAAGTAAGTTCCTTAGAATATTATTTTTCCT<br>ACTGAAAGTTACCACATGCGTCGTTGTTTATACAGTAATAGGAACAAGAAAAAA<br>GTCACCTAAGCTCACCCTCATCAATTGTGGAGTTCCTTTATATCCCATCTTCTCTC<br>CAAACACATACGCA (SEQ ID NO: 39) |
| ISD | ggagt (SEQ ID NO: 12) |
| CUG repeat targeting sequence | CAGCAGCAGCAGCAGCAGCAGCAGCAGCAGCAGCAGCAGCAGCAG (SEQ ID NO: 165) |
| SMOPT | AATTTTTGGAGTA (SEQ ID NO: 164) |
| Human stem loop (eSL) | ggctttctggctccttaccggaaagcc (SEQ ID NO: 1) |
| Human U7 terminator | CCTCTTATGATGTTTGTTGCCAATGATAGATTGTTTTCACTGTGCAAAAATTATGG<br>GTAGTTTTGGTGGTCTTGATGCAGTTGTAAGCTTGGAG (SEQ ID NO: 49) |
| Human U1 promoter | TAAGGACCAGCTTCTTTGGGAGAGAACAGACGCAGGGGCGGGAGGGAAAAAGG<br>GAGAGGCAGACGTCACTTCCCCTTGGCGGCTCTGGCAGCAGATTGGTCGGTTGA<br>GTGGCAGAAAGGCAGACGGGGACTGGGCAAGGCACTGTCGGTGACATCACGGA<br>CAGGGCGACTTCTATGTAGATGAGGCAGCGCAGAGGCTGACGTCTTCGCCACTT<br>GCTGCTTCACCACGAAGGAGTTCCCGTGCCCTGGGAGCGGGTTCAGGACCGCTG<br>ATCGGAAGTGAGAATCCCAGCTGTGTGTCAGGGCTGGAAAGGGCTCGGGAGTGC<br>GCGGGGCAAGTGACCGTGTGTGTAAAGAGTGAGGCGTATGAGGCTGTGTCGGGG<br>CAGAGGCacaacgtttc (SEQ ID NO: 40) |
| ISD | ggagt (SEQ ID NO: 12) |
| spacer | CAGCAGCAGCAGCAGCAGCAGCAGCAGCAGCAGCAGCAGCAGCAG (SEQ ID NO: 165) |
| SMOPT | AATTTTTGGAGTA (SEQ ID NO: 164) |

| Plasmid Element | Nucleotide Sequence 5' to 3' |
| --- | --- |
| Human stem loop (eSL) | ggctttctggctccttaccggaaagcc (SEQ ID NO: 1) |
| human U1 terminator | ACTTTCTGGAGTTTCAAAAACAGACTGTACGCCAAGGGTCATATCTTTTT (SEQ ID NO: 50) |
| 3'mut ITR | CCACTCCCTCTCTGCGCGCTCGCTCGCTCACTGAGGCCGGGCGACCAAAGGTCGCCCGACGCCCGGGCTTTGCCCGGGCGGCCTCAGTGAGCGAGCGAGCGCGCAGAGAGGGA (SEQ ID NO: 61) |

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a U1 promoter sequence, a CUG repeat targeting U7 esnRNA sequence, a U1 downstream terminator sequence, and a second ITR sequence. In some aspects, a nucleic acid sequence encoding AAV vector A04234 encoding CUG repeat targeting snRNA sequences comprises SEQ ID NO: 177.

A04234: scAAV-hU7-CUG×15-hU1-CUG×15 (5' mut ITR)

| Plasmid Element | Nucleotide Sequence 5' to 3' |
| --- | --- |
| 5' mut ITR | ctgcgcgctcgctcgctcactgaggccgcccgggcaaagcccgggcgtcgggcgaccttt ggtcgcccggcctcagtgagcgagcgagcgcgcagagagggagtgggtt (SEQ ID NO: 162) |
| human U7 promoter | TACTGCCGAATCCAGGTCTCCGGGCTTAACAACAACGAAGGGGCTGTGACTGGCTGCTTTCTCAACCAATCAGCACCGAACTCATTTGCATGGGCTGAGAACAAATGTTCGCGAACTCTAGAAATGAATGACTTAAGTAAGTTCCTTAGAATATTATTTTTCCTACTGAAAGTTACCACATGCGTCGTTGTTTATACAGTAATAGGAACAAGAAAAAAGTCACCTAAGCTCACCCTCATCAATTGTGGAGTTCCTTTATATCCCATCTTCTCTCCAAACACATACGCA (SEQ ID NO: 39) |
| ISD | ggagt (SEQ ID NO: 12) |
| spacer | CAGCAGCAGCAGCAGCAGCAGCAGCAGCAGCAGCAGCAGCAG (SEQ ID NO: 165) |
| SMOPT | AATTTTTGGAGTA (SEQ ID NO: 164) |
| Human stem loop (eSL) | ggctttctggctccttaccggaaagcc (SEQ ID NO: 1) |
| Human U7 terminator | CCTCTTATGATGTTTGTTGCCAATGATAGATTGTTTTCACTGTGCAAAAATTATGGGTAGTTTTGGTGGTCTTGATGCAGTTGTAAGCTTGGAG (SEQ ID NO: 49) |
| Human U1 promoter | TAAGGACCAGCTTCTTTGGGAGAGAACAGACGCAGGGGCGGGAGGGAAAAAGGGAGAGGCAGACGTCACTTCCCCTTGGCGGCTCTGGCAGCAGATTGGTCGGTTGAGTGGCAGAAAGGCAGACGGGGACTGGGCAAGGCACTGTCGGTGACATCACGGACAGGGCGACTTCTATGTAGATGAGGCAGCGCAGAGGCTGACGTCTTCGCCACTTGCTGCTTCACCACGAAGGAGTTCCCGTGCCCTGGGAGCGGGTTCAGGACCGCTGATCGGAAGTGAGAATCCCAGCTGTGTGTCAGGGCTGGAAAGGGCTCGGGAGTGCGCGGGGCAAGTGACCGTGTGTGTAAAGAGTGAGGCGTATGAGGCTGTGTCGGGGCAGAGGCacaacgtttc (SEQ ID NO: 40) |
| ISD | ggagt (SEQ ID NO: 12) |
| spacer | CAGCAGCAGCAGCAGCAGCAGCAGCAGCAGCAGCAGCAGCAG (SEQ ID NO: 165) |
| SMOPT | AATTTTTGGAGTA (SEQ ID NO: 164) |
| Human stem loop (eSL) | ggctttctggctccttaccggaaagcc (SEQ ID NO: 1) |
| human U1 terminator | ACTTTCTGGAGTTTCAAAAACAGACTGTACGCCAAGGGTCATATCTTTTT (SEQ ID NO: 50) |
| 3'ITR | aaggaaccctagtgatggagttggccactccctctctgcgcgctcgctcgctcactgaggccgggcgaccaaaggtcgcccgacgcccgggctttgcccgggggcctcagtgagcgagcgagcgcgccagc (SEQ ID NO: 166) |

An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a U1 promoter sequence, a CAG repeat targeting U7 esnRNA sequence, a U1 downstream terminator sequence, and a second ITR sequence. In some aspects, a nucleic acid sequence encoding AAV vector A04390 encoding CAG repeat targeting snRNA sequences comprises SEQ ID NO: 178.

A04390: scAA 5'mITR hU7-CAG15x-hU1-CAG×15

| Plasmid Element | Nucleotide Sequence 5' to 3' |
| --- | --- |
| 5' mut ITR | ctgcgcgctcgctcgctcactgaggccgcccgggcaaagcccgggcgtcgggcgacctttggtcgcccggcctcag tgagcgagcgagcgcgcagagagggagtggggtt (SEQ ID NO: 162) |
| human U7 promoter | TACTGCCGAATCCAGGTCTCCGGGCTTAACAACAACGAAGGGGCTGTGACTGGC TGCTTTCTCAACCAATCAGCACCGAACTCATTTGCATGGGCTGAGAACAAATGTT CGCGAACTCTAGAAATGAATGACTTAAGTAAGTTCCTTAGAATATTATTTTTCCT ACTGAAAGTTACCACATGCGTCGTTGTTTATACAGTAATAGGAACAAGAAAAAA GTCACCTAAGCTCACCCTCATCAATTGTGGAGTTCCTTTATATCCCATCTTCTCTC CAAACACATACGCA (SEQ ID NO: 39) |
| ISD | ggagt (SEQ ID NO: 12) |
| CAG targeting sequence | CTGCTGCTGCTGCTGCTGCTGCTGCTGCTGCTGCTGCTGCTGCTG (SEQ ID NO: 167) |
| SMOPT | AATTTTTGGAGTA (SEQ ID NO: 164) |
| Human stem loop (eSL) | ggctttctggctccttaccggaaagcc (SEQ ID NO: 1) |
| Human U7 terminator | CCTCTTATGATGTTTGTTGCCAATGATAGATTGTTTTCACTGTGCAAAAATTATGG GTAGTTTTGGTGGTCTTGATGCAGTTGTAAGCTTGGAG (SEQ ID NO: 49) |
| Human U1 promoter | TAAGGACCAGCTTCTTTGGGAGAGAACAGACGCAGGGGCGGGAGGGAAAAAGG GAGAGGCAGACGTCACTTCCCCTTGGCGGCTCTGGCAGCAGATTGGTCGGTTGA GTGGCAGAAAGGCAGACGGGGACTGGGCAAGGCACTGTCGGTGACATCACGGA CAGGGCGACTTCTATGTAGATGAGGCAGCGCAGAGGCTGACGTCTTCGCCACTT GCTGCTTCACCACGAAGGAGTTCCCGTGCCCTGGGAGCGGGTTCAGGACCGCTG ATCGGAAGTGAGAATCCCAGCTGTGTGTCAGGGCTGGAAAGGGCTCGGGAGTGC GCGGGGCAAGTGACCGTGTGTGTAAAGAGTGAGGCGTATGAGGCTGTGTCGGGG CAGAGGCacaacgtttc (SEQ ID NO: 40) |
| ISD | ggagt (SEQ ID NO: 12) |
| CAG targeting sequence | CTGCTGCTGCTGCTGCTGCTGCTGCTGCTGCTGCTGCTGCTGCTG (SEQ ID NO: 167) |
| SMOPT | AATTTTTGGAGTA (SEQ ID NO: 164) |
| Human stem loop (eSL) | ggctttctggctccttaccggaaagcc (SEQ ID NO: 1) |
| human U1 terminator | ACTTTCTGGAGTTTCAAAAACAGACTGTACGCCAAGGGTCATATCTTTTT (SEQ ID NO: 50) |
| 3'ITR | aaggaaccctagtgatggagttggccactccctctctgcgcgctcgctcgctcactgaggccgggcgaccaaa ggtcgcccgacgcccgggctttgcccgggcggcctcagtgagcgagcgagcgcgccagc (SEQ ID NO: 166) |

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a U1 promoter sequence, a CUG repeat targeting U7 esnRNA sequence, a U1 downstream terminator sequence, and a second ITR sequence. In some aspects, a nucleic acid sequence encoding AAV vector A04530 encoding CUG repeat targeting snRNA sequences comprises SEQ ID NO: 231.

A04530: scAAV-mU7p-CUGx15-mU1p-CUGx15; Mouse Loop with ISD and eSL

| Plasmid Element | Nucleotide Sequence 5' to 3' |
|---|---|
| 5' mut ITR | ctgcgcgctcgctcgctcactgaggccgcccgggcaaagcccgggcgtcgggcgacctttggtc gcccggcctcagtgagcgagcgagcgcgcagagagggagtggggtt (SEQ ID NO: 162) |
| mouse U7 promoter | taacaacataggagctgtgattggctgttttcagccaatcagcactgActcatttgcatagcctttac aagcggtcacaaactcaagaaacgagcggttttaatagtcttttagaatattgtttatcgaaccgaata aggaactgtgctttgtgattcacatatcagtggaggggtgtggaaatggcaccttgatctcaccctc atcgaaagtggagttgatgtcctTccctggctcgctacagacgcacttccgcaa (SEQ ID NO: 48) |
| ISD | ggagt (SEQ ID NO: 12) |
| spacer | CAGCAGCAGCAGCAGCAGCAGCAGCAGCAGCAGCAG CAGCAG (SEQ ID NO: 165) |
| SMOPT | aATTTTTGGAGca (SEQ ID NO: 161) |
| Mouse stem loop (eSL) | ggttttctgacctccgtcggaaaacccct (SEQ ID NO: 12) |
| Mouse U7 terminator | cccaatttcactggtctacaatgaaagcaaaacagttctcttcccgctcccggtgtgtgagaggg gctttgatccttctctggtttcctaggaaacgcgtatgtg (SEQ ID NO: 156) |
| Mouse U1 promoter | TTGTTCCTCTTAGTGTTAATTCACACTAAAGACTGTGCATCC GACTCCTACATTTATGAAAGTAAATGCCTGTTGTTAGAACA AAAAAGGCTACAGAACAAAAAACAAAGCGAAATACCATCT GCTTTAGGTTCAGTGTGGTATTTTCCCGCTGACAGGGAGGC GGGTTTTTGGGTACAGGAAACGAGTCACTATGGAGGCGGT ACTATGTAGATGAGAATTCAGGTGCAAACTGGGAAAAGCA ACTGCTTCCAAATATTTGTGATTTTTACAGTGTAGTTTTGGA AAAACTCTTAGCCTACCAATTCTTCTAAGTGTTTTAAAATG TGGGAGCCAGTACACATGAAGTTATAGAGTGTTTTAATGAG GCTTAAATATTTACCGTAACTATGAAATGCTACGCATATCA TGCTGTTCAGGCTCCGTGGCCACGCAACTC (SEQ ID NO: 47) |
| ISD | ggagt (SEQ ID NO: 12) |
| spacer | CAGCAGCAGCAGCAGCAGCAGCAGCAGCAGCAGCAG CAGCAG (SEQ ID NO: 165) |
| SMOPT | aATTTTTGGAGca (SEQ ID NO: 161) |
| Mouse stem loop (eSL) | ggttttctgacctccgtcggaaaacccct (SEQ ID NO: 12) |
| Mouse U1 terminator | GTTTACTTGGTTTTAAAAATAGCTTGCACTAGCGATACGGA ATATGGTTATTAGGTTTGTTAGGCATCATGTCGTGTCTTACT ATAGAAAAATAACGTAGTGTTCATTTTAGCCTGCCTGTATG TGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3'ITR | aggaaccctagtgatggagttggccactccctctctgcgcgctcgctcgctcactgaggccggg cgaccaaaggtcgcccgacgcccgggctttgcccgggcggcctcagtgagcgagcgagcgcg cagctgcctgcagg (SEQ ID NO: 60) |

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a U1 promoter sequence, a CUG repeat targeting U7 esnRNA sequence, a U1 downstream terminator sequence, and a second ITR sequence. In some aspects, a nucleic acid sequence encoding AAV vector A04940 encoding CUG repeat targeting snRNA sequences comprises SEQ ID NO: 232.

A04940: scAAV-mU7D-CUGx10-mU1p-CUGx10: Mouse Loop with ISD and eSL No CCU

| Plasmid Element | Nucleotide Sequence 5' to 3' |
|---|---|
| 5' mut ITR | ctgcgcgctcgctcgctcactgaggccgcccgggcaaagcccgggcgtcgggcgacctttggtc gcccggcctcagtgagcgagcgagcgcgcagagagggagtggggtt (SEQ ID NO: 162) |
| mouse U7 promoter | taacaacataggagctgtgattggctgttttcagccaatcagcactgActcatttgcatagcctttac aagcggtcacaaactcaagaaacgagcggttttaatagtcttttagaatattgtttatcgaaccgaata |

| Plasmid Element | Nucleotide Sequence 5' to 3' |
|---|---|
| | aggaactgtgctttgtgattcacatatcagtggaggggtgtggaaatggcaccttgatctcaccctc atcgaaagtggagttgatgtcctTccctggctcgctacagacgcacttccgcaa (SEQ ID NO: 48) |
| ISD | ggagt (SEQ ID NO: 12) |
| spacer | CAGCAGCAGCAGCAGCAGCAGCAGCAGCAG (SEQ ID NO: 165) |
| SMOPT | aATTTTTGGAGca (SEQ ID NO: 161) |
| Mouse stem loop (eSL) | ggttttctgacctccgtcggaaaacc (SEQ ID NO: 148) |
| Mouse U7 terminator | cccaatttcactggtctacaatgaaagcaaaacagttctcttcccgctccccggtgtgtgagaggg gctttgatccttctctggtttcctaggaaacgcgtatgtg (SEQ ID NO: 156) |
| Mouse U1 promoter | TTGTTCCTCTTAGTGTTAATTCACACTAAAGACTGTGCATCC GACTCCTACATTTATGAAAGTAAATGCCTGTTGTTAGAACA AAAAAGGCTACAGAACAAAAAACAAAGCGAAATACCATCT GCTTTAGGTTCAGTGTGGTATTTTCCCGCTGACAGGGAGGC GGGTTTTTGGGTACAGGAAACGAGTCACTATGGAGGCGGT ACTATGTAGATGAGAATTCAGGTGCAAACTGGGAAAAGCA ACTGCTTCCAAATATTTGTGATTTTTACAGTGTAGTTTTGGA AAAACTCTTAGCCTACCAATTCTTCTAAGTGTTTTAAAATG TGGGAGCCAGTACACATGAAGTTATAGAGTGTTTTAATGAG GCTTAAATATTTACCGTAACTATGAAATGCTACGCATATCA TGCTGTTCAGGCTCCGTGGCCACGCAACTC (SEQ ID NO: 47) |
| ISD | ggagt (SEQ ID NO: 12) |
| spacer | CAGCAGCAGCAGCAGCAGCAGCAGCAGCAG (SEQ ID NO: 165) |
| SMOPT | aATTTTTGGAGca (SEQ ID NO: 161) |
| Mouse stem loop (eSL) | ggttttctgacctccgtcggaaaaccct (SEQ ID NO: 12) |
| Mouse U1 terminator | GTTTACTTGGTTTTAAAAATAGCTTGCACTAGCGATACGGA ATATGGTTATTAGGTTTGTTAGGCATCATGTCGTGTCTTACT ATAGAAAAATAACGTAGTGTTCATTTTAGCCTGCCTGTATG TGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3'ITR | aggaaccccctagtgatggagttggccactccctctctgcgcgctcgctcgctcactgaggccggg cgaccaaaggtcgcccgacgcccgggctttgcccgggcggcctcagtgagcgagcgagcgcg cagctgcctgcagg (SEQ ID NO: 60) |

An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a U1 promoter sequence, a CAG repeat targeting U7 esnRNA sequence, a U1 downstream terminator sequence, and a second ITR sequence. In some aspects, a nucleic acid sequence encoding AAV vector A04533 encoding CAG repeat targeting snRNA sequences comprises SEQ ID NO: 233.

A04533: scAAV-mU7p-CAGx15-mU1p-CAGx15; Mouse Loop with ISD and eSL

| Plasmid Element | Nucleotide Sequence 5' to 3' |
|---|---|
| 5' mut ITR | ctgcgcgctcgctcgctcactgaggccgcccgggcaaagcccggcgtcgggcgacctttggtc gcccggcctcagtgagcgagcgagcgcgcagagagggagtggggtt (SEQ ID NO: 162) |
| mouse U7 promoter | taacaacataggagctgtgattggctgttttcagccaatcagcactgActcatttgcatagcctttac aagcggtcacaaactcaagaaacgagcggttttaatagtcttttagaatattgtttatcgaaccgaata aggaactgtgctttgtgattcacatatcagtggaggggtgtggaaatggcaccttgatctcaccctc atcgaaagtggagttgatgtcctTccctggctcgctacagacgcacttccgcaa (SEQ ID NO: 48) |
| ISD | ggagt (SEQ ID NO: 12) |
| spacer | CTGCTGCTGCTGCTGCTGCTGCTGCTGCTGCTGCTGCTG CTG (SEQ ID NO: 167) |

| Plasmid Element | Nucleotide Sequence 5' to 3' |
|---|---|
| SMOPT | aATTTTTGGAGca (SEQ ID NO: 161) |
| Mouse stem loop (eSL) | ggttttctgacctccgtcggaaaacccct (SEQ ID NO: 12) |
| Mouse U7 terminator | cccaatttcactggtctacaatgaaagcaaaacagttctcttccccgctccccggtgtgtgagaggg gctttgatccttctctggtttcctaggaaacgcgtatgtg (SEQ ID NO: 156) |
| Mouse U1 promoter | TTGTTCCTCTTAGTGTTAATTCACACTAAAGACTGTGCATCC GACTCCTACATTTATGAAAGTAAATGCCTGTTGTTAGAACA AAAAAGGCTACAGAACAAAAAACAAAGCGAAATACCATCT GCTTTAGGTTCAGTGTGGTATTTTCCCGCTGACAGGGAGGC GGGTTTTTGGGTACAGGAAACGAGTCACTATGGAGGCGGT ACTATGTAGATGAGAATTCAGGTGCAAACTGGGAAAAGCA ACTGCTTCCAAATATTTGTGATTTTTACAGTGTAGTTTTGGA AAAACTCTTAGCCTACCAATTCTTCTAAGTGTTTTAAAATG TGGGAGCCAGTACACATGAAGTTATAGAGTGTTTTAATGAG GCTTAAATATTTACCGTAACTATGAAATGCTACGCATATCA TGCTGTTCAGGCTCCGTGGCCACGCAACTC (SEQ ID NO: 47) |
| ISD | ggagt (SEQ ID NO: 12) |
| spacer | CTGCTGCTGCTGCTGCTGCTGCTGCTGCTGCTGCTGCTG CTG (SEQ ID NO: 167) |
| SMOPT | aATTTTTGGAGca (SEQ ID NO: 161) |
| Mouse stem loop (eSL) | ggttttctgacctccgtcggaaaacccct (SEQ ID NO: 12) |
| Mouse U1 terminator | GTTTACTTGGTTTTAAAAATAGCTTGCACTAGCGATACGGA ATATGGTTATTAGGTTTGTTAGGCATCATGTCGTGTCTTACT ATAGAAAAATAACGTAGTGTTCATTTTAGCCTGCCTGTATG TGTTAATTTGTCCTTATTGCGCATTGTTCTTGTTAAGTCTTC TGTAAGGAGTTGCGGGTTTCAAACTGTCAGTCTGAGAGCA (SEQ ID NO: 57) |
| 3' ITR | Aggaacccctagtgatggagttggccactccctctctgcgcgctcgctcgctcactgaggccgg gcgaccaaaggtcgcccgacgcccgggctttgcccggcggcctcagtgagcgagcgagcgc gcagctgcctgcagg (SEQ ID NO: 60) |

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, and a second ITR sequence. In some aspects, a nucleic acid sequence encoding AAV vector A02962 encoding CUG repeat targeting snRNA sequences comprises SEQ ID NO: 120. A02962 ss pAAV-4×U7(15×CUG) (derivative of P00369) targeting CUG repeats

```
ITR
                                                      (SEQ ID NO: 59)
Cctgcaggcagctgcgcgctcgctcgctcactgaggccgcccgggcgtcgggcgacctttggtcgc ccggcctcagtgagcgagcgagcgcgcagagagggagtggccaactccatcactaggggttcct U7 promoter
                                                      (SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAA

AGTTACCACATGCGTCGTTGTTTATACAGTAATAGGAACAAG

AAAAAAGTCACCTAAGCTCACCCTCATCAATTGTGGAGTTCC

TTTATATCCCATCTTCTCTCCAAACACATACGCA
```

U7 snRNA
(SEQ ID NO: 65)
ggagtCAGCAGCAGCAGCAGCAGCAGCAGCAGCAGCAGCA

GCAGCAGAATTTTTGGAGTAggctttctggctcccttaccggaaagcc

U7 Downstream (terminator)
(SEQ ID NO: 49)
CCTCTTATGATGTTTGTTGCCAATGATAGATTGTTTTCACTGT

GCAAAAATTATGGGTAGTTTTGGTGGTCTTGATGCAGTTGTA

AGCTTGGAG 30 bp buffer 1
(SEQ ID NO: 24)
CAAACTACAGAGCCAAGTGCTATCCACAGA

U7 promoter
(SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAA

AGTTACCACATGCGTCGTTGTTTATACAGTAATAGGAACAAG

AAAAAAGTCACCTAAGCTCACCCTCATCAATTGTGGAGTTCC

TTTATATCCCATCTTCTCTCCAAACACATACGCA

U7 snRNA
(SEQ ID NO: 65)
ggagtCAGCAGCAGCAGCAGCAGCAGCAGCAGCAGCAGCA

GCAGCAGAATTTTTGGAGTAggctttctggctcccttaccggaaagcc

U7 Downstream (terminator)
(SEQ ID NO: 49)
CCTCTTATGATGTTTGTTGCCAATGATAGATTGTTTTCACTGT

GCAAAAATTATGGGTAGTTTTGGTGGTCTTGATGCAGTTGTA

AGCTTGGAG 30 bp buffer 2
(SEQ ID NO: 25)
GAGCTTTCTGGGTTGCCATCTCAAGCAGAC

U7 promoter
(SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAA

AGTTACCACATGCGTCGTTGTTTATACAGTAATAGGAACAAG

AAAAAAGTCACCTAAGCTCACCCTCATCAATTGTGGAGTTCC

TTTATATCCCATCTTCTCTCCAAACACATACGCA

U7 snRNA
(SEQ ID NO: 65)
ggagtCAGCAGCAGCAGCAGCAGCAGCAGCAGCAGCAGCA

GCAGCAGAATTTTTGGAGTAggctttctggctcccttaccggaaagcc

U7 Downstream (terminator)
(SEQ ID NO: 49)
CCTCTTATGATGTTTGTTGCCAATGATAGATTGTTTTCACTGT

GCAAAAATTATGGGTAGTTTTGGTGGTCTTGATGCAGTTGTA

AGCTTGGAG

```
30 bp buffer 3
                                                            (SEQ ID NO: 26)
TACAAGGCCATCAGCTCATACTCACAATTG U7 promoter
                                                            (SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAA

AGTTACCACATGCGTCGTTGTTTATACAGTAATAGGAACAAG

AAAAAAGTCACCTAAGCTCACCCTCATCAATTGTGGAGTTCC

TTTATATCCCATCTTCTCTCCAAACACATACGCA

U7 snRNA
                                                            (SEQ ID NO: 65)
ggagtCAGCAGCAGCAGCAGCAGCAGCAGCAGCAGCAGCAGCA GCAGCAGAATTTTTGGAGTAggctttctggctccttaccggaaagcc U7 Downstream (terminator)
                                                            (SEQ ID NO: 49)
CCTCTTATGATGTTTGTTGCCAATGATAGATTGTTTTCACTGT

GCAAAAATTATGGGTAGTTTTGGTGGTCTTGATGCAGTTGTA

AGCTTGGAG

ITR
                                                            (SEQ ID NO: 60)
Aggaacccctagtgatggagttggccactccctctctgcgcgctcgctcgctcactgaggccgggcg accaaaggtcgcccgacgcccgggctttgcccgggcggcctcagtgagcgagcgagcgcgcagct gcctgcagg
```

An exemplary AAV vector of the disclosure comprises from 5' to 3': a first inverted terminal repeat (ITR) sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, and a second ITR sequence. In some aspects, a nucleic acid sequence encoding AAV vector A02963 encoding a non-targeting snRNA sequences comprises SEQ ID NO: 121.

A02963 ss pAAV-4×U7(NT1) (Derivative of P00369)

```
ITR
                                                            (SEQ ID NO: 59)
Cctgcaggcagctgcgcgctcgctcgctcactgaggccgcccgggcgtcgggcgacctttggtcgcc cggcctcagtgagcgagcgagcgcgcagagagggagtggccaactccatcactaggggttcct U7 promoter
                                                            (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAA

AGTCACCTAAGCTCACCCTCATCAATTGTGGAGTTCCTTTATAT

CCCATCTTCTCTCCAAACACATACGCA

U7 snRNA
                                                            (SEQ ID NO: 66)
ggagtTCACCAGAAGCGTACCATACTCACGAAATTTTTGGAGTAgg
```

```
ctttctggctccttaccggaaagcc
```

U7 Downstream (terminator)                                        (SEQ ID NO: 49)
```
CCTCTTATGATGTTTGTTGCCAATGATAGATTGTTTTCACTGTG
CAAAAATTATGGGTAGTTTTGGTGGTCTTGATGCAGTTGTAAGC
TTGGAG
```

30 bp buffer 1                                                    (SEQ ID NO: 24)
```
CAAACTACAGAGCCAAGTGCTATCCACAGA
```

U7 promoter                                                       (SEQ ID NO: 39)
```
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTT
ACCACATGCGTCGTTGTTTATACAGTAATAGGAACAAGAAAAA
AGTCACCTAAGCTCACCCTCATCAATTGTGGAGTTCCTTTATAT
CCCATCTTCTCTCCAAACACATACGCA
```

U7 snRNA                                                          (SEQ ID NO: 66)
```
ggagtTCACCAGAAGCGTACCATACTCACGAAATTTTTGGAGTAgg
ctttctggctccttaccggaaagcc
```

U7 Downstream (terminator)                                        (SEQ ID NO: 49)
```
CCTCTTATGATGITTGTTGCCAATGATAGATTGTTTTCACTGTG
CAAAAATTATGGGTAGTTTTGGTGGTCTTGATGCAGTTGTAAGC
TTGGAG
```

30 bp buffer 2                                                    (SEQ ID NO: 25)
```
GAGCTTTCTGGGTTGCCATCTCAAGCAGAC
```

U7 promoter                                                       (SEQ ID NO: 39)
```
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTT
ACCACATGCGTCGTTGTTTATACAGTAATAGGAACAAGAAAAA
AGTCACCTAAGCTCACCCTCATCAATTGTGGAGTTCCTTTATAT
CCCATCTTCTCTCCAAACACATACGCA
```

U7 snRNA                                                          (SEQ ID NO: 66)
```
ggagtTCACCAGAAGCGTACCATACTCACGAAATTTTTGGAGTAgg
ctttctggctccttaccggaaagcc
```

U7 Downstream (terminator)                                        (SEQ ID NO: 49)
```
CCTCTTATGATGTTTGTTGCCAATGATAGATTGTTTTCACTGTG
CAAAAATTATGGGTAGTTTTGGTGGTCTTGATGCAGTTGTAAGC
TTGGAG
```

-continued

```
30 bp buffer 3
                                                        (SEQ ID NO: 26)
TACAAGGCCATCAGCTCATACTCACAATTG U7 promoter
                                                        (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA

U7 snRNA
                                                        (SEQ ID NO: 66)
ggagtTCACCAGAAGCGTACCATACTCACGAAATTTTTGGAGTAgg ctttctggctccttaccggaaagcc U7 Downstream (terminator)
                                                        (SEQ ID NO: 49)
CCTCTTATGATGTTTGTTGCCAATGATAGATTGTTTTCACTGTG

CAAAAATTATGGGTAGTTTTGGTGGTCTTGATGCAGTTGTAAGC

TTGGAG

ITR
                                                        (SEQ ID NO: 60)
Aggaaccccta gtgatggagttggccactccctctctgcgcgctcgctcgctcactgaggccgggcga ccaaaggtcgcccgacgcccgggctttgcccgggggcctcagtgagcgagcgagcgcgcagctgc ctgcagg
```

An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, and a second ITR sequence. In some aspects, a nucleic acid sequence encoding AAV vector A02967 encoding a CAG repeat targeting snRNA sequences comprises SEQ ID NO: 122.

A02967 ss pAAV-4XU7(15XCAG) Targeting CAG Repeats

```
ITR
                                                        (SEQ ID NO: 59)
Cctgcaggcagctgcgcgctcgctcgctcactgaggccgcccgggcgtcgggcgacctttggtcgc ccggcctcagtgagcgagcgagcgcgcagagagggagtggccaactccatcactagggggttcct U7 promoter
                                                        (SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAAA

GTTACCACATGCGTCGTTGTTTATACAGTAATAGGAACAAGAA

AAAGTCACCTAAGCTCACCCTCATCAATTGTGGAGTTCCTTT

ATATCCCATCTTCTCTCCAAACACATACGCA

U7 snRNA
                                                        (SEQ ID NO: 67)
ggagtCTGCTGCTGCTGCTGCTGCTGCTGCTGCTGCTGCTGCTGC
```

-continued

TGCTGAATTTTTGGAGTAggctttctggctccttaccggaaagcc

U7 Downstream (terminator) (SEQ ID NO: 49)
CCTCTTATGATGTTTGTTGCCAATGATAGATTGTTTTCACTGTG

CAAAAATTATGGGTAGTTTTGGTGGTCTTGATGCAGTTGTAAG

CTTGGAG 30 bp buffer 1 (SEQ ID NO: 24)
CAAACTACAGAGCCAAGTGCTATCCACAGA

U7 promoter (SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAAA

GTTACCACATGCGTCGTTGTTTATACAGTAATAGGAACAAGAA

AAAAGTCACCTAAGCTCACCCTCATCAATTGTGGAGTTCCTTT

ATATCCCATCTTCTCTCCAAACACATACGCA

U7 snRNA (SEQ ID NO: 67)
ggagtCTGCTGCTGCTGCTGCTGCTGCTGCTGCTGCTGCTGC

TGCTGAATTTTTGGAGTAggctttctggctccttaccggaaagcc

U7 Downstream (terminator) (SEQ ID NO: 49)
CCTCTTATGATGTTTGTTGCCAATGATAGATTGTTTTCACTGTG

CAAAAATTATGGGTAGTTTTGGTGGTCTTGATGCAGTTGTAAG

CTTGGAG 30 bp buffer 2 (SEQ ID NO: 25)
GAGCTTTCTGGGTTGCCATCTCAAGCAGAC

U7 promoter (SEQ ID NO: 39)
TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAAA

GTTACCACATGCGTCGTTGTTTATACAGTAATAGGAACAAGAA

AAAAGTCACCTAAGCTCACCCTCATCAATTGTGGAGTTCCTTT

ATATCCCATCTTCTCTCCAAACACATACGCA

U7 snRNA (SEQ ID NO: 67)
ggagtCTGCTGCTGCTGCTGCTGCTGCTGCTGCTGCTGCTGC

TGCTGAATTTTTGGAGTAggctttctggctccttaccggaaagcc

U7 Downstream (terminator) (SEQ ID NO: 49)
CCTCTTATGATGTTTGTTGCCAATGATAGATTGTTTTCACTGTG

CAAAAATTATGGGTAGTTTTGGTGGTCTTGATGCAGTTGTAAG
CTTGGAG

30bp buffer 3 (SEQ ID NO: 26)
TACAAGGCCATCAGCTCATACTCACAATTG

-continued

U7 promoter (SEQ ID NO: 39)

TACTGCCGAATCCAGGTCTCCGGGCTTAACAACAACGAAGGG

GCTGTGACTGGCTGCTTTCTCAACCAATCAGCACCGAACTCAT

TTGCATGGGCTGAGAACAAATGTTCGCGAACTCTAGAAATGA

ATGACTTAAGTAAGTTCCTTAGAATATTATTTTTCCTACTGAAA

GTTACCACATGCGTCGTTGTTTATACAGTAATAGGAACAAGAA

AAAAGTCACCTAAGCTCACCCTCATCAATTGTGGAGTTCCTTT

ATATCCCATCTTCTCTCCAAACACATACGCA

U7 snRNA (SEQ ID NO: 67)

ggagtCTGCTGCTGCTGCTGCTGCTGCTGCTGCTGCTGCTGCTGC

TGCTGAATTTTTGGAGTAggctttctggctccttaccggaaagcc

U7 Downstream (terminator) (SEQ ID NO: 49)

CCTCTTATGATGTTTGTTGCCAATGATAGATTGTTTTCACTGTG

CAAAAATTATGGGTAGTTTTGGTGGTCTTGATGCAGTTGTAAG

CTTGGAG

ITR (SEQ ID NO: 60)

Aggaacccctagtgatggagttggccactccctctctgcgcgctcgctcgctcactgaggccgggcg accaaaggtcgcccgacgcccgggctttgcccgggcggcctcagtgagcgagcgagcgcgcagct gcctgcagg An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, and a second ITR sequence. In some aspects, a nucleic acid sequence encoding AAV vector A03079 encoding a CUG repeat targeting snRNA sequences comprises SEQ ID NO: 123.

A03079 sc pAAV-4XU7(15XCUG) (Derivative of P00369) Targeting CUG Repeats

ITR (SEQ ID NO: 59)

Cctgcaggcagctgcgcgctcgctcgctcactgaggccgcccgggcgtcgggcgacctttggtcgcc cggcctcagtgagcgagcgagcgcgcagagagggagtggccaactccatcactaggggttcct U7 promoter (SEQ ID NO: 39)

TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA

U7 snRNA (SEQ ID NO: 65)

ggagtCAGCAGCAGCAGCAGCAGCAGCAGCAGCAGCAGCAGCAG

CAGCAGAATTTTTGGAGTAggctttctggctccttaccggaaagcc

-continued

U7 Downstream (terminator) (SEQ ID NO: 49)
CCTCTTATGATGTTTGTTGCCAATGATAGATTGTTTTCACTGTGC
AAAAATTATGGGTAGTTTTGGTGGTCTTGATGCAGTTGTAAGCT
TGGAG 30 bp buffer 1 (SEQ ID NO: 24)
CAAACTACAGAGCCAAGTGCTATCCACAGA U7 promoter (SEQ ID NO: 39)
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTT
ACCACATGCGTCGTTGTTTATACAGTAATAGGAACAAGAAAAA
AGTCACCTAAGCTCACCCTCATCAATTGTGGAGTTCCTTTATAT
CCCATCTTCTCTCCAAACACATACGCA U7 snRNA (SEQ ID NO: 65)
ggagtCAGCAGCAGCAGCAGCAGCAGCAGCAGCAGCAGCAGCAG
CAGCAGAATTTTTGGAGTAggctttctggctccttaccggaaagcc U7 Downstream (terminator) (SEQ ID NO: 49)
CCTCTTATGATGTTTGTTGCCAATGATAGATTGTTTTCACTGTGC
AAAAATTATGGGTAGTTTTGGTGGTCTTGATGCAGTTGTAAGCT
TGGAG 30 bp buffer 2 (SEQ ID NO: 25)
GAGCTTTCTGGGTTGCCATCTCAAGCAGAC U7 promoter (SEQ ID NO: 39)
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTT
ACCACATGCGTCGTTGTTTATACAGTAATAGGAACAAGAAAAA
AGTCACCTAAGCTCACCCTCATCAATTGTGGAGTTCCTTTATAT
CCCATCTTCTCTCCAAACACATACGCA U7 snRNA (SEQ ID NO: 65)
ggagtCAGCAGCAGCAGCAGCAGCAGCAGCAGCAGCAGCAGCAG
CAGCAGAATTTTTGGAGTAggctttctggctccttaccggaaagcc U7 Downstream (terminator) (SEQ ID NO: 49)
CCTCTTATGATGTTTGTTGCCAATGATAGATTGTTTTCACTGTGC
AAAAATTATGGGTAGTTTTGGTGGTCTTGATGCAGTTGTAAGCT
TGGAG 30 bp buffer 3 (SEQ ID NO: 26)
TACAAGGCCATCAGCTCATACTCACAATTG U7 promoter -continued

```
                                                          (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA

U7 snRNA
                                                          (SEQ ID NO: 65)
ggagtCAGCAGCAGCAGCAGCAGCAGCAGCAGCAGCAGCAGCAG CAGCAGAATTTTTGGAGTAggctttctggctccttaccggaaagcc U7 Downstream (terminator)
                                                          (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG

ITR
                                                          (SEQ ID NO: 61)
CCACTCCCTCTCTGCGCGCTCGCTCGCTCACTGAGGCCGGGCGA

CCAAAGGTCGCCCGACGCCCGGGCTTTGCCCGGGCGGCCTCAG

TGAGCGAGCGAGCGCGCAGAGAGGGA
```

An exemplary AAV vector of the disclosure comprises from 5' to 3': a first inverted terminal repeat (ITR) sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, and a second ITR sequence. In some aspects, a nucleic acid sequence encoding AAV vector A03080 encoding a non-repeat targeting snRNA sequences comprises SEQ ID NO: 124.

A03080 sc pAAV-4XU7(NT1) (Derivative of P00369)

```
ITR
                                                          (SEQ ID NO: 59)
Cctgcaggcagctgcgcgctcgctcgctcactgaggccgcccgggcgtcgggcgacctttggtcgccc ggcctcagtgagcgagcgagcgcgcagagagggagtggccaactccatcactaggggttcct U7 promoter
                                                          (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAA

GTCACCTAAGCTCACCCTCATCAATTGTGGAGTTCCTTTATATCC

CATCTTCTCTCCAAACACATACGCA

U7 snRNA
                                                          (SEQ ID NO: 66)
ggagtTCACCAGAAGCGTACCATACTCACGAAATTTTTGGAGTAggc tttctggctccttaccggaaagcc U7 Downstream (terminator)
                                                          (SEQ ID NO: 49)
CCTCTTATGATGTTTGTTGCCAATGATAGATTGTTTTCACTGTGC
```

-continued

```
AAAAATTATGGGTAGTTTTGGTGGTCTTGATGCAGTTGTAAGCT

TGGAG
```

30 bp buffer 1 (SEQ ID NO: 24)

```
CAAACTACAGAGCCAAGTGCTATCCACAGA
```

U7 promoter (SEQ ID NO: 39)

```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA
```

U7 snRNA (SEQ ID NO: 66)

```
ggagtTCACCAGAAGCGTACCATACTCACGAAATTTTTGGAGTAggc tttctggctccttaccggaaagcc
```

U7 Downstream (terminator) (SEQ ID NO: 49)

```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

30 bp buffer 2 (SEQ ID NO: 25)

```
GAGCTTTCTGGGTTGCCATCTCAAGCAGAC
```

U7 promoter (SEQ ID NO: 39)

```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA
```

U7 snRNA (SEQ ID NO: 66)

```
ggagtTCACCAGAAGCGTACCATACTCACGAAATTTTTGGAGTAggc tttctggctccttaccggaaagcc
```

U7 Downstream (terminator) (SEQ ID NO: 49)

```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

30 bp buffer 3 (SEQ ID NO: 26)

```
TACAAGGCCATCAGCTCATACTCACAATTG
```

U7 promoter (SEQ ID NO: 39)

```
TACTGCCGAATCCAGGTCTCCGGGCTTAACAACAACGAAGGGG
```

```
CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA                                          (SEQ ID NO: 66)

ggagtTCACCAGAAGCGTACCATACTCACGAAATTTTTGGAGTAggc tttctggctccttaccggaaagcc

U7 Downstream (terminator)                        (SEQ ID NO: 49)

CCTCTTATGATGTTTGTTGCCAATGATAGATTGTTTTCACTGTGC

AAAAATTATGGGTAGTTTTGGTGGTCTTGATGCAGTTGTAAGCT

TGGAG

ITR                                               (SEQ ID NO: 61)

CCACTCCCTCTCTGCGCGCTCGCTCGCTCACTGAGGCCGGGCGA

CCAAAGGTCGCCCGACGCCCGGGCTTTGCCCGGGCGGCCTCAGT

GAGCGAGCGAGCGCGCAGAGAGGGA
```

An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, and a second ITR sequence. In some aspects, a nucleic acid sequence encoding AAV vector A03081 encoding a CAG repeat targeting snRNA sequences comprises SEQ ID NO: 125.

A03081 sc pAAV-4XU7(15XCAG) Targeting CAG Repeats

```
ITR                                               (SEQ ID NO: 59)
Cctgcaggcagctgcgcgctcgctcgctcactgaggccgcccgggcgtcgggcgacctttggtcgccc ggcctcagtgagcgagcgagcgcgcagagagggagtggccaactccatcactaggggttcct U7 promoter                                       (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA                                          (SEQ ID NO: 67)
ggagtCTGCTGCTGCTGCTGCTGCTGCTGCTGCTGCTGCTGCTG CTGAATTTTTGGAGTAggctttctggctccttaccggaaagcc U7 Downstream (terminator)                        (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT
```

-continued

TGGAG 30 bp buffer 1 (SEQ ID NO: 24)
CAAACTACAGAGCCAAGTGCTATCCACAGA

U7 promoter (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA (SEQ ID NO: 67)
ggagtCTGCTGCTGCTGCTGCTGCTGCTGCTGCTGCTGCTGCTG

CTGAATTTTTGGAGTAggctttctggctccttaccggaaagcc

U7 Downstream (terminator) (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG 30 bp buffer 2 (SEQ ID NO: 25)
GAGCTTTCTGGGTTGCCATCTCAAGCAGAC

U7 promoter (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA (SEQ ID NO: 67)
ggagtCTGCTGCTGCTGCTGCTGCTGCTGCTGCTGCTGCTGCTG

CTGAATTTTTGGAGTAggctttctggctccttaccggaaagcc

U7 Downstream (terminator) (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG 30 bp buffer 3 (SEQ ID NO: 26)
TACAAGGCCATCAGCTCATACTCACAATTG

U7 promoter (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

```
ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
                                                            (SEQ ID NO: 67)
ggagtCTGCTGCTGCTGCTGCTGCTGCTGCTGCTGCTGCTGCTGCTG CTGAATTTTTGGAGTAggctttctggctccttaccggaaagcc U7 Downstream (terminator)
                                                            (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG

ITR
                                                            (SEQ ID NO: 61)
CCACTCCCTCTCTGCGCGCTCGCTCGCTCACTGAGGCCGGGCGA

CCAAAGGTCGCCCGACGCCCGGGCTTTGCCCGGGCGGCCTCAGT

GAGCGAGCGAGCGCGCAGAGAGGGA
```

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02888 encoding a CUG repeat targeting snRNA sequence comprises SEQ ID NO: 126.

A02888 pAAV_1×U7(15XCUG)_CMV_GFP (No Buffer) Targeting CUG Repeats

```
ITR
                                                            (SEQ ID NO: 59)
Cctgcaggcagctgcgcgctcgctcgctcactgaggccgcccgggcgtcgggcgacctttggtcgccc ggcctcagtgagcgagcgagcgcgcagagagggagtggccaactccatcactaggggttcct U7 promoter
                                                            (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
                                                            (SEQ ID NO: 65)
ggagtCAGCAGCAGCAGCAGCAGCAGCAGCAGCAGCAGCAGCAG CAGCAGAATTTTTGGAGTAggctttctggctccttaccggaaagcc U7 Downstream (terminator)
                                                            (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG

CMV promoter
                                                            (SEQ ID NO: 62)
Ccttacataacttacggtaaatggcccgcctggctgaccgcccaacgacccccgcccattgacgtcaata
```

-continued

```
atgacgtatgttcccatagtaacgccaatagggactttccattgacgtcaatgggtggagtatttacggtaaa ctgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccaccccattgacgtcaatgggagtttgttttggcaccaaaatcaacgggactttccaaaatg tcgtaacaactccgccccattgacgcaaatgggcggtaggcgtgtacggtgggaggtctatataagcaga gct
``` eGFP (SEQ ID NO: 63)

```
ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgcctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacaccctggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc cgccctgagcaaagaccccaacgagaagcgcgatcacatggtcctgctggagttcgtgaccgccgccg ggatcactctcggcatggacgagctgtacaagTAA
```

SV40 Poly A (SEQ ID NO: 64)

```
Aacttgtttattgcagcttataatggttacaaataaagcaatagcatcacaaatttcacaaataaagcattttttt cactgcattctagttgtggtttgtccaaactcatcaatgtatctta
```

ITR (SEQ ID NO: 60)

```
Aggaaccccctagtgatggagttggccactccctctctgcgcgctcgctcgctcactgaggccgggcgac caaaggtcgcccgacgcccgggctttgcccgggggcctcagtgagcgagcgagcgcgcagctgcct gcagg
```

An exemplary AAV vector of the disclosure comprises from 5' to 3': a first inverted terminal repeat (ITR) sequence, a U7 promoter sequence, a non-targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02889 encoding a non-targeting repeat targeting snRNA sequence comprises SEQ ID NO: 127.

A02889 pAAV_1×U7(NT1)_CMV_GFP (No Buffer)

ITR (SEQ ID NO: 59)

```
Cctgcaggcagctgcgcgctcgctcgctcactgaggccgcccgggcgtcgggcgacctttggtcgccc ggcctcagtgagcgagcgagcgcgcagagagggagtggccaactccatcactagggggttcct
```

U7 promoter (SEQ ID NO: 39)

```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC
```

CATCTTCTCTCCAAACACATACGCA

U7 snRNA (SEQ ID NO: 66)

ggagtTCACCAGAAGCGTACCATACTCACGAAATTTTTGGAGTAggc tttctggctccttaccggaaagcc

U7 Downstream (terminator)

(SEQ ID NO: 49)

CCTCTTATGATGTTTGTTGCCAATGATAGATTGTTTTCACTGTGC

AAAAATTATGGGTAGTTTTGGTGGTCTTGATGCAGTTGTAAGCT

TGGAG

CMV promoter (SEQ ID NO. 62)

Cgttacataacttacggtaaatggcccgcctggctgaccgcccaacgacccccgcccattgacgtcaata atgacgtatgttcccatagtaacgccaatagggactttccattgacgtcaatgggtggagtatttacggtaaa ctgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccaccccattgacgtcaatgggagtttgttttggcaccaaaatcaacgggactttccaaaatg tcgtaacaactccgccccattgacgcaaatgggcggtaggcgtgtacggtgggaggtctatataagcaga gct eGFP (SEQ ID NO: 63)

ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacaccctggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc cgccctgagcaaagaccccaacgagaagcgcgatcacatggtcctgctggagttcgtgaccgccgccg ggatcactctcggcatggacgagctgtacaagTAA SV40 Poly A (SEQ ID NO: 64)

Aacttgtttattgcagcttataatggttacaaataaagcaatagcatcacaaatttcacaaataaagcatttttttt cactgcattctagttgtggtttgtccaaactcatcaatgtatctta

ITR (SEQ ID NO: 60)

Aggaacccctagtgatggagttggccactccctctctgcgcgctcgctcgctcactgaggccgggcgac caaaggtcgcccgacgcccgggctttgcccgggcggcctcagtgagcgagcgagcgcgcagctgcct gcagg An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02925 encoding a CAG repeat targeting repeat targeting snRNA sequence comprises SEQ ID NO: 128.

A02925 pAAV_1×U7(15XCAG)_CMV_GFP (No Buffer) Targeting CAG Repeats

ITR
(SEQ ID NO: 59)
Cctgcaggcagctgcgcgctcgctcgctcactgaggccgcccgggcgtcgggcgacctttggtcgccc ggcctcagtgagcgagcgagcgcgcagagagggagtggccaactccatcactagggttcct U7 promoter
(SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
(SEQ ID NO: 67)
ggagtCTGCTGCTGCTGCTGCTGCTGCTGCTGCTGCTGCTGCTG

CTGAATTTTTGGAGTAggctttctggctccttaccggaaagcc

U7 Downstream (terminator)
(SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG

CMV promoter
(SEQ ID NO: 62)
Cgttacataacttacggtaaatggcccgcctggctgaccgcccaacgacccccgcccattgacgtcaata atgacgtatgttcccatagtaacgccaatagggactttccattgacgtcaatgggtggagtatttacggtaaa ctgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccacccattgacgtcaatgggagtttgttttggcaccaaaatcaacgggactttccaaaatg tcgtaacaactccgccccattgacgcaaatgggcggtaggcgtgtacggtgggaggtctatataagcaga gct eGFP
(SEQ ID NO: 63)
ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacacccctggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc

```
cgccctgagcaaagaccccaacgagaagcgcgatcacatggtcctgctggagttcgtgaccgccgcg ggatcactctcggcatggacgagctgtacaagTAA SV40 Poly A
                                                             (SEQ ID NO: 64)
Aacttgtttattgcagcttataatggttacaaataaagcaatagcatcacaaatttcacaaataaagcatttttt cactgcattctagttgtggtttgtccaaactcatcaatgtatctta ITR
                                                             (SEQ ID NO: 60)
Aggaacccctagtgatggagttggccactccctctctgcgcgctcgctcgctcactgaggccgggcgac caaaggtcgcccgacgcccgggctttgcccggggcctcagtgagcgagcgagcgcgcagctgcct gcagg
```

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02894 encoding a CUG repeat targeting repeat targeting snRNA sequence comprises SEQ ID NO: 129.

A02894 pAAV_3×U7(15XCUG)_CMV_GFP (100 bp Buffer) Targeting CUG Repeats

```
ITR
                                                             (SEQ ID NO: 59)
Cctgcaggcagctgcgcgctcgctcgctcactgaggccgcccgggcgtcgggcgaccttttggtcgccc ggcctcagtgagcgagcgagcgcgcagagagggagtggccaactccatcactagggggttcct U7 promoter
                                                             (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
                                                             (SEQ ID NO: 65)
ggagtCAGCAGCAGCAGCAGCAGCAGCAGCAGCAGCAGCAGCAG CAGCAGAATTTTTGGAGTAggctttctggctccttaccggaaagcc U7 Downstream (terminator)
                                                             (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG 100 bp buffer 1
                                                             (SEQ ID NO: 31)
CAAACTACAGAGCCAAGTGCTATCCACAGAGAGCTTTCTGGGTT

GCCATCTCAAGCAGACTACAAGGCCATCAGCTCATACTCACAAT

TGACTTTGAGAG

U7 promoter
                                                             (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT
```

```
GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA
```

U7 snRNA (SEQ ID NO: 65)
```
ggagtCAGCAGCAGCAGCAGCAGCAGCAGCAGCAGCAGCAGCAG

CAGCAGAATTTTTGGAGTAggctttctggctccttaccggaaagcc
```

U7 Downstream (terminator)

(SEQ ID NO: 49)
```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

100 bp buffer 2

(SEQ ID NO: 28)
```
TTGACCACATACGTGCTCTTTCAAAGTTCTGTGTTTGAAGTTATG

TTAGTAACAACTGATGCCCATCCTGCAATGACAAATCCAATTCT

CAGTGCAGCTC
```

U7 promoter (SEQ ID NO: 39)
```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA
```

U7 snRNA (SEQ ID NO: 65)
```
ggagtCAGCAGCAGCAGCAGCAGCAGCAGCAGCAGCAGCAGCAG

CAGCAGAATTTTTGGAGTAggctttctggctccttaccggaaagcc
```

U7 Downstream (terminator)

(SEQ ID NO: 49)
```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

CMV promoter (SEQ ID NO: 62)
```
Cgttacataacttacggtaaatggcccgcctggctgaccgcccaacgacccccgcccattgacgtcaata atgacgtatgttcccatagtaacgccaataggggactttccattgacgtcaatgggtggagtatttacggtaaa ctgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccaccccattgacgtcaatgggagtttgttttggcaccaaaatcaacgggactttccaaaatg
```

```
tcgtaacaactccgccccattgacgcaaatgggcggtaggcgtgtacggtgggaggtctatataagcaga gct
``` eGFP (SEQ ID NO: 63)

```
ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacaccctggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc cgccctgagcaaagaccccaacgagaagcgcgatcacatggtcctgctggagttcgtgaccgccgcg ggatcactctcggcatggacgagctgtacaagTAA
```

SV40 Poly A (SEQ ID NO: 64)

```
Aacttgtttattgcagcttataatggttacaaataaagcaatagcatcacaaatttcacaaataaagcatttttttt cactgcattctagttgtggtttgtccaaactcatcaatgtatctta
```

ITR (SEQ ID NO: 60)

```
Aggaacccctagtgatggagttggccactccctctctgcgcgctcgctcgctcactgaggccgggcgac caaaggtcgcccgacgcccgggctttgcccgggcggcctcagtgagcgagcgagcgcgcagctgcct gcagg
```

An exemplary AAV vector of the disclosure comprises from 5' to 3': a first inverted terminal repeat (ITR) sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02895 encoding a non-targeting snRNA sequence comprises SEQ ID NO: 130.

A02895 pAAV_3×U7(NT1)_CMV_GFP (100 bp Buffer)

ITR (SEQ ID NO: 59)

```
Cctgcaggcagctgcgcgctcgctcgctcactgaggccgcccgggcgtcgggcgacctttggtcgccc ggcctcagtgagcgagcgagcgcgcagagagggagtggccaactccatcactaggggttcct
```

U7 promoter (SEQ ID NO: 39)

```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA
```

U7 snRNA (SEQ ID NO: 66)

```
ggagtTCACCAGAAGCGTACCATACTCACGAAATTTTTGGAGTAggc
```

```
tttctggctccttaccggaaagcc
```

U7 Downstream (terminator)                                                    (SEQ ID NO: 49)
```
CCTCTTATGATGTTTGTTGCCAATGATAGATTGTTTTCACTGTGC
AAAAATTATGGGTAGTTTTGGTGGTCTTGATGCAGTTGTAAGCT
TGGAG
```

100 bp buffer 1                                                               (SEQ ID NO: 27)
```
CAAACTACAGAGCCAAGTGCTATCCACAGAGAGCTTTCTGGGTT
GCCATCTCAAGCAGACTACAAGGCCATCAGCTCATACTCACAAT
TGACTTTGAGAG
```

U7 promoter                                                                   (SEQ ID NO: 39)
```
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTTA
CCACATGCGTCGTTGTTTATACAGTAATAGGAACAAGAAAAAA
GTCACCTAAGCTCACCCTCATCAATTGTGGAGTTCCTTTATATCC
CATCTTCTCTCCAAACACATACGCA
```

U7 snRNA                                                                      (SEQ ID NO: 66)
```
ggagtTCACCAGAAGCGTACCATACTCACGAAATTTTTGGAGTAggc
tttctggctccttaccggaaagcc
```

U7 Downstream (terminator)                                                    (SEQ ID NO: 49)
```
CCTCTTATGATGTTTGTTGCCAATGATAGATTGTTTTCACTGTGC
AAAAATTATGGGTAGTTTTGGTGGTCTTGATGCAGTTGTAAGCT
TGGAG
```

100 bp buffer 2                                                               (SEQ ID NO: 28)
```
TTGACCACATACGTGCTCTTTCAAAGTTCTGTGTTTGAAGTTATG
TTAGTAACAACTGATGCCCATCCTGCAATGACAAATCCAATTCT
CAGTGCAGCTC
```

U7 promoter                                                                   (SEQ ID NO: 39)
```
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTTA
CCACATGCGTCGTTGTTTATACAGTAATAGGAACAAGAAAAAA
GTCACCTAAGCTCACCCTCATCAATTGTGGAGTTCCTTTATATCC
CATCTTCTCTCCAAACACATACGCA
```

U7 snRNA                                                                      (SEQ ID NO: 66)
```
ggagtTCACCAGAAGCGTACCATACTCACGAAATTTTTGGAGTAggc
tttctggctccttaccggaaagcc
```

U7 Downstream (terminator)                                                    (SEQ ID NO: 49)
```
CCTCTTATGATGTTTGTTGCCAATGATAGATTGTTTTCACTGTGC
```

AAAAATTATGGGTAGTTTTGGTGGTCTTGATGCAGTTGTAAGCT
TGGAG

CMV promoter
(SEQ ID NO: 62)
Cgttacataacttacggtaaatggcccgcctggctgaccgcccaacgaccccgcccattgacgtcaata atgacgtatgttcccatagtaacgccaatagggactttccattgacgtcaatgggtggagtatttacggtaaa ctgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccaccccattgacgtcaatgggagtttgttttggcaccaaaatcaacgggactttccaaaatg tcgtaacaactccgccccattgacgcaaatgggcggtaggcgtgtacggtgggaggtctatataagcaga gct eGFP
(SEQ ID NO: 63)
ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacaccctggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc cgccctgagcaaagaccccaacgagaagcgcgatcacatggtcctgctggagttcgtgaccgccgcc ggatcactctcggcatggacgagctgtacaagTAA SV40 Poly A
(SEQ ID NO: 64)
Aacttgtttattgcagcttataatggttacaaataaagcaatagcatcacaaatttcacaaataaagcatttttttt cactgcattctagttgtggtttgtccaaactcatcaatgtatctta ITR
(SEQ ID NO: 60)
Aggaacccctagtgatggagttggccactccctctctgcgcgctcgctcgctcactgaggccgggcgac caaaggtcgcccgacgcccgggctttgcccgggcggcctcagtgagcgagcgagcgcgcagctgcct gcagg An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02968 encoding a CAG repeat targeting repeat targeting snRNA sequence comprises SEQ ID NO: 131.

A02968 pAAV_3×U7(15XCAG)_CMV_GFP (100 bp Buffer) Targeting CAG Repeats

ITR
(SEQ ID NO: 59)
Cctgcaggcagctgcgcgctcgctcgctcactgaggccgcccgggcgtcgggcgacctttggtcgcc cggcctcagtgagcgagcgagcgcgcagagagggagtggccaactccatcactaggggttcct U7 promoter -continued U7 promoter (SEQ ID NO: 39)
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTT
ACCACATGCGTCGTTGTTTATACAGTAATAGGAACAAGAAAAA
AGTCACCTAAGCTCACCCTCATCAATTGTGGAGTTCCTTTATAT
CCCATCTTCTCTCCAAACACATACGCA U7 snRNA (SEQ ID NO: 67)
ggagtCTGCTGCTGCTGCTGCTGCTGCTGCTGCTGCTGCTGCT
GCTGAATTTTTGGAGTAggctttctggctccttaccggaaagcc U7 Downstream (terminator) (SEQ ID NO: 49)
CCTCTTATGATGTTTGTTGCCAATGATAGATTGTTTTCACTGTGC
AAAAATTATGGGTAGTTTTGGTGGTCTTGATGCAGTTGTAAGCT
TGGAG 100bp buffer 1 (SEQ ID NO: 27)
CAAACTACAGAGCCAAGTGCTATCCACAGAGAGCTTTCTGGGT
TGCCATCTCAAGCAGACTACAAGGCCATCAGCTCATACTCACA
ATTGACTTTGAGAG U7 promoter (SEQ ID NO: 39)
TACTGCCGAATCCAGGTCTCCGGGCTTAACAACAACGAAGGGG
CTGTGACTGGCTGCTTTCTCAACCAATCAGCACCGAACTCATTT
GCATGGGCTGAGAACAAATGTTCGCGAACTCTAGAAATGAATG
ACTTAAGTAAGTTCCTTAGAATATTATTTTTCCTACTGAAAGTT
ACCACATGCGTCGTTGTTTATACAGTAATAGGAACAAGAAAAA
AGTCACCTAAGCTCACCCTCATCAATTGTGGAGTTCCTTTATAT
CCCATCTTCTCTCCAAACACATACGCA U7 snRNA (SEQ ID NO: 67)
ggagtCTGCTGCTGCTGCTGCTGCTGCTGCTGCTGCTGCTGCT
GCTGAATTTTTGGAGTAggctttctggctccttaccggaaagcc U7 Downstream (terminator) (SEQ ID NO: 49)
CCTCTTATGATGTTTGTTGCCAATGATAGATTGTTTTCACTGTGC
AAAAATTATGGGTAGTTTTGGTGGTCTTGATGCAGTTGTAAGCT
TGGAG 100 bp buffer 2 (SEQ ID NO: 28)
TTGACCACATACGTGCTCTTTCAAAGTTCTGTGTTTGAAGTTAT
GTTAGTAACAACTGATGCCCATCCTGCAATGACAAATCCAATT
CTCAGTGCAGCTC U7 promoter (SEQ ID NO: 39)
TACTGCCGAATCCAGGTCTCCGGGCTTAACAACAACGAAGGGG
CTGTGACTGGCTGCTTTCTCAACCAATCAGCACCGAACTCATTT

```
GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA
```

U7 snRNA
(SEQ ID NO: 67)
```
ggagtCTGCTGCTGCTGCTGCTGCTGCTGCTGCTGCTGCTGCT

GCTGAATTTTTGGAGTAggctttctggctccttaccggaaagcc
```

U7 Downstream (terminator)
(SEQ ID NO: 49)
```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

CMV promoter
(SEQ ID NO: 62)
```
Cgttacataacttacggtaaatggcccgcctggctgaccgcccaacgacccccgcccattgacgtcaat aatgacgtatgttcccatagtaacgccaatagggactttccattgacgtcaatgggtggagtatttacggta aactgcccacttggcagtacatcaagtgtatcatatgccaagtacgccccctattgacgtcaatgacggta aatggcccgcctggcattatgcccagtacatgaccttatgggactttcctacttggcagtacatctacgtatt agtcatcgctattaccatggtgatgcggttttggcagtacatcaatgggcgtggatagcggtttgactcacg gggatttccaagtctccacccattgacgtcaatgggagtttgttttggcaccaaaatcaacgggactttcc aaaatgtcgtaacaactccgccccattgacgcaaatgggcggtaggcgtgtacggtgggaggtctatata agcagagct
``` eGFP
(SEQ ID NO: 63)
```
ATGgtgagcaagggcgaggagctgttcaccggggtggtgcccatcctggtcgagctggacggcga cgtaaacggccacaagttcagcgtgtccggcgagggcgagggcgatgccacctacggcaagctgacc ctgaagttcatctgcaccaccggcaagctgcccgtgccctggcccaccctcgtgaccaccctgacctac ggcgtgcagtgcttcagccgctaccccgaccacatgaagcagcacgacttcttcaagtccgccatgccc gaaggctacgtccaggagcgcaccatcttcttcaaggacgacggcaactacaagacccgcgccgaggt gaagttcgagggcgacaccctggtgaaccgcatcgagctgaagggcatcgacttcaaggaggacggc aacatcctggggcacaagctggagtacaactacaacagccacaacgtctatatcatggccgacaagcag aagaacggcatcaaggtgaacttcaagatccgccacaacatcgaggacggcagcgtgcagctcgccg accactaccagcagaacacccccatcggcgacggccccgtgctgctgcccgacaaccactacctgagc acccagtccgccctgagcaaagaccccaacgagaagcgcgatcacatggtcctgctggagttcgtgac cgccgccgggatcactctcggcatggacgagctgtacaagTAA
```

SV40 Poly A
(SEQ ID NO: 64)
```
Aacttgtttattgcagcttataatggttacaaataaagcaatagcatcacaaatttcacaaataaagcattttttt tcactgcattctagttgtggtttgtccaaactcatcaatgtatctta
```

ITR
(SEQ ID NO: 60)
```
Aggaacccctagtgatggagttggccactccctctctgcgcgctcgctcgctcactgaggccgggcga ccaaaggtcgcccgacgcccgggctttgcccgggcggcctcagtgagcgagcgagcgcgcagctgc ctgcagg
```

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a buffer sequence, a U7 promoter sequence, a CUG repeat targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02896 encoding a CUG repeat targeting repeat targeting snRNA sequence comprises SEQ ID NO: 132.

A02896 pAAV_3×U7(15XCUG)_CMV_GFP (500 bp Buffer)

```
ITR
                                                                (SEQ ID NO: 59)
Cctgcaggcagctgcgcgctcgctcgctcactgaggccgcccgggcgtcgggcgacctttggtcgccc ggcctcagtgagcgagcgagcgcgcagagagggagtggccaactccatcactaggggttcct U7 promoter
                                                                (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
                                                                (SEQ ID NO: 65)
ggagtCAGCAGCAGCAGCAGCAGCAGCAGCAGCAGCAGCAGCAG CAGCAGAATTTTTGGAGTAggctttctggctccttaccggaaagcc U7 Downstream (terminator)
                                                                (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG 500 bp buffer 1
                                                                (SEQ ID NO: 29)
CAAACTACAGAGCCAAGTGCTATCCACAGAGAGCTTTCTGGGTT

GCCATCTCAAGCAGACTACAAGGCCATCAGCTCATACTCACAAT

TGACTTTGAGAGTCATTTTCCAATGCTCCTACACACCCCTTCTTC

ACAATCCCCAACAAATCTGAGGCTGGAACTTGGTACCATAACAA

TCATTACATTATTTCACCAGAAGTACACCTTGCCTGGAAGATTG

GCATTATAGCATCTTCTAACATTGTGAAAGTTAGTGACCAATGA

GGAGATCCAAGTCAGTTCCAGTTGGATTTCTCTATACTCTATAAT

AAATATATATGGTGTCTTCAACAATAGGACTTTGCCATCCAGTG

ATGCTAAAAATCAATAACAATGGCAATAACCTGCCCTGTTTGGA

AAGCCTCTGGCTTCCATGACTAACAATTCAAGGCAGGTCTCCTA

TACCTAGTACTGAGATTTTTATTTGATAAACTATATCTTCTGGGA

GGAGAAGCATTGT

U7 promoter
                                                                (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG
```

-continued
ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
(SEQ ID NO: 65)
ggagtCAGCAGCAGCAGCAGCAGCAGCAGCAGCAGCAGCAGCAG

CAGCAGAATTTTTGGAGTAggctttctggctccttaccggaaagcc

U7 Downstream (terminator)
(SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG 500 bp buffer 2
(SEQ ID NO: 30)
TTGACCACATACGTGCTCTTTCAAAGTTCTGTGTTTGAAGTTATG

TTAGTAACAACTGATGCCCATCCTGCAATGACAAATCCAATTCT

CAGTGCAGCTCTCTGAAATAGTTTTGCTTTCTCTCTCTAGGTCTG

TTCTATACTCCTAACTCTCCAGGAGTTTACAAGGAATAAAATCT

CTTCCAAATGCTTTCTGTTGCAACAACTGGACCATACTGAAAGC

TGAGGCCCACAATTGCAATCTAGGTTAGCAGGTAATCATTGTTG

GTGAGGTCCTCCCTTTCCCCAGGCTCGTGTTTGTATTGGGGAGC

AGGAAATTTTTGCTAGAGCAGCACTGCCATCTCTCTACACTCCA

CCTGATTGGTGGGATGGACCAGAGAAATGGACATTCCCAACAC

AGTCCCTCCTTTCACATCTGCTCACCTGCCCACAGGATACTTTCC

ACCATGCATACTGGGCTCTGCACCAACCATTCAGCAGTGATGAA

GAGGAAACTTGAAC

U7 promoter
(SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
(SEQ ID NO: 65)
ggagtCAGCAGCAGCAGCAGCAGCAGCAGCAGCAGCAGCAGCAG

CAGCAGAATTTTTGGAGTAggctttctggctccttaccggaaagcc

U7 Downstream (terminator)
(SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG

CMV promoter
(SEQ ID NO: 62)
Cgttacataacttacggtaaatggcccgcctggctgaccgcccaacgacccccgcccattgacgtcaata -continued

```
atgacgtatgttcccatagtaacgccaatagggactttccattgacgtcaatgggtggagtatttacggtaaa ctgcccacttggcagtacatcaagtgtatcatatgccaagtacgcccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccaccccattgacgtcaatgggagtttgttttggcaccaaaatcaacgggactttccaaaatg tcgtaacaactccgccccattgacgcaaatgggcggtaggcgtgtacggtgggaggtctatataagcaga gct
``` eGFP (SEQ ID NO: 63)

```
ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacaccctggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc cgccctgagcaaagaccccaacgagaagcgcgatcacatggtcctgctggagttcgtgaccgccgccg ggatcactctcggcatggacgagctgtacaagTAA
```

SV40 Poly A (SEQ ID NO: 64)

```
Aacttgtttattgcagcttataatggttacaaataaagcaatagcatcacaaatttcacaaataaagcattttttt cactgcattctagttgtggtttgtccaaactcatcaatgtatctta
```

ITR (SEQ ID NO: 60)

```
Aggaaccccttagtgatggagttggccactccctctctgcgcgctcgctcgctcactgaggccgggcgac caaaggtcgcccgacgcccgggctttgcccgggcggcctcagtgagcgagcgagcgcgcagctgcct gcagg
```

An exemplary AAV vector of the disclosure comprises from 5' to 3': a first inverted terminal repeat (ITR) sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a buffer sequence, a U7 promoter sequence, a non-targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02897 encoding a non-targeting repeat targeting snRNA sequence comprises SEQ ID NO: 133.

A02897 pAAV_3xU7(NT1)_CMV_GFP (500 bp Buffer)

ITR (SEQ ID NO: 59)

```
Cctgcaggcagctgcgcgctcgctcgctcactgaggccgcccgggcgtcgggcgacctttggtcgcc cggcctcagtgagcgagcgagcgcgcagagagggagtggccaactccatcactaggggttcct
```

U7 promoter (SEQ ID NO: 39)

```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT
```

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA

U7 snRNA
(SEQ ID NO: 66)

ggagtTCACCAGAAGCGTACCATACTCACGAAATTTTTGGAGTAgg ctttctggctccttaccggaaagcc

U7 (terminator) Downstream
(SEQ ID NO: 49)

CCTCTTATGATGTTTGTTGCCAATGATAGATTGTTTTCACTGTGC

AAAAATTATGGGTAGTTTTGGTGGTCTTGATGCAGTTGTAAGCT

TGGAG 500 bp buffer 1
(SEQ ID NO: 29)

CAAACTACAGAGCCAAGTGCTATCCACAGAGAGCTTTCTGGGT

TGCCATCTCAAGCAGACTACAAGGCCATCAGCTCATACTCACA

ATTGACTTTGAGAGTCATTTTCCAATGCTCCTACACACCCCTTC

TTCACAATCCCCAACAAATCTGAGGCTGGAACTTGGTACCATA

ACAATCATTACATTATTTCACCAGAAGTACACCTTGCCTGGAAG

ATTGGCATTATAGCATCTTCTAACATTGTGAAAGTTAGTGACCA

ATGAGGAGATCCAAGTCAGTTCCAGTTGGATTTCTCTATACTCT

ATAATAAATATATATGGTGTCTTCAACAATAGGACTTTGCCATC

CAGTGATGCTAAAAATCAATAACAATGGCAATAACCTGCCCTG

TTTGGAAAGCCTCTGGCTTCCATGACTAACAATTCAAGGCAGG

TCTCCTATACCTAGTACTGAGATTTTTATTTGATAAACTATATCT

TCTGGGAGGAGAAGCATTGT

U7 promoter
(SEQ ID NO: 39)

TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCAT

U7 snRNA
(SEQ ID NO: 66)

ggagtTCACCAGAAGCGTACCATACTCACGAAATTTTTGGAGTAgg ctttctggctccttaccggaaagcc

U7 Downstream (terminator)
(SEQ ID NO: 49)

CCTCTTATGATGTTTGTTGCCAATGATAGATTGTTTTCACTGTGC

AAAAATTATGGGTAGTTTTGGTGGTCTTGATGCAGTTGTAAGCT

TGGAG 500 bp buffer 2
(SEQ ID NO: 30)

TTGACCACATACGTGCTCTTTCAAAGTTCTGTGTTTGAAGTTAT

```
GTTAGTAACAACTGATGCCCATCCTGCAATGACAAATCCAATT

CTCAGTGCAGCTCTCTGAAATAGTTTTGCTTTCTCTCTAGGTC

TGTTCTATACTCCTAACTCTCCAGGAGTTTACAAGGAATAAAAT

CTCTTCCAAATGCTTTCTGTTGCAACAACTGGACCATACTGAAA

GCTGAGGCCCACAATTGCAATCTAGGTTAGCAGGTAATCATTG

TTGGTGAGGTCCTCCCTTTCCCCAGGCTCGTGTTTGTATTGGGG

AGCAGGAAATTTTTGCTAGAGCAGCACTGCCATCTCTCTACACT

CCACCTGATTGGTGGGATGGACCAGAGAAATGGACATTCCCAA

CACAGTCCCTCCTTTCACATCTGCTCACCTGCCCACAGGATACT

TTCCACCATGCATACTGGGCTCTGCACCAACCATTCAGCAGTGA

TGAAGAGGAAACTTGAAC
```

U7 promoter (SEQ ID NO: 39)

```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA
```

U7 snRNA (SEQ ID NO: 66)

```
ggagtTCACCAGAAGCGTACCATACTCACGAAATTTTTGGAGTAgg ctttctggctccttaccggaaagcc
```

U7 Downstream (terminator) (SEQ ID NO: 49)

```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

CMV promoter (SEQ ID NO: 62)

```
Cgttacataacttacggtaaatggcccgcctggctgaccgcccaacgacccccgcccattgacgtcaat aatgacgtatgttcccatagtaacgccaatagggactttccattgacgtcaatgggtggagtatttacggta aactgcccacttggcagtacatcaagtgtatcatatgccaagtacgccccctattgacgtcaatgacggta aatggcccgcctggcattatgcccagtacatgaccttatgggactttcctacttggcagtacatctacgtatt agtcatcgctattaccatggtgatgcggttttggcagtacatcaatgggcgtggatagcggtttgactcacg gggatttccaagtctccaccccattgacgtcaatgggagtttgttttggcaccaaaatcaacgggactttcc aaaatgtcgtaacaactccgccccattgacgcaaatgggcggtaggcgtgtacggtgggaggtctatata agcagagct
``` eGFP (SEQ ID NO: 63)

```
ATGgtgagcaagggcgaggagctgttcaccggggtggtgcccatcctggtcgagctggacggcga cgtaaacggccacaagttcagcgtgtccggcgagggcgagggcgatgccacctacggcaagctgacc ctgaagttcatctgcaccaccggcaagctgcccgtgccctggcccaccctcgtgaccaccctgacctac ggcgtgcagtgcttcagccgctaccccgaccacatgaagcagcacgacttcttcaagtccgccatgccc gaaggctacgtccaggagcgcaccatcttcttcaaggacgacggcaactacaagacccgcgccgaggt
```

```
gaagttcgagggcgacaccctggtgaaccgcatcgagctgaagggcatcgacttcaaggaggacggc aacatcctggggcacaagctggagtacaactacaacagccacaacgtctatatcatggccgacaagcag aagaacggcatcaaggtgaacttcaagatccgccacaacatcgaggacggcagcgtgcagctcgccg accactaccagcagaacacccccatcggcgacggccccgtgctgctgcccgacaaccactacctgagc acccagtccgccctgagcaaagaccccaacgagaagcgcgatcacatggtcctgctggagttcgtgac cgccgccgggatcactctcggcatggacgagctgtacaagTAA SV40 Poly A
                                                                (SEQ ID NO: 64)
Aacttgtttattgcagcttataatggttacaaataaagcaatagcatcacaaatttcacaaataaagcattttt tcactgcattctagttgtggtttgtccaaactcatcaatgtatctta ITR
                                                                (SEQ ID NO: 60)
Aggaacccctagtgatggagttggccactccctctctgcgcgctcgctcgctcactgaggccgggcga ccaaaggtcgcccgacgcccgggctttgcccgggcggcctcagtgagcgagcgagcgcgcagctgc ctgcagg
```

An exemplary AAV vector of the disclosure comprises from 5' to 3': a first inverted terminal repeat (ITR) sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a buffer sequence, a U7 promoter sequence, a CAG repeat targeting U7 esnRNA sequence, a U7 downstream terminator sequence, a CMV promoter sequence, a sequence encoding green fluorescent protein (GFP), a sv40 polyA sequence, and a second ITR sequence. In some aspects, a nucleic acid sequence encoding AAV vector A02969 encoding a CAG repeat targeting repeat targeting snRNA sequence comprises SEQ ID NO: 134.

A02969 pAAV_3×U7(15XCAG)_CMV_GFP (500 bp Buffer) Targeting CAG Repeats

```
ITR
                                                                (SEQ ID NO: 59)
Cctgcaggcagctgcgcgctcgctcgctcactgaggccgcccgggcgtcgggcgacctttggtcgccc ggcctcagtgagcgagcgagcgcgcagagagggagtggccaactccatcactaggggttcct U7 promoter
                                                                (SEQ ID NO: 39)
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA
                                                                (SEQ ID NO: 67)
ggagtCTGCTGCTGCTGCTGCTGCTGCTGCTGCTGCTGCTGCTG CTGAATTTTTGGAGTAggctttctggctccttaccggaaagcc U7 Downstream (terminator)
                                                                (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG 500 bp buffer 1
                                                                (SEQ ID NO: 29)
CAAACTACAGAGCCAAGTGCTATCCACAGAGAGCTTTCTGGGTT

GCCATCTCAAGCAGACTACAAGGCCATCAGCTCATACTCACAAT
```

```
TGACTTTGAGAGTCATTTTCCAATGCTCCTACACACCCCTTCTTC

ACAATCCCCAACAAATCTGAGGCTGGAACTTGGTACCATAACAA

TCATTACATTATTTCACCAGAAGTACACCTTGCCTGGAAGATTG

GCATTATAGCATCTTCTAACATTGTGAAAGTTAGTGACCAATGA

GGAGATCCAAGTCAGTTCCAGTTGGATTTCTCTATACTCTATAAT

AAATATATGGTGTCTTCAACAATAGGACTTTGCCATCCAGTG

ATGCTAAAAATCAATAACAATGGCAATAACCTGCCCTGTTTGGA

AAGCCTCTGGCTTCCATGACTAACAATTCAAGGCAGGTCTCCTA

TACCTAGTACTGAGATTTTATTTGATAAACTATATCTTCTGGGA

GGAGAAGCATTGT
```

U7 promoter (SEQ ID NO: 39)
```
TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA
```

U7 snRNA (SEQ ID NO: 67)
```
ggagtCTGCTGCTGCTGCTGCTGCTGCTGCTGCTGCTGCTGCTG

CTGAATTTTTGGAGTAggctttctggctccttaccggaaagcc
```

U7 Downstream (terminator) (SEQ ID NO: 49)
```
CCTCTTATGATGTTTGTTGCCAATGATAGATTGTTTTCACTGTGC

AAAAATTATGGGTAGTTTTGGTGGTCTTGATGCAGTTGTAAGCT

TGGAG
```

500 bp buffer 2 (SEQ ID NO: 30)
```
TTGACCACATACGTGCTCTTTCAAAGTTCTGTGTTTGAAGTTATG

TTAGTAACAACTGATGCCCATCCTGCAATGACAAATCCAATTCT

CAGTGCAGCTCTCTGAAATAGTTTTGCTTTCTCTCTCTAGGTCTG

TTCTATACTCCTAACTCTCCAGGAGTTTACAAGGAATAAAATCT

CTTCCAAATGCTTTCTGTTGCAACAACTGGACCATACTGAAAGC

TGAGGCCCACAATTGCAATCTAGGTTAGCAGGTAATCATTGTTG

GTGAGGTCCTCCCTTTCCCCAGGCTCGTGTTTGTATTGGGGAGC

AGGAAATTTTTGCTAGAGCAGCACTGCCATCTCTCTACACTCCA

CCTGATTGGTGGGATGGACCAGAGAAATGGACATTCCCAACAC

AGTCCCTCCTTTCACATCTGCTCACCTGCCCACAGGATACTTTCC

ACCATGCATACTGGGCTCTGCACCAACCATTCAGCAGTGATGAA

GAGGAAACTTGAAC
```

U7 promoter (SEQ ID NO: 39)
```
TACTGCCGAATCCAGGTCTCCGGGCTTAACAACAACGAAGGGG
```

-continued
CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTTA

CCACATGCGTCGTTGTTTATACAGTAATAGGAACAAGAAAAAA

GTCACCTAAGCTCACCCTCATCAATTGTGGAGTTCCTTTATATCC

CATCTTCTCTCCAAACACATACGCA

U7 snRNA (SEQ ID NO: 67)
ggagtCTGCTGCTGCTGCTGCTGCTGCTGCTGCTGCTGCTGCTG

CTGAATTTTTGGAGTAggctttctggctccttaccggaaagcc

U7 Downstream (terminator) (SEQ ID NO: 49)
CCTCTTATGATGTTTGTTGCCAATGATAGATTGTTTTCACTGTGC

AAAAATTATGGGTAGTTTTGGTGGTCTTGATGCAGTTGTAAGCT

TGGAG

CMV promoter (SEQ ID NO: 62)
Cgttacataacttacggtaaatggcccgcctggctgaccgcccaacgacccccgcccattgacgtcaata atgacgtatgttcccatagtaacgccaatagggactttccattgacgtcaatgggtggagtatttacggtaaa ctgcccacttggcagtacatcaagtgtatcatatgccaagtacgccccctattgacgtcaatgacggtaaat ggcccgcctggcattatgcccagtacatgaccttatgggactttcctacttggcagtacatctacgtattagtc atcgctattaccatggtgatgcggttttggcagtacatcaatgggcgtggatagcggtttgactcacgggga tttccaagtctccaccccattgacgtcaatgggagtttgttttggcaccaaaatcaacgggactttccaaaatg tcgtaacaactccgccccattgacgcaaatgggcggtaggcgtgtacggtgggaggtctatataagcaga gct eGFP (SEQ ID NO: 63)
ATGgtgagcaagggcgaggagctgttcaccggggtggtgcccatcctggtcgagctggacggcgac gtaaacggccacaagttcagcgtgtccggcgagggcgagggcgatgccacctacggcaagctgaccct gaagttcatctgcaccaccggcaagctgcccgtgccctggcccaccctcgtgaccaccctgacctacggc gtgcagtgcttcagccgctaccccgaccacatgaagcagcacgacttcttcaagtccgccatgcccgaag gctacgtccaggagcgcaccatcttcttcaaggacgacggcaactacaagacccgcgccgaggtgaagt tcgagggcgacacccttggtgaaccgcatcgagctgaagggcatcgacttcaaggaggacggcaacatc ctggggcacaagctggagtacaactacaacagccacaacgtctatatcatggccgacaagcagaagaac ggcatcaaggtgaacttcaagatccgccacaacatcgaggacggcagcgtgcagctcgccgaccactac cagcagaacacccccatcggcgacggccccgtgctgctgcccgacaaccactacctgagcacccagtc cgccctgagcaaagaccccaacgagaagcgcgatcacatggtcctgctggagttcgtgaccgccgccg ggatcactctcggcatggacgagctgtacaagTAA SV40 Poly A (SEQ ID NO: 64)
Aacttgtttattgcagcttataatggttacaaataaagcaatagcatcacaaatttcacaaataaagcatttttttt cactgcattctagttgtggtttgtccaaactcatcaatgtatctta ITR (SEQ ID NO: 60)
Aggaacccctagtgatggagttggccactccctctctgcgcgctcgctcgctcactgaggccgggcgac caaaggtcgcccgacgcccgggctttgcccgggggcctcagtgagcgagcgagcgcgcagctgcct gcagg An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A03980 encoding a DMD exon 51 targeting snRNA sequences comprises SEQ ID NO: 135.

A03980: pAAV(ssAAV) U7promoter-esnRNA-z38/42-U7 Termination-U1promoter-esnRNAz38/z42-U1 Termination ITR
(SEQ ID NO: 59)
cctgcaggcagctgcgcgctcgctcgctcactgaggccgcccgggcgtcgggcgacctttggtcgcccggcc tcagtgagcgagcgagcgcgcagagagggagtggccaactccatcactagggggttcct U7 promoter
(SEQ ID NO: 39)
TACTGCCGAATCCAGGTCTCCGGGCTTAACAACAACGAAGGGGCTG

TGACTGGCTGCTTTCTCAACCAATCAGCACCGAACTCATTTGCATGG

GCTGAGAACAAATGTTCGCGAACTCTAGAAATGAATGACTTAAGTA

AGTTCCTTAGAATATTATTTTTCCTACTGAAAGTTACCACATGCGTC

GTTGTTTATACAGTAATAGGAACAAGAAAAAAGTCACCTAAGCTCA

CCCTCATCAATTGTGGAGTTCCTTTATATCCCATCTTCTCTCCAAAC

ACATACGCA z38/42 esnRNA (DMD exon 51)
(SEQ ID NO: 68)
ggagtTACCTCCAACATCAAGGAAGATGGCAGTAACCACAGGTTGTGT CACCAGAGTAACAAATTTTTGGAGTAggctttctggctccttaccggaaagcc U7 termination
(SEQ ID NO: 49)
CCTCTTATGATGTTTGTTGCCAATGATAGATTGTTTTCACTGTGCAA

AAATTATGGGTAGTTTTGGTGGTCTTGATGCAGTTGTAAGCTTGGAG

U1 promoter
(SEQ ID NO: 40)
TAAGGACCAGCTTCTTTGGGAGAGAACAGACGCAGGGGCGGGAGG

GAAAAAGGGAGAGGCAGACGTCACTTCCCCTTGGCGGCTCTGGCAG

CAGATTGGTCGGTTGAGTGGCAGAAAGGCAGACGGGGACTGGGCA

AGGCACTGTCGGTGACATCACGGACAGGGCGACTTCTATGTAGATG

AGGCAGCGCAGAGGCTGACGTCTTCGCCACTTGCTGCTTCACCACG

AAGGAGTTCCCGTGCCCTGGGAGCGGGTTCAGGACCGCTGATCGGA

AGTGAGAATCCCAGCTGTGTGTCAGGGCTGGAAAGGGCTCGGGAGT

GCGCGGGGCAAGTGACCGTGTGTGTAAAGAGTGAGGCGTATGAGG

CTGTGTCGGGGCAGAGGCacaacgtttc z38/42 esnRNA (DMD exon 51)
(SEQ ID NO: 68)
ggagtTACCTCCAACATCAAGGAAGATGGCAGTAACCACAGGTTGTGT CACCAGAGTAACAAATTTTTGGAGTAggctttctggctccttaccggaaagcc U1 termination
(SEQ ID NO: 50)
ACTTTCTGGAGTTTCAAAAACAGACTGTACGCCAAGGGTCATATCTT

TTT

ITR
(SEQ ID NO: 60)
aggaaccccctagtgatggagttggccactccctctctgcgcgctcgctcgctcactgaggccgggcgaccaaa ggtcgcccgacgcccgggctttgcccggggggcctcagtgagcgagcgagcgcgcagctgcctgcagg An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A03981 encoding a DMD exon 51 targeting snRNA sequences comprises SEQ ID NO: 136.

A03981: pAAV(ssAAV)_U7promoter-esnRNA-z42-U7termination-U1promoter-esnRNA-z38-U1 Termination ITR (SEQ ID NO: 59)
cctgcaggcagctgcgcgctcgctcgctcactgaggccgcccgggcgtcgggcgacctttggtcgcccggcc tcagtgagcgagcgagcgcgcagagagggagtggccaactccatcactagggggttcct U7 promoter (SEQ ID NO: 39)
TACTGCCGAATCCAGGTCTCCGGGCTTAACAACAACGAAGGGGCTG

TGACTGGCTGCTTTCTCAACCAATCAGCACCGAACTCATTTGCATGG

GCTGAGAACAAATGTTCGCGAACTCTAGAAATGAATGACTTAAGTA

AGTTCCTTAGAATATTATTTTTCCTACTGAAAGTTACCACATGCGTC

GTTGTTTATACAGTAATAGGAACAAGAAAAAAGTCACCTAAGCTCA

CCCTCATCAATTGTGGAGTTCCTTTATATCCCATCTTCTCTCCAAAC

ACATACGCA z42 esnRNA (DMD exon 51) (SEQ ID NO: 69)
ggagtGTAACCACAGGTTGTGTCACCAGAGTAACAAATTTTTGGAGTA ggctttctggctccttaccggaaagcc U7 termination (SEQ ID NO: 49)
CCTCTTATGATGTTTGTTGCCAATGATAGATTGTTTTCACTGTGCAA

AAATTATGGGTAGTTTTGGTGGTCTTGATGCAGTTGTAAGCTTGGAG

U1 promoter (SEQ ID NO: 40)
TAAGGACCAGCTTCTTTGGGAGAGAACAGACGCAGGGGCGGGAGG

GAAAAAGGGAGAGGCAGACGTCACTTCCCCTTGGCGGCTCTGGCAG

CAGATTGGTCGGTTGAGTGGCAGAAAGGCAGACGGGGACTGGGCA

AGGCACTGTCGGTGACATCACGGACAGGGCGACTTCTATGTAGATG

AGGCAGCGCAGAGGCTGACGTCTTCGCCACTTGCTGCTTCACCACG

AAGGAGTTCCCGTGCCCTGGGAGCGGGTTCAGGACCGCTGATCGGA

AGTGAGAATCCCAGCTGTGTGTCAGGGCTGGAAAGGGCTCGGGAGT

GCGCGGGGCAAGTGACCGTGTGTGTAAAGAGTGAGGCGTATGAGG

CTGTGTCGGGGCAGAGGCacaacgtttc z38 esnRNA (DMD exon 51) (SEQ ID NO: 70)
ggagtTACCTCCAACATCAAGGAAGATGGCAAATTTTTGGAGTAggctttc tggctccttaccggaaagcc U1 termination (SEQ ID NO: 50)
ACTTTCTGGAGTTTCAAAAACAGACTGTACGCCAAGGGTCATATCTT

TTT

ITR (SEQ ID NO: 60)
aggaacccctagtgatggagttggccactccctctctgcgcgctcgctcgctcactgaggccgggcgaccaaa ggtcgcccgacgcccgggctttgcccgggggcctcagtgagcgagcgagcgcgcagctgcctgcagg An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a U1 promoter sequence, a DMD exon 51 targeting U7 esnRNA sequence, a U1 downstream terminator sequence, and a second ITR sequence. In some aspects, a nucleic acid sequence encoding AAV vector A04229 encoding a DMD exon 51 targeting snRNA sequences comprises SEQ ID NO: 137.

A04229: pAAV(scAAV) U7promoter-esnRNA-z38/42-U7 Termination-U1promoter-esnRNAz38/z42-U1 Termination-Mut ITR

```
ITR
                                                           (SEQ ID NO: 59)
cctgcaggcagctgcgcgctcgctcgctcactgaggccgcccgggcgtcgggcgacctttggtcgcccggc ctcagtgagcgagcgagcgcgcagagagggagtggccaactccatcactagggttcct U7 promoter
                                                           (SEQ ID NO: 39)
TACTGCCGAATCCAGGTCTCCGGGCTTAACAACAACGAAGGGGCT

GTGACTGGCTGCTTTCTCAACCAATCAGCACCGAACTCATTTGCAT

GGGCTGAGAACAAATGTTCGCGAACTCTAGAAATGAATGACTTAA

GTAAGTTCCTTAGAATATTATTTTTCCTACTGAAAGTTACCACATGC

GTCGTTGTTTATACAGTAATAGGAACAAGAAAAAAGTCACCTAAG

CTCACCCTCATCAATTGTGGAGTTCCTTTATATCCCATCTTCTCTCC

AAACACATACGCA z38/42 esnRNA (DMD exon 51)
                                                           (SEQ ID NO: 68)
ggagtTACCTCCAACATCAAGGAAGATGGCAGTAACCACAGGTTGTG TCACCAGAGTAACAAATTTTTGGAGTAggctttctggctccttaccggaaagcc U7 termination
                                                           (SEQ ID NO: 49)
CCTCTTATGATGTTTGTTGCCAATGATAGATTGTTTTCACTGTGCAA

AAATTATGGGTAGTTTTGGTGGTCTTGATGCAGTTGTAAGCTTGGA
G

U1 promoter
                                                           (SEQ ID NO: 40)
TAAGGACCAGCTTCTTTGGGAGAGAACAGACGCAGGGGCGGGAGG

GAAAAAGGGAGAGGCAGACGTCACTTCCCCTTGGCGGCTCTGGCA

GCAGATTGGTCGGTTGAGTGGCAGAAAGGCAGACGGGGACTGGGC

AAGGCACTGTCGGTGACATCACGGACAGGGCGACTTCTATGTAGA

TGAGGCAGCGCAGAGGCTGACGTCTTCGCCACTTGCTGCTTCACCA

CGAAGGAGTTCCCGTGCCCTGGGAGCGGGTTCAGGACCGCTGATC

GGAAGTGAGAATCCCAGCTGTGTGTCAGGGCTGGAAAGGGCTCGG

GAGTGCGCGGGCAAGTGACCGTGTGTGTAAAGAGTGAGGCGTAT

GAGGCTGTGTCGGGGCAGAGGCacaacgtttc z38/42 esnRNA (DMD exon 51)
                                                           (SEQ ID NO: 68)
TCACCAGAGTAACAAATTTTTGGAGTAggctttctggctccttaccggaaagcc ggagtTACCTCCAACATCAAGGAAGATGGCAGTAACCACAGGTTGTG U1 termination
                                                           (SEQ ID NO: 50)
ACTTTCTGGAGTTTCAAAAACAGACTGTACGCCAAGGGTCATATCT

TTTT
``` mITR (SEQ ID NO: 61)

CCACTCCCTCTCTGCGCGCTCGCTCGCTCACTGAGGCCGGGCGACC

AAAGGTCGCCCGACGCCCGGGCTTTGCCCGGGCGGCCTCAGTGAG

CGAGCGAGCGCGCAGAGAGGGA

An exemplary AAV vector of the disclosure comprises from 5' to 3': a first inverted terminal repeat (ITR) sequence, a U7 promoter sequence, a DMD exon 51 targeting U7 esnRNA sequence, a U7 downstream terminator sequence, a buffer sequence, a U1 promoter sequence, a DMD exon 51 targeting U7 esnRNA sequence, a U1 downstream terminator sequence, a buffer sequence, and a second ITR sequence.

In some aspects, a nucleic acid sequence encoding AAV vector A04184 encoding a DMD exon 51 targeting snRNA sequences comprises SEQ ID NO: 138.

A04184: pAAV(ssAAV)-U7promoter-z38/42-U7term_U1promoter-z38/42-U1term_Buffer Combination Sequence

ITR (SEQ ID NO: 59)

cctgcaggcagctgcgcgctcgctcgctcactgaggccgcccgggcgtcgggcgacctttggtcgccc ggcctcagtgagcgagcgagcgcgcagagagggagtggccaactccatcactaggggttcct U7 promoter (SEQ ID NO: 39)

TACTGCCGAATCCAGGTCTCCGGGCTTAACAACAACGAAGGGG

CTGTGACTGGCTGCTTTCTCAACCAATCAGCACCGAACTCATTT

GCATGGGCTGAGAACAAATGTTCGCGAACTCTAGAAATGAATG

ACTTAAGTAAGTTCCTTAGAATATTATTTTTCCTACTGAAAGTT

ACCACATGCGTCGTTGTTTATACAGTAATAGGAACAAGAAAAA

AGTCACCTAAGCTCACCCTCATCAATTGTGGAGTTCCTTTATAT

CCCATCTTCTCTCCAAACACATACGCA z38/42 esnRNA (DMD exon 51) (SEQ ID NO: 68)

ggagtTACCTCCAACATCAAGGAAGATGGCAGTAACCACAGGTTG

TGTCACCAGAGTAACAAATTTTTGGAGTAggctttctggctccttaccggaaa gcc

U7 termination (SEQ ID NO: 49)

CCTCTTATGATGTTTGTTGCCAATGATAGATTGTTTTCACTGTGC

AAAAATTATGGGTAGTTTTGGTGGTCTTGATGCAGTTGTAAGCT

TGGAG

U1 promoter (SEQ ID NO: 40)

TAAGGACCAGCTTCTTTGGGAGAGAACAGACGCAGGGGCGGGA

GGGAAAAAGGGAGAGGCAGACGTCACTTCCCCTTGGCGGCTCT

GGCAGCAGATTGGTCGGTTGAGTGGCAGAAAGGCAGACGGGG

ACTGGGCAAGGCACTGTCGGTGACATCACGGACAGGGCGACTT

CTATGTAGATGAGGCAGCGCAGAGGCTGACGTCTTCGCCACTT

GCTGCTTCACCACGAAGGAGTTCCCGTGCCCTGGGAGCGGGTT

CAGGACCGCTGATCGGAAGTGAGAATCCCAGCTGTGTGTCAGG

GCTGGAAAGGGCTCGGAGTGCGCGGGGCAAGTGACCGTGTGT

GTAAAGAGTGAGGCGTATGAGGCTGTGTCGGGGCAGAGGCacaa cgtttc

-continued z38/42 esnRNA (DMD exon 51)
(SEQ ID NO: 68)
ggagtTACCTCCAACATCAAGGAAGATGGCAGTAACCACAGGTTG TGTCACCAGAGTAACAAATTTTTGGAGTAggctttctggctccttaccggaaa gcc U1 termination
(SEQ ID NO: 50)
ACTTTCTGGAGTTTCAAAAACAGACTGTACGCCAAGGGTCATAT

CTTTTT

Buffer combo sequence
(SEQ ID NO: 144)
CAAACTACAGAGCCAAGTGCTATCCACAGAGAGCTTTCTGGGT

TGCCATCTCAAGCAGACTACAAGGCCATCAGCTCATACTCACA

ATTGACTTTGAGAGTCATTTTCCAATGCTCCTACACACCCCTTCT

TCACAATCCCCAACAAATCTGAGGCTGGAACTTGGTACCATAA

CAATCATTACATTATTTCACCAGAAGTACACCTTGCCTGGAAGA

TTGGCATTATAGCATCTTCTAACATTGTGAAAGTTAGTGACCAA

TGAGGAGATCCAAGTCAGTTCCAGTTGGATTTCTCTATACTCTA

TAATAAATATATATGGTGTCTTCAACAATAGGACTTTGCCATCC

AGTGATGCTAAAAATCAATAACAATGGCAATAACCTGCCCTGT

TTGGAAAGCCTCTGGCTTCCATGACTAACAATTCAAGGCAGGTC

TCCTATACCTAGTACTGAGATTTTTATTTGATAAACTATATCTTC

TGGGAGGAGAAGCATTGTTTGACCACATACGTGCTCTTTCAAA

GTTCTGTGTTTGAAGTTATGTTAGTAACAACTGATGCCCATCCT

GCAATGACAAATCCAATTCTCAGTGCAGCTCTCTGAAATAGTTT

TGCTTTCTCTCTCTAGGTCTGTTCTATACTCCTAACTCTCCAGGA

GTTTACAAGGAATAAAATCTCTTCCAAATGCTTTCTGTTGCAAC

AACTGGACCATACTGAAAGCTGAGGCCCACAATTGCAATCTAG

GTTAGCAGGTAATCATTGTTGGTGAGGTCCTCCCTTTCCCCAGG

CTCGTGTTTGTATTGGGGAGCAGGAAATTTTTGCTAGAGCAGCA

CTGCCATCTCTCTACACTCCACCTGATTGGTGGGATGGACCAGA

GAAATGGACATTCCCAACACAGTCCCTCCTTTCACATCTGCTCA

CCTGCCCACAGGATACTTTCCACCATGCATACTGGGCTCTGCAC

CAACCATTCAGCAGTGATGAAGAGGAAACTTGAACCCATGCAG

AGTACCTCTAGAGAAAAGTTTCTAAAGTTGGTTTTGCCTTGCTT

AGAAAGGAGGTCAAAGGTGAAGCCTAGGAGAAACATTCAGCA

ATGTTGCACAAAGACATGAGAATAAATGATTTTAGCATCCTGA

AATGAAGAGCATAGTGATCTCACCATAGCTACCCACCTACCCA

GAGAACTTCCAGGCTTTCACTGTCTCTTTTCTGAATCACCCACA

TTACAGAATATCAGTCATTGTGTAATTAGATAACAGATTGTGAG

GTGCCCAAACAGAAACAAACTTTACAGGAGGAGAGAGAAAT

CAAGGTGATGACTATGGAGAACAAAATGAGAAGGAGAGGTGG

AGTTCCTGCTGCATGAACACCTATCCTGCTATAGAGCCCATTTC

TTCCATAAATAATACAACTCTGTAACTCCATAGGTCAGAAAGA

```
AACAGTGTTCTGTGTCTTCCCATCTAGCACCACAAACCCCCACA

AGATTAATTTGTTTCTAGGGACCCTTAAATCTCTATCAAAATTC

TGGAAACCTCTACTTTAGAAAATCTTATATTTATTATTCAGGCT

ACTTTCCAGAGTGATAAGCTACTGAGTCTCCTAAGTGTCATCTA

TGGTACACAGGGATAAGATCAGGAATAAACCTGGG

ITR
                                                            (SEQ ID NO: 60)
aggaacccctagtgatggagttggccactccctctctgcgcgctcgctcgctcactgaggccgggcgac caaaggtcgcccgacgcccgggctttgcccggggcctcagtgagcgagcgagcgcgcagctgcct gcagg
```

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U1 promoter sequence, a CUG repeat targeting U7 esnRNA sequence, a U1 downstream terminator sequence, an eCMV promoter sequence, a sequence encoding GFP, a polyA sequence, and a second ITR sequence. In some aspects, a nucleic acid sequence encoding AAV vector A03681 encoding a CUG repeat targeting snRNA sequences comprises SEQ ID NO: 139.

A03681: pAAV(ssAAV)-U7 Promoter-zCUGx15-U7 Term_U1 Promoter-zCUGx15-U1 Term-eCMV-eGFP

```
ITR
                                                            (SEQ ID NO: 59)
cctgcaggcagctgcgcgctcgctcgctcactgaggccgcccgggcgtcgggcgacctttggtcgcccggcct cagtgagcgagcgagcgcgcagagagggagtggccaactccatcactagggggttcct U7 promoter
                                                            (SEQ ID NO: 39)
TACTGCCGAATCCAGGTCTCCGGGCTTAACAACAACGAAGGGGCTG

TGACTGGCTGCTTTCTCAACCAATCAGCACCGAACTCATTTGCATGG

GCTGAGAACAAATGTTCGCGAACTCTAGAAATGAATGACTTAAGTA

AGTTCCTTAGAATATTATTTTTCCTACTGAAAGTTACCACATGCGTCG

TTGTTTATACAGTAATAGGAACAAGAAAAAAGTCACCTAAGCTCAC

CCTCATCAATTGTGGAGTTCCTTTATATCCCATCTTCTCTCCAAACAC

ATACGCA zCUGx15 esnRNA
                                                            (SEQ ID NO: 65)
ggagtCAGCAGCAGCAGCAGCAGCAGCAGCAGCAGCAGCAGCAGCAG CAGAATTTTTGGAGTAggctttctggctccttaccggaaagcc U7 termination
                                                            (SEQ ID NO: 49)
CCTCTTATGATGTTTGTTGCCAATGATAGATTGTTTTCACTGTGCAAA

AATTATGGGTAGTTTTGGTGGTCTTGATGCAGTTGTAAGCTTGGAG

U1 promoter
                                                            (SEQ ID NO: 40)
TAAGGACCAGCTTCTTTGGGAGAGAACAGACGCAGGGGCGGGAGGG

AAAAAGGGAGAGGCAGACGTCACTTCCCCTTGGCGGCTCTGGCAGC

AGATTGGTCGGTTGAGTGGCAGAAAGGCAGACGGGGACTGGGCAAG

GCACTGTCGGTGACATCACGGACAGGGCGACTTCTATGTAGATGAG

GCAGCGCAGAGGCTGACGTCTTCGCCACTTGCTGCTTCACCACGAAG

GAGTTCCCGTGCCCTGGGAGCGGGTTCAGGACCGCTGATCGGAAGT

GAGAATCCCAGCTGTGTGTCAGGGCTGGAAAGGGCTCGGGAGTGCG
```

```
CGGGGCAAGTGACCGTGTGTGTAAAGAGTGAGGCGTATGAGGCTGT

GTCGGGGCAGAGGCacaacgtttc

ZCUGx15 esnRNA
                                                              (SEQ ID NO: 65)
ggagtCAGCAGCAGCAGCAGCAGCAGCAGCAGCAGCAGCAGCAGCAG CAGAATTTTTGGAGTAggctttctggctccttaccggaaagcc U1 termination
                                                              (SEQ ID NO: 50)
ACTTTCTGGAGTTTCAAAAACAGACTGTACGCCAAGGGTCATATCTT

TTT eCMV promoter
                                                              (SEQ ID NO: 62)
cgttacataacttacggtaaatggcccgcctggctgaccgcccaacgaccccgcccattgacgtcaataatgac gtatgttcccatagtaacgccaatagggactttccattgacgtcaatgggtggagtatttacggtaaactgcccactt ggcagtacatcaagtgtatcatatgccaagtacgccccctattgacgtcaatgacggtaaatggcccgcctggcatt atgcccagtacatgaccttatgggactttcctacttggcagtacatctacgtattagtcatcgctattaccatg eGFP
                                                              (SEQ ID NO: 63)
ATGgtgagcaagggcgaggagctgttcaccggggtggtgcccatcctggtcgagctggacggcgacgtaaa cggccacaagttcagcgtgtccggcgagggcgagggcgatgccacctacggcaagctgaccctgaagttcatct gcaccaccggcaagctgcccgtgccctggcccaccctcgtgaccaccctgacctacggcgtgcagtgcttcagc cgctaccccgaccacatgaagcagcacgacttcttcaagtccgccatgcccgaaggctacgtccaggagcgcac catcttcttcaaggacgacggcaactacaagacccgcgccgaggtgaagttcgagggcgacaccctggtgaacc gcatcgagctgaagggcatcgacttcaaggaggacggcaacatcctggggcacaagctggagtacaactacaa cagccacaacgtctatatcatggccgacaagcagaagaacggcatcaaggtgaacttcaagatccgccacaaca tcgaggacggcagcgtgcagctcgccgaccactaccagcagaacacccccatcggcgacggccccgtgctgc tgcccgacaaccactacctgagcacccagtccgcccctgagcaaagacccaacgagaagcgcgatcacatggt cctgctggagttcgtgaccgccgcgggatcactctcggcatggacgagctgtacaagTAA SV40 pA
                                                              (SEQ ID NO: 64)
aacttgtttattgcagcttataatggttacaaataaagcaatagcatcacaaatttcacaaataaagcatttttttcactg cattctagttgtggtttgtccaaactcatcaatgtatctta ITR
                                                              (SEQ ID NO: 60)
aggaacccctagtgatggagttggccactccctctctgcgcgctcgctcgctcactgaggccgggcgaccaaag gtcgcccgacgcccgggctttgcccgggggcctcagtgagcgagcgagcgcgcagctgcctgcagg
```

An exemplary AAV vector of the disclosure comprises from 5' to 3': a first inverted terminal repeat (ITR) sequence, a U1 promoter sequence, a CUG repeat targeting U7 esnRNA sequence, a U1 downstream terminator sequence, a buffer sequence, a U7 promoter sequence, a CUG repeat targeting U7 esnRNA sequence, a U7 downstream terminator sequence, an eCMV promoter sequence, a sequence encoding GFP, a polyA sequence, and a second ITR sequence. In some aspects, a nucleic acid sequence encoding AAV vector A03682 encoding a CUG repeat targeting snRNA sequences comprises SEQ ID NO: 140.

A03682: pAAV(ssAAV)-U1 Promoter-zCUGx15-U1 Term_U7 Promoter-zCUGx15-U7 Term-eCMV-eGFP

```
ITR
                                                              (SEQ ID NO: 59)
cctgcaggcagctgcgcgctcgctcgctcactgaggccgcccgggcgtcgggcgacctttggtcgcccggcc tcagtgagcgagcgagcgcgcagagagggagtggccaactccatcactaggggttcct U1 promoter
                                                              (SEQ ID NO: 40)
TAAGGACCAGCTTCTTTGGGAGAGAACAGACGCAGGGGCGGGAGG
```

```
GAAAAAGGGAGAGGCAGACGTCACTTCCCCTTGGCGGCTCTGGCAG

CAGATTGGTCGGTTGAGTGGCAGAAAGGCAGACGGGACTGGGCA

AGGCACTGTCGGTGACATCACGGACAGGGCGACTTCTATGTAGATG

AGGCAGCGCAGAGGCTGACGTCTTCGCCACTTGCTGCTTCACCACG

AAGGAGTTCCCGTGCCCTGGGAGCGGGTTCAGGACCGCTGATCGGA

AGTGAGAATCCCAGCTGTGTGTCAGGGCTGGAAAGGGCTCGGGAGT

GCGCGGGGCAAGTGACCGTGTGTGTAAAGAGTGAGGCGTATGAGG

CTGTGTCGGGGCAGAGGCacaacgtttc
```

ZCUGx15 esnRNA                                          (SEQ ID NO: 65)
```
ggagtCAGCAGCAGCAGCAGCAGCAGCAGCAGCAGCAGCAGCAGCAG CAGAATTTTTGGAGTAggctttctggctccttaccggaaagcc
```

U1 termination                                          (SEQ ID NO: 50)
```
ACTTTCTGGAGTTTCAAAAACAGACTGTACGCCAAGGGTCATATCTT

TTT
```

U7 promoter                                             (SEQ ID NO: 39)
```
AATCCAGGTCTCCGGGCTTAACAACAACGAAGGGGCTGTGACTGGC

TGCTTTCTCAACCAATCAGCACCGAACTCATTTGCATGGGCTGAGA

ACAAATGTTCGCGAACTCTAGAAATGAATGACTTAAGTAAGTTCCT

TAGAATATTATTTTTCCTACTGAAAGTTACCACATGCGTCGTTGTTT

ATACAGTAATAGGAACAAGAAAAAAGTCACCTAAGCTCACCCTCAT

CAATTGTGGAGTTCCTTTATATCCCATCTTCTCTCCAAACACATACG

CA
``` zCUGx15 esnRNA                                          (SEQ ID NO: 65)
```
ggagtCAGCAGCAGCAGCAGCAGCAGCAGCAGCAGCAGCAGCAGCAG CAGAATTTTTGGAGTAggctttctggctccttaccggaaagcc
```

U7 termination                                          (SEQ ID NO: 49)
```
CCTCTTATGATGTTTGTTGCCAATGATAGATTGTTTTCACTGTGCAA

AAATTATGGGTAGTTTTGGTGGTCTTGATGCAGTTGTAAGCTTGGAG
``` eCMV promoter                                           (SEQ ID NO: 62)
```
cgttacataacttacggtaaatggcccgcctggctgaccgcccaacgacccccgcccattgacgtcaataatgac gtatgttcccatagtaacgccaatagggactttccattgacgtcaatgggtggagtatttacggtaaactgcccactt ggcagtacatcaagtgtatcatatgccaagtacgccccctattgacgtcaatgacggtaaatggcccgcctggca ttatgcccagtacatgaccttatgggactttcctacttggcagtacatctacgtattagtcatcgctattaccatg
``` eGFP                                                    (SEQ ID NO: 63)
```
ATGgtgagcaagggcgaggagctgttcaccggggtggtgcccatcctggtcgagctggacggcgacgtaa acggccacaagttcagcgtgtccggcgagggcgagggcgatgccacctacggcaagctgaccctgaagttca tctgcaccaccggcaagctgcccgtgccctggcccaccctcgtgaccaccctgacctacggcgtgcagtgcttc agccgctaccccgaccacatgaagcagcacgacttcttcaagtccgccatgcccgaaggctacgtccaggagc gcaccatcttcttcaaggacgacggcaactacaagacccgcgccgaggtgaagttcgagggcgacaccctggt gaaccgcatcgagctgaagggcatcgacttcaaggaggacggcaacatcctggggcacaagctggagtacaa
```

-continued

```
ctacaacagccacaacgtctatatcatggccgacaagcagaagaacggcatcaaggtgaacttcaagatccgc cacaacatcgaggacggcagcgtgcagctcgccgaccactaccagcagaacaccccatcggcgacggccc cgtgctgctgcccgacaaccactacctgagcaccagtccgccctgagcaaagacccaacgagaagcgcga tcacatggtcctgctggagttcgtgaccgccgcgggatcactctcggcatggacgagctgtacaagTAA
```

SV40 pA (SEQ ID NO: 64)
```
aacttgtttattgcagcttataatggttacaaataaagcaatagcatcacaaatttcacaaataaagcattttttttcactg cattctagttgtggtttgtccaaactcatcaatgtatctta
```

ITR (SEQ ID NO: 60)
```
aggaaccccctagtgatggagttggccactccctctctgcgcgctcgctcgctcactgaggccgggcgaccaaa ggtcgcccgacgcccgggctttgcccgggggcctcagtgagcgagcgagcgcgcagctgcctgcagg
```

An exemplary AAV vector of the disclosure comprises from 5' to 3': a first inverted terminal repeat (ITR) sequence, a U7 promoter sequence, a non-targeting U7 esnRNA sequence, a U7 downstream terminator sequence, a buffer sequence, a U1 promoter sequence, a non-targeting U7 esnRNA sequence, a U1 downstream terminator sequence, an eCMV promoter sequence, a sequence encoding GFP, a polyA sequence, and a second ITR sequence. In some aspects, a nucleic acid sequence encoding AAV vector A03683 encoding a non-targeting snRNA sequences comprises SEQ ID NO: 141.

A03683: pAAV(ssAAV)-U7 Promoter-Znt-U7 Term_U1 Promoter-Znt-U1 Term-eCMV-eGFP

ITR (SEQ ID NO: 59)
```
cctgcaggcagctgcgcgctcgctcgctcactgaggccgcccgggcgtcgggcgacctttggtcgcccggcc tcagtgagcgagcgagcgcgcagagagggagtggccaactccatcactaggggttcct
```

U7 promoter (SEQ ID NO: 39)
```
TACTGCCGAATCCAGGTCTCCGGGCTTAACAACAACGAAGGGGCTG

TGACTGGCTGCTTTCTCAACCAATCAGCACCGAACTCATTTGCATGG

GCTGAGAACAAATGTTCGCGAACTCTAGAAATGAATGACTTAAGTA

AGTTCCTTAGAATATTATTTTTCCTACTGAAAGTTACCACATGCGTC

GTTGTTTATACAGTAATAGGAACAAGAAAAAAGTCACCTAAGCTCA

CCCTCATCAATTGTGGAGTTCCTTTATATCCCATCTTCTCTCCAAAC

ACATACGCA
``` z-nt esnRNA (SEQ ID NO: 66)
```
ggagtTCACCAGAAGCGTACCATACTCACGAAATTTTTGGAGTAggctttct ggctccttaccggaaagcc
```

U7 termination (SEQ ID NO: 49)
```
CCTCTTATGATGTTTGTTGCCAATGATAGATTGTTTTCACTGTGCAA

AAATTATGGGTAGTTTTGGTGGTCTTGATGCAGTTGTAAGCTTGGAG
```

U1 promoter (SEQ ID NO: 40)
```
TAAGGACCAGCTTCTTTGGGAGAGAACAGACGCAGGGGCGGGAGG

GAAAAAGGGAGAGGCAGACGTCACTTCCCCTTGGCGGCTCTGGCAG

CAGATTGGTCGGTTGAGTGGCAGAAAGGCAGACGGGGACTGGGCA

AGGCACTGTCGGTGACATCACGGACAGGGCGACTTCTATGTAGATG

AGGCAGCGCAGAGGCTGACGTCTTCGCCACTTGCTGCTTCACCACG

AAGGAGTTCCCGTGCCCTGGGAGCGGGTTCAGGACCGCTGATCGGA

AGTGAGAATCCCAGCTGTGTGTCAGGGCTGGAAAGGGCTCGGGAGT
```

```
GCGCGGGGCAAGTGACCGTGTGTGTAAAGAGTGAGGCGTATGAGG

CTGTGTCGGGGCAGAGGCacaacgtttc
```

Z-nt esnRNA (SEQ ID NO: 66)

```
ggagtTCACCAGAAGCGTACCATACTCACGAAATTTTTGGAGTAggctttct ggctccttaccggaaagcc
```

U1 termination (SEQ ID NO: 50)

```
ACTTTCTGGAGTTTCAAAAACAGACTGTACGCCAAGGGTCATATCTT

TTT
``` eCMV promoter (SEQ ID NO: 62)

```
cgttacataacttacggtaaatggcccgcctggctgaccgcccaacgaccccgcccattgacgtcaataatgac gtatgttcccatagtaacgccaatagggactttccattgacgtcaatgggtggagtatttacggtaaactgcccactt ggcagtacatcaagtgtatcatatgccaagtacgccccctattgacgtcaatgacggtaaatggcccgcctggca ttatgcccagtacatgaccttatgggactttcctacttggcagtacatctacgtattagtcatcgctattaccatg
``` eGFP (SEQ ID NO: 63)

```
ATGgtgagcaagggcgaggagctgttcaccggggtggtgcccatcctggtcgagctggacggcgacgtaa acggccacaagttcagcgtgtccggcgagggcgagggcgatgccacctacggcaagctgaccctgaagttca tctgcaccaccggcaagctgcccgtgccctggcccaccctcgtgaccaccctgacctacggcgtgcagtgcttc agccgctaccccgaccacatgaagcagcacgacttcttcaagtccgccatgcccgaaggctacgtccaggagc gcaccatcttcttcaaggacgacggcaactacaagacccgcgccgaggtgaagttcgagggcgacaccctggt gaaccgcatcgagctgaagggcatcgacttcaaggaggacggcaacatcctggggcacaagctggagtacaa ctacaacagccacaacgtctatatcatggccgacaagcagaagaacggcatcaaggtgaacttcaagatccgc cacaacatcgaggacggcagcgtgcagctcgccgaccactaccagcagaacacccccatcggcgacggccc cgtgctgctgcccgacaaccactacctgagcacccagtccgccctgagcaaagaccccaacgagaagcgcga tcacatggtcctgctggagttcgtgaccgccgccgggatcactctcggcatggacgagctgtacaagTAA
```

SV40 pA (SEQ ID NO: 64)

```
aacttgtttattgcagcttataatggttacaaataaagcaatagcatcacaaatttcacaaataaagcatttttttcactg cattctagttgtggtttgtccaaactcatcaatgtatctta
```

ITR (SEQ ID NO: 60)

```
Aggaacccctagtgatggagttggccactccctctctgcgcgctcgctcgctcactgaggccgggcgaccaaa ggtcgcccgacgcccgggctttgcccgggggcctcagtgagcgagcgagcgcgcagctgcctgcagg
```

An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U1 promoter sequence, a CUG repeat targeting U7 esnRNA sequence, a U1 downstream terminator sequence, and a second ITR sequence. In some aspects, a nucleic acid sequence encoding AAV vector A03684 encoding a CUG repeat targeting snRNA sequences comprises SEQ ID NO: 142.

A03864: pAAV(ssAAV)-U7 Promoter-zCUGx15-U7 Term_U1 Promoter-zCUGx15-U1 Term (Minus GFP—Derivative of 3681)

ITR (SEQ ID NO: 59)

```
cctgcaggcagctgcgcgctcgctcgtcactgaggccgcccgggcgtcgggcgaccttggtcgcccggcc tcagtgagcgagcgagcgcgcagagagggagtggccaactccatcactagggttcct
```

U7 promoter (SEQ ID NO: 39)

TACTGCCGAATCCAGGTCTCCGGGCTTAACAACAACGAAGGGGCTG

TGACTGGCTGCTTTCTCAACCAATCAGCACCGAACTCATTTGCATGG

GCTGAGAACAAATGTTCGCGAACTCTAGAAATGAATGACTTAAGTA

AGTTCCTTAGAATATTATTTTTCCTACTGAAAGTTACCACATGCGTC

GTTGTTTATACAGTAATAGGAACAAGAAAAAAGTCACCTAAGCTCA

CCCTCATCAATTGTGGAGTTCCTTTATATCCCATCTTCTCTCCAAAC

ACATACGCA

ZCUGx15 esnRNA (SEQ ID NO: 65)

ggagtCAGCAGCAGCAGCAGCAGCAGCAGCAGCAGCAGCAGCAGCAG

CAGAATTTTTGGAGTAggctttctggctccttaccggaaagcc

U7 termination (SEQ ID NO: 49)

CCTCTTATGATGTTTGTTGCCAATGATAGATTGTTTTCACTGTGCAA

AAATTATGGGTAGTTTTGGTGGTCTTGATGCAGTTGTAAGCTTGGAG

U1 promoter (SEQ ID NO: 40)

TAAGGACCAGCTTCTTTGGGAGAGAACAGACGCAGGGGCGGGAGG

GAAAAAGGGAGAGGCAGACGTCACTTCCCCTTGGCGGCTCTGGCAG

CAGATTGGTCGGTTGAGTGGCAGAAAGGCAGACGGGGACTGGGCA

AGGCACTGTCGGTGACATCACGGACAGGGCGACTTCTATGTAGATG

AGGCAGCGCAGAGGCTGACGTCTTCGCCACTTGCTGCTTCACCACG

AAGGAGTTCCCGTGCCCTGGGAGCGGGTTCAGGACCGCTGATCGGA

AGTGAGAATCCCAGCTGTGTGTCAGGGCTGGAAAGGGCTCGGGAGT

GCGCGGGCAAGTGACCGTGTGTGTAAAGAGTGAGGCGTATGAGG

CTGTGTCGGGGCAGAGGCacaacgtttc

ZCUGx15 esnRNA (SEQ ID NO: 65)

ggagtCAGCAGCAGCAGCAGCAGCAGCAGCAGCAGCAGCAGCAGCAG

CAGAATTTTTGGAGTAggctttctggctccttaccggaaagcc

U1 termination (SEQ ID NO: 50)

ACTTTCTGGAGTTTCAAAAACAGACTGTACGCCAAGGGTCATATCTT

TTT

ITR (SEQ ID NO: 60)

aggaacccctagtgatggagttggccactccctctctgcgcgctcgctcgctcactgaggccgggcgaccaaa ggtcgcccgacgcccgggctttgcccgggggcctcagtgagcgagcgagcgcgcagctgcctgcagg An exemplary AAV vector of the disclosure comprises from 5' to 3': a first inverted terminal repeat (ITR) sequence, a U7 promoter sequence, a CUG repeat targeting U7 esnRNA sequence, a U7 downstream terminator sequence, a buffer sequence, a U1 promoter sequence, a CUG repeat targeting U7 esnRNA sequence, a U1 downstream terminator sequence, and a second ITR sequence. In some aspects, a nucleic acid sequence encoding AAV vector A04233 encoding a CUG repeat targeting snRNA sequences comprises SEQ ID NO: 143.

A04233: pAAV(scAAV)-U7promoter-zCUGx15-U7termination-U1promoter-zCUGx15-U1termination (Derivative of A03681 No GFP in scAAV)

ITR (SEQ ID NO: 59)

cctgcaggcagctgcgcgctcgctcgctcactgaggccgcccggcgtc gggcgacctttggtcgcccggcctcagtgagcgagcgagcgcgcagaga gggagtggccaactccatcactagggggttcct -continued U7 promoter
(SEQ ID NO: 39)
TACTGCCGAATCCAGGTCTCCGGGCTTAACAACAACGAAGGGGCTG

TGACTGGCTGCTTTCTCAACCAATCAGCACCGAACTCATTTGCATGG

GCTGAGAACAAATGTTCGCGAACTCTAGAAATGAATGACTTAAGTA

AGTTCCTTAGAATATTATTTTTCCTACTGAAAGTTACCACATGCGTC

GTTGTTTATACAGTAATAGGAACAAGAAAAAAGTCACCTAAGCTCA

CCCTCATCAATTGTGGAGTTCCTTTATATCCCATCTTCTCTCCAAAC

ACATACGCA zCUGx15 esnRNA
(SEQ ID NO: 65)
ggagtCAGCAGCAGCAGCAGCAGCAGCAGCAGCAGCAGCAGCAGCAG CAGAATTTTTGGAGTAggctttctggctccttaccggaaagcc U7 termination
(SEQ ID NO: 49)
CCTCTTATGATGTTTGTTGCCAATGATAGATTGTTTTCACTGTGCAA

AAATTATGGGTAGTTTTGGTGGTCTTGATGCAGTTGTAAGCTTGGAG

U1 promoter
(SEQ ID NO: 40)
TAAGGACCAGCTTCTTTGGGAGAGAACAGACGCAGGGGCGGGAGG

GAAAAAGGGAGAGGCAGACGTCACTTCCCCTTGGCGGCTCTGGCAG

CAGATTGGTCGGTTGAGTGGCAGAAAGGCAGACGGGGACTGGGCA

AGGCACTGTCGGTGACATCACGGACAGGGCGACTTCTATGTAGATG

AGGCAGCGCAGAGGCTGACGTCTTCGCCACTTGCTGCTTCACCACG

AAGGAGTTCCCGTGCCCTGGGAGCGGGTTCAGGACCGCTGATCGGA

AGTGAGAATCCCAGCTGTGTGTCAGGGCTGGAAAGGGCTCGGGAGT

GCGCGGGGCAAGTGACCGTGTGTGTAAAGAGTGAGGCGTATGAGG

CTGTGTCGGGGCAGAGGCacaacgtttc

ZCUGx15 esnRNA
(SEQ ID NO: 65)
ggagtCAGCAGCAGCAGCAGCAGCAGCAGCAGCAGCAGCAGCAGCAG

CAGAATTTTTGGAGTAggctttctggctccttaccggaaagcc

U1 termination
(SEQ ID NO: 50)
ACTTTCTGGAGTTTCAAAAACAGACTGTACGCCAAGGGTCATATCTT

TTT mITR
(SEQ ID NO: 61)
CCACTCCCTCTCTGCGCGCTCGCTCGCTCACTGAGGCCGGGCGACCA

AAGGTCGCCCGACGCCCGGGCTTTGCCCGGGCGGCCTCAGTGAGCG

AGCGAGCGCGCAGAGAGGGA

Promoter Sequences

Gene therapy and RNA-targeting snRNA gene therapy compositions of the disclosure comprise promoter sequences derived from an snRNA.

A "promoter" is a control sequence that is a region of a polynucleotide sequence at which initiation and rate of transcription are controlled. It may contain genetic elements at which regulatory proteins and molecules may bind such as RNA polymerase and other transcription factors.

In some embodiments of the compositions and methods of the disclosure, an expression vector, viral vector or non-viral vector provided herein, includes without limitation, an expression control element. An "expression control element" as used herein refers to any sequence that regulates the expression of a coding sequence, such as a gene. Exemplary expression control elements include but are not limited to promoters, enhancers, microRNAs, post-transcriptional regulatory elements, polyadenylation signal sequences, and introns. Expression control elements may be constitutive, inducible, repressible, or tissue-specific, for example. A "promoter" is a control sequence that is a region of a polynucleotide sequence at which initiation and rate of transcription are controlled. It may contain genetic elements at which regulatory proteins and molecules may bind such as RNA polymerase and other transcription factors. An "enhancer" is a region of DNA that can be bound by activating proteins to increase the likelihood or frequency of transcription.

In some embodiments of the compositions and methods of the disclosure, an expression vector, viral vector or non-viral vector provided herein, includes without limitation, vector elements such as a buffer sequence derived human genomic sequences downstream from an snRNA and as such will have the capability to encoding multiple snRNAs from a single construct.

In some embodiments, with the incorporation of coding sequences into the compositions disclosed herein, multicistronic vectors can simultaneously express two or more separate proteins from the same mRNA. The two strategies most widely used for constructing multicistronic configurations are through the use of an IRES or a 2A self-cleaving site. An "IRES" refers to an internal ribosome entry site or portion thereof of viral, prokaryotic, or eukaryotic origin which are used within polycistronic vector constructs. In some embodiments, an IRES is an RNA element that allows for translation initiation in a cap-independent manner. The term "self-cleaving peptides" or "sequences encoding self-cleaving peptides" or "2A self-cleaving site" refer to linking sequences which are used within vector constructs to incorporate sites to promote ribosomal skipping and thus to generate two polypeptides from a single promoter, such self-cleaving peptides include without limitation, T2A, and P2A peptides or other sequences encoding the self-cleaving peptides.

In another embodiment, the vector configurations can comprise linker(s), signal sequence(s), and/or tag(s).

In some embodiments, the vector is a viral vector. In some embodiments, the vector is an adenoviral vector, an adeno-associated viral (AAV) vector, or a lentiviral vector. In some embodiments, the vector is a retroviral vector, an adenoviral/retroviral chimera vector, a herpes simplex viral I or II vector, a parvoviral vector, a reticuloendotheliosis viral vector, a poliovirol vector, a papillomaviral vector, a vaccinia viral vector, or any hybrid or chimeric vector incorporating favorable aspects of two or more viral vectors. In some embodiments, the vector further comprises one or more expression control elements operably linked to the polynucleotide. In some embodiments, the vector further comprises one or more selectable markers. In some embodiments, the AAV vector has low toxicity. In some embodiments, the AAV vector does not incorporate into the host genome, thereby having a low probability of causing insertional mutagenesis. In some embodiments, the AAV vector can encode a range of total polynucleotides from 4.5 kb to 4.75 kb. In some embodiments, exemplary AAV vectors that may be used in any of the herein described compositions, systems, methods, and kits can include an AAV1 vector, a modified AAV1 vector, an AAV2 vector, a modified AAV2 vector, an AAV2-Tyr mutant vector, an AAV3 vector, a modified AAV3 vector, an AAV4 vector, a modified AAV4 vector, an AAV5 vector, a modified AAV5 vector, an AAV6 vector, a modified AAV6 vector, an AAV7 vector, a modified AAV7 vector, an AAV8 vector, an AAVrh8 vector, an AAV9 vector, an AAV.rh10 vector, a modified AAV.rh10 vector, an AAVrh.74, an AAV.rh32/33 vector, a modified AAV.rh32/33 vector, an AAV.rh43 vector, a modified AAV.rh43 vector, an AAV.rh64R1 vector, and a modified AAV.rh64R1 vector, an AAV-Tyr mutant vector, AAV-Tyr-Ser mutant vector, AAV-Tyr-Ser-Thr mutant vector and any combinations or equivalents thereof. In some embodiments, the lentiviral vector is an integrase-competent lentiviral vector (ICLV). In some embodiments, the lentiviral vector can refer to the transgene plasmid vector as well as the transgene plasmid vector in conjunction with related plasmids (e.g., a packaging plasmid, a rev expressing plasmid, an envelope plasmid) as well as a lentiviral-based particle capable of introducing exogenous nucleic acid into a cell through a viral or viral-like entry mechanism.

Lentiviral vectors are well-known in the art (see, e.g., Trono D. (2002) Lentiviral vectors, New York: Spring-Verlag Berlin Heidelberg and Durand et al. (2011) Viruses 3(2):132-159 doi: 10.3390/v3020132). In some embodiments, exemplary lentiviral vectors that may be used in any of the herein described compositions, systems, methods, and kits can include a human immunodeficiency virus (HIV) 1 vector, a modified human immunodeficiency virus (HIV) 1 vector, a human immunodeficiency virus (HIV) 2 vector, a modified human immunodeficiency virus (HIV) 2 vector, a sooty mangabey simian immunodeficiency virus (SIVsm) vector, a modified sooty mangabey simian immunodeficiency virus (SIVsm) vector, a African green monkey simian immunodeficiency virus (SIVAGM) vector, a modified African green monkey simian immunodeficiency virus (SIVAGM) vector, an equine infectious anemia virus (EIAV) vector, a modified equine infectious anemia virus (EIAV) vector, a feline immunodeficiency virus (FIV) vector, a modified feline immunodeficiency virus (FIV) vector, a Visna/maedi virus (VNV/VMV) vector, a modified Visna/maedi virus (VNV/VMV) vector, a caprine arthritis-encephalitis virus (CAEV) vector, a modified caprine arthritis-encephalitis virus (CAEV) vector, a bovine immunodeficiency virus (BIV), or a modified bovine immunodeficiency virus (BIV).

Nucleic Acids

An NOI (nucleotide sequence of interest) includes, without limitation, any nucleotide sequence or transgene capable of being delivered by a vector. NOIs can be synthetic, derived from naturally occurring DNA or RNA, codon optimized, recombinant RNA/DNA, cDNA, partial genomic DNA, and/or combinations thereof. The NOI can be a coding region or partial coding region, but need not be a coding region. An NOI can be RNA/DNA in a sense or anti-sense orientation. An NOI can be an snRNA. NOIs are also referred herein, without limitation, as transgenes, heterologous sequences, genes, therapeutic genes. An NOI may also encode an RNA (ribonucleoprotein complex) a POI (protein of interest), a partial POI, a mutated version or variant of a POI. A POI may be analogous to or correspond to a wild-type protein. A POI may also be a fusion protein or ribonucleoprotein complex such as an snRNP. In some aspects, RNA sequences disclosed herein may be represented as DNA sequences and it is within the ability of the skilled artisan to derive the sequence of an RNA sequence from a DNA sequence.

Codon Optimization

In some embodiments, NOIs or transgenes or GOIs such as nucleic acid sequences encoding RNA-targeting snRNAs of the disclosure are codon optimized nucleic acid sequences. In some embodiments, the codon optimized sequence exhibits at least 5%, at least 10%, at least 20%, at least 30%, at least 50%, at least 75%, at least 100%, at least 200%, at least 300%, at least 500%, or at least 1000% increased transcription or translation in a human subject relative to a wild-type or non-codon optimized nucleic acid sequence.

In some aspects, a codon optimized nucleic acid sequence exhibits increased stability. In some aspects, a codon optimized nucleic acid sequence exhibits increased stability through increased resistance to hydrolysis. In some embodiments, the codon optimized sequence exhibits at least 5%, at least 10%, at least 20%, at least 30%, at least 50%, at least 75%, at least 100%, at least 200%, at least 300%, at least 500%, or at least 1000% increased stability relative to a wild-type or non-codon optimized nucleic acid sequence. In some embodiments, the codon optimized sequence exhibits at least 5%, at least 10%, at least 20%, at least 30%, at least 50%, at least 75%, at least 100%, at least 200%, at least 300%, at least 500%, or at least 1000% increased resistance to hydrolysis in a human subject relative to a wild-type or non-codon optimized nucleic acid sequence.

In some aspects, a codon optimized nucleic acid sequence can comprise no donor splice sites. In some aspects, a codon optimized nucleic acid sequence can comprise no more than about one, or about two, or about three, or about four, or about five, or about six, or about seven, or about eight, or about nine, or about ten donor splice sites. In some aspects, a codon optimized nucleic acid sequence comprises at least one, or at least two, or at least three, or at least four, or at least five, or at least six, or at least seven, or at least eight, or at least nine, or at least ten fewer donor splice sites as compared to a non-codon optimized nucleic acid sequence.

Without wishing to be bound by theory, the removal of donor splice sites in the codon optimized nucleic acid sequence can unexpectedly and unpredictably increase expression of protein of interest in vivo, as cryptic splicing is prevented. Moreover, cryptic splicing may vary between different subjects, meaning that the expression level of a protein comprising donor splice sites may unpredictably vary between different subjects. Such unpredictability is unacceptable in the context of human therapy. Accordingly, the codon optimized nucleic acid sequences which lacks donor splice sites, unexpectedly and surprisingly allows for increased expression of the protein in human subjects and regularizes expression of the protein across different human subjects.

In some aspects, a codon optimized nucleic acid sequence can have a GC content that differs from the GC content of the non-codon optimized nucleic acid sequence encoding the RNA-targeting snRNA. In some aspects, the GC content of a codon optimized nucleic acid sequence is more evenly distributed across the entire nucleic acid sequence, as compared to the non-codon optimized nucleic acid sequence.

Without wishing to be bound by theory, by more evenly distributing the GC content across the entire nucleic acid sequence, the codon optimized nucleic acid sequence exhibits a more uniform melting temperature ("Tm") across the length of the transcript. The uniformity of melting temperature results unexpectedly in increased expression of the codon optimized nucleic acid in a human subject, as transcription and/or translation of the nucleic acid sequence occurs with less stalling of the polymerase and/or ribosome.

In some aspects, a codon optimized nucleic acid sequence can have fewer repressive microRNA target binding sites as compared to the non-codon optimized nucleic acid sequence. In some aspects, a codon optimized nucleic acid sequence can have at least one, or at least two, or at least three, or at least four, or at least five, or at least six, or at least seven, or at least eight, or at least nine, or at least ten, or at least ten fewer repressive microRNA target binding sites as compared to the non-codon optimized nucleic acid sequence.

Without wishing to be bound by theory, by having fewer repressive microRNA target binding sites, the codon optimized nucleic acid sequence unexpectedly exhibits increased expression in a human subject.

Provided herein are the nucleic acid sequences encoding the gene therapy compositions or RNA-targeting snRNA systems for use in gene transfer and expression techniques described herein. It should be understood, although not always explicitly stated that the sequences provided herein can be used to provide the expression product as well as substantially identical sequences that encode an RNA or express and produce a protein that has the same biological properties. These "biologically equivalent" or "biologically active" or "equivalent" polypeptides are encoded by equivalent polynucleotides as described herein. They may possess at least 60%, or alternatively, at least 65%, or alternatively, at least 70%, or alternatively, at least 75%, or alternatively, at least 80%, or alternatively at least 85%, or alternatively at least 90%, or alternatively at least 95% or alternatively at least 98%, identical primary amino acid sequence to the reference polypeptide when compared using sequence identity methods run under default conditions. Specific polypeptide sequences are provided as examples of particular embodiments. Modifications to the sequences to amino acids with alternate amino acids that have similar charge. Additionally, an equivalent polynucleotide is one that hybridizes under stringent conditions to the reference polynucleotide or its complement or in reference to a polypeptide, a polypeptide encoded by a polynucleotide that hybridizes to the reference encoding polynucleotide under stringent conditions or its complementary strand. Alternatively, an equivalent polypeptide or protein is one that is expressed from an equivalent polynucleotide.

The NOIs or nucleic acid sequences (e.g., polynucleotide sequences) disclosed herein may be codon-optimized which is a technique well known in the art. Codon optimization refers to the fact that different cells differ in their usage of particular codons. This codon bias corresponds to a bias in the relative abundance of particular tRNAs in the cell type. By altering the codons in the sequence to match with the relative abundance of corresponding tRNAs, it is possible to increase expression. It is also possible to decrease expression by deliberately choosing codons for which the corresponding tRNAs are known to be rare in a particular cell type. Codon usage tables are known in the art for mammalian cells, as well as for a variety of other organisms. Based on the genetic code, nucleic acid sequences coding for, e.g., an esnRNA, esnRNA can be generated. In some embodiments, such a sequence is optimized for expression in a host or target cell, such as a host cell used to express the esnRNA or a cell in which the disclosed methods are practiced (such as in a mammalian cell, e.g., a human cell). Codon preferences and codon usage tables for a particular species can be used to engineer isolated nucleic acid molecules encoding an esnRNA that takes advantage of the codon usage preferences of that particular species. For example, the esnRNA disclosed herein can be designed to have codons that are preferentially used by a particular organism of interest. In one example, an esnRNA nucleic acid sequence is optimized for expression in human cells, such as one having at least 70%, at least 80%, at least 85%, at least 90%, at least 92%, at least 95%, at least 98%, or at least 99% sequence identity to its corresponding wild-type or originating nucleic acid sequence. In some embodiments, an isolated nucleic acid molecule encoding at least one esnRNA (which can be part of a vector) includes at least one esnRNA coding sequence that is codon optimized for expression in a eukaryotic cell, or at least one esnRNA coding sequence codon optimized for expression in a human cell. In one embodiment, such a codon optimized esnRNA coding sequence has at least 80%, at least 85%, at least 90%, at least 92%, at least 95%, at least 96%, at least 97%, at least 98%, at least 99%, or 100% sequence identity to its corresponding wild-type or originating sequence. In another embodiment, a eukaryotic cell codon optimized nucleic acid sequence encodes esnRNA having at least 85%, at least 90%, at least 92%, at least 95%, at least 96%, at least 97%, at least 98%, at least 99%, or 100% sequence identity to its corresponding wild-type or originating sequence. In another embodiment, a variety of clones containing functionally equivalent nucleic acids may be routinely generated, such as nucleic acids which differ in sequence but which encode the same esnRNA sequence. Silent mutations in the coding sequence result from the degeneracy (i.e., redundancy) of the genetic code, whereby more than one codon can encode the same amino acid residue. Thus, for example, leucine can be encoded by CTT, CTC, CTA, CTG, TTA, or TTG; serine can be encoded by TCT, TCC, TCA, TCG, AGT, or AGC; asparagine can be encoded by AAT or AAC; aspartic acid can be encoded by GAT or GAC; cysteine can be encoded by TGT or TGC; alanine can be encoded by GCT, GCC, GCA, or GCG; glutamine can be encoded by CAA or CAG; tyrosine can be encoded by TAT or TAC; and isoleucine can be encoded by ATT, ATC, or ATA. Tables showing the standard genetic code can be found in various sources (see, for example, Stryer, 1988, Biochemistry, 3.sup.rd Edition, W.H. 5 Freeman and Co., NY).

"Hybridization" refers to a reaction in which one or more polynucleotides react to form a complex that is stabilized via hydrogen bonding between the bases of the nucleotide residues. The hydrogen bonding may occur by Watson-Crick base pairing, Hoogstein binding, or in any other sequence-specific manner. The complex may comprise two strands forming a duplex structure, three or more strands forming a multi-stranded complex, a single self-hybridizing strand, or any combination of these. A hybridization reaction may constitute a step in a more extensive process, such as the initiation of a PC reaction, or the enzymatic cleavage of a polynucleotide by a ribozyme.

Examples of stringent hybridization conditions include: incubation temperatures of about 25° C. to about 37° C.; hybridization buffer concentrations of about 6×SSC to about 10×SSC; formamide concentrations of about 0% to about 25%; and wash solutions from about 4×SSC to about 8×SSC. Examples of moderate hybridization conditions include: incubation temperatures of about 40° C. to about 50° C.; buffer concentrations of about 9×SSC to about 2×SSC; formamide concentrations of about 30% to about 50%; and wash solutions of about 5×SSC to about 2×SSC. Examples of high stringency conditions include: incubation temperatures of about 55° C. to about 68° C.; buffer concentrations of about 1×SSC to about 0.1×SSC; formamide concentrations of about 55% to about 75%; and wash solutions of about 1×SSC, 0.1×SSC, or deionized water. In general, hybridization incubation times are from 5 minutes to 24 hours, with 1, 2, or more washing steps, and wash incubation times are about 1, 2, or 15 minutes. SSC is 0.15 M NaCl and 15 mM citrate buffer. It is understood that equivalents of SSC using other buffer systems can be employed.

"Homology" or "identity" or "similarity" refers to sequence similarity between two peptides or between two nucleic acid molecules. Homology can be determined by comparing a position in each sequence which may be aligned for purposes of comparison. When a position in the compared sequence is occupied by the same base or amino acid, then the molecules are homologous at that position. A degree of homology between sequences is a function of the number of matching or homologous positions shared by the sequences. An "unrelated" or "non-homologous" sequence shares less than 40% identity, or alternatively less than 25% identity, with one of the sequences of the present invention.

Cells

In some embodiments of the compositions and methods of the disclosure, a cell of the disclosure is a prokaryotic cell.

In some embodiments of the compositions and methods of the disclosure, a cell of the disclosure is a eukaryotic cell. In some embodiments, the cell is a mammalian cell. In some embodiments, the cell is a bovine, murine, feline, equine, porcine, canine, simian, or human cell. In some embodiments, the cell is a non-human mammalian cell such as a non-human primate cell.

In some embodiments, a cell of the disclosure is a somatic cell. In some embodiments, a cell of the disclosure is a germline cell. In some embodiments, a germline cell of the disclosure is not a human cell.

In some embodiments of the compositions and methods of the disclosure, a cell of the disclosure is a stem cell. In some embodiments, a cell of the disclosure is an embryonic stem cell. In some embodiments, an embryonic stem cell of the disclosure is not a human cell. In some embodiments, a cell of the disclosure is a multipotent stem cell or a pluripotent stem cell. In some embodiments, a cell of the disclosure is an adult stem cell. In some embodiments, a cell of the disclosure is an induced pluripotent stem cell (iPSC). In some embodiments, a cell of the disclosure is a hematopoietic stem cell (HSC).

In some embodiments of the compositions and methods of the disclosure, a somatic cell of the disclosure is a neuronal cell. In one embodiment, a cell or cells of a patient treated with compositions disclosed herein include, without limitation, central nervous system (neurons), peripheral nervous system (neurons), peripheral motor neurons, and/or sensory neurons. In one embodiment, a neuronal cell is a glial cell.

In some embodiments of the compositions and methods of the disclosure, a somatic cell of the disclosure is a fibroblast or an epithelial cell. In some embodiments, an epithelial cell of the disclosure forms a squamous cell epithelium, a cuboidal cell epithelium, a columnar cell epithelium, a stratified cell epithelium, a pseudostratified columnar cell epithelium or a transitional cell epithelium. In some embodiments, an epithelial cell of the disclosure forms a gland including, but not limited to, a pineal gland, a thymus gland, a pituitary gland, a thyroid gland, an adrenal gland, an apocrine gland, a holocrine gland, a merocrine gland, a serous gland, a mucous gland and a sebaceous gland. In some embodiments, an epithelial cell of the disclosure contacts an outer surface of an organ including, but not limited to, a lung, a spleen, a stomach, a pancreas, a bladder, an intestine, a kidney, a gallbladder, a liver, a larynx or a pharynx. In some embodiments, an epithelial cell of the disclosure contacts an outer surface of a blood vessel or a vein.

In some embodiments of the disclosure, a somatic cell is an ocular cell. An ocular cell includes, without limitation, corneal epithelial cells, keratyocytes, retinal pigment epithelial (RPE) cells, lens epithelial cells, iris pigment epithelial cells, conjunctival fibroblasts, non-pigmented ciliary epithelial cells, trabecular meshwork cells, ocular choroid fibroblasts, conjunctival epithelial cells, In some embodiments, an ocular cell is a retinal cell or a corneal cell. In one embodiment, a retinal cell is a photoreceptor cell or a retinal pigment epithelial cell. In another embodiment, a retinal cell is a ganglion cell, an amacrine cell, a bipolar cell, a horizontal cell, a Müller glial cell, a rod cell, or a cone cell.

In some embodiments of the compositions and methods of the disclosure, a somatic cell of the disclosure is a primary cell.

In some embodiments of the compositions and methods of the disclosure, a somatic cell of the disclosure is a cultured cell.

In some embodiments of the compositions and methods of the disclosure, a somatic cell of the disclosure is in vivo, in vitro, ex vivo or in situ.

In some embodiments of the compositions and methods of the disclosure, a somatic cell of the disclosure is autologous or allogeneic.

Methods of Use

The disclosure provides a method of encoding an RNA or expressing an NOI in a cell using the snRNA systems disclosed herein. In one embodiment, the disclosure provides a method of modifying an RNA or the activity of a protein encoded by an RNA molecule comprising contacting the composition of the disclosure and the target RNA molecule under conditions suitable for binding to the RNA molecule.

The disclosure provides a method of modifying the level of expression of an RNA molecule of the disclosure or a protein encoded by the RNA molecule comprising contacting the composition of the disclosure and a cell comprising the RNA molecule under conditions suitable for binding to the RNA molecule. In some embodiments, the cell is in vivo, in vitro, ex vivo or in situ. In some embodiments, the composition of the disclosure comprises a vector comprising snRNA sequences. In some embodiments, the vector is an AAV.

The disclosure provides a method of modifying the level of expression of an RNA molecule of the disclosure or a protein encoded by the RNA molecule comprising contacting the composition of the disclosure and the RNA molecule under conditions suitable for knocking down, blocking, splicing, multi-targeting, or editing the target RNA. In some embodiments, the vector is an AAV.

The disclosure provides a method of modifying a target RNA or an activity of a protein encoded by an RNA molecule comprising contacting the composition and a cell comprising the RNA molecule under conditions suitable knocking down, blocking, splicing, multi-targeting, or editing the target RNA. In some embodiments, the cell is in vivo, in vitro, ex vivo or in situ. In some embodiments, the composition comprises a vector comprising the snRNA sequences disclosed herein. In some embodiments, the vector is an AAV.

The disclosure provides a method of treating a disease or disorder comprising administering to a subject a therapeutically effective amount of an snRNA composition of the disclosure.

The disclosure provides a method of treating a disease in a patient in need of such treatment comprising administering to the patient a therapeutically effective amount of an snRNA composition of the disclosure, wherein the composition comprises a vector comprising snRNA sequences disclosed herein, wherein the composition modifies, reduces, destroys, knocks down or ablates a level of expression of a toxic repeat RNA (compared to the level of expression of a toxic repeat RNA treated with a non-targeting (NT) control or compared to no treatment). In another embodiment, the level of reduction is 1-fold or greater. In another embodiment, the level of reduction is 2-fold, 3-fold, 4-fold, 5-fold, 6-fold, 7-fold, 8-fold, 9-fold or 10-fold. In another embodiment, the level of reduction is 10-fold or greater. In another embodiment, the level of reduction is between 10-fold and 20-fold. In another embodiment, the level of reduction is 11-fold, 12-fold, 13-fold, 14-fold, 15-fold, 16-fold, 17-fold, 18-fold, 19-fold, or 20-fold. In another embodiment, the gene therapy compositions disclosed herein when administered to a patient lead to 20%-100% destruction of the toxic repeat RNA. In one embodiment, the % elimination of the toxic repeat RNA is any of 20-99%, 25%-99%, 50%-99%, 80%-99%, 90%-99%, 95%-99%. In one embodiment, the % elimination is 90%, 91%, 92%, 93%, 94%, 95%, 96%, 97%, 98%, or 99%. In another embodiment, % elimination is complete elimination or 100% elimination of the toxic repeat RNA.

The disclosure provides a method of treating a disease or disorder in a subject comprising administering an RNA-targeting nucleic acid molecule (i.e. an esnRNA of the disclosure) or an AAV vector comprising an esnRNA of the disclosure.

In some aspects, the disease or disorder is associated with a toxic repeat RNA sequence. In some aspects, the toxic repeat RNA sequence is a CAG, CUG, GGCCCC, CCGGG, or GGCCC+CCGGGG RNA repeat.

In some aspects, the disease or disorder is myotonic dystrophy (DM1) or Huntington's disease (HD).

In some aspects, the disease or disorder is Duchenne Muscular Dystrophy. In some aspects, the RNA-targeting nucleic acid molecule or AAV vector targets an RNA sequence encoding dystrophin (DMD). In some aspects, the RNA sequence encoding DMD comprises an intronic or exonic sequence. In some aspects, the exonic sequence comprises exon 51, or a flanking region thereof, of DMD.

In some embodiments of the methods of the disclosure, a subject of the disclosure has been diagnosed with a disease to be treated. In some embodiments, the subject of the disclosure presents at least one sign or symptom of a disorder or disease to be treated. In some embodiments, the subject of the disclosure presents at least one sign or symptom of a disease.

In some embodiments of the methods of the disclosure, a subject of the disclosure is female. In some embodiments of the methods of the disclosure, a subject of the disclosure is male. In some embodiments, a subject of the disclosure has two XX or XY chromosomes. In some embodiments, a subject of the disclosure has two XX or XY chromosomes and a third chromosome, either an X or a Y.

In some embodiments of the methods of the disclosure, a subject of the disclosure is a neonate, an infant, a child, an adult, a senior adult, or an elderly adult. In some embodiments of the methods of the disclosure, a subject of the disclosure is at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or 31 days old. In some embodiments of the methods of the disclosure, a subject of the disclosure is at least 1, 2, 3, 4, 5, 6, 7, 8, 9, 10, 11 or 12 months old. In some embodiments of the methods of the disclosure, a subject of the disclosure is at least 1, 2, 3, 4, 5, 6, 7, 8, 9, 10, 15, 20, 25, 30, 35, 40, 45, 50, 55, 65, 70, 75, 80, 85, 90, 95, 100 or any number of years or partial years in between of age.

In some embodiments of the methods of the disclosure, a subject of the disclosure is a mammal. In some embodiments, a subject of the disclosure is a non-human mammal.

In some embodiments of the methods of the disclosure, a subject of the disclosure is a human.

In some embodiments of the methods of the disclosure, a therapeutically effective amount comprises a single dose of a composition of the disclosure. In some embodiments, a therapeutically effective amount comprises a therapeutically effective amount comprises at least one dose of a composition of the disclosure. In some embodiments, a therapeutically effective amount comprises a therapeutically effective amount comprises one or more dose(s) of a composition of the disclosure.

In some embodiments of the methods of the disclosure, a therapeutically effective amount eliminates a sign or symptom of the disease or disorder. In some embodiments, a therapeutically effective amount reduces a severity of a sign or symptom of the disease or disorder.

In some embodiments of the methods of the disclosure, a therapeutically effective amount eliminates the disease or disorder.

In some embodiments of the methods of the disclosure, a therapeutically effective amount prevents an onset of a disease or disorder. In some embodiments, a therapeutically effective amount delays the onset of a disease or disorder. In some embodiments, a therapeutically effective amount reduces the severity of a sign or symptom of the disease or disorder. In some embodiments, a therapeutically effective amount improves a prognosis for the subject.

In some embodiments of the methods of the disclosure, a composition of the disclosure is administered to the subject via intracerebral administration. In some embodiments, the composition of the disclosure is administered to the subject by an intrastriatal route. In some embodiments, the composition of the disclosure is administered to the subject by a stereotaxic injection or an infusion. In some embodiments, the composition is administered to the brain. In some embodiments of the methods of the disclosure, a composition of the disclosure is administered to the subject locally.

In some embodiments, the compositions disclosed herein are formulated as pharmaceutical compositions. Briefly, pharmaceutical compositions for use as disclosed herein may comprise a protein(s) or a polynucleotide encoding the protein(s), optionally comprised in an AAV, which is optionally also immune orthogonal, in combination with one or more pharmaceutically or physiologically acceptable carriers, diluents or excipients. Such compositions may comprise buffers such as neutral buffered saline, phosphate buffered saline and the like; carbohydrates such as glucose, mannose, sucrose or dextrans, mannitol; proteins; polypeptides or amino acids such as glycine; antioxidants; chelating agents such as EDTA or glutathione; adjuvants (e.g., aluminum hydroxide); and preservatives. Compositions of the disclosure may be formulated for routes of administration, such as e.g., oral, enteral, topical, transdermal, intranasal, and/or inhalation; and for routes of administration via injection or infusion such as, e.g., intravenous, intramuscular, subpial, intrathecal, intraparenchymal, intrathecal, intrastriatal, subcutaneous, intradermal, intraperitoneal, intratumoral, intravenous, intraocular, and/or parenteral administration. In certain embodiments, the compositions of the present disclosure are formulated for intracerebral or intrastriatal administration.

EXAMPLES

Example 1: esnRNA Targeting CUG Repeats in DM1 Cell Model

Materials and Methods:

CTG480 HeLa cells were seeded at 100,000 cells/ml in 12 well plate. Next day snRNAs were transfected using lipofectamine (2 µL P3000 and 2.5 µl lipofectamine per sample). 24 h our later cells were trypsinized and ½ of the cells seeded in chamber slides for FISH and the other ½ in a 24-well plate for RNA analysis.

Next day RNA was extracted for RNA analysis and cells were fixed for FISH. For FISH CUG foci was labeled with CUG fluorescent probe, and the cell nuclei was stained with DAPI.

Purpose: To determine whether engineered snRNPs comprising the engineered stem loop are capable of knocking down CUG expansions and therefore decrease the number of RNA foci in a DM1 cell model.

Rationale: The U7 snRNA can be programmed to target mRNAs by replacing its histone mRNA annealing sequence with a sequence complementary to a target of interest. U7 with 15×CAG repeats has been shown by others to reduce CUG repeat expansions, which cause DM1 (Francois et al NSMB 2011). We optimized this snRNA system by engineering the stem loop (SEQ ID NO: 1) to better stabilize the secondary structure of U7 snRNA in cells. We compared our engineered U7 stem loop to the U7 stem loop known in the art (Francois et al NSMB 2011). The constructs contain 15×CAG repeats and an optimized Sm binding domain, which further helps to stabilize the programmed U7. The CUG-targeting constructs were tested to determine whether they can deplete CUG foci by binding to and blocking CUG repeats in an appropriate cell model and compared to U7s that contained a non-targeting (NT) sequence. See FIGS. 1A-D and 2A-C.

Constructs and controls were transiently transfected into HeLa(CTG480) which has 480 CTG repeats inserted into its genome by CRISPR to model DM1 and express CUG foci as shown by in-situ hybridization. Cells were seeded and fixed onto chamber slides, and RNA in-situ hybridization was performed on the cells using a probe for CUG and dapi for nuclear staining. The co-localization of the CUG probe and DAPI signal was quantified using Halo.

Treatment with 15×CAG esnRNA constructs (to target/block CUG repeats) significantly decreased CUG RNA foci.

Compared to their respective non-targeting control, the non-engineered snRNA and esnRNA constructs led to a 39% and 68% reduction in average #foci/cell, respectively.

Example 2: esnRNA Targeting CAG Repeats

Materials and Methods:

HEK293T cells were seeded at 150,000 cells/ml in a 12 well plate. Next day snRNAs were transfected using lipofectamine (2 µL P3000 and 2.5 µl lipofectamine per sample). Cells were transfected with the CAG reporter construct (containing 80 CAG repeats) and increasing doses (from 100 to 1000 ng) of the snRNA plasmids targeting CAG repeats (referred as CUG- or the control non-targeting (nt).

RNA was extracted for RNA analysis 48 h post transfection using the QiaCube Connect. qRT-PCR was performed to detect the expression levels of the CAG reporter and normalized to the expression levels of the GAPDH reference gene.

Another set of cells was used for Western blot analysis with a myc tag antibody to detect the protein levels of Poly-Q CAG containing reporter. GAPDH was used as loading control.

Purpose: Mutant HTT is caused by the existence of microsatellite repeats in exon one of HTT. Here, we explored whether engineered snRNPs comprising the engineered stem loop are capable of knocking down CAG microsatellite repeat RNA in a CAG80 reporter assay.

Rationale:

The U7 snRNA can be programmed to target mRNAs by replacing its histone mRNA annealing sequence with a sequence complementary to a target of interest. The esnRNA system reprogrammed to target CAG repeats comprises an eSL of SEQ ID NO: 1 to better stabilize the secondary structure of U7 snRNA in cells. The constructs contain 15×CUG repeats to target CAG expansions. These constructs also contained an optimized Sm binding domain, which further helps to stabilize the programmed U7. The CAG-targeting constructs were tested to determine whether they can knock down CAG repeats and poly-Q containing protein compared to eSLs that contained a non-targeting sequence.

Complete knockdown of detectable PolyQ protein was achieved by the highest 3 doses of U7. An almost complete knockdown was achieved at the lowest U7 dose. Accordingly, we show herein a dose-dependent knockdown of CAG80 reporter mRNA to baseline levels. See FIGS. 3A-3C.

Example 3: esnRNA Modulation of USH2A Minigene Exon 13 Splicing

Materials and Methods:

HEK293T cells were seeded at 150,000/ml in 12 well plate. Next day cells were transfected with 50 ng of USH2A minigene with a total of 250 ng, 500 ng, 1 ug of pcDNA expressing non-targeting esnRNA or USH2A exon 13-targeting esnRNA with lipofectamine.

Cells were harvested 48 h post-transfection. RNA was extracted using Qiacube connect, reverse transcribed, and semiquantitative PCR performed with primers that anneal to USH2A exon 12 and 14.

Quantitation of U7 was performed by PCR with primers annealing to the non-targeting esnRNA.

Rationale: USH2A exon 13 mutations lead to Usher Syndrome Type 2A. Exon 13 is an in-frame exon and a therapeutic strategy includes skipping exon 13. We designed esnRNAs comprising an eSL disclosed herein that target and anneal to exon splicing enhancers on exon 13 of USH2A and block the inclusion of exon 13. Our programmed esnRNA system to target USH2A exon 13 results in efficient exon 13 skipping on minigene. PCR results suggest higher steady state levels of the esnRNA system compared to non-engineered SL. See FIGS. 4A-4D. See also FIG. 1A.

Example 4: Splicing Correction by esnRNA-Mediated CUG-Repeat Blocking in DM1 Patient Myotubes Materials and Methods:

DM1 patient myotubes containing 2600 CUG repeats in the 3'UTR of DMPK were differentiated for 13 days before introduction of esnRNA comprising eSL disclosed herein targeting 15×CUG repeats. RNA was extracted from cells 24 hours after treatment, RNA was reverse transcribed and semiquantitative PCR was performed to DM1 disease splicing biomarkers LDB3 exon 11, BIN1 exon 11 and DMD exon 78. Analysis of splicing isoforms was performed by calculating the percentage of the healthy splice isoform (LDB3 exon 11 excluded, BIN1 exon 11 included and DMD exon 78 included) over the total signal from both the disease and healthy isoforms.

Rationale:

DM1 is caused by CUG repeat expansions in the 3'UTR of the DMPK gene that sequesters MBNL protein and as a result lead to dysregulation of alternative splicing. esnRNAs comprising an eSL disclosed herein were programmed to target CUG (15×CUGs) and this resulted in a dose dependent increase in healthy splice isoforms for all three tested disease splicing biomarkers compared to the non-targeting control. See FIGS. 5A-5F. See also FIG. 2C.

Example 5: Testing Alternative 5' Stabilizing Motifs in U7-Based eSLs and ISDs

Figure 1C:
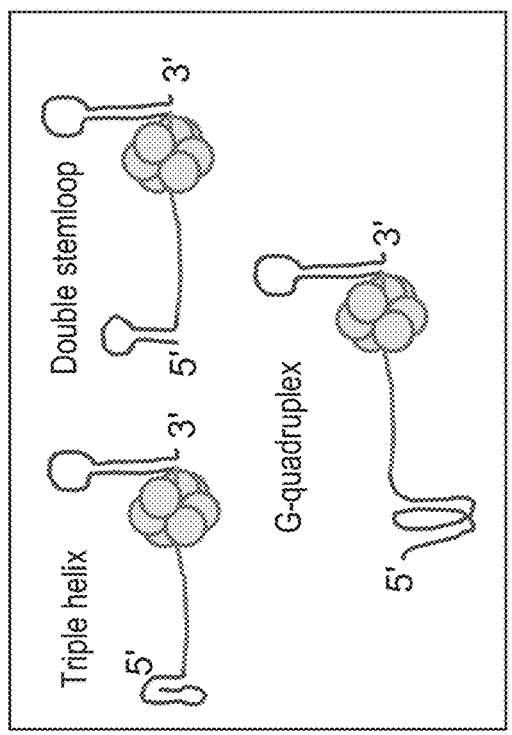
FIG. 1A-D.
Figure 1D:
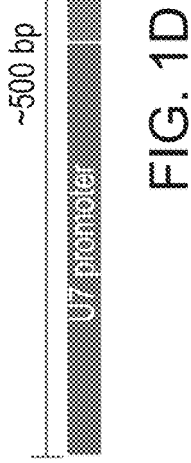
Figure 1A:
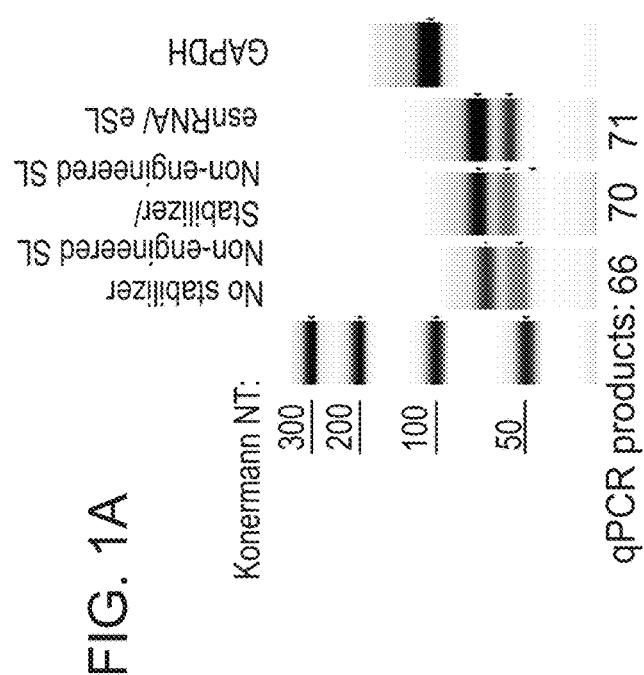
Figure 1B:
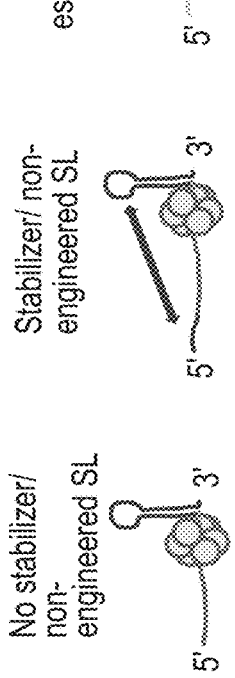
Figure 2A:
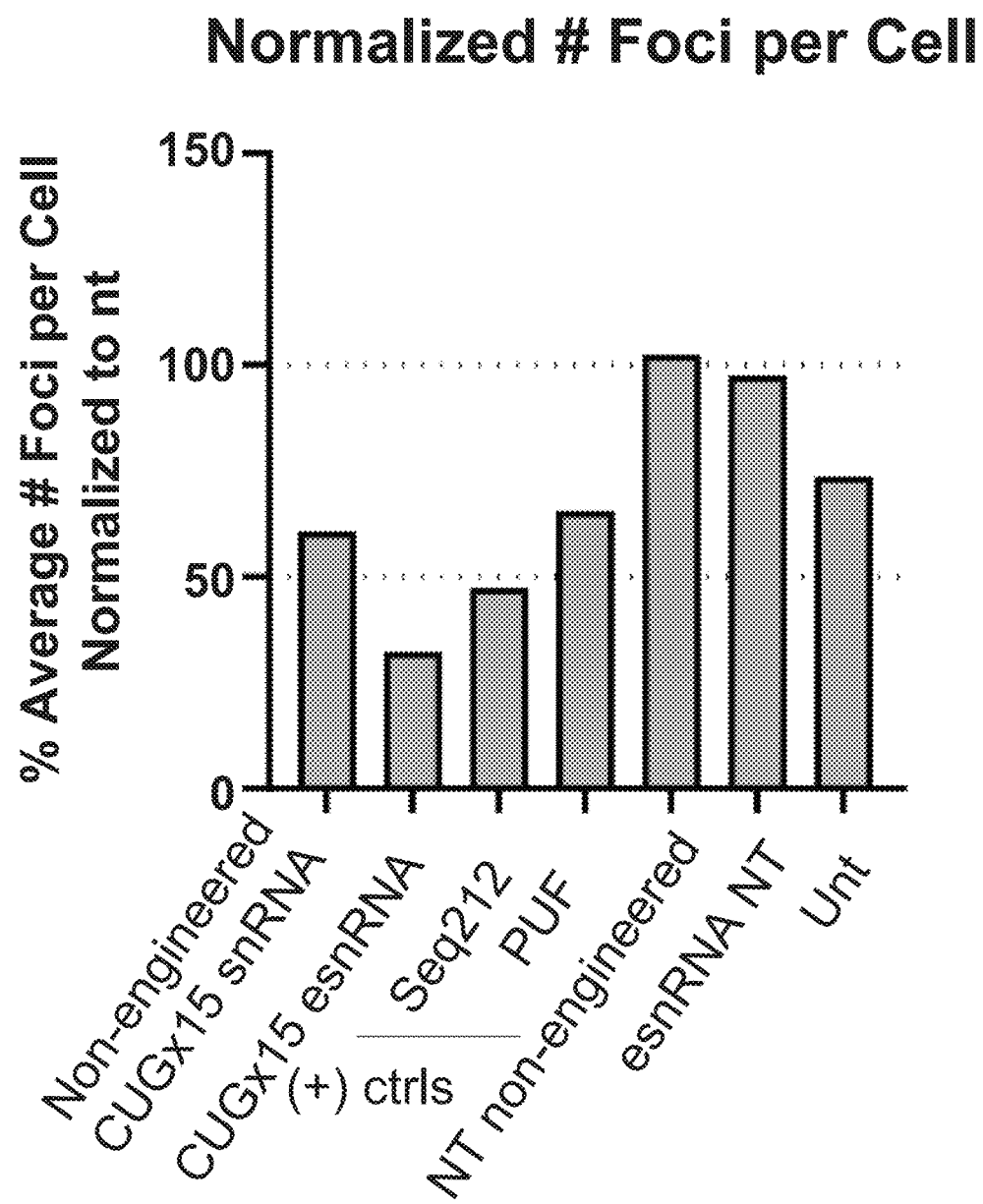
Figure 2B:
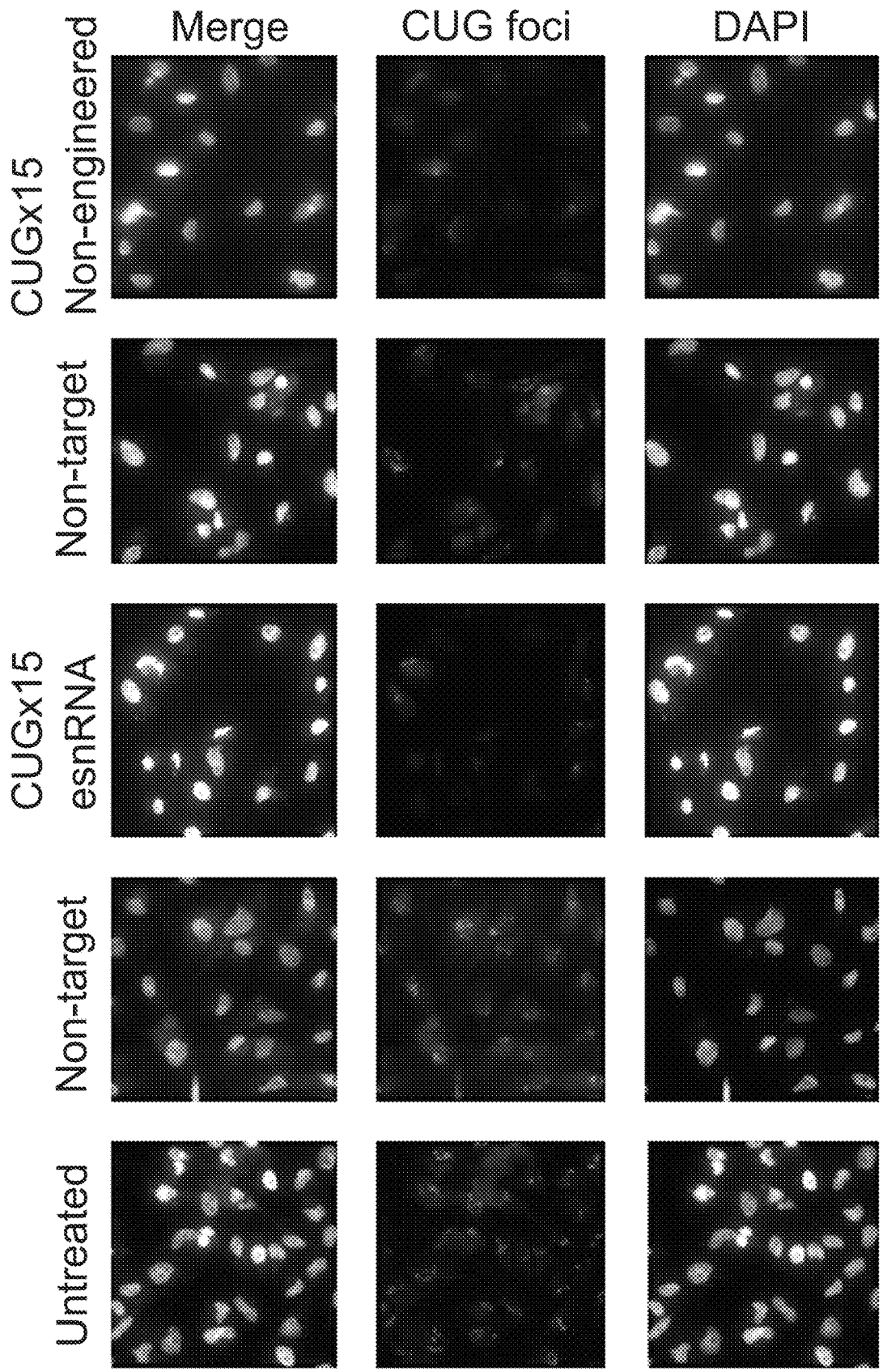
Figure 4A:
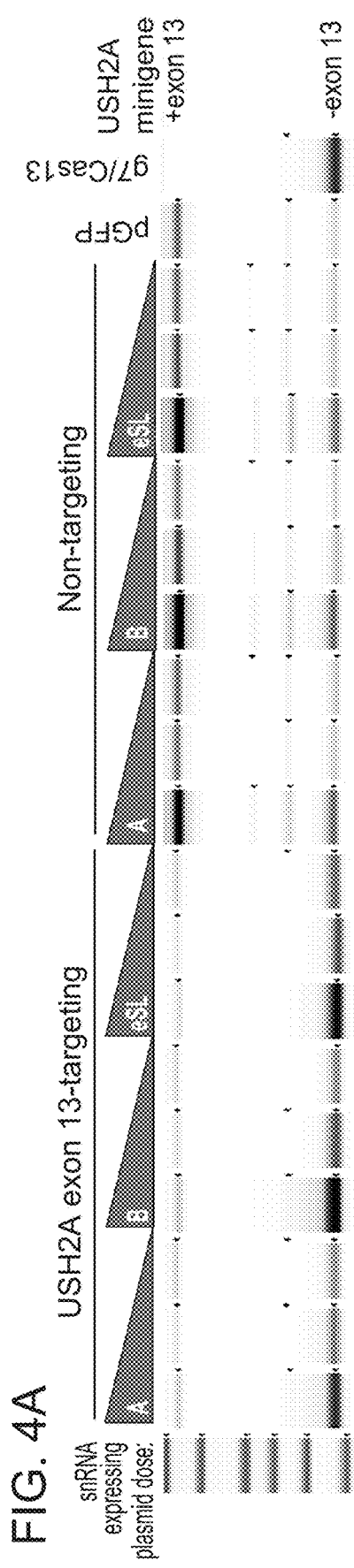
FIG. 4A-D.
Figure 4B:
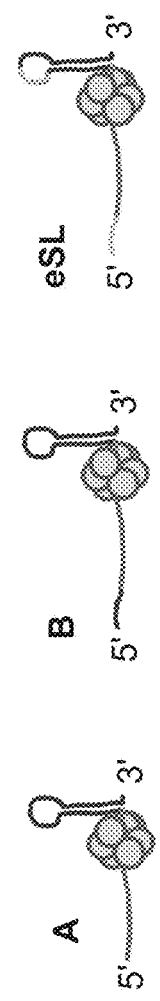
Figure 4C:
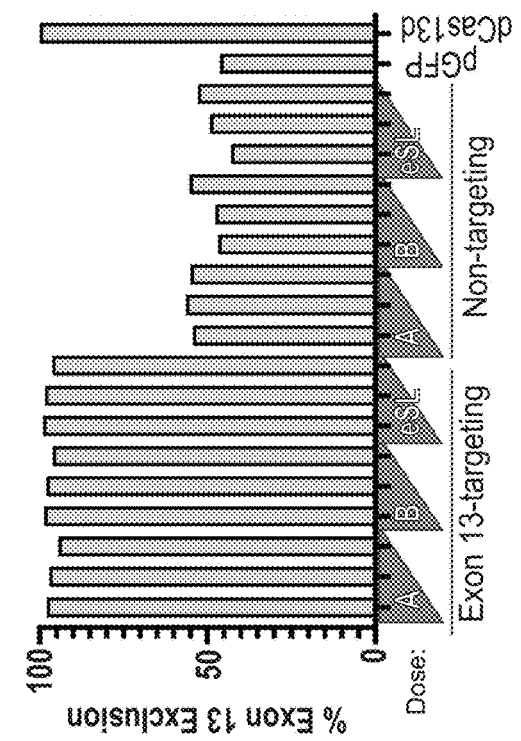
Figure 4D:
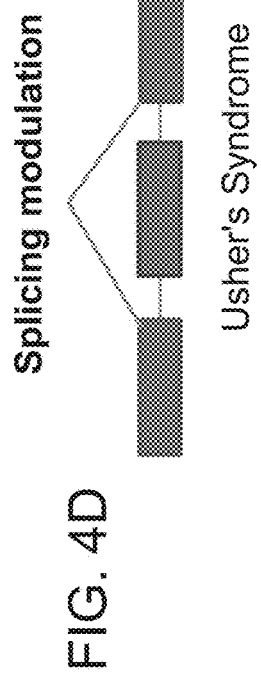
Figure 6A:
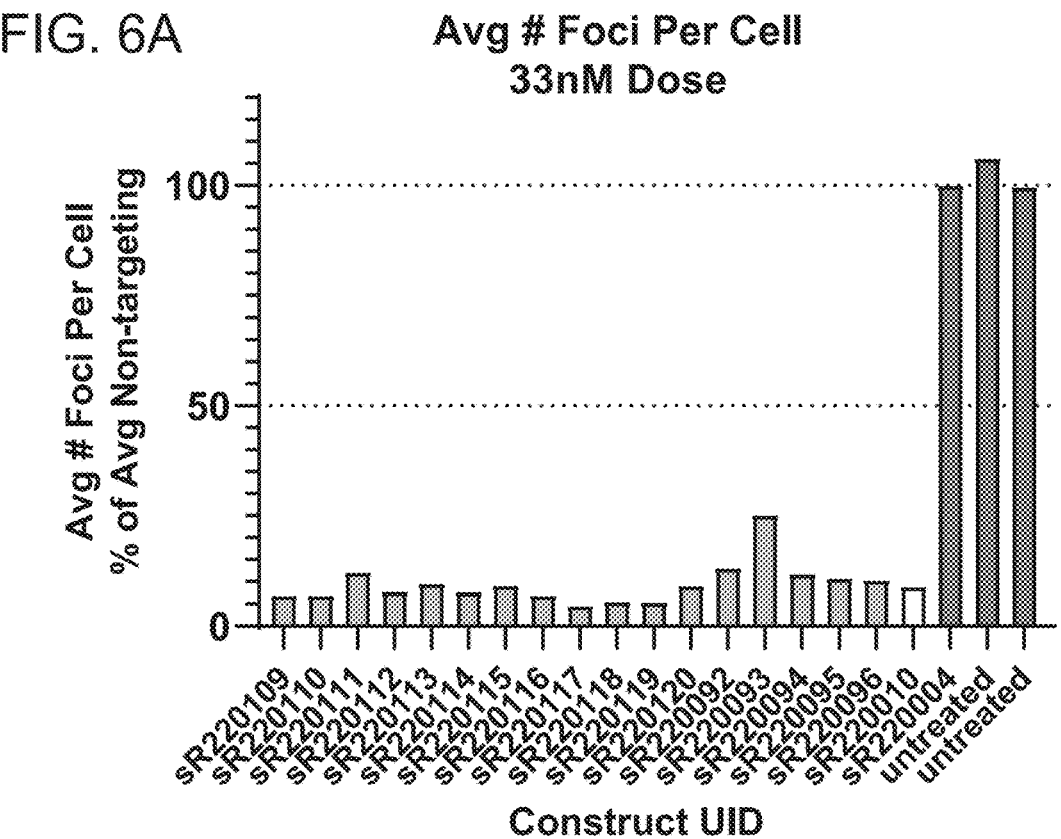
FIG. 6A-6B shows quantification of efficacy of esnRNA with alternative 5' interaction stabilizing domain (ISD) in knocking down CUG RNA foci, synthetic snRNA transfection in CTG480 HeLa cells followed by fluorescent in-situ hybridization for CUG RNA foci. (Bars sR220109, sR220110, sR220111, sR220112, sR220113, sR220114, sR220115, sR220116, sR220117, sR220118, sR220119, sR220120, sR2200092, sR2200093, sR2200094, sR2200095, and sR2200096=alternative engineered stem loops with corresponding 5' ISDs. Bar sR220010=selected engineered stem loop and corresponding 5' ISD. sR220004=non-targeting snRNA). Synthetic snRNAs were transfected at 33 nM (A) or 11 nM (B) dose.
Figure 6B:
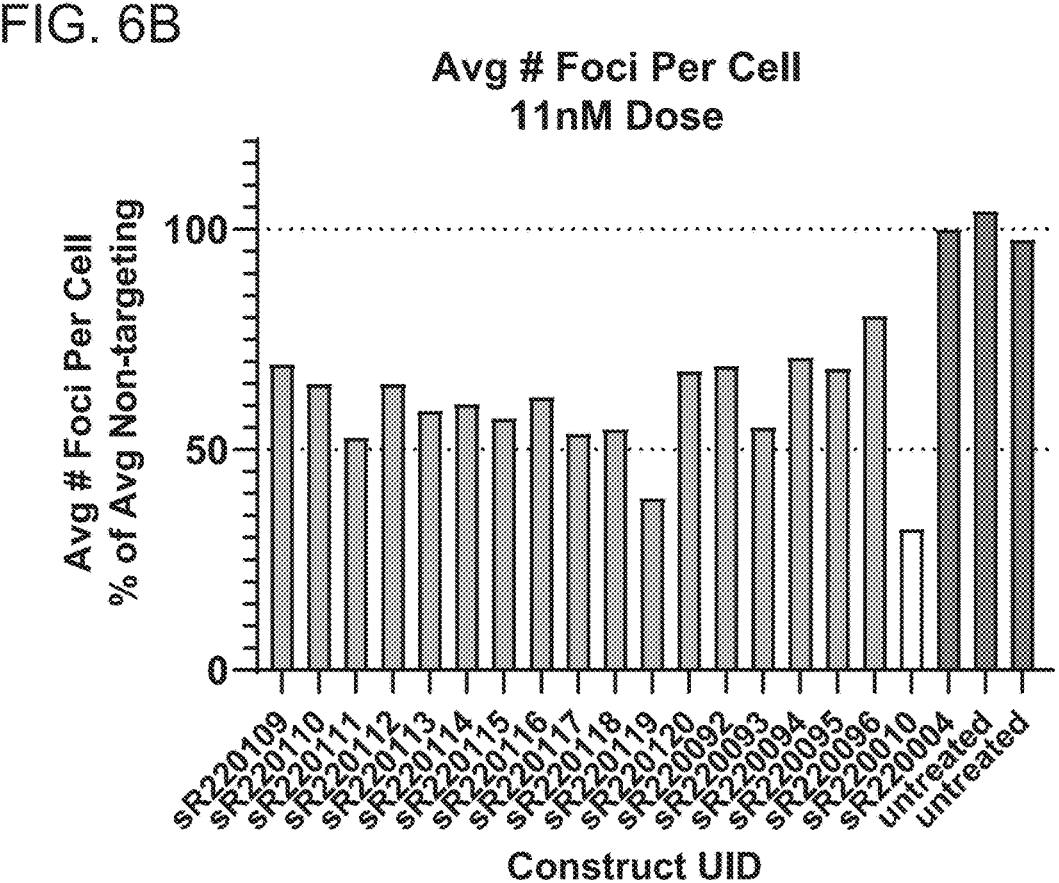

Efficacy of CUGx15 targeting snRNA with alternative 5' interaction stabilizing domain (ISD) in reducing RNA foci was shown and determined by synthetic snRNA transfection in CTG480 HeLa cells followed by fluorescent in-situ hybridization for CUG RNA foci. See FIG. 6A-6B. (sR220109, sR220110, sR220111, sR220112, sR220113, sR220114, sR220115, sR220116, sR220117, sR220118, sR220119, sR220120, sR2200092, sR2200093, sR2200094, sR2200095, and sR2200096=alternative engineered stem loops with corresponding 5' ISDs. sR220010=selected engineered stem loop and corresponding 5' ISD. sR220004=non-targeting snRNA.

Figure 7A:
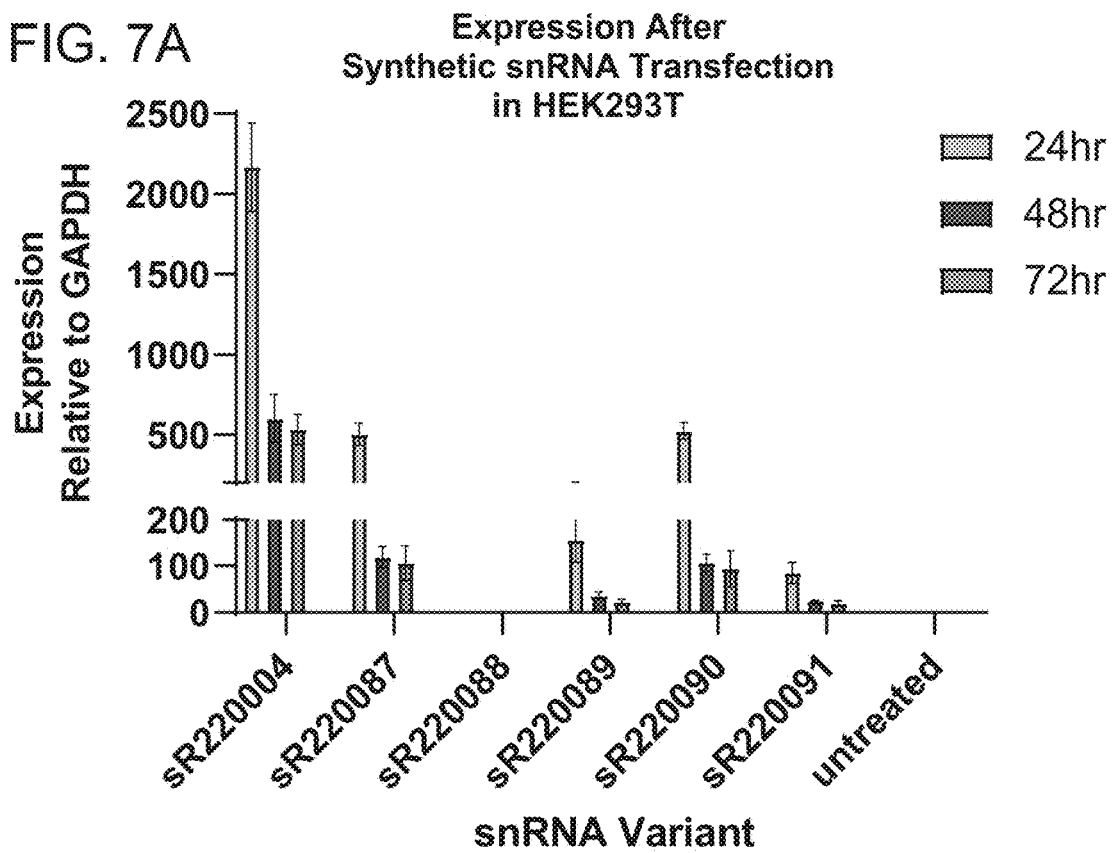
FIG. 7A-7B shows that different ISDs lead to varying levels of stability over time.
Figure 7B:
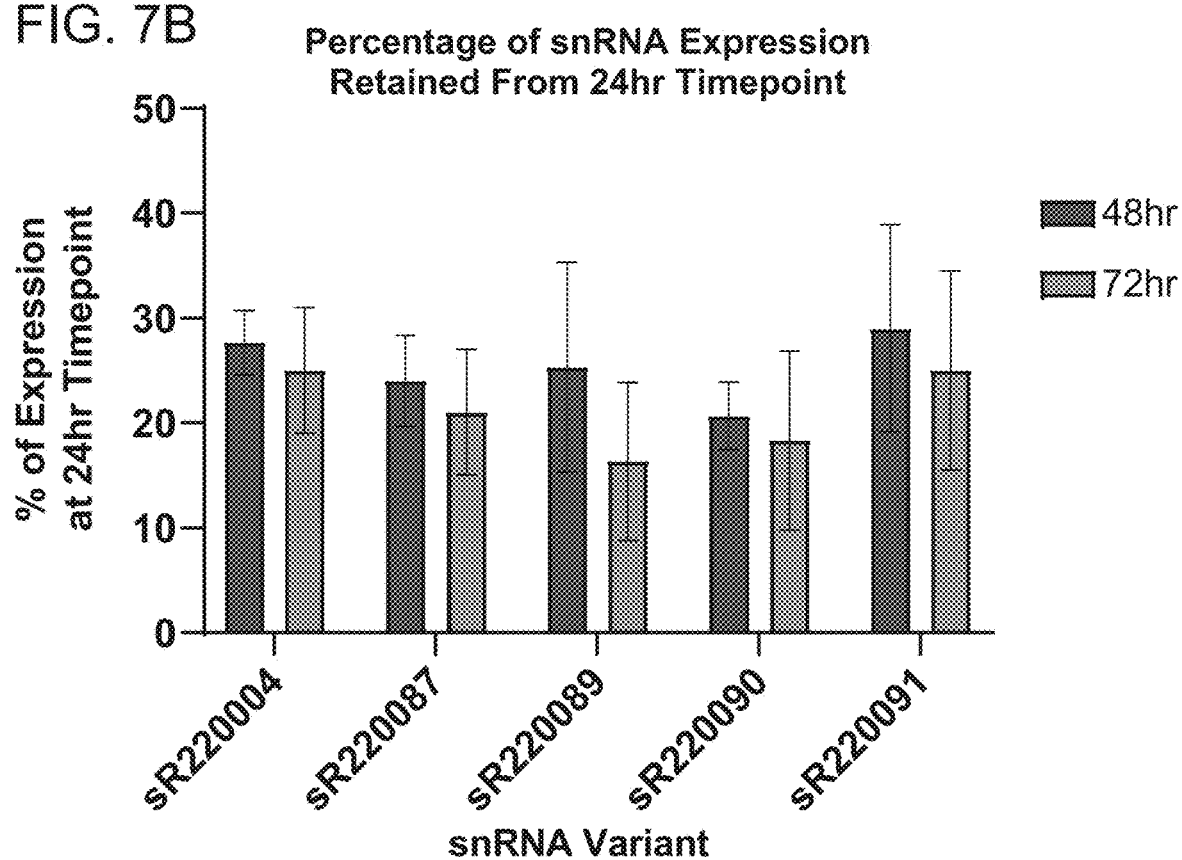

Expression levels of non-targeting snRNAs with alternative 5' stabilizing domains at 24 hr, 48 hr, and 72 hr time points after transfection of synthetic snRNA were evaluated. See FIG. 7A-7B. sR220004 had the highest expression at all time points. sR220088 had no detectable expression. eSL/5'ISD found in 004 was selected for future constructs. sR220004 and sR220091 had the highest retention of expression at 48 hr and 72 hr time points.

Figure 8:
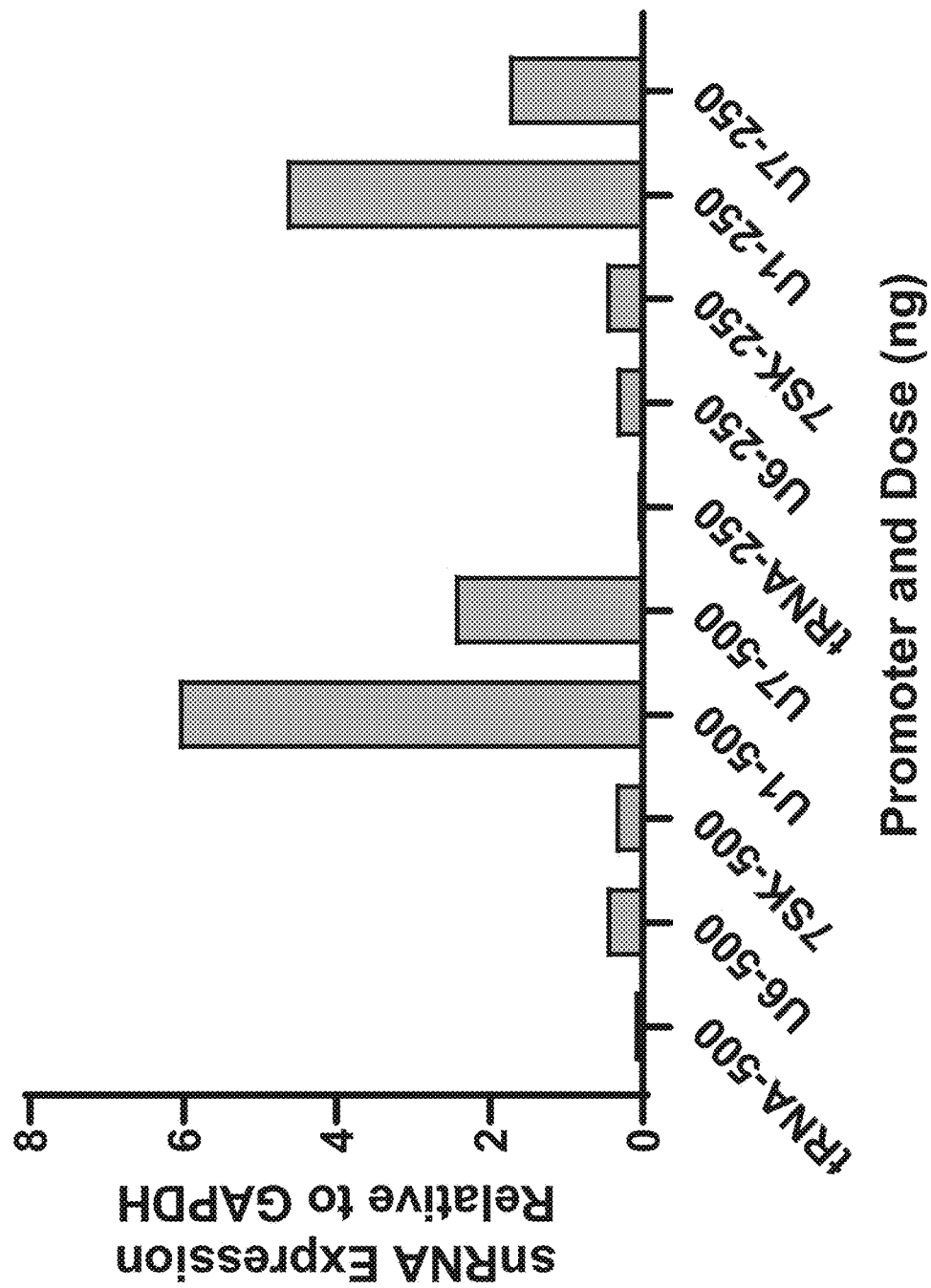
FIG. 8 shows levels of snRNA expression by qPCR in CTG480 HeLa cells when snRNAs are expressed under distinct PolIII and PolII promoters. Y axis depicts snRNA expression levels relative to GAPDH reference gene, and x axis depicts the different snRNAs promoters used to express snRNAs (Pol II U1 and U7 promoters or PolIII: U6, tRNA and 7SK). Plasmids with varying promoters were transfected at two different doses (250 and 500 ng).

Example 6: U7 snRNA Efficacy and Expression by PolIII and PolII Promoters snRNA expression was evaluated by qPCR in CTG480 HeLa cells when snRNA expression was driven by different human PolIII and PolII promoters. See FIG. 8. The U1 promoter drives the highest level of snRNAs, followed by the U7 promoter. The PolIII promoters U6 and 7SK had low expression, and the PolIII tRNA promoter had lowest expression.

Figure 9A:
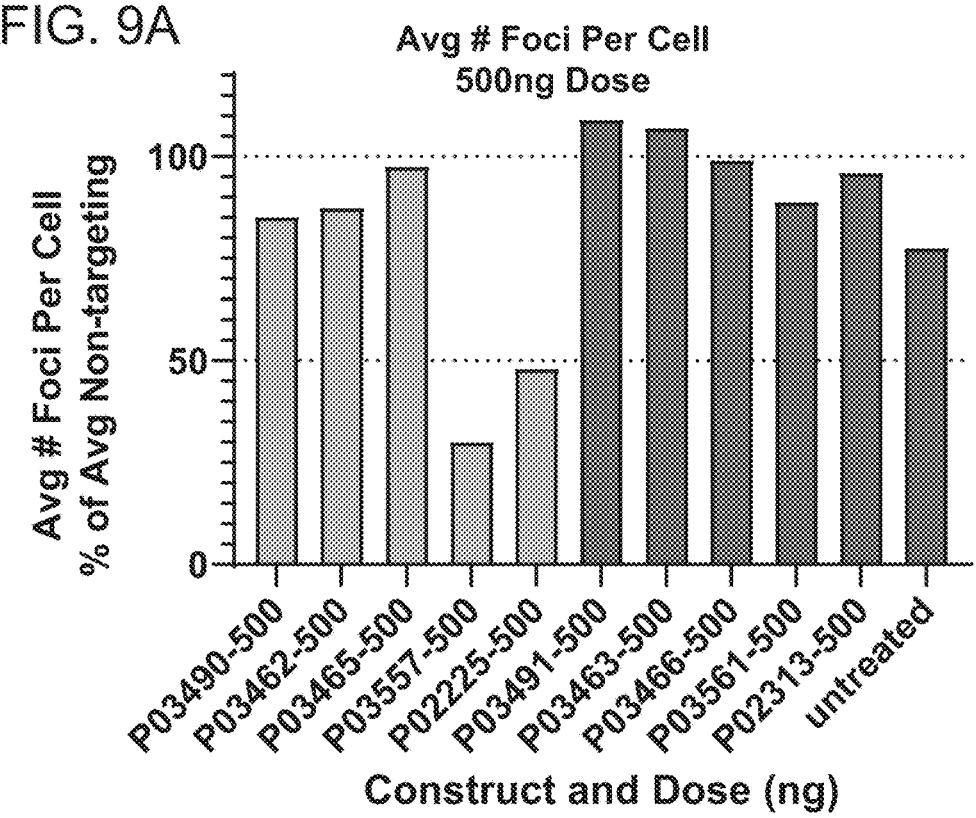
FIG. 9A-9B shows quantification of CUG foci by RNA FISH in CTG480 HeLa cells after transfection of 500 ng (A) or 250 ng (B) engineered snRNA constructs with varying Pol III and Pol II promoters and respective DT sequences. Constructs with Pol II promoters (P02225 and P03557) driving expression of engineered snRNAs are more effective at depleting microsatellite repeat-containing foci than constructs with Pol III promoters driving snRNAs. Bars P03491, P03463, P03466, P03561, and P02313 represent NT esnRNA and bars P03490, P03462, P03465, P03557, and P02225 represent CUG targeting esnRNAs.
Figure 9B:
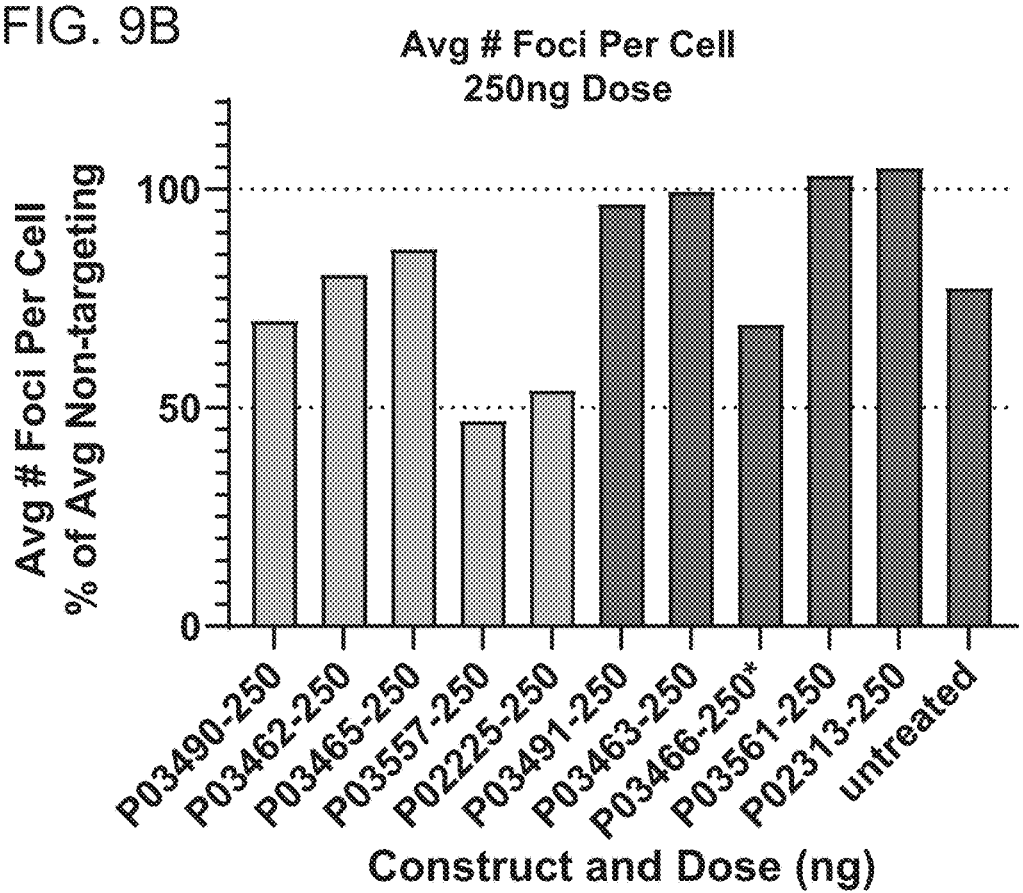

CUG foci quantification was evaluated by RNA FISH in CTG480 HeLa cells. See FIG. 9A-9B. Only U1 and U7 promoters were clearly efficacious in reducing the number of CUG foci, with U1 being more efficacious than U7 (P03490, P03462, P03465, P03557, and P02225=CUG-targeting; P03491, P03463, P03466, P03561, and P02313=non-targeting).

Figure 10:
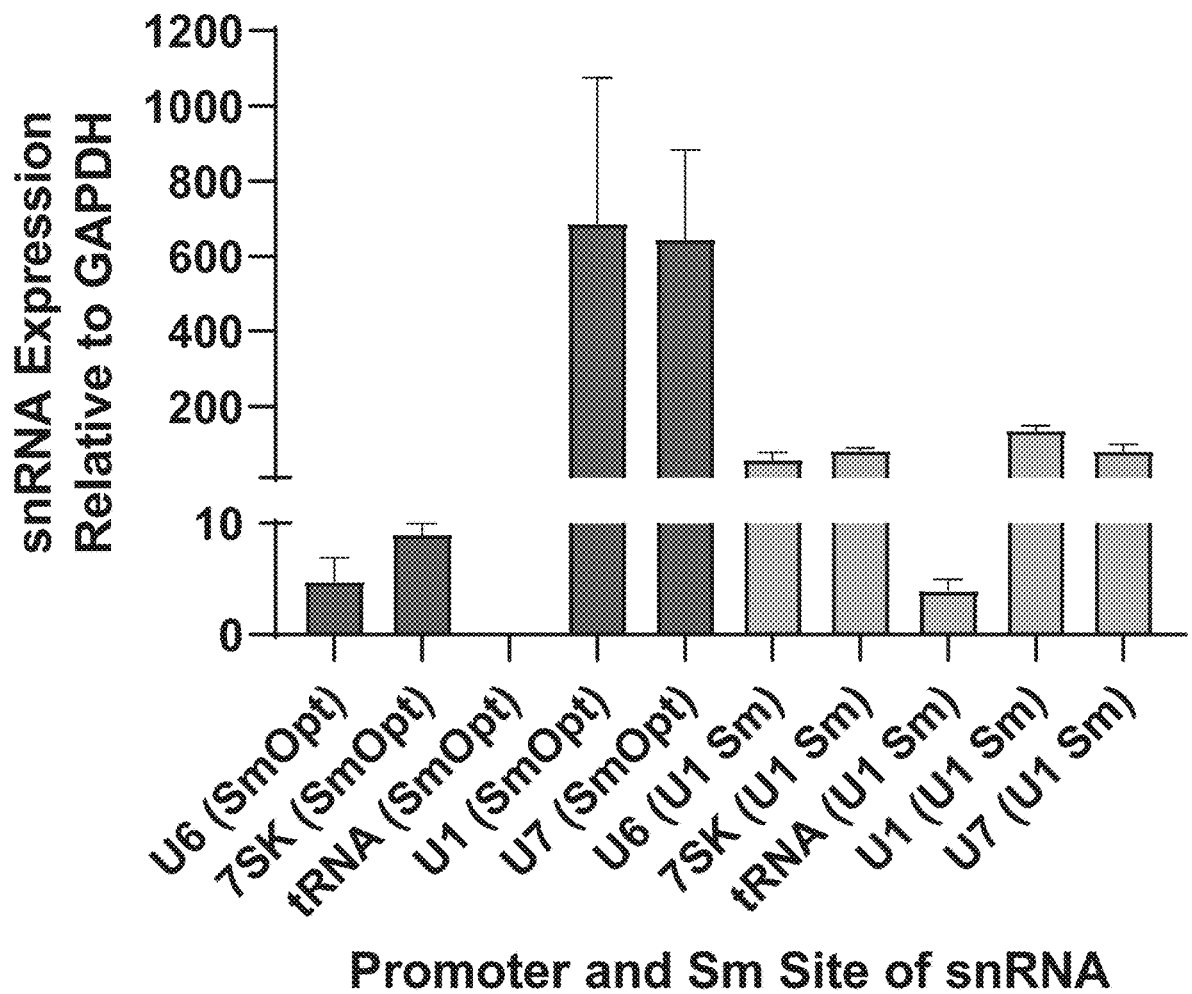
FIG. 10 shows levels of snRNA expression by qPCR in HEK293T cells when snRNAs are expressed under PolIII (U6, tRNA and 7SK) or PolII promoters (U7 and U1) and contain the SmOpt or the U1 Sm binging sites.
Figure 11B:
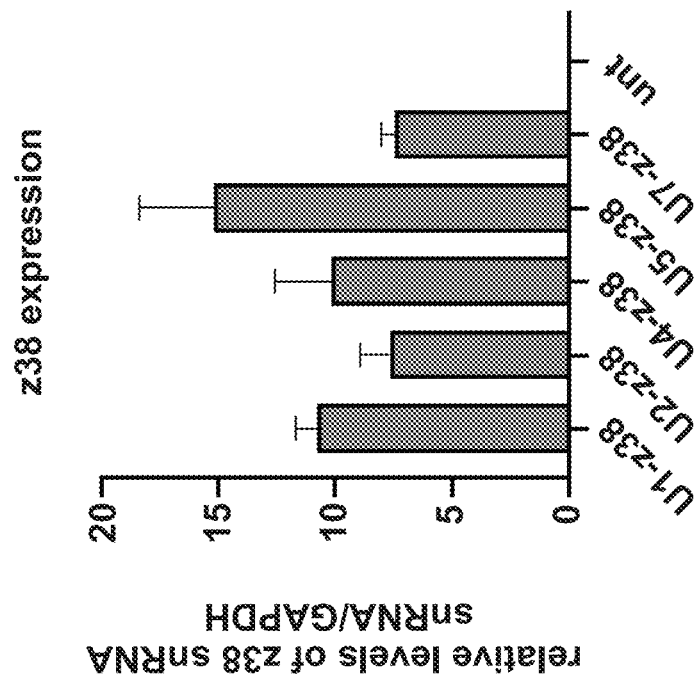
FIG. 11A-11B shows levels of snRNA expression relative to GAPDH reference gene after transfection into HEK293 cells. Primers specific for each snRNA (z) were used for qPCR to determine relative promoter strength. Y axis depicts snRNA expression levels relative to GAPDH and x axis depicts the snRNA spacer znt (non-targeting control, in A) and z38 (targeting spacer, B) when they are expressed under snRNA distinct promoters (U1, U2, U4, U5 and U7; unt refers to untreated). Primer sets specific to z-nt (FIG. A) or z-38 (FIG. B) were used.
Figure 11A:
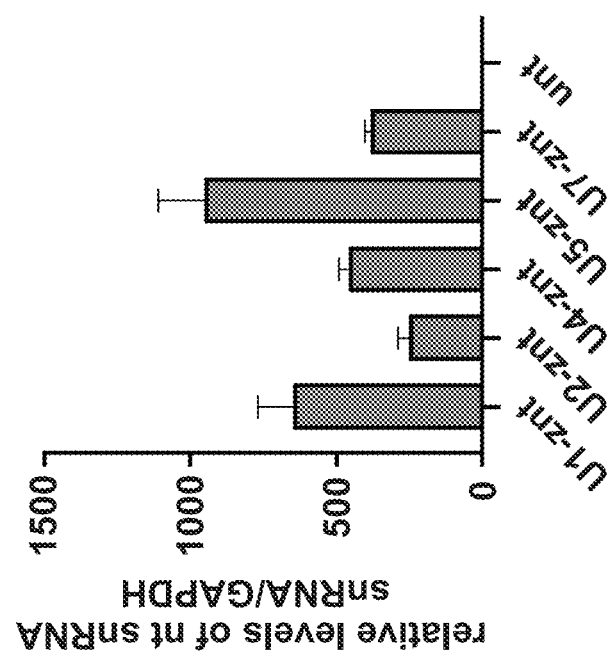

| UID | Promoter, target |
|---|---|
| P03490 | tRNA (CUGx15) |
| P03462 | U6 (CUGx15) |
| P03465 | 7SK (CUGx15) |
| P03557 | U1 (CUGx15) |
| P02225 | U7 (CUGx15) |
| P03491 | tRNA (nt) |
| P03463 | U6 (nt) |
| P03466 | 7SK (nt) |
| P03561 | U1 (nt) |
| P02313 | U7 (nt) | snRNA expression was determined by qPCR in HEK293T cells (see FIG. 10). Expression of U7 snRNAs under PolIII promoters increased up to 25× when SmOpt was converted to U1 Sm binding site. Expression by PolII U1 and U7 promoters decreased when Sm site was converted to U1 Sm. Expression by U1 and U7 promoters are superior to Pol III promoters.

snRNA transfection into HEK293T cells was conducted. See FIG. 11A-11B. Here znt esnRNA and z38 esnRNA expression was driven by distinct snRNA promoters. Those constructs were transfected into HEK293T cells. 48 h post-transfection RNA was extracted and cDNA was made. Primers specific for each snRNA (z) were used for qPCR to determine snRNA expression and relative promoter strength.

Figure 12B:
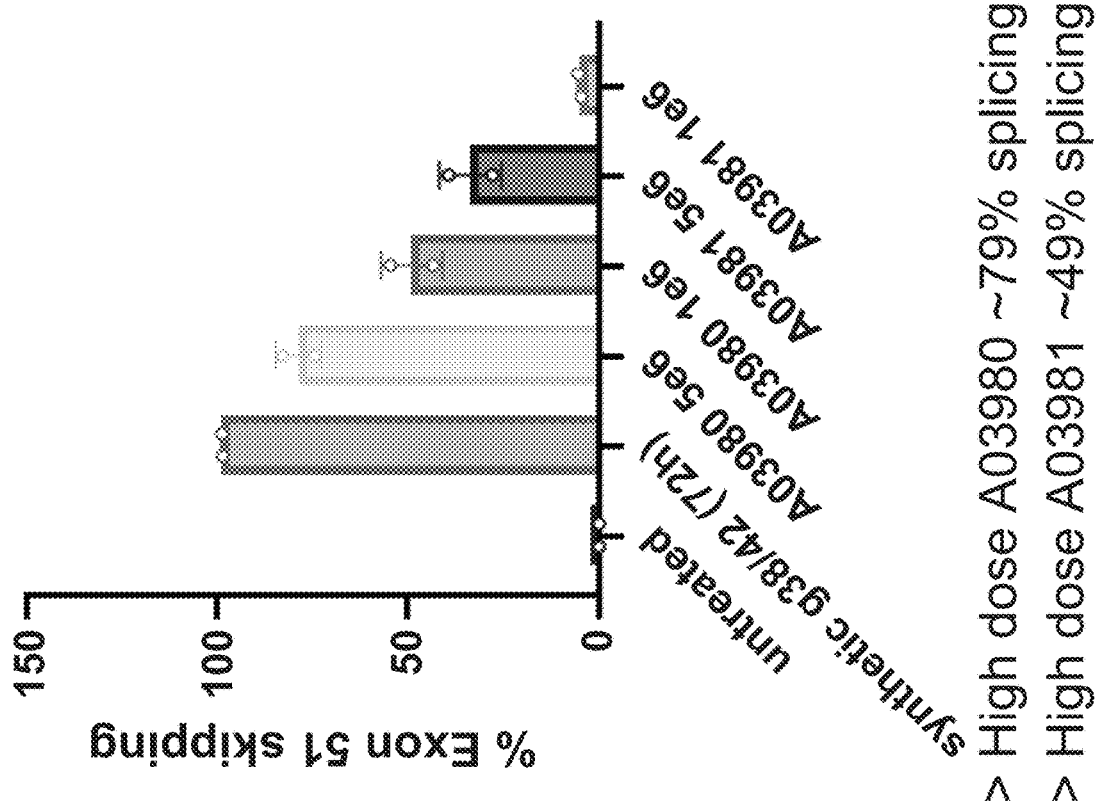

Example 7: esnRNA Constructs Result in DMD Exon Skipping of Exon 51 in Patient Myotubes Transduction of human delta exon 52 myotubes with snRNA disclosed herein was conducted. See FIG. 12A-12B. Quantification of the band intensities using amplification primers determined % exon 51 skipping.

Figure 13B:
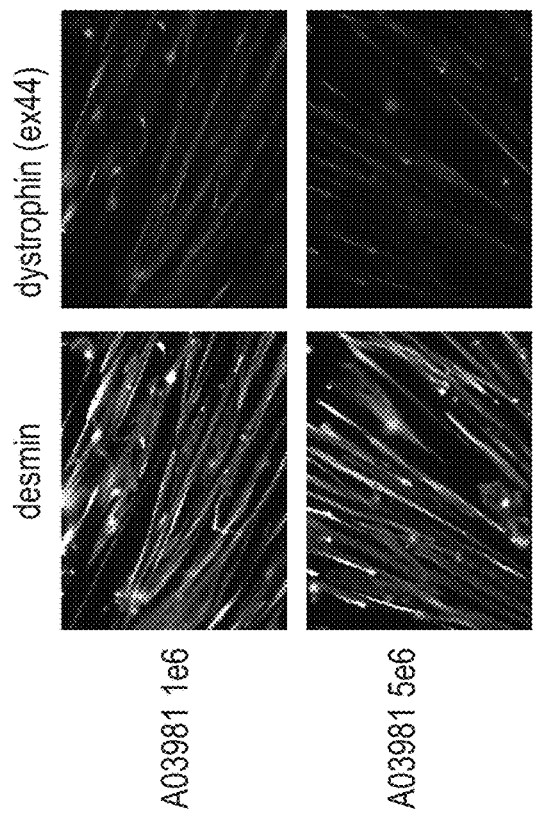
FIG. 13A-13B shows dystrophin staining and restoration of human delta exon 52 myotubes after treatment with snRNAs for exon 51 skipping.
Figure 13A:
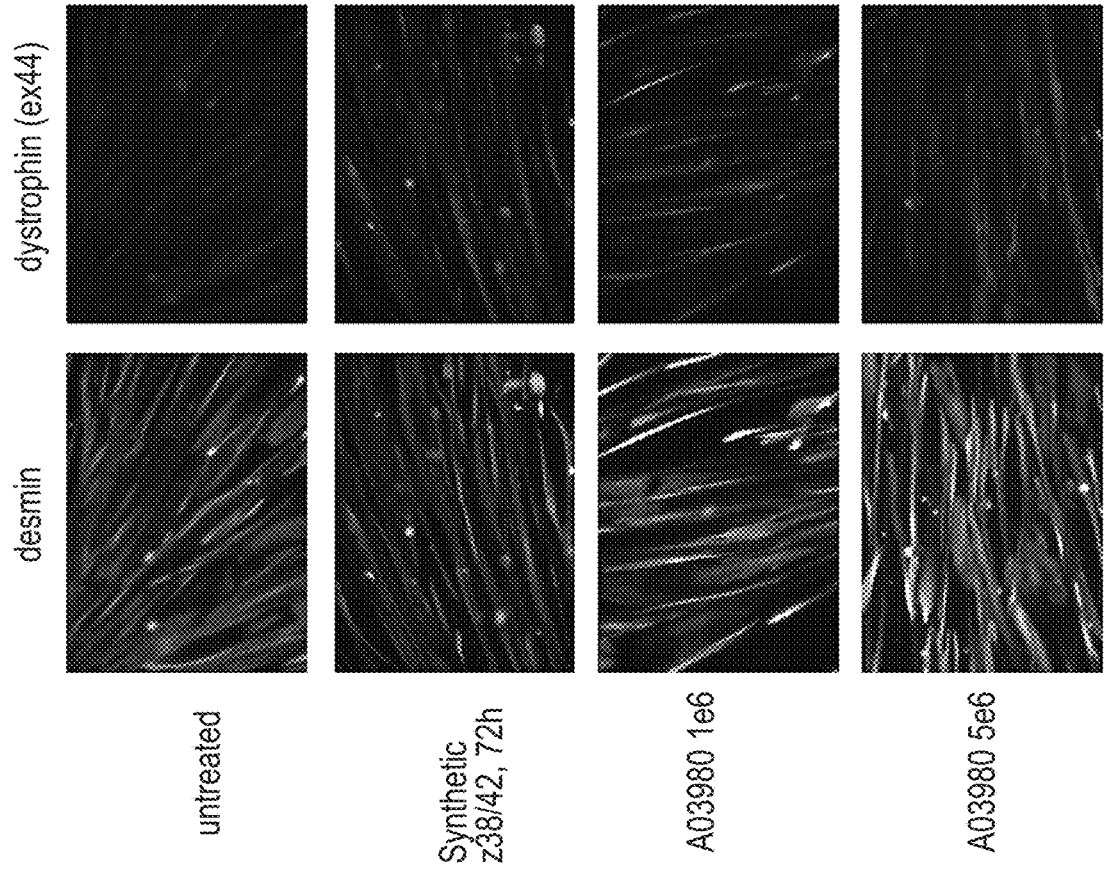
Figures 14A, 14B:
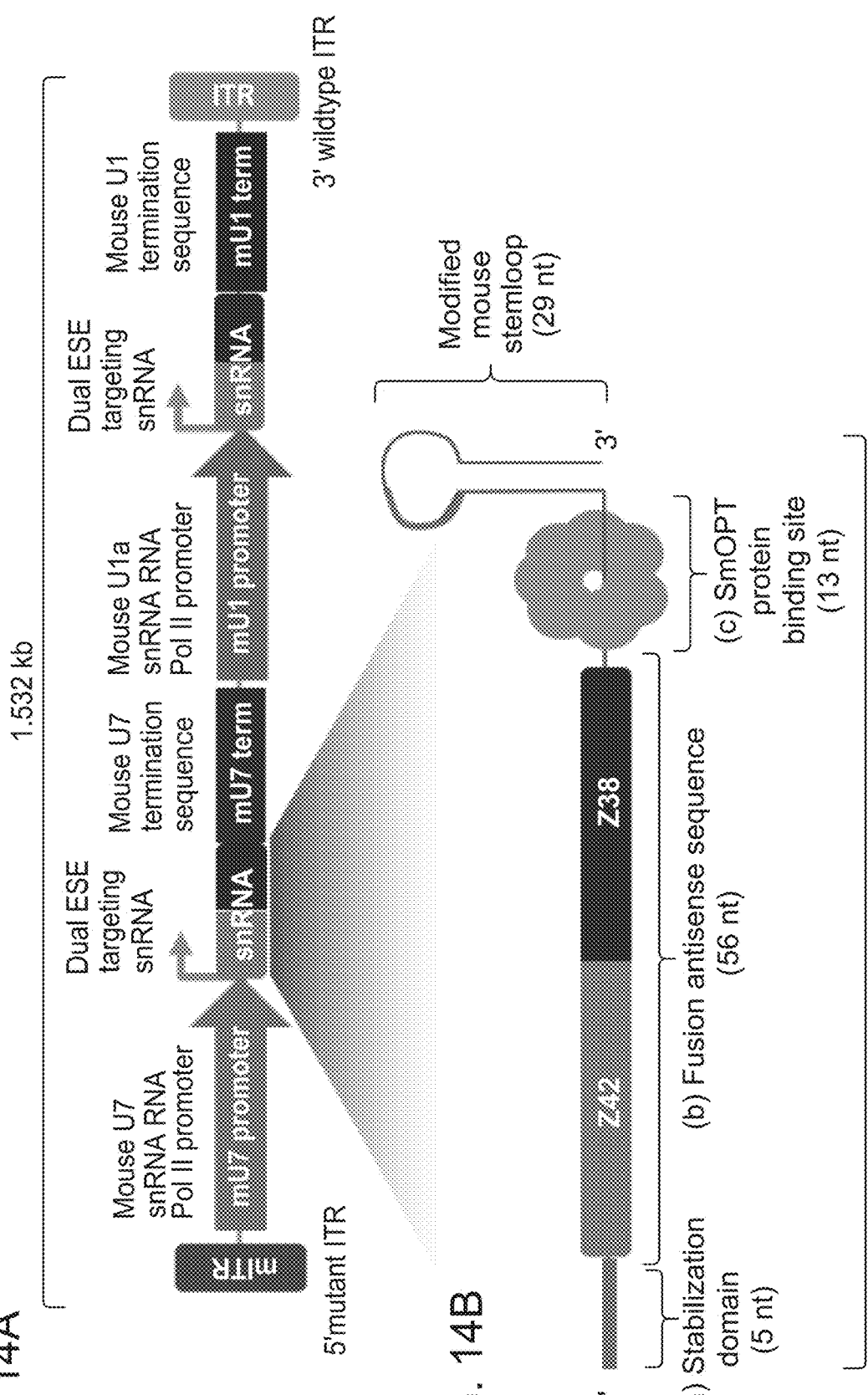
FIG. 14A illustrates the vector genome of A04569, which expresses 2 fusion snRNAs of identical sequence, as depicted in FIG. 14B.
Figure 14C:
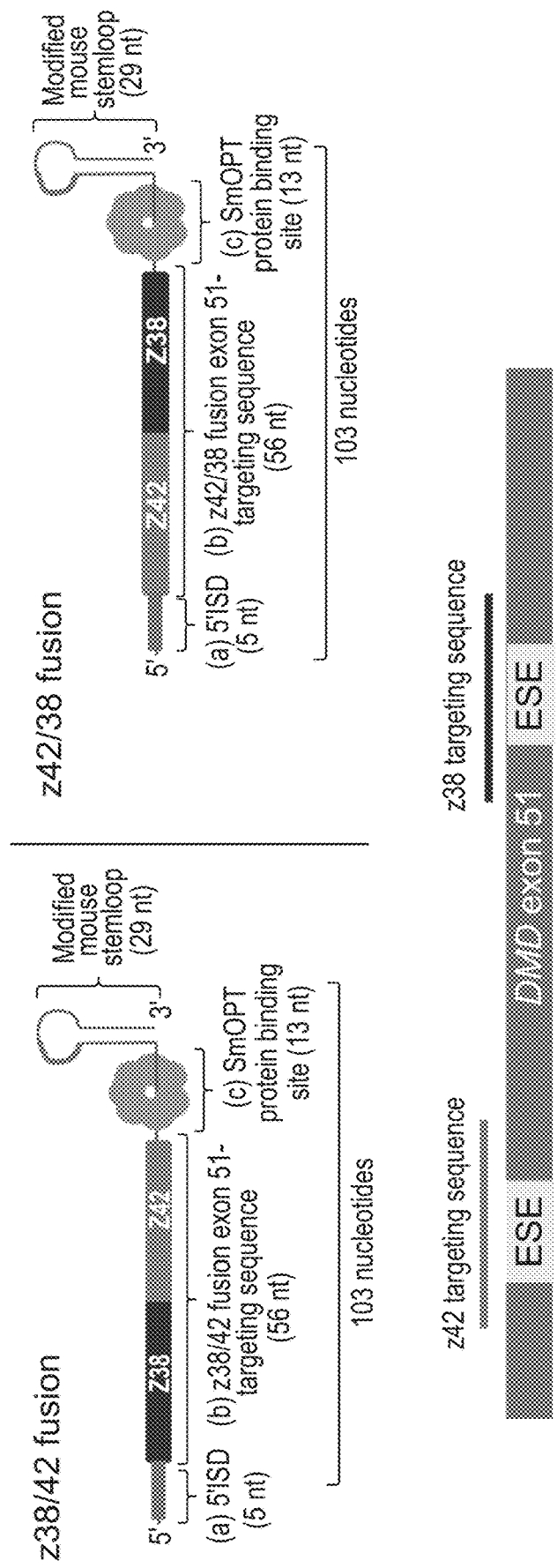
FIG. 14C shows that exon 51 Exon Splicing Enhancer (ESE)-targeting fusion snRNAs can be constructed such z38-targeting sequence is in the 5'-most position in the antisense sequence with z42-targeting sequence downstream of the z38 sequence (z73) or in the opposite orientation with z42-targeting sequence in the 5'-most position and z38 downstream (z187). In both cases, the antisense sequence of the snRNAs is composed of 2 targeting sequences, each of which targets a separate and unique ESE in exon 51 (FIG. 14C bottom diagram).

Human delta exon 52 myotubes were transduced with AAV9 carrying snRNAs disclosed herein. Immunofluorescence was performed to desmin and dystrophin. Dystrophin can be detected after treatment with exon 51-targeting snRNAs. See FIG. 13A-13B.

Example 8: Exon 51 Skipping Skeletal Myotubes and a DMD Mouse Model

Figure 15C:
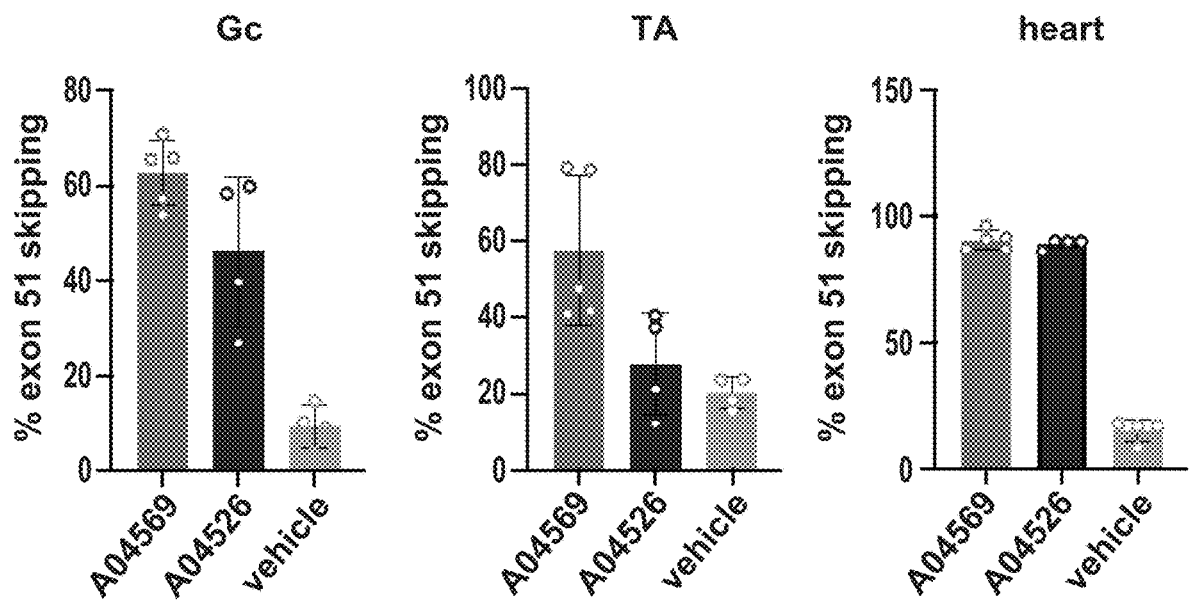
Figure 15D:
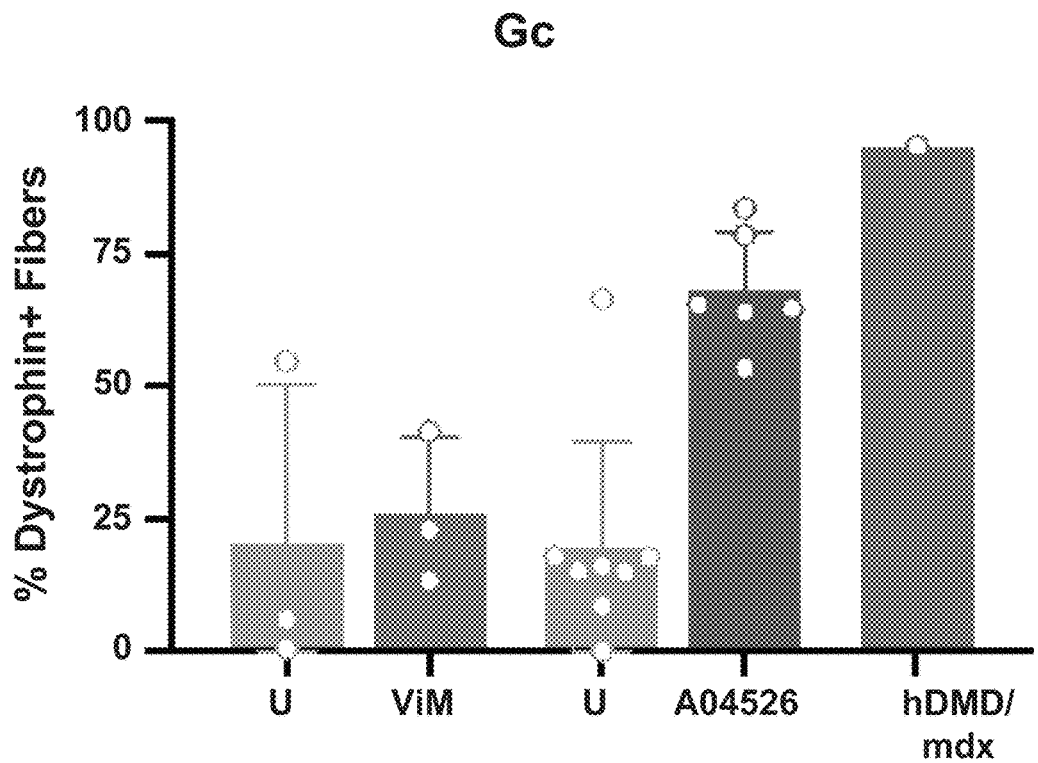

Human skeletal myotubes with exon 52 deleted were transfected with exon 51 RNA-targeting snRNAs carrying fusion antisense sequences (z73=z38/z42) and z187=z42/z38) which target exon splicing enhancers (ESEs). 24 hours after transfection of a low dose of the snRNAs exon 51 skipping levels were quantified (tape station image FIG. 15A). Human skeletal myotubes (with DMD exon 52 deleted) were transduced with AAV9-A04526 (2× z73) and A04569 (2× z187). The myotubes were transduced for 7 days with MOIs of 2.5e4, 1e5 and 5e5. AAV9-based exon 51 skipping was quantified (FIG. 15B). Mice carrying hDMD with exon 52 deleted (del52hDMD/mdx) were injected retro-orbitally with 3e12 vector genomes of A04526 and A04569. Following 3-week survival, RNA was extracted from the tibialis anterior muscle (TA), the Gastrocnemius (Gc) and the heart. Semi-quantitative RT-PCR was performed to detect exon 51 included and excluded bands. (FIG. 15C) shows quantification of exon 51 skipping in the humanized DMD mouse model. Intramuscular delivery of a 3e11 vg/muscle dose of A04526 or an exon 51 ESE-targeting Morpholino (ViM) to the Gastrocnemius of del52hDMD/mdx mice. FIG. 15D shows the quantification of dystrophin positive fibers after 4 weeks. hDMD/mdx mice (gray bar) which expresses wildtype human dystrophin serves as a positive control for dystrophin expression. U=untreated.

Example 9: AAV9-based Splicing Reversal and CUG Repeat Knockdown in DM1 Patient-Derived Myotubes DM1 patient fibroblasts were differentiated into myotubes by transduction with myoD Adenovirus vector (for 5 days). Myotubes were transduced with MOIs of 5e4, 2e5 and 1e6 of A04233 and A04234 (scAAV9 with dual snRNA cassettes targeting CUG repeats) and harvested 7 days post-transduction. Splicing reversal of DMD and LBD3 RNAs and knockdown of DMPK after treatment with U7 snRNA targeting CUG repeats in patient derived myotubes (containing 1700 CUG repeats). See FIGS. 16A-D. Cell nuclei were stained with DAPI and CUG FISH was performed with a CUG labeled probe. Cells were processed 7 days post-transduction for quantification of average number of CUG foci per cell. See FIGS. 17A-B.

Example 10: AAV9-based HTT Knockdown in HD Patient Cells and HD Mouse Model

HD patient iPSc (containing 66 CAG repeats) were differentiated into cortical neurons for 2 weeks and then transduced with 2 different MOIs of AAV-A04390 snRNA vector (2× snRNA cassette targeting CAG repeats) for an additional 2 weeks. Then cortical neurons were harvested and mutant soluble HTT quantified by Meso scale discovery immunoassay. See FIGS. 18A-18C. Then, an in vivo study was designed to target CAG repeats in an R6/2 HD mouse model. An AAV-snRNA vector targeting CAG repeats (A03081: AAVrh10-snRNA (4× snRNAs with CAG×15 TS)) was administered intrastriatal at 2e10 vector genomes and post-treatment mutant soluble HTT protein was quantified via Meso scale discovery immunoassay (MSD) on untreated and snRNA treated mice (n=10). See FIGS. 19A-B.

Example 11: Higher Levels of Expression with Engineered Stem Loop snRNA Vectors Compared to Native Stem Loop snRNA Vectors CHO-Lec2 cells were transduced at an MOI of 1e6 with AAV9-A04527 vector (native stem loop expressing z38/42 targeting DMD exon 51 ESEs) or AAV9-A04526 vector (engineered stem loop expressing z38/42 targeting DMD exon 51 ESEs). Expression of z38/42 is higher in cells transduced with engineered snRNA vector compared to expression of z38/42 in cells transduced with native stem loop snRNA vector. See FIGS. 20A-B.

INCORPORATION BY REFERENCE

Every document cited herein, including any cross referenced or related patent or application is hereby incorporated herein by reference in its entirety unless expressly excluded or otherwise limited. The citation of any document is not an admission that it is prior art with respect to any invention disclosed or embodimented herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

OTHER EMBODIMENTS

While particular embodiments of the disclosure have been illustrated and described, various other changes and modifications can be made without departing from the spirit and scope of the disclosure. The scope of the appended claims includes all such changes and modifications that are within the scope of this disclosure.

What is claimed is:

1. An RNA-targeting nucleic acid molecule comprising an engineered snRNA (esnRNA), wherein the esnRNA comprises an engineered stem loop (eSL) comprising ggttttctgacctccgtcggaaaaccccct (SEQ ID NO: 146).

2. The RNA-targeting nucleic acid molecule of claim 1, wherein the esnRNA comprises a targeting sequence (TS) that targets a target RNA of interest.

3. The RNA-targeting nucleic acid molecule of claim 2, wherein the target RNA is a pre-mRNA or mRNA sequence.

4. The RNA-targeting nucleic acid molecule of claim 2, wherein the target RNA of interest is a microsatellite repeat RNA.

5. The RNA-targeting nucleic acid molecule of claim 2, wherein the target RNA is a sequence encoding dystrophin (DMD).

6. The RNA-targeting nucleic acid molecule of claim 1, wherein the esnRNA comprises two targeting sequences that target two RNA sequences of interest.

7. The RNA-targeting nucleic acid molecule of claim 6, wherein the two targeting sequences are a fusion sequence.

8. The RNA-targeting nucleic acid molecule of claim 1, wherein the esnRNA comprises an Sm binding domain (SmBD) selected from the group consisting of a U1, U2, U4, and U5 SmBD.

9. The RNA-targeting nucleic acid molecule of claim 1, wherein the esnRNA comprises a 5' interaction stabilizer domain (5'ISD).

10. A vector comprising one or more esnRNA of claim 1.

11. The vector of claim 10, wherein the vector is an AAV vector.

12. The AAV vector of claim 11, wherein the esnRNA is operably linked to a promoter.

13. The AAV vector of claim 12, wherein the promoter is a murine promoter.

14. The AAV vector of claim 11, wherein the esnRNA is operably linked to a U7 promoter or a U1 promoter.

15. The AAV vector of claim 11, wherein the esnRNA is operably linked to a downstream terminator (DT).

16. The AAV vector of claim 15, wherein the DT is a U7 DT or a U1 DT.

17. The AAV vector of claim 15, wherein the DT is a murine DT.

18. The AAV vector of claim 11, wherein the vector comprises at least one, at least two, at least three, at least four, or at least five esnRNA.

19. A vector comprising an engineered snRNA (esnRNA) of SEQ ID NO: 179.

20. The vector of claim 19, comprising at least two esnRNA.

\* \* \* \* \*

SEQUENCE LISTING

```
Sequence total quantity: 233
SEQ ID NO: 1            moltype = DNA  length = 27
FEATURE                 Location/Qualifiers
source                  1..27
                        mol_type = other DNA
                        organism = synthetic construct
SEQUENCE: 1
ggctttctgg ctccttaccg gaaagcc                                      27

SEQ ID NO: 2            moltype = DNA  length = 27
FEATURE                 Location/Qualifiers
source                  1..27
                        mol_type = other DNA
                        organism = synthetic construct
SEQUENCE: 2
ggctttctgg gaggttaccg gaaagcc                                      27

SEQ ID NO: 3            moltype = DNA  length = 28
FEATURE                 Location/Qualifiers
source                  1..28
                        mol_type = other DNA
                        organism = synthetic construct
SEQUENCE: 3
ggctttctgg cctccttacc ggaaagcc                                     28

SEQ ID NO: 4            moltype = DNA  length = 28
FEATURE                 Location/Qualifiers
```

```
source                    1..28
                          mol_type = other DNA
                          organism = synthetic construct
SEQUENCE: 4
ggctttctgg ggaggttacc ggaaagcc                                              28

SEQ ID NO: 5              moltype = DNA  length = 27
FEATURE                   Location/Qualifiers
source                    1..27
                          mol_type = other DNA
                          organism = synthetic construct
SEQUENCE: 5
ggctttctgg ctggctaccg gaaagcc                                               27

SEQ ID NO: 6              moltype = DNA  length = 25
FEATURE                   Location/Qualifiers
source                    1..25
                          mol_type = other DNA
                          organism = synthetic construct
SEQUENCE: 6
ggctttctgg cttccccgga aagcc                                                 25

SEQ ID NO: 7              moltype = DNA  length = 27
FEATURE                   Location/Qualifiers
source                    1..27
                          mol_type = other DNA
                          organism = synthetic construct
SEQUENCE: 7
ggctttctgg cttcttcccg gaaagcc                                               27

SEQ ID NO: 8              moltype = DNA  length = 27
FEATURE                   Location/Qualifiers
source                    1..27
                          mol_type = other DNA
                          organism = synthetic construct
SEQUENCE: 8
ggctttctgg caacttaccg gaaagcc                                               27

SEQ ID NO: 9              moltype = DNA  length = 27
FEATURE                   Location/Qualifiers
source                    1..27
                          mol_type = other DNA
                          organism = synthetic construct
SEQUENCE: 9
ggctttctgg ttcggtaccg gaaagcc                                               27

SEQ ID NO: 10             moltype = DNA  length = 28
FEATURE                   Location/Qualifiers
source                    1..28
                          mol_type = other DNA
                          organism = synthetic construct
SEQUENCE: 10
ggctttctgg aagccttacc ggaaagcc                                              28

SEQ ID NO: 11             moltype = DNA  length = 27
FEATURE                   Location/Qualifiers
source                    1..27
                          mol_type = other DNA
                          organism = synthetic construct
SEQUENCE: 11
ggctttctgg cttcttaccg gaaagcc                                               27

SEQ ID NO: 12             moltype =    length =
SEQUENCE: 12
000

SEQ ID NO: 13             moltype =    length =
SEQUENCE: 13
000

SEQ ID NO: 14             moltype =    length =
SEQUENCE: 14
000

SEQ ID NO: 15             moltype =    length =
SEQUENCE: 15
000

SEQ ID NO: 16             moltype =    length =
```

```
SEQUENCE: 16
000

SEQ ID NO: 17           moltype =    length =
SEQUENCE: 17
000

SEQ ID NO: 18           moltype =    length =
SEQUENCE: 18
000

SEQ ID NO: 19           moltype =    length =
SEQUENCE: 19
000

SEQ ID NO: 20           moltype =    length =
SEQUENCE: 20
000

SEQ ID NO: 21           moltype =    length =
SEQUENCE: 21
000

SEQ ID NO: 22           moltype =    length =
SEQUENCE: 22
000

SEQ ID NO: 23           moltype =    length =
SEQUENCE: 23
000

SEQ ID NO: 24           moltype = DNA   length = 30
FEATURE                 Location/Qualifiers
source                  1..30
                        mol_type = other DNA
                        organism = synthetic construct
SEQUENCE: 24
caaactacag agccaagtgc tatccacaga                                      30

SEQ ID NO: 25           moltype = DNA   length = 30
FEATURE                 Location/Qualifiers
source                  1..30
                        mol_type = other DNA
                        organism = synthetic construct
SEQUENCE: 25
gagctttctg ggttgccatc tcaagcagac                                      30

SEQ ID NO: 26           moltype = DNA   length = 30
FEATURE                 Location/Qualifiers
source                  1..30
                        mol_type = other DNA
                        organism = synthetic construct
SEQUENCE: 26
tacaaggcca tcagctcata ctcacaattg                                      30

SEQ ID NO: 27           moltype = DNA   length = 100
FEATURE                 Location/Qualifiers
source                  1..100
                        mol_type = other DNA
                        organism = synthetic construct
SEQUENCE: 27
caaactacag agccaagtgc tatccacaga gagctttctg ggttgccatc tcaagcagac     60
tacaaggcca tcagctcata ctcacaattg actttgagag                          100

SEQ ID NO: 28           moltype = DNA   length = 100
FEATURE                 Location/Qualifiers
source                  1..100
                        mol_type = other DNA
                        organism = synthetic construct
SEQUENCE: 28
ttgaccacat acgtgctctt tcaaagttct gtgtttgaag ttatgttagt aacaactgat     60
gcccatcctg caatgacaaa tccaattctc agtgcagctc                          100

SEQ ID NO: 29           moltype = DNA   length = 500
FEATURE                 Location/Qualifiers
source                  1..500
                        mol_type = other DNA
                        organism = synthetic construct
SEQUENCE: 29
```

```
caaactacag agccaagtgc tatccacaga gagctttctg ggttgccatc tcaagcagac    60
tacaaggcca tcagctcata ctcacaattg actttgagag tcattttcca atgctcctac   120
acacccttc ttcacaatcc ccaacaaatc tgaggctgga acttggtacc ataacaatca   180
ttacattatt tcaccagaag tacaccttgc ctggaagatt ggcattatag catcttctaa   240
cattgtgaaa gttagtgacc aatgaggaga tccaagtcag ttccagttgg atttctctat   300
actctataat aaatatatat ggtgtcttca acaataggac tttgccatcc agtgatgcta   360
aaaatcaata acaatggcaa taacctgccc tgtttggaaa gcctctggct tccatgacta   420
acaattcaag gcaggtctcc tatacctagt actgagattt ttatttgata aactatatct   480
tctgggagga gaagcattgt                                              500

SEQ ID NO: 30         moltype = DNA   length = 500
FEATURE               Location/Qualifiers
source                1..500
                      mol_type = other DNA
                      organism = synthetic construct
SEQUENCE: 30
ttgaccacat acgtgctctt tcaaagttct gtgtttgaag ttatgttagt aacaactgat    60
gcccatcctg caatgacaaa tccaattctc agtgcagctc tctgaaatag ttttgctttc   120
tctctctagg tctgttctat actcctaact ctccaggagt ttacaaggaa taaaatctct   180
tccaaatgct ttctgttgca acaactggac catactgaaa gctgaggccc acaattgcaa   240
tctaggttag caggtaatca ttgttggtga ggtcctccct ttccccaggc tcgtgttgt    300
attggggagc aggaaatttt tgctagagca gcactctac ctctctacac tccacctgat   360
tggtgggatg gaccagagaa atggacattc ccaacacagt ccctcctttc acatctgctc   420
acctgcccac aggatacttt ccaccatgca tactgggctc tgcaccaacc attcagcagt   480
gatgaagagg aaacttgaac                                              500

SEQ ID NO: 31         moltype =   length =
SEQUENCE: 31
000

SEQ ID NO: 32         moltype =   length =
SEQUENCE: 32
000

SEQ ID NO: 33         moltype =   length =
SEQUENCE: 33
000

SEQ ID NO: 34         moltype =   length =
SEQUENCE: 34
000

SEQ ID NO: 35         moltype =   length =
SEQUENCE: 35
000

SEQ ID NO: 36         moltype =   length =
SEQUENCE: 36
000

SEQ ID NO: 37         moltype =   length =
SEQUENCE: 37
000

SEQ ID NO: 38         moltype =   length =
SEQUENCE: 38
000

SEQ ID NO: 39         moltype = DNA   length = 288
FEATURE               Location/Qualifiers
source                1..288
                      mol_type = other DNA
                      organism = synthetic construct
SEQUENCE: 39
tactgccgaa tccaggtctc cgggcttaac aacaacgaag gggctgtgac tggctgcttt    60
ctcaaccaat cagcaccgaa tcatttgca tgggctgaga acaaatgttc gcgaactcta   120
gaaatgaatg acttaagtaa gttccttaga atattatttt tcctactgaa agttaccaca   180
tgcgtcgttg tttatacagt aataggaaca agaaaaagt cacctaagct caccctcatc   240
aattgtggag ttccttata tcccatcttc tctccaaaca catacgca                288

SEQ ID NO: 40         moltype = DNA   length = 392
FEATURE               Location/Qualifiers
source                1..392
                      mol_type = other DNA
                      organism = synthetic construct
SEQUENCE: 40
aaggaccagc ttctttggga gagaacagac gcagggcgg gagggaaaaa gggagaggca    60
gacgtcactt cccccttggcg gctctggcag cagattggtc ggttgagtgg cagaaaggca   120
gacgggact gggcaaggca ctgtcggtga catcacggac agggcgactt ctatgtagat   180
```

```
gaggcagcgc agaggctgac gtcttcgcca cttgctgctt caccacgaag gagtttcccgt    240
gccctgggag cggggttcagg accgctgatc ggaagtgaga atcccagctg tgtgtcaggg    300
ctggaaaggg ctcgggagtg cgcggggcaa gtgaccgtgt gtgtaaagag tgaggcgtat    360
gaggctgtgt cggggcagag gcacaacgtt tc                                  392

SEQ ID NO: 41           moltype = DNA   length = 247
FEATURE                 Location/Qualifiers
source                  1..247
                        mol_type = other DNA
                        organism = synthetic construct
SEQUENCE: 41
ccacgccctc tgtgaaaggg cggggcatgc aaattcgaaa tgaaagcccg ggaacgccgg     60
aagaagcacg ggtgtaagat ttcccttttc aaaggcagag aataagaaat cagcccgaga    120
gtgtaagggc gtcaatagcg ctgtggacga gacagaggga atggggcaag gagcgaggct    180
ggggctctca ccgcgacttg aatgtggatg agagtgggac ggtgacggcg ggcgcgaagg    240
cgagcgc                                                              247

SEQ ID NO: 42           moltype = DNA   length = 250
FEATURE                 Location/Qualifiers
source                  1..250
                        mol_type = other DNA
                        organism = synthetic construct
SEQUENCE: 42
ttcgcagtct ctgaattaag tctattagca tgttcctccc atagtgcttt gcttcatatc     60
aacaaaaacc tagctaagtg aaatcagcaa cgatatgcag aaaccaccta cgcaggtcac    120
aaacatcttt ctatgattgt ataatttca agcaagcaat aagtgaagat ttttccatag     180
gccctaaact cacctttgcg aaataggaag ctggtttatt gggagtgatg agcaggggc    240
gtaacaaatt                                                           250

SEQ ID NO: 43           moltype = DNA   length = 300
FEATURE                 Location/Qualifiers
source                  1..300
                        mol_type = other DNA
                        organism = synthetic construct
SEQUENCE: 43
gcagcaaggc ctccacttca cccctaaag gttgccccaa gagcaccgtg tgactgctaa      60
ggtatttccg gagtctaaag acgattattc aggtctcatt tgcataccca taatacactg    120
caaacagtat ttttttcgga aaaacattta tatattgctt gacatttta agtatgagaa     180
ttttgcatgc agaatttttt tgtataaact ttctcaggta gtaaccccttg ggattagtag   240
acaccatcag tgtactagga attgcagtta cccgaaaatt gagttacaga agtaactggt    300

SEQ ID NO: 44           moltype = DNA   length = 296
FEATURE                 Location/Qualifiers
source                  1..296
                        mol_type = other DNA
                        organism = synthetic construct
SEQUENCE: 44
gtttattaca gggacagcag agatccagtt tggttaatta aggtaccgag ggcctatttc     60
ccatgattcc ttcatatttg catatacgat acaaggctgt tagagagata attagaatta   120
atttgactgt aaacacaaag atattagtac aaaaatacgtg acgtagaaag taataatttc   180
ttgggtagtt tgcagttta aaattatgtt ttaaaatgga ctatcatatg cttaccgtaa    240
cttgaaagta tttcgatttc ttggctttat atatcttgtg gaaaggacga aacacc        296

SEQ ID NO: 45           moltype = DNA   length = 243
FEATURE                 Location/Qualifiers
source                  1..243
                        mol_type = other DNA
                        organism = synthetic construct
SEQUENCE: 45
ctgcagtatt tagcatgccc cacccatctg caaggcattc tggatagtgt caaaacagcc     60
ggaaatcaag tccgtttatc tcaaacttta gcatttggg aataaatgat atttgctatg    120
ctggttaaat tagattttag ttaaatttcc tgctgaagct ctagtacgat aagtaacttg    180
acctaagtgt aaagttgaga tttccttcag gtttatatag cttgtgcgcc gcctgggtac    240
ctc                                                                  243

SEQ ID NO: 46           moltype = DNA   length = 106
FEATURE                 Location/Qualifiers
source                  1..106
                        mol_type = other DNA
                        organism = synthetic construct
SEQUENCE: 46
caggactagt cttttaggtc aaaaagaaga agctttgtaa ccgttggttt ccgtagtgta     60
gtggttatca cgttcgccta acacgcgaaa ggtccccggt tcgaag                   106

SEQ ID NO: 47           moltype = DNA   length = 439
FEATURE                 Location/Qualifiers
source                  1..439
                        mol_type = other DNA
                        organism = synthetic construct
```

```
SEQUENCE: 47
ttgttcctct tagtgttaat tcacactaaa gactgtgcat ccgactccta catttatgaa    60
agtaaatgcc tgttgttaga acaaaaaagg ctacagaaca aaaaacaaag cgaaatacca   120
tctgctttag gttcagtgtg gtattttccc gctgacaggg aggcgggttt ttgggtacag   180
gaaacgagtc actatggagg cggtactatg tagatgaaga ttcaggtgca aactgggaaa   240
agcaactgct tccaaatatt tgtgattttt acagtgtagt tttggaaaaa ctcttagcct   300
accaattctt ctaagtgttt taaaatgtgg gagccagtac acatgaagtt atagagtgtt   360
ttaatgaggc ttaaatattt accgtaacta tgaaatgcta cgcatatcat gctgttcagg   420
ctccgtggcc acgcaactc                                                439

SEQ ID NO: 48          moltype = DNA   length = 258
FEATURE                Location/Qualifiers
source                 1..258
                       mol_type = other DNA
                       organism = synthetic construct
SEQUENCE: 48
taacaacata ggagctgtga ttggctgttt tcagccaatc agcactgact catttgcata    60
gcctttacaa gcggtcacaa actcaagaaa cgagcggttt taatagtctt ttagaatatt   120
gtttatcgaa ccgaataagg aactgtgctt tgtgattcac atatcagtgg aggggtgtgg   180
aaatggcacc ttgatctcac cctcatcgaa agtggagttg atgtccttcc ctggctcgct   240
acagacgcac ttccgcaa                                                 258

SEQ ID NO: 49          moltype = DNA   length = 94
FEATURE                Location/Qualifiers
source                 1..94
                       mol_type = other DNA
                       organism = synthetic construct
SEQUENCE: 49
cctcttatga tgtttgttgc caatgataga ttgttttcac tgtgcaaaaa ttatgggtag    60
ttttggtggt cttgatgcag ttgtaagctt ggag                                94

SEQ ID NO: 50          moltype = DNA   length = 50
FEATURE                Location/Qualifiers
source                 1..50
                       mol_type = other DNA
                       organism = synthetic construct
SEQUENCE: 50
actttctgga gtttcaaaaa cagactgtac gccaagggtc atatctttt                50

SEQ ID NO: 51          moltype = DNA   length = 50
FEATURE                Location/Qualifiers
source                 1..50
                       mol_type = other DNA
                       organism = synthetic construct
SEQUENCE: 51
ccggggatac aacgtgtttc ctaaaagtag agggaggtaa gagacggtag                50

SEQ ID NO: 52          moltype = DNA   length = 50
FEATURE                Location/Qualifiers
source                 1..50
                       mol_type = other DNA
                       organism = synthetic construct
SEQUENCE: 52
ctgaattttc ttgcagttga acaacagagg ctttttttgt gtgtgtgggg                50

SEQ ID NO: 53          moltype = DNA   length = 50
FEATURE                Location/Qualifiers
source                 1..50
                       mol_type = other DNA
                       organism = synthetic construct
SEQUENCE: 53
atatgtggta atccaacaat agaaattatt tttaagtttg tgtgttcctt                50

SEQ ID NO: 54          moltype =    length =
SEQUENCE: 54
000

SEQ ID NO: 55          moltype =    length =
SEQUENCE: 55
000

SEQ ID NO: 56          moltype =    length =
SEQUENCE: 56
000

SEQ ID NO: 57          moltype = DNA   length = 206
FEATURE                Location/Qualifiers
source                 1..206
                       mol_type = other DNA
```

-continued

```
                                organism = synthetic construct
SEQUENCE: 57
gtttacttgg tttaaaaat agcttgcact agcgatacgg aatatggtta ttaggtttgt    60
taggcatcat gtcgtgtctt actatagaaa aataacgtag tgttcatttt agcctgcctt   120
tatgtgttaa tttgtcctta ttgcgcattg ttcttgttaa gtcttctgta aggagttgcg   180
ggtttcaaac tgtcagtctg agagca                                       206

SEQ ID NO: 58           moltype = DNA   length = 110
FEATURE                 Location/Qualifiers
source                  1..110
                        mol_type = other DNA
                        organism = synthetic construct
SEQUENCE: 58
cccaatttca ctggtctaca atgaaagcaa aacagttctc ttccccgctc cccggtgtgt    60
gagaggggct ttgatccttc tctggtttcc taggaaacgc gtatgtgtac              110

SEQ ID NO: 59           moltype = DNA   length = 130
FEATURE                 Location/Qualifiers
source                  1..130
                        mol_type = other DNA
                        organism = synthetic construct
SEQUENCE: 59
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct                                                         130

SEQ ID NO: 60           moltype = DNA   length = 141
FEATURE                 Location/Qualifiers
source                  1..141
                        mol_type = other DNA
                        organism = synthetic construct
SEQUENCE: 60
aggaacccct agtgatggag ttggccactc cctctctgcg cgctcgctcg ctcactgagg    60
ccgggcgacc aaaggtcgcc cgacgcccgg gctttgcccg gcggcctcag tgagcgagc   120
gagcgcgcag ctgcctgcag g                                            141

SEQ ID NO: 61           moltype = DNA   length = 113
FEATURE                 Location/Qualifiers
source                  1..113
                        mol_type = other DNA
                        organism = synthetic construct
SEQUENCE: 61
ccactccctc tctgcgcgct cgctcgctca ctgaggccgg ggcgaccaaag gtcgcccgac    60
gcccgggctt tgcccgggcg gcctcagtga gcgagcgagc gcgcagagag gga          113

SEQ ID NO: 62           moltype = DNA   length = 508
FEATURE                 Location/Qualifiers
source                  1..508
                        mol_type = other DNA
                        organism = synthetic construct
SEQUENCE: 62
cgttacataa cttacggtaa atggcccgcc tggctgaccg cccaacgacc cccgcccatt    60
gacgtcaata atgacgtatg ttcccatagt aacgccaata gggactttcc attgacgtca   120
atgggtggag tatttacggt aaactgccca cttggcagta catcaagtgt atcatatgcc   180
aagtacgccc cctattgacg tcaatgacgg taaatggccc gcctggcatt atgcccagta   240
catgacccta tgggactttc ctacttggca gtacatctac gtattagtca tcgctattac   300
catggtgatg cggttttggc agtacatcaa tgggcgtgga tagcggtttg actcacgggg   360
atttccaagt ctccaccccca ttgacgtcaa tgggagtttg ttttggcacc aaaatcaacg   420
ggactttcca aaatgtcgta caactccgcc ccattgacgc aaatgggcg gtaggcgtgt    480
acggtgggag gtctatataa gcagagct                                     508

SEQ ID NO: 63           moltype = DNA   length = 720
FEATURE                 Location/Qualifiers
source                  1..720
                        mol_type = other DNA
                        organism = synthetic construct
SEQUENCE: 63
atggtgagca agggcgagga gctgttcacc ggggtggtgc ccatcctggt cgagctggac    60
ggcgacgtaa acggccacaa gttcagcgtg tccggcgagg gcgagggcga tgccacctac   120
ggcaagctga ccctgaagtt catctgcacc accggcaagc tgcccgtgcc ctggcccacc   180
ctcgtgacca ccctgaccta cggcgtgcag tgcttcagcc gctaccccga ccacatgaag   240
cagcacgact tcttcaagtc cgccatgccc gaaggctacg tccaggagcg caccatcttc   300
ttcaaggacg acggcaacta caagacccgc gccgaggtga agttcgaggg cgacaccctg   360
gtgaaccgca tcgagctgaa gggcatcgac ttcaaggagg acggcaacat cctggggcac   420
aagctggagt acaactacaa cagccacaac gtctatatca tggccgacaa gcagaagaac   480
ggcatcaagg tgaacttcaa gatccgccac aacatcgagg acggcagcgt gcagctcgcc   540
gaccactacc agcagaacac ccccatcggc gacggccccg tgctgctgcc cgacaaccac   600
tacctgagca cccagtccgc cctgagcaaa gaccccaacg agaagcgcga tcacatggtc   660
ctgctggagt tcgtgaccgc cgccgggatc actctcggca tggacgagct gtacaagtaa   720
```

```
SEQ ID NO: 64          moltype = DNA   length = 122
FEATURE                Location/Qualifiers
source                 1..122
                       mol_type = other DNA
                       organism = synthetic construct
SEQUENCE: 64
aacttgttta ttgcagctta taatggttac aaataaagca atagcatcac aaatttcaca      60
aataaagcat ttttttcact gcattctagt tgtggtttgt ccaaactcat caatgtatct     120
ta                                                                    122

SEQ ID NO: 65          moltype = DNA   length = 90
FEATURE                Location/Qualifiers
source                 1..90
                       mol_type = other DNA
                       organism = synthetic construct
SEQUENCE: 65
ggagtcagca gcagcagcag cagcagcagc agcagcagca gcagcagcag aattttggga      60
gtaggctttc tggctcctta ccggaaagcc                                       90

SEQ ID NO: 66          moltype = DNA   length = 71
FEATURE                Location/Qualifiers
source                 1..71
                       mol_type = other DNA
                       organism = synthetic construct
SEQUENCE: 66
ggagttcacc agaagcgtac catactcacg aaattttggg agtaggcttt ctggctcctt      60
accggaaagc c                                                           71

SEQ ID NO: 67          moltype = DNA   length = 90
FEATURE                Location/Qualifiers
source                 1..90
                       mol_type = other DNA
                       organism = synthetic construct
SEQUENCE: 67
ggagtctgct gctgctgctg ctgctgctgc tgctgctgct gctgctgctg aattttggga      60
gtaggctttc tggctcctta ccggaaagcc                                       90

SEQ ID NO: 68          moltype = DNA   length = 101
FEATURE                Location/Qualifiers
source                 1..101
                       mol_type = other DNA
                       organism = synthetic construct
SEQUENCE: 68
ggagttacct ccaacatcaa ggaagatggc agtaaccaca ggttgtgtca ccagagtaac      60
aaattttggg agtaggcttt ctggctcctt accggaaagc c                         101

SEQ ID NO: 69          moltype = DNA   length = 75
FEATURE                Location/Qualifiers
source                 1..75
                       mol_type = other DNA
                       organism = synthetic construct
SEQUENCE: 69
ggagtgtaac cacaggttgt gtcaccagag taacaaattt ttggagtagg ctttctggct      60
ccttaccgga aagcc                                                       75

SEQ ID NO: 70          moltype = DNA   length = 71
FEATURE                Location/Qualifiers
source                 1..71
                       mol_type = other DNA
                       organism = synthetic construct
SEQUENCE: 70
ggagttacct ccaacatcaa ggaagatggc aaattttggg agtaggcttt ctggctcctt      60
accggaaagc c                                                           71

SEQ ID NO: 71          moltype = DNA   length = 90
FEATURE                Location/Qualifiers
source                 1..90
                       mol_type = other DNA
                       organism = synthetic construct
SEQUENCE: 71
ggagtcagca gcagcagcag cagcagcagc agcagcagca gcagcagcag aatttgtgga      60
gtaggctttc tggctcctta ccggaaagcc                                       90

SEQ ID NO: 72          moltype = DNA   length = 90
FEATURE                Location/Qualifiers
source                 1..90
                       mol_type = other DNA
                       organism = synthetic construct
```

```
SEQUENCE: 72
ggagtcagca gcagcagcag cagcagcagc agcagcagca gcagcagcag tcgagttgga    60
gtaggctttc tggctcctta ccggaaagcc                                     90

SEQ ID NO: 73           moltype = DNA  length = 81
FEATURE                 Location/Qualifiers
source                  1..81
                        mol_type = other DNA
                        organism = synthetic construct
SEQUENCE: 73
ggagtcagca gcagcagcag cagcagcagc agcagcagca gcagcagcag agtaggcttt    60
ctggctcctt accggaaagc c                                              81

SEQ ID NO: 74           moltype = DNA  length = 71
FEATURE                 Location/Qualifiers
source                  1..71
                        mol_type = other DNA
                        organism = synthetic construct
SEQUENCE: 74
ggagttcacc agaagcgtac catactcacg aaatttgtgg agtaggcttt ctggctcctt    60
accggaaagc c                                                         71

SEQ ID NO: 75           moltype = DNA  length = 71
FEATURE                 Location/Qualifiers
source                  1..71
                        mol_type = other DNA
                        organism = synthetic construct
SEQUENCE: 75
ggagttcacc agaagcgtac catactcacg atcgagttgg agtaggcttt ctggctcctt    60
accggaaagc c                                                         71

SEQ ID NO: 76           moltype = DNA  length = 62
FEATURE                 Location/Qualifiers
source                  1..62
                        mol_type = other DNA
                        organism = synthetic construct
SEQUENCE: 76
ggagttcacc agaagcgtac catactcacg aagtaggctt tctggctcct taccggaaag    60
cc                                                                   62

SEQ ID NO: 77           moltype = DNA  length = 90
FEATURE                 Location/Qualifiers
source                  1..90
                        mol_type = other DNA
                        organism = synthetic construct
SEQUENCE: 77
ggagtctgct gctgctgctg ctgctgctgc tgctgctgct gctgctgctg aatttgtgga    60
gtaggctttc tggctcctta ccggaaagcc                                     90

SEQ ID NO: 78           moltype = DNA  length = 90
FEATURE                 Location/Qualifiers
source                  1..90
                        mol_type = other DNA
                        organism = synthetic construct
SEQUENCE: 78
ggagtctgct gctgctgctg ctgctgctgc tgctgctgct gctgctgctg tcgagttgga    60
gtaggctttc tggctcctta ccggaaagcc                                     90

SEQ ID NO: 79           moltype = DNA  length = 81
FEATURE                 Location/Qualifiers
source                  1..81
                        mol_type = other DNA
                        organism = synthetic construct
SEQUENCE: 79
ggagtctgct gctgctgctg ctgctgctgc tgctgctgct gctgctgctg agtaggcttt    60
ctggctcctt accggaaagc c                                              81

SEQ ID NO: 80           moltype = DNA  length = 60
FEATURE                 Location/Qualifiers
source                  1..60
                        mol_type = other DNA
                        organism = synthetic construct
SEQUENCE: 80
ggagtctgct gctgctgctg aatttgtgga gtaggctttc tggctcctta ccggaaagcc    60

SEQ ID NO: 81           moltype = DNA  length = 60
FEATURE                 Location/Qualifiers
source                  1..60
                        mol_type = other DNA
```

```
                               organism = synthetic construct
SEQUENCE: 81
ggagtctgct gctgctgctg tcgagttgga gtaggctttc tggctcctta ccggaaagcc      60

SEQ ID NO: 82              moltype = DNA   length = 51
FEATURE                    Location/Qualifiers
source                     1..51
                           mol_type = other DNA
                           organism = synthetic construct
SEQUENCE: 82
ggagtctgct gctgctgctg agtaggcttt ctggctcctt accggaaagc c               51

SEQ ID NO: 83              moltype = DNA   length = 58
FEATURE                    Location/Qualifiers
source                     1..58
                           mol_type = other DNA
                           organism = synthetic construct
SEQUENCE: 83
ggagttacct ccaacatcaa ggaagatggc aggctttctg gctccttacc ggaaagcc        58

SEQ ID NO: 84              moltype = DNA   length = 96
FEATURE                    Location/Qualifiers
source                     1..96
                           mol_type = other DNA
                           organism = synthetic construct
SEQUENCE: 84
gttcccgaag taaccttcg ggaacggagt tcaccagaag cgtaccatac tcacgaaatt       60
tttggagtag gctttctggc tccttaccgg aaagcc                                96

SEQ ID NO: 85              moltype = DNA   length = 91
FEATURE                    Location/Qualifiers
source                     1..91
                           mol_type = other DNA
                           organism = synthetic construct
SEQUENCE: 85
gttcccgaag taaccttcg ggaactcacc agaagcgtac catactcacg aaattttttgg     60
agtaggcttt ctggctcctt accggaaagc c                                     91

SEQ ID NO: 86              moltype = DNA   length = 91
FEATURE                    Location/Qualifiers
source                     1..91
                           mol_type = other DNA
                           organism = synthetic construct
SEQUENCE: 86
gttcccgaag ggagtcttcg ggaactcacc agaagcgtac catactcacg aaattttttgg    60
agtaggcttt ctggctcctt accggaaagc c                                     91

SEQ ID NO: 87              moltype = DNA   length = 72
FEATURE                    Location/Qualifiers
source                     1..72
                           mol_type = other DNA
                           organism = synthetic construct
SEQUENCE: 87
gggccctcac cagaagcgta ccatactcac gaaattttg gagtaggctt tctggctcct       60
taccggaaag cc                                                          72

SEQ ID NO: 88              moltype = DNA   length = 96
FEATURE                    Location/Qualifiers
source                     1..96
                           mol_type = other DNA
                           organism = synthetic construct
SEQUENCE: 88
gagaagattc gtcttctctc tctctcttct tcaccagaag cgtaccatac tcacgaaatt      60
tttggagtag gctttctggc tccttaccgg aaagcc                                96

SEQ ID NO: 89              moltype = DNA   length = 115
FEATURE                    Location/Qualifiers
source                     1..115
                           mol_type = other DNA
                           organism = synthetic construct
SEQUENCE: 89
gttcccgaag taaccttcg ggaacggagt cagcagcagc agcagcagca gcagcagcag       60
cagcagcagc agcagaattt ttggagtagg ctttctggct ccttaccgga aagcc          115

SEQ ID NO: 90              moltype = DNA   length = 110
FEATURE                    Location/Qualifiers
source                     1..110
                           mol_type = other DNA
                           organism = synthetic construct
```

```
SEQUENCE: 90
gttcccgaag taaccttcg ggaaccagca gcagcagcag cagcagcagc agcagcagca    60
gcagcagcag aatttttgga gtaggctttc tggctcctta ccggaaagcc              110

SEQ ID NO: 91           moltype = DNA   length = 110
FEATURE                 Location/Qualifiers
source                  1..110
                        mol_type = other DNA
                        organism = synthetic construct
SEQUENCE: 91
gttcccgaag ggagtcttcg ggaaccagca gcagcagcag cagcagcagc agcagcagca    60
gcagcagcag aatttttgga gtaggctttc tggctcctta ccggaaagcc              110

SEQ ID NO: 92           moltype = DNA   length = 91
FEATURE                 Location/Qualifiers
source                  1..91
                        mol_type = other DNA
                        organism = synthetic construct
SEQUENCE: 92
gggcccagc agcagcagca gcagcagcag cagcagcagc agcagcagca gaatttttgg     60
agtaggcttt ctggctcctt accgaaaagc c                                   91

SEQ ID NO: 93           moltype = DNA   length = 115
FEATURE                 Location/Qualifiers
source                  1..115
                        mol_type = other DNA
                        organism = synthetic construct
SEQUENCE: 93
gagaagattc gtcttctctc tctctcttct cagcagcagc agcagcagca gcagcagcag    60
cagcagcagc agcagaattt ttggagtagg ctttctggct ccttaccgga aagcc        115

SEQ ID NO: 94           moltype = DNA   length = 71
FEATURE                 Location/Qualifiers
source                  1..71
                        mol_type = other DNA
                        organism = synthetic construct
SEQUENCE: 94
ggagttcacc agaagcgtac catactcacg aaatttttgg agtaggcttt ctggctcctt    60
accggaaagc c                                                         71

SEQ ID NO: 95           moltype = DNA   length = 71
FEATURE                 Location/Qualifiers
source                  1..71
                        mol_type = other DNA
                        organism = synthetic construct
SEQUENCE: 95
cctcttcacc agaagcgtac catactcacg aaatttttgg agtaggcttt ctgggaggtt    60
accggaaagc c                                                         71

SEQ ID NO: 96           moltype = DNA   length = 73
FEATURE                 Location/Qualifiers
source                  1..73
                        mol_type = other DNA
                        organism = synthetic construct
SEQUENCE: 96
ggaggttcac cagaagcgta ccatactcac gaaattttg gagtaggctt tctggcctcc     60
ttaccggaaa gcc                                                       73

SEQ ID NO: 97           moltype = DNA   length = 73
FEATURE                 Location/Qualifiers
source                  1..73
                        mol_type = other DNA
                        organism = synthetic construct
SEQUENCE: 97
cctccttcac cagaagcgta ccatactcac gaaattttg gagtaggctt tctggggagg     60
ttaccggaaa gcc                                                       73

SEQ ID NO: 98           moltype = DNA   length = 72
FEATURE                 Location/Qualifiers
source                  1..72
                        mol_type = other DNA
                        organism = synthetic construct
SEQUENCE: 98
agccagtcac cagaagcgta ccatactcac gaaattttg gagtaggctt tctggctggc     60
taccggaaag cc                                                        72

SEQ ID NO: 99           moltype = DNA   length = 69
FEATURE                 Location/Qualifiers
source                  1..69
```

```
                        mol_type = other DNA
                        organism = synthetic construct
SEQUENCE: 99
ggaagtcacc agaagcgtac catactcacg aaattttgg agtaggcttt ctggcttccc    60
cggaaagcc                                                           69

SEQ ID NO: 100          moltype = DNA   length = 73
FEATURE                 Location/Qualifiers
source                  1..73
                        mol_type = other DNA
                        organism = synthetic construct
SEQUENCE: 100
gaagaagtca ccagaagcgt accatactca cgaaattttt ggagtaggct ttctggcttc    60
ttcccggaaa gcc                                                      73

SEQ ID NO: 101          moltype = DNA   length = 70
FEATURE                 Location/Qualifiers
source                  1..70
                        mol_type = other DNA
                        organism = synthetic construct
SEQUENCE: 101
gttgtcacca gaagcgtacc atactcacga aattttgga gtaggctttc tggcaactta    60
ccggaaagcc                                                          70

SEQ ID NO: 102          moltype = DNA   length = 71
FEATURE                 Location/Qualifiers
source                  1..71
                        mol_type = other DNA
                        organism = synthetic construct
SEQUENCE: 102
ccgaatcacc agaagcgtac catactcacg aaattttgg agtaggcttt ctggttcggt    60
accggaaagc c                                                        71

SEQ ID NO: 103          moltype = DNA   length = 73
FEATURE                 Location/Qualifiers
source                  1..73
                        mol_type = other DNA
                        organism = synthetic construct
SEQUENCE: 103
taaggagtca ccagaagcgt accatactca cgaaattttt ggagtaggct ttctggctcc    60
ttaccggaaa gcc                                                      73

SEQ ID NO: 104          moltype = DNA   length = 70
FEATURE                 Location/Qualifiers
source                  1..70
                        mol_type = other DNA
                        organism = synthetic construct
SEQUENCE: 104
gaagtcacca gaagcgtacc atactcacga aattttgga gtaggctttc tggcttcttc    60
ccggaaagcc                                                          70

SEQ ID NO: 105          moltype = DNA   length = 72
FEATURE                 Location/Qualifiers
source                  1..72
                        mol_type = other DNA
                        organism = synthetic construct
SEQUENCE: 105
ggctttcacc agaagcgtac catactcacg aaattttgg agtaggcttt ctggaagcct    60
taccggaaag cc                                                       72

SEQ ID NO: 106          moltype = DNA   length = 70
FEATURE                 Location/Qualifiers
source                  1..70
                        mol_type = other DNA
                        organism = synthetic construct
SEQUENCE: 106
gaagtcacca gaagcgtacc atactcacga aattttgga gtaggctttc tggcttctta    60
ccggaaagcc                                                          70

SEQ ID NO: 107          moltype = DNA   length = 90
FEATURE                 Location/Qualifiers
source                  1..90
                        mol_type = other DNA
                        organism = synthetic construct
SEQUENCE: 107
ggagtcagca gcagcagcag cagcagcag agcagcagca gcagcagcag aattttgga     60
gtaggctttg tggctccttta ccggaaagcc                                   90

SEQ ID NO: 108          moltype = DNA   length = 90
```

```
FEATURE                 Location/Qualifiers
source                  1..90
                        mol_type = other DNA
                        organism = synthetic construct
SEQUENCE: 108
cctctcagca gcagcagcag cagcagcagc agcagcagca gcagcagcag aattttttgga    60
gtaggctttc tgggaggtta ccggaaagcc                                      90

SEQ ID NO: 109          moltype = DNA  length = 92
FEATURE                 Location/Qualifiers
source                  1..92
                        mol_type = other DNA
                        organism = synthetic construct
SEQUENCE: 109
ggaggtcagc agcagcagca gcagcagcag cagcagcagc agcagcagca gaattttttgg    60
agtaggcttt ctggcctcct taccggaaag cc                                   92

SEQ ID NO: 110          moltype = DNA  length = 92
FEATURE                 Location/Qualifiers
source                  1..92
                        mol_type = other DNA
                        organism = synthetic construct
SEQUENCE: 110
cctcctcagc agcagcagca gcagcagcag cagcagcagc agcagcagca gaattttttgg    60
agtaggcttt ctggggaggt taccggaaag cc                                   92

SEQ ID NO: 111          moltype = DNA  length = 91
FEATURE                 Location/Qualifiers
source                  1..91
                        mol_type = other DNA
                        organism = synthetic construct
SEQUENCE: 111
agccagcagc agcagcagca gcagcagcag cagcagcagc agcagcagca gaattttttgg    60
agtaggcttt ctggctggct accggaaagc c                                    91

SEQ ID NO: 112          moltype = DNA  length = 88
FEATURE                 Location/Qualifiers
source                  1..88
                        mol_type = other DNA
                        organism = synthetic construct
SEQUENCE: 112
ggaagcagca gcagcagcag cagcagcagc agcagcagca gcagcagcag aattttttgga    60
gtaggctttc tggcttcccc ggaaagcc                                        88

SEQ ID NO: 113          moltype = DNA  length = 92
FEATURE                 Location/Qualifiers
source                  1..92
                        mol_type = other DNA
                        organism = synthetic construct
SEQUENCE: 113
gaagaagcag cagcagcagc agcagcagca gcagcagcag cagcagcagc agaattttttg    60
gagtaggctt tctggcttct tcccggaaag cc                                   92

SEQ ID NO: 114          moltype = DNA  length = 89
FEATURE                 Location/Qualifiers
source                  1..89
                        mol_type = other DNA
                        organism = synthetic construct
SEQUENCE: 114
gttgcagcag cagcagcagc agcagcagca gcagcagcag cagcagcaga attttttggag    60
taggctttct ggcaacttac cggaaagcc                                       89

SEQ ID NO: 115          moltype = DNA  length = 90
FEATURE                 Location/Qualifiers
source                  1..90
                        mol_type = other DNA
                        organism = synthetic construct
SEQUENCE: 115
ccgaacagca gcagcagcag cagcagcagc agcagcagca gcagcagcag aattttttgga    60
gtaggctttc tggttcggta ccggaaagcc                                      90

SEQ ID NO: 116          moltype = DNA  length = 92
FEATURE                 Location/Qualifiers
source                  1..92
                        mol_type = other DNA
                        organism = synthetic construct
SEQUENCE: 116
taaggagcag cagcagcagc agcagcagca gcagcagcag cagcagcagc agaattttttg    60
gagtaggctt tctggctcct taccggaaag cc                                   92
```

```
SEQ ID NO: 117         moltype = DNA  length = 89
FEATURE                Location/Qualifiers
source                 1..89
                       mol_type = other DNA
                       organism = synthetic construct
SEQUENCE: 117
gaagcagcag cagcagcagc agcagcagca gcagcagcag cagcagcaga attttttggag   60
taggctttct ggcttcttcc cggaaagcc                                      89

SEQ ID NO: 118         moltype = DNA  length = 91
FEATURE                Location/Qualifiers
source                 1..91
                       mol_type = other DNA
                       organism = synthetic construct
SEQUENCE: 118
ggcttcagca gcagcagcag cagcagcagc agcagcagca gcagcagcag aattttttgga   60
gtaggctttt tggaagcctt accggaaagc c                                   91

SEQ ID NO: 119         moltype = DNA  length = 89
FEATURE                Location/Qualifiers
source                 1..89
                       mol_type = other DNA
                       organism = synthetic construct
SEQUENCE: 119
gaagcagcag cagcagcagc agcagcagca gcagcagcag cagcagcaga attttttggag   60
taggctttct ggcttcttac cggaaagcc                                      89

SEQ ID NO: 120         moltype = DNA  length = 2469
FEATURE                Location/Qualifiers
source                 1..2469
                       mol_type = other DNA
                       organism = synthetic construct
SEQUENCE: 120
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact   120
aggggttcct gcggccggtc gcgtctagta acttcgcgat gtacgggcca gatatatact   180
gccgaatcca ggtctccggg cttaacaaca acgaaggggc tgtgactggc tgcttttctca  240
accaatcagc accgaactca tttgcatggg ctgagaacaa atgttcgcga actctagaaa   300
tgaatgactt aagtaagttc cttagaatat tattttttcct actgaaagtt accacatgcg  360
tcgttgttta tacagtaata ggaacaagaa aaaagtcacc taagctcacc ctcatcaatt   420
gtggagttcc tttatatccc atcttctctc caaacacata cgcaggagtc agcagcagca   480
gcagcagca cagcagcagc agcagcagca gcagaatttt ggagtaggc tttctgctc      540
cttaccggaa agcccctctt atgatgttt ttgccaatga tagattgttt tcactgtgca    600
aaaattatgg gtagttttgg tggtcttgat gcagttgtaa gcttggagga tccgagctcg   660
gtaccaagca aactacagag ccaagtgcta tccacagact tcgcgatgta cgggccagat   720
atatactgcc gaatccaggt ctccgggctt aacaacaacg aaggggctgt gactggctgc   780
tttctcaacc aatcagcacc gaactcattt gcatgggctg agaacaaatg ttcgcgaact   840
ctagaaatga atgacttaag taagttcctt agaatattat ttttcctact gaaagttacc   900
acatgcgtcg ttgtttatac agtaatagga caagaaaaa gtcacctaa gctcaccctc    960
atcaattgtg gagttccttt atatcccatc ttctctccaa acacatacgc aggagtcag  1020
agcagcagca gcagcagcag cagcagcagc agcagcagca gaattttttgg agtaggcttt  1080
ctggctcctt accggaaagc ccctcttatg atgtttgttg ccaatgatag attgttttca  1140
ctgtgcaaaa attatgggta gttttggtgg tcttgatgca gttgtaagct tggaggatcc  1200
gagctcggta ccaaggagct ttctgggttg ccatctcaag cagaccttcg cgatgtacgg  1260
gccagatata tactgccgaa tccaggtctc cgggcttaac aacaacgaag gggctgtgac  1320
tggctgcttt ctcaaccaat cagcaccgaa ctcatttgca tgggctgaga acaaatgttc  1380
gcgaactcta gaaatgaatg acttaagtaa gttccttaga atattatttt tcctactgaa  1440
agttaccaca tgcgtcgttg tttatacagt aataggaaca agaaaaaag cacctaagct  1500
caccctcatc aattgtggag ttcctttata tcccatcttc tctccaaaca catacgcagg  1560
agtcagcagc agcagcagca gcagcagcag cagcagcagc agcagcagaa attttttggagt  1620
aggctttctg ctccttaccc ggaaagcccc tcttatgatg tttgttgcca atgatagatt  1680
gttttcactg tgcaaaaatt atgggtagtt ttggtggtct tgatgcagtt gtaagcttgg  1740
aggatccgag ctcggtacca gtacaaggc catcagctca tactcacaat tgcttcgcga  1800
tgtacgggcc agatatatac tgccgaatcc aggtctccgg gcttaacaac aacgaagggg  1860
ctgtgactgg ctgctttctc aaccaatcag caccgaactc atttgcatgg ctgagaaca  1920
aatgttcgcg aactctagaa atgaatgact taagtaagtt ccttagaata ttattttttcc  1980
tactgaaagt taccacatgc gtcgttgttt atacagtaat aggaacaaga aaaaagtcac  2040
ctaagctcac cctcatcaat tgtggagttc ctttatatcc catcttctct ccaaacacat  2100
acgcaggagt cagcagcagc agcagcagca gcagcagcag cagcagcagc agcagaattt  2160
ttggagtagg ctttctggct ccttaccgga aagcccctct tatgatgttt gttgccaatg  2220
atagattgtt tcactgtgc aaaaattatg gtagttttg tggtcttga tgcagttgta    2280
agcttggagg atccgagctc ggtaccaagg tgcggaccca acggccgcag gaaccctag  2340
tgatggagtt ggccactccc tctctgcgcg ctcgctcgct cactgaggcc gggcgaccaa  2400
aggtcgcccg acgcccgggc tttgcccggg cggcctcagt gagcgagcga gcgcgcagct  2460
gcctgcagg                                                         2469

SEQ ID NO: 121         moltype = DNA  length = 2393
FEATURE                Location/Qualifiers
```

```
source                  1..2393
                        mol_type = other DNA
                        organism = synthetic construct
SEQUENCE: 121
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggccggtc gcgtctagta acttcgcgat gtacgggcca gatatatact  180
gccgaatcca ggtctccggg cttaacaaca acgaaggggc tgtgactggc tgctttctca  240
accaatcagc accgaactca tttgcatggg ctgagaacaa atgttcgcga actctagaaa  300
tgaatgactt aagtaagttc cttagaatat tattttcct actgaaagtt accacatgcg  360
tcgttgttta tacagtaata ggaacaagaa aaaagtcacc taagctcacc ctcatcaatt  420
gtggagttcc tttatatccc atcttctctc caaacacata cgcaggagtt caccagaagc  480
gtaccatact cacgaaattt tggagtaggc ttctggctcc ccttaccgga agcccctct   540
tatgatgttt gttgccaatg atagattgtt ttcactgtgc aaaaattatg ggtagttttg  600
gtggtcttga tgcagttgta agcttggagg atccgagctc ggtaccaagc aaactacaga  660
gccaagtgct atccacagac ttcgcgatgt acgggccaga tatatactgc cgaatccagg  720
tctccgggct taacaacaac gaaggggctg tgactggctg ctttctcaac caatcagcac  780
cgaactcatt tgcatgggct gagaacaaat gttcgcgaac tctagaaatg aatgacttaa  840
gtaagttcct tagaatatta ttttcctac tgaaagttac cacatgcgtc gttgtttata  900
cagtaatagg aacaagaaaa agtcaccta agctcaccct catcaattgt ggagttcctt  960
tatatcccat cttctctcca aacacatacg caggagttca ccagaagcgt accatactca 1020
cgaaatttt ggagtaggct ttctggctcc ttaccggaaa gcccctctta tgatgtttgt 1080
tgccaatgat agattgtttt cactgtgcaa aaattatggg tagttttggt ggtcttgatg 1140
cagttgtaag cttggaggat ccgagctcgg taccaaggag ctttctgggt tgccatctca 1200
agcagacctt cgcgatgtac gggccagata tactgccgaa tccaggtctc cgggcttaa  1260
acaacaacga aggggctgtg actggctgct tctcaaccaa tcagcaccg aactcatttg  1320
catgggctga gaacaaatgt tcgcgaactc tagaaatgaa tgacttaagt aagttcctta 1380
gaatattatt tttcctactg aaagttacca catgcgtcgt tgtttataca gtaataggaa 1440
caagaaaaaa gtcacctaag ctcaccctca tcaattgtgg agttccttta tcccatct   1500
tctctccaaa cacatacgca ggagttcacc agaagcgtac catactcacg aaattttgt  1560
agtaggcttt ctggctcctt accggaaagc ccctcttatg atgtttgttg ccaatgatag 1620
attgttttca ctgtgcaaaa attatgggta gttttggtgg tcttgatgca gttgtaagct 1680
tggaggatcc gagctcggta ccaagtacaa ggccatcagc tcatactcac aattgcttcg 1740
cgatgtacgg gccagatata tactgccgaa tccaggtctc cgggcttaac aacaacgaag 1800
gggctgtgac tggctgcttt ctcaaccaat cagcaccgaa ctcatttgca tgggctgag  1860
acaaatgttc gcgaactcta gaaatgaatg acttaagtaa gttccttaga atattattt  1920
tcctactgaa agttaccaca tgcgtcgttg tttatacagt aataggaaca agaaaaaagt 1980
cacctaagct caccctcatc aattgtggag ttcctttata tcccatcttc tctccaaaca 2040
catacgcagg agttcaccag aagcgtacca tactcacgaa aattttggag tagactttct 2100
ggctccttac cggaaagccc ctcttatgat gtttgttgcc aatgatagat tgttttcact 2160
gtgcaaaaat tatgggtagt tttggtggtc ttgatgcagt tgtaagcttg gaggatccga 2220
gctcggtacc aaggtgcgga cccaacggcc gcaggaaccc ctagtgatgg agttggccac 2280
tccctctctg cgcgctcgct cgctcactga ggccgggcga ccaaaggtcg cccgacgccc 2340
gggctttgcc cgggcggcct cagtgagcga gcgagcgcg agctgcctgc agg         2393

SEQ ID NO: 122          moltype = DNA  length = 2469
FEATURE                 Location/Qualifiers
source                  1..2469
                        mol_type = other DNA
                        organism = synthetic construct
SEQUENCE: 122
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact  120
aggggttcct gcggccggtc gcgtctagta acttcgcgat gtacgggcca gatatatact  180
gccgaatcca ggtctccggg cttaacaaca acgaaggggc tgtgactggc tgctttctca  240
accaatcagc accgaactca tttgcatggg ctgagaacaa atgttcgcga actctagaaa  300
tgaatgactt aagtaagttc cttagaatat tattttcct actgaaagtt accacatgcg  360
tcgttgttta tacagtaata ggaacaagaa aaaagtcacc taagctcacc ctcatcaatt  420
gtggagttcc tttatatccc atcttctctc caaacacata cgcaggagtt cgtgctgct  480
gctgctgctg ctgctgctgc tgctgctgct gctgaatttt tggagtaggc tttctggctc  540
cttaccggaa agcccctctt atgatgtttt tgccaatga tagattgttt tcactgtgca  600
aaaattatgg gtagttttgg tggtcttgat gcagttgtaa gcttggagga tccgagctcg  660
gtaccaagca aactacagag ccaagtgcta tccacagact tcgcgatgta cgggccagat  720
atatactgcc gaatccaggt ctccgggctt aacaacaacg aaggggctgt gactggctgc  780
tttctcaacc aatcagcacc gaactcattt gcatgggctg agaacaaatg ttcgcgaact  840
ctagaaatga atgacttaag taagttcctt agaatattat tttcctact gaaagttacc  900
acatgcgtcg ttgtttatac agtaatagga acaagaaaaa gtcacctaa gctcaccctc  960
atcaattgtg gagttccttt atcccatc ttctctccaa acacatacgc aggagttcgc 1020
tgctgctgct gctgctgctg ctgctgctgc tgctgctgct gaatttttgg agtaggcttt 1080
ctggctcctt accggaaagc ccctcttatg atgtttgttg ccaatgatag attgttttca 1140
ctgtgcaaaa attatgggta gttttggtgg tcttgatgca gttgtaagct tggaggatcc 1200
gagctcggta ccaaggagct ttctgggttg ccatctcaag cagaccttcg cgatgtacgg 1260
gccagatata tactgccgaa tccaggtctc cgggcttaac aacaacgaag gggctgtgac 1320
tggctgcttt ctcaaccaat cagcaccgaa ctcatttgca tgggctgaga acaaatgttc 1380
gcgaactcta gaaatgaatg acttaagtaa gttccttaga atattatttt tcctactgaa 1440
agttaccaca tgcgtcgttg tttatacagt aataggaaca agaaaaaagt cacctaagct 1500
caccctcatc aattgtggag ttcctttata tcccatcttc tccaaaca catacgcagg 1560
agtctgctgc tgctgctgct gctgctgctg ctgctgaa ttttggagt              1620
aggctttctg gctccttacc ggaaagcccc tcttatgatg tttgttgcca atgatagatt 1680
```

```
gttttcactg tgcaaaaatt atgggtagtt ttggtggtct tgatgcagtt gtaagcttgg    1740
aggatccgag ctcggtacca agtacaaggc catcagctca tactcacaat tgcttcgcga    1800
tgtacgggcc agatatatac tgccgaatcc aggtctccgg gcttaacaac aacgaagggg    1860
ctgtgactgg ctgctttctc aaccaatcag caccgaactc atttgcatgg gctgagaaca    1920
aatgttcgcg aactctagaa atgaatgact taagtaagtt ccttagaata ttattttcc     1980
tactgaaagt taccacatgc gtcgttgttt atacagtaat aggaacaaga aaaagtcac     2040
ctaagctcac cctcatcaat tgtggagttc ctttatatcc catcttctct ccaaacacat    2100
acgcaggagt ctgctgctgc tgctgctgct gctgctgctg ctgctgctgc tgctgaattt    2160
ttggagtagg ctttctggct ccttaccgga aagcccctct tatgatgttt gttgccaatg    2220
atagattgtt ttcactgtgc aaaaattatg ggtagttttg gtggtcttga tgcagttgta    2280
agcttggagg atccgagctc ggtaccaagg tgcggaccca acggccgcag gaacccctag    2340
tgatggagtt ggccactccc tctctgcgcg ctcgctcgct cactgaggcc gggcgaccaa    2400
aggtcgcccg acgccgggc tttgcccggg cggcctcagt gagcgagcga gcgcgcagct    2460
gcctgcagg                                                           2469

SEQ ID NO: 123          moltype = DNA   length = 2451
FEATURE                 Location/Qualifiers
source                  1..2451
                        mol_type = other DNA
                        organism = synthetic construct
SEQUENCE: 123
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcgccggtc gcgtctagta accggtcttc gcgatgtacg ggccagatat     180
atactgccga atccaggtct ccgggcttaa caacaacgaa ggggctgtga ctggctgctt    240
tctcaaccaa tcagcaccga actcatttgc atgggctgag aacaaatgtt cgcgaactct    300
agaaatgaat gacttaagta agttccttag aatattattt tcctactga aagttaccac    360
atgcgtcgtt gtttatacag taataggaac aagaaaaaag tcacctaagc tcaccctcat    420
caattgtgga gttcctttat atcccatctt ctctccaaac atacgcag gagtcagcag      480
cagcagcagc agcagcagca gcagcagcag attttttggag taggcttt               540
ggctccttac cggaaagccc ctcttatgat gtttgttgcc aatgatagat tgttttcact    600
gtgcaaaaat tatgggtagt tttggtggtc ttgatgcagt tgtaagcttg gaggatccga    660
gctcggtacc aagcaaacta cagagccaag tgctatccac agacttcgcg atgtacgggc    720
cagatatata ctgccgaatc caggtctccg ggcttaacaa caacgaaggg gctgtgactg    780
gctgctttct caaccaatca gcaccgaact catttgcatg ggctgagaac aaatgttcgc    840
gaactctaga aatgaatgac ttaagtaagt tccttagaat attattttc ctactgaaag    900
ttaccacatg cgtcgttgtt tatacagtaa taggaacaag aaaaagtca cctaagctca    960
ccctcatcaa ttgtggagtt cctttatatc ccatcttctc tccaaacaca tacgcaggag   1020
tcagcagcag cagcagcagc agcagcagca gcagcagcag caatt tttggagtag        1080
gctttctggc tccttaccgg aaagcccctc ttatgatgtt tgttgccaat gatagattg    1140
tttcactgtg caaaaattat gggtagtttt ggtggtcttg atgcagttgt aagcttggag   1200
gatccgagct cggtaccaag gagctttctg gttgccatc tcaagcagac cttcgcgatg    1260
tacgggccag atatatactg ccgaatccag gtctccggc ttaacaacaa cgaagggct    1320
gtgactggct gctttctcaa ccaatcagca ccgaactcat ttgcatgggc tgagaacaaa    1380
tgttcgcgaa ctctagaaat gaatgactta agtaagttcc ttagaatatt attttccta    1440
ctgaaagtta ccacatgcgt cgttgtttat acagtaatag gaacaagaaa aaagtcacct    1500
aagctcaccc tcatcaattg tggagttcct ttatatccc tcttctctcc aaacacatac    1560
gcaggagtca gcagcagcag cagcagcagc agcagcagca gcagcagcag cagaattttt    1620
ggagtaggct ttctggctcc ttaccggaaa gcccctctta tgatgtttgt tgccaatgat    1680
agattgtttt cactgtgcaa aaattatggg tagttttggt ggtcttgatg cagttgtaag    1740
cttggaggat ccgagctcgg taccaagtac aaggccatca gctcatactc acaattgctt    1800
cgcgatgtac gggccagata tatactgccg aatccaggtc tccgggctta acaacaacga    1860
aggggctgtg actggctgct ttctcaacca atcagcaccg aactcatttg catgggctga    1920
gaacaaatgt tcgcgaactc tagaaatgaa tgacttaagt aagttccta gaatattatt    1980
tttcctactg aaagttacca catgcgtcgt tgtttataca gtaataggaa caagaaaaaa    2040
gtcacctaag ctcaccctca tcaattgtgg agttccttta tatcccatct tctctccaaa    2100
cacatacgca ggagtcagca gcagcagcag cagcagcagc agcagcagca gcagcagcag    2160
aattttggga gtaggctttc tggctcctta ccggaaagcc cctcttatga tgtttgttgc    2220
caatgataga ttgttttcac tgtgcaaaaa ttatgggtag ttttggtggt cttgatgcag    2280
ttgtaagctt ggaggatccg agctcggtac caaggtgcgg acccaacggc cgcagtcc    2340
actccctctc tgcgcgctcg ctcgctcact gaggccgggc gaccaaaggt cgcccgacgc    2400
ccgggctttg cccgggcggc ctcagtgagc gagcgagcgc gcagagaggg a             2451

SEQ ID NO: 124          moltype = DNA   length = 2375
FEATURE                 Location/Qualifiers
source                  1..2375
                        mol_type = other DNA
                        organism = synthetic construct
SEQUENCE: 124
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcgccggtc gcgtctagta accggtcttc gcgatgtacg ggccagatat     180
atactgccga atccaggtct ccgggcttaa caacaacgaa ggggctgtga ctggctgctt    240
tctcaaccaa tcagcaccga actcatttgc atgggctgag aacaaatgtt cgcgaactct    300
agaaatgaat gacttaagta agttccttag aatattattt tcctactga aagttaccac    360
atgcgtcgtt gtttatacag taataggaac aagaaaaaag tcacctaagc tcaccctcat    420
caattgtgga gttcctttat atcccatctt ctctccaaac atacgcag gagttcacca     480
gaagcgtacc atactcacga aatttggga gtaggctttc tggctcctta ccggaaagcc    540
cctcttatga tgtttgttgc caatgataga ttgttttcac tgtgcaaaaa ttatgggtag    600
```

```
ttttggtggt cttgatgcag ttgtaagctt ggaggatccg agctcggtac caagcaaact    660
acagagccaa gtgctatcca cagacttcgc gatgtacggg ccagatatat actgccgaat    720
ccaggtctcc gggcttaaca acaacgaagg ggctgtgact ggctgctttc tcaaccaatc    780
agcaccgaac tcatttgcat gggctgagaa caaatgttcg cgaactctag aaatgaatga    840
cttaagtaag ttccttagaa tattattttt cctactgaaa gttaccacat gcgtcgttgt    900
ttatacagta ataggaacaa gaaaaaagtc acctaagctc accctcatca attgtggagt    960
tcctttatat cccatcttct ctccaaacac atacgcagga gttaccagag agcgtaccat   1020
actcacgaaa tttttggagt aggctttctg gctccttacc ggaaagcccc tcttatgatg   1080
tttgttgcca atgataagtt gttttcactg tgcaaaaatt atgggtagtt ttggtggtct   1140
tgatgcagtt gtaagcttgg aggatccgag ctcggtacca aggagctttc tgggttgcca   1200
tctcaagcag accttcgcga tgtacgggcc agatatatac tgccgaatcc aggtctccgg   1260
gcttaacaac aacgaagggg ctgtgactgg ctgctttctc aaccaatcag caccgaactc   1320
atttgcatgg gctgagaaca aatgttcgcg aactctagaa atgaatgact taagtaagtt   1380
ccttagaata ttattttcc tactgaaagt taccacatgc gtcgttgttt atacagtaat   1440
aggaacaaga aaaaagtcac ctaagctcac cctcatcaat tgtggagttc ctttatatcc   1500
catcttctct ccaaacacat acgcaggagt tcaccagaag cgtaccatac tcacgaaatt   1560
tttggagtag gctttctggc tccttaccgg aaagcccctc ttatgatgtt tgttgccaat   1620
gatagattgt tttcactgtg caaaaattat gggtagtttt ggtggtcttg atgcagttgt   1680
aagcttggag gatccgagct cggtaccaag tacaaggcca tcagctcata ctcacaattg   1740
cttcgcgatg tacgggccag atatatactg ccgaatccag gtctccgggc ttaacaacaa   1800
cgaagggggc gtgactggct gctttctcaa ccaatcagca ccgaactcat ttgcatgggc   1860
tgagaacaaa tgttcgcgaa ctctagaaat gaatgactta agtaagttcc ttagaatatt   1920
attttccta ctgaaagtta ccacatgcgt cgttgtttat acagtaatag gaacaagaaa   1980
aaagtcacct aagctcaccc tcatcaattg tggagttcct ttatatccca tcttctctcc   2040
aaacacatac gcaggagttc accagaagcg taccatactc acgaaatttt tggagtaggc   2100
tttctggctc cttaccggaa agcccctctt atgatgtttg ttgccaatga tagattgttt   2160
tcactgtgca aaaattatgg gtagttttgg tggtcttgat gcagttgtaa gcttggagga   2220
tccgagctcg gtaccaaggt gcggaccaa cggccgccta gtccactccc tctctgcgcg   2280
ctcgctcgct cactgaggcc gggcgaccaa aggtcgcccg acgcccgggc tttgcccggg   2340
cggcctcagt gagcgagcga gcgcgcagag aggga                              2375

SEQ ID NO: 125         moltype = DNA   length = 2451
FEATURE                Location/Qualifiers
source                 1..2451
                       mol_type = other DNA
                       organism = synthetic construct
SEQUENCE: 125
cctgcaggca gctgcgcgct cgctcgctca ctgaggccgc ccgggcgtcg ggcgaccttt     60
ggtcgcccgg cctcagtgag cgagcgagcg cgcagagagg gagtggccaa ctccatcact    120
aggggttcct gcggccggtc gcgtctagta accggtcttc gcgatgtacg ggccagatat    180
atactgccga atccaggtct ccgggcttaa caacaacgaa ggggctgtga ctggctgctt    240
tctcaaccaa tcagcaccga actcatttgc atgggctgag aacaaatgtt cgcgaactct    300
agaaatgaat gacttaagta gttccttag aatattattt tcctactga aagttaccac    360
atgcgtcgtt gtttatacag taataggaac aagaaaaaag tcacctaagc tcaccctcat    420
caattgtgga gttcctttat atccatcttc tctccaaaca catacgcagg agtctgctg    480
ctgctgctgc tgctgctgct gctgctgctg ctgctgctga ttttggagta ggctttct    540
ggctccttac cggaaagccc ctcttatgat gtttgttgcc aatgataga gttgttttcact   600
gtgcaaaaat tatgggtagt tttggtggtc ttgatgcagt tgtaagcttg gaggatccga    660
gctcggtacc aagcaaacta cagagccaag tgctatccac agacttcgcg atgtacgggc    720
cagatatata ctgccgaatc caggtctccg gcttaacaa caacgaaggg gctgtgactg    780
gctgctttct caaccaatca gcaccgaact catttgcatg ggctgagaac aaatgttcg    840
gaactctaga aatgaatgac ttaagtaagt tccttagaat attattttc ctactgaaag    900
ttaccacatg cgtcgttgtt tatacagtaa taggaacaag aaaaagtca cctaagctca    960
ccctcatcaa ttgtggagtt cctttatatc ccatcttctc tccaaacaca tacgcaggag   1020
tctgctgctg ctgctgctgc tgctgctgct gctgctgctg ctgctgaatt tttggagtag   1080
gctttctggc tccttaccgg aaagcccctc ttatgatgtt tgttgccaat gatagattgt   1140
tttcactgtg caaaaattat gggtagtttt ggtggtcttg atgcagttgt aagcttggag   1200
gatccgagct cggtaccaag gagctttctg ggttgccatc tcaagcagac cttcgcgatg   1260
tacgggccag atatatactg ccgaatccag gtctccgggc ttaacaacaa cgaagggggct   1320
gtgactggct gctttctcaa ccaatcagca ccgaactcat ttgcatgggc tgagaacaaa   1380
tgttcgcgaa ctctagaaat gaatgactta agtaagttcc ttagaatatt attttccta   1440
ctgaaagtta ccacatgcgt cgttgtttat acagtaatag gaacaagaaa aaagtcacct   1500
aagctcaccc tcatcaattg tggagttcct ttatatccca tcttctctcc aaacacatac   1560
gcaggagtct gctgctgctg ctgctgctgc tgctgctgc tgctgaatttt                1620
ggagtaggct ttctgctcc ttaccggaaa gcccctctta tgatgtttgt tgccaatgat   1680
agattgtttt cactgtgcaa aaattatggg tagttttggt ggtcttgatg cagttgtaag   1740
cttggaggat ccgagctcgg taccaagtac aaggccatca gctcatactc acaattgctt   1800
cgcgatgtac gggccagata tatactgccg aatccaggtc tccgggctta acaacaacga   1860
aggggctgtg actggctgct ttctcaacca atcagcacg aactcatttg catgggctgt   1920
gaacaaatgt tcgcgaactc tagaaatgaa tgacttaagt aagttcctta gaatattatt   1980
tttcctactg aaagttacca catgcgtcgt tgtttataca gtataggaa caagaaaaaa   2040
gtcacctaag ctcaccctca tcaattgtgg agttccttta tcccatct tctctccaaa   2100
cacatacgca ggagtctgct gctgctgctg ctgctgctg tgctgctgct gctgctgtg   2160
aattttggag taggctttct ggctccttac cggaaagccc ctcttatgat gtttgttgc   2220
caatgataga ttgttttcac tgtgcaaaaa ttatgggtag ttttggtggt cttgatgcag   2280
ttgtaagctt ggaggatccg agctcggtac caagggtgcgg acccaacggc cgcctagtcc   2340
actccctctc tgcgcgctcg ctcgctcact gaggccggg gaccaaaggt cgcccgacgc   2400
ccgggctttg cccgggcggc ctcagtgagc gagcgagcgc gcagagaggg a             2451
```

| SEQ ID NO: 126 | moltype = DNA length = 2516 |
|---|---|
| FEATURE | Location/Qualifiers |
| source | 1..2516 |
| | mol_type = other DNA |
| | organism = synthetic construct |

SEQUENCE: 126
```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg cttttctcaac caatcagcac   240
cgaactcatt tgcatgggct gagaacaaat gttcgcgaac tctagaaatg aatgacttaa   300
gtaagttcct tagaatatta ttttctcctac tgaaagttac cacatgcgtc gttgtttata   360
cagtaatagg aacaagaaaa aagtcaccta agctcaccct catcaattgt ggagttcctt   420
tatatcccat cttctctcca aacacatacg caggagtcag cagcagcag agcagcagca   480
gcagcagcag cagcagcagc agaattttg gagtaggctt tctggctcct taccggaaag   540
cccctcttat gatgtttgtt gccaatgata gattgttttc actgtgcaaa aattatgggt   600
agttttggtg gtcttgatgc agttgtaagc ttggaggatc cgagctcggt accaagctag   660
tcgcgtcgac ggatccgaat tcgatatcgc tagcataata gtaatcaatt acgggtcat   720
tagttcatag cccatatatg gagttccgcg ttacataact tacggtaaat ggcccgcctg   780
gctgaccgcc caacgacccc cgcccattga cgtcaataat gacgtatgtt cccatagtaa   840
cgccaatagg gactttccat tgacgtcaat gggtggagta tttacggtaa actgcccact   900
tggcagtaca tcaagtgtat catatgccaa gtacgccccc tattgacgtc aatgacggta   960
aatggcccgc ctggcattat gcccagtaca tgaccttatg ggactttcct acttggcagt  1020
acatctacgt attagtcatc gctattacca tggtgatgcg gttttggcag tacatcaatg  1080
ggcgtggata gcggtttgac tcacgggat ttccaagtct ccaccccatt gacgtcaatg  1140
ggagtttgtt ttggcaccaa aatcaacggg actttccaaa atgtcgtaac aactccgcc  1200
cattgacgca aatgggcggt aggcgtgtac ggtgggaggt ctatataagc agagctggtt  1260
tagtgaaccg tcagatccgc tagcgctacc ggactcagat ctcgagctca agcttcgaat  1320
tctgcagtcg acggtaccgc gggcccggga tccaccggtc gccaccatgg tgagcaaggg  1380
cgaggagctg ttcaccgggg tggtgcccat cctggtcgag ctggacggcg acgtaaacgg  1440
ccacaagttc agcgtgtccg gcgagggcga gggcgatgcc acctacggca agctgaccct  1500
gaagttcatc tgcaccaccg gcaagctgcc cgtgcctgg cccaccctcg tgaccaccct  1560
gacctacggc gtgcagtgct tcagccgcta ccccgaccac atgaagcagc acgacttctt  1620
caagtccgcc atgcccgaag gctacgtcca ggagcgcacc atcttcttca aggacgacgg  1680
caactacaag acccgcgcg aggtgaagtt cgagggcgac accctggtga accgcatcga  1740
gctgaagggc atcgacttca aggaggacgg caacatcctg gggcacaagc tggagtacaa  1800
ctacaacagc cacaacgtct atatcatggc cgacaagcag aagaacggca tcaaggtgaa  1860
cttcaagatc cgccacaaca tcgaggacgg cagcgtgcag ctcgccgacc actaccagca  1920
gaacaccccc atcggcgacg gccccgtgct gctgcccgac aaccactacc tgagcaccca  1980
gtccgccctg agcaaagacc ccaacgagaa gcgcgatcac atggtcctgc tggagttcgt  2040
gaccgccgcc gggatcactc tcggcatgga cgagctgtac aagtaaagcg gccgcgactc  2100
tagatcaataa tcagccatac cacatttgta gaggttttac ttgctttaaa aaacctccca  2160
cacctcccc tgaacctgaa acataaaatg aatgcaattg ttgttgttatt cttgtttatt  2220
gcagcttata atggttacaa ataaagcaat agcatcacaa atttcacaaa taaagcattt  2280
ttttcactgc attctagttg tggtttgtcc aaactcatca atgtatctta agatatctag  2340
atctcgaggt aaccacgtgc ggaccgagcg ccgcaggaa cccctagtga tggagttggc  2400
cactccctct ctgcgcgctc gctcgctcac tgaggccggg cgaccaaagg tcgcccgacg  2460
cccgggcttt gcccgggcgg cctcagtgag cgagcgagcg cgcagctgcc tgcagg      2516
```

| SEQ ID NO: 127 | moltype = DNA length = 2497 |
|---|---|
| FEATURE | Location/Qualifiers |
| source | 1..2497 |
| | mol_type = other DNA |
| | organism = synthetic construct |

SEQUENCE: 127
```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg cttttctcaac caatcagcac   240
cgaactcatt tgcatgggct gagaacaaat gttcgcgaac tctagaaatg aatgacttaa   300
gtaagttcct tagaatatta ttttcctac tgaaagttac cacatgcgtc gttgtttata   360
cagtaatagg aacaagaaaa aagtcaccta agctcaccct catcaattgt ggagttcctt   420
tatatcccat cttctctcca aacacatacg caggagttca ccagaagcgt accatactca   480
cgaaattttt ggagtaggct ttctggctcc ttaccgaaa gccccctctta tgatgtttgtt   540
tgccaatgat agattgtttt cactgtgcaa aaattatggg tagttttggt ggtcttgatg   600
cagttgtaag cttggaggat ccgagctcgg taccaagcta gtcgcgtcga cggatccgaa   660
ttcgatatcg ctagcataat agtaatcaat tacgggtca ttagttcata gcccatatat   720
ggagttccgc gttacataac ttacggtaaa tggcccgcct ggctgaccgc ccaacgaccc   780
ccgcccattg acgtcaataa tgacgtatgt tcccatagta acgccaatag ggactttcca   840
ttgacgtcaa tgggtggagt atttacggta aactgcccac ttggcagtac atcaagtgta   900
tcatatgcca agtacgcccc ctattgacgt caatgacggt aaatggcccg cctggcatta   960
tgcccagtac atgaccttat gggactttcc tacttggcag tacatctacg tattagtcat  1020
cgctattacc atggtgatgc ggttttggca gtacatcaat gggcgtggat agcggtttga  1080
ctcacgggga tttccaagtc tccaccccat tgacgtcaat gggagtttgt tttggcacca  1140
aaatcaacgg gactttccaa aatgtcgtaa caactccgcc cattgacgc aaatgggcgg  1200
taggcgtgta cggtgggagg tctatataag cagagctggt ttagtgaacc gtcagatccg  1260
ctagcgctac cggactcaga tctcgagctc aagcttcgaa ttctgcagtc gacggtaccg  1320
cgggcccggg atccaccggt cgccaccatg gtgagcaagg gcgaggagct gttcaccggg  1380
gtggtgccca tcctggtcga gctggacggc gacgtaaacg gccacaagtt cagcgtgtcc  1440
```

```
ggcgagggcg agggcgatgc cacctacggc aagctgaccc tgaagttcat ctgcaccacc  1500
ggcaagctgc ccgtgccctg gcccacccte gtgaccaccc tgacctacgg cgtgcagtgc  1560
ttcagccgct accccgacca catgaagcag cacgacttct tcaagtccgc catgcccgaa  1620
ggctacgtcc aggagcgcac catcttcttc aaggacgacg gcaactacaa gacccgcgcc  1680
gaggtgaagt tcgagggcga caccctggtg aaccgcatcg agctgaaggg catcgacttc  1740
aaggaggacg gcaacatcct ggggcacaag ctggagtaca actacaacag ccacaacgtc  1800
tatatcatgg ccgacaagca gaagaacggc atcaaggtga acttcaagat ccgccacaac  1860
atcgaggacg gcagcgtgca gctcgccgac cactaccagc agaacacccc catcggcgac  1920
ggccccgtgc tgctgcccga caaccactac ctgagcaccc agtccgccct gagcaaagac  1980
cccaacgaga agcgcgatca catggtcctg ctggagttcg tgaccgccgc cgggatcact  2040
ctcggcatgg acgagctgta caagtaaagc ggccgcgact ctagatcata atcagccata  2100
ccacatttgt agaggtttta cttgctttaa aaaacctccc acacctcccc ctgaacctga  2160
aacataaaat gaatgcaatt gttgttgtta acttgtttat tgcagcttat aatggttaca  2220
aataaagcaa tagcatcaca aatttcacaa ataaagcatt ttttcactgc cattctagtt  2280
gtggtttgtc caaactcatc aatgtatctt aagatatcta gatctcgagg taaccacgtg  2340
cggaccgagc ggccgcagga accccctagtg atggagttgg ccactccctc tctgcgcgct  2400
cgctcgctca ctgaggccgg gcgaccaaag gtcgcccgac gcccgggctt tgcccggcg  2460
gcctcagtga gcgagcgagc gcgcagctgc ctgcagg  2497

SEQ ID NO: 128              moltype = DNA   length = 2516
FEATURE                     Location/Qualifiers
source                      1..2516
                            mol_type = other DNA
                            organism = synthetic construct
SEQUENCE: 128
cctgcaggca gctgcgcgct cgctcgctca ctgaggccgc ccgggcgtcg ggcgaccttt  60
ggtcgcccgg cctcagtgag cgagcgagcg cgcagagagg gagtggccaa ctccatcact  120
aggggttcct gcggccgcac ttcgcgatgt acgggccaga tatatactgc cgaatccagg  180
tctccgggct taacaacaac gaaggggctg tgactggctg cttttctcaac caatcagcac  240
cgaactcatt tgcatgggct gagaacaaat gttcgcgaac tctagaaatg aatgacttaa  300
gtaagttcct tagaatatta ttttttcctac tgaaagttac cacatgcgtc gttgtttata  360
cagtaatagg aacaagaaaa aagtcaccta agctcaccct catcaattgt ggagttcctt  420
tatatcccat cttctctcca aacacatacg caggagtctg ctgctgctgc tgctgctgct  480
gctgctgctg ctgctgctgc tgaattttg gagtaggctt tctggctcct taccggaaag  540
cccctcttat gatgttttgt gccaatgata gattgtttc actgtgcaaa aattatggt  600
agttttggtg gtcttgatgc agttgtaagc ttggaggatc cgagctcggt accaagctag  660
tcgcgtcgac ggatccgaat tcgatatcgc tagcataata gtaatcaatt acgggggtcat  720
tagttcatag cccatatatg gagttccgcg ttacataact tacggtaaat ggcccgcctg  780
gctgaccgcc caacgacccc cgcccattga cgtcaataat gacgtatgtt cccatagtaa  840
cgccaatagg gactttccat tgacgtcaat gggtggagta tttacggtaa actgcccact  900
tggcagtaca tcaagtgtat catatgccaa gtacgccccc tattgacgtc aatgacggta  960
aatgcccgc ctggcattat gcccagtaca tgaccttatg gactttcct acttggcagt  1020
acatctacgt attagtcatc gctattacca tggtgatgcg gttttggcag tacatcaatg  1080
ggcgtggata gcggtttgac tcacggggat ttccaagtct ccaccccatt gacgtcaatg  1140
ggagtttgtt ttggcaccaa aatcaacggg acttttccaa aatgtcgtaac aactccgccc  1200
cattgacgca aatgggcggt aggcgtgtac ggtgggaggt ctatataagc agagctggtt  1260
tagtgaaccg tcagatccgc tagcgctacc ggactcagat ctcgagctca agcttcgaat  1320
tctgcagtcg acggtaccgc gggcccggga tccaccggtc gccaccatgg tgagcaaggg  1380
cgaggagctg ttcaccgggg tggtgcccat cctggtcgag ctggacggcg acgtaaacgg  1440
ccacaagttc agcgtgtccg gcgagggcga gggcgatgcc acctacggca agctgaccct  1500
gaagttcatc tgcaccaccg gcaagctgcc cgtgccctgg cccaccctcg tgaccaccctg  1560
gacctacggc gtgcagtgct tcagccgcta ccccgaccac atgaagcagc acgacttctt  1620
caagtccgcc atgcccgaag gctacgtcca ggagcgcacc atcttcttca aggacgacgg  1680
caactacaag acccgcgccg aggtgaagtt cgagggcgac accctggtga accgcatcga  1740
gctgaagggc atcgacttca aggaggacgg caacatcctg gggcacaagc tggagtacaa  1800
ctacaacagc cacaacgtct atatcatggc cgacaagcag aagaacggca tcaaggtgaa  1860
cttcaagatc cgccacaaca tcgaggacgg cagcgtgcag ctcgccgacc actaccagca  1920
gaacaccccc atcggcgacg gccccgtgct gctgcccgac aaccactacc tgagcaccca  1980
gtccgccctg agcaaagacc ccaacgagaa gcgcgatcac atggtcctgc tggagttcgt  2040
gaccgccgcc gggatcactc tcggcatgga cgagctgtac aagtaaagcg gccgcgactc  2100
tagatcataa tcagccatac cacatttgta gaggttttac ttgctttaaa aaacctccca  2160
cacctcccc tgaacctgaa acataaaatg aatgcaattg ttgttgttaa cttgtttatt  2220
gcagcttata atggttacaa ataaagcaat agcatcacaa atttcacaaa taaagcattt  2280
ttttcactgc attctagttg tggtttgtcc aaactcatca atgtatctta agatatctag  2340
atctcgaggt aaccacgtgc ggaccgagcg gccgcaggaa cccctagtga tggagttggc  2400
cactccctct ctgcgcgctc gctcgctcac tgaggccggg cgaccaaagg tcgcccgacg  2460
cccgggcttt gcccggcgg cctcagtgag cgagcgagcg cgcagctgcc tgcagg  2516

SEQ ID NO: 129              moltype = DNA   length = 3756
FEATURE                     Location/Qualifiers
source                      1..3756
                            mol_type = other DNA
                            organism = synthetic construct
SEQUENCE: 129
cctgcaggca gctgcgcgct cgctcgctca ctgaggccgc ccgggcgtcg ggcgaccttt  60
ggtcgcccgg cctcagtgag cgagcgagcg cgcagagagg gagtggccaa ctccatcact  120
aggggttcct gcggccgcac gcgtcttcgc gatgtacggg ccagatatat actgccgaat  180
ccaggtctcc gggcttaaca caacgaagg ggctgtgact ggctgctttc tcaaccaatc  240
agcaccgaac tcatttgcat gggctgagaa caaatgttcg cgaactctag aaatgaatga  300
```

```
cttaagtaag ttccttagaa tattattttt cctactgaaa gttaccacat gcgtcgttgt   360
ttatacagta ataggaacaa gaaaaaagtc acctaagctc accctcatca attgtggagt   420
tcctttatat cccatcttct ctccaaacac atacgcagga gtcagcagca gcagcagcag   480
cagcagcagc agcagcagca gcagcagaat ttttggagta ggctttctgg ctccttaccg   540
gaaagcccct cttatgatgt ttgttgccaa tgatagattg ttttcactgt gcaaaaatta   600
tgggtagttt tggtggtctt gatgcagttg taagcttgga ggatccgagc tcggtaccaa   660
gcaaactaca gagccaagtg ctatccacag agagctttct gggttgccat ctcaagcaga   720
ctacaaggcc atcagctcat actcacaatt gactttgaga gcttcgcgat gtacgggcca   780
gatatatact gccgaatcca ggtctccggg cttaacaaca acgaaggggc tgtgactggc   840
tgctttctca accaatcagc accgaactca tttgcatggg ctgagaacaa atgttcgcga   900
actctagaaa tgaatgactt aagtaagttc cttagaatat tattttttcct actgaaagtt   960
accacatgcg tcgttgttta tacagtaata ggaacaagaa aaaagtcacc taagctcacc  1020
ctcatcaatt gtggagttcc tttatatccc atcttctctc caaacacata cgcaggagtc  1080
agcagcagca gcagcagcag cagcagcagc agcagcagca gcagaatttt tggagtaggc  1140
tttctggctc cttaccggaa agcccctctt atgatgtttg ttgccaatga tagattgttt  1200
tcactgtgca aaaattatgg gtagttttgg tggtcttgat gcagttgtaa gcttggagga  1260
tccgagctcg gtaccaagtt gaccacatac gtgctctttc aaagttctgt gtttgaagtt  1320
atgttagtaa caactgaatgc ccatcctgca atgacaaatc caattctcag tgcagctcct  1380
tcgcgatgta cgggccagat atatactgcc gaatccaggt ctccgggctt aacaacaacg  1440
aaggggctgt gactggctgc tttctcaacc aatcagcacc gaactcattt gcatgggctg  1500
agaacaaatg ttcgcgaact ctagaaatga atgacttaag taagttcctt agaatattat  1560
ttttcctact gaaagttacc acatgcgtcg ttgtttatac agtaatagga acaagaaaaa  1620
agtcacctaa gctcaccctc atcaattgtg gagttccttt atatcccatc ttctctccaa  1680
acacatacgc aggagtcagc agcagcagca gcagcagcag cagcagcagc agcagcagca  1740
gaattttggg agtaggcttt ctggctcctt accggaaagc ccctcttatg atgtttgttg  1800
ccaatgatag attgttttca ctgtgcaaaa attattgttgg tggtcttgat gcagttgtaa  1860
gcttggagga tccgagctcg gtaccaagtt gaccacatac gtgctctttc aaagttctgt  1860
gttgtaagct tggaggatcc gagctcggta ccaagactag tcgcgtcgac ggatccgaat  1920
tcgatatcgc tagcataata gtaatcaatt acggggtcat tagttcatag cccatatatg  1980
gagttccgcg ttacataact tacggtaaat ggcccgcctg gctgaccgcc caacgacccc  2040
cgcccattga cgtcaataat gacgtatgtt cccatagtaa cgccaatagg gactttccat  2100
tgacgtcaat gggtggagta tttacggtaa actgcccact tggcagtaca tcaagtgtat  2160
catatgccaa gtacgccccc tattgacgtc aatgacggta aatggcccgc ctggcattat  2220
gcccagtaca tgaccttatg gactttcct acttggcagt acatctacgt attagtcatc  2280
gctattacca tggtgatgcg gttttggcag tacatcaatg ggcgtggata gcggtttgac  2340
tcacggggat ttccaagtct caccccatt gacgtcaatg ggagtttgtt ttggccaaa  2400
aatcaacggg actttccaaa atgtcgtaac aactccgccc cattgacgca aatgggcggt  2460
aggcgtgtac ggtgggaggt ctatataagc agagctggtt tagtgaaccg tcagatccgc  2520
tagcgctacc ggactcagat ctcgagctca agcttcgaat tctgcagtcg acggtaccgc  2580
gggcccggta tccaccggtc gccaccatgg tgagcaaggg cgaggagctg ttcaccgggg  2640
tggtgcccat cctggtcgag ctggacggcg acgtaaacgg ccacaagttc agcgtgtccg  2700
gcgagggcga gggcgatgcc acctacggca agctgaccct gaagttcatc tgcaccaccg  2760
gcaagctgcc cgtgccctgg cccaccctcg tgaccaccct gacctacggc gtgcagtgct  2820
tcagccgcta ccccgaccac atgaagcagc acgacttctt caagtccgcc atgcccgaag  2880
gctacgtcca ggagcgcacc atcttcttca aggacgacgg caactacaag acccgcgccg  2940
aggtgaagtt cgagggcgac accctggtga accgcatcga gctgaagggc atcgacttca  3000
aggaggacgg caacatcctg gggcacaagc tggagtacaa ctacaacagc cacaacgtct  3060
atatcatggc cgacaagcag aagaacggca tcaaggtgaa cttcaagatc cgccacaaca  3120
tcgaggacgg cagcgtgcag ctcgccgacc actaccagca gaacacccc atcggcgacg  3180
gccccgtgct gctgcccgac aaccactacc tgagcaccca gtccgccctg agcaaagacc  3240
ccaacgagaa gcgcgatcac atggtcctgc tggagttcgt gaccgccgcc gggatcactc  3300
tcggcatgga cgagctgtac aagtaaagcg gccgcgactc tagatcataa tcagccatac  3360
cacatttgta gaggttttac ttgctttaaa aaacctccca cacctccccc tgaacctgaa  3420
acataaaatg aatgcaattg ttgttgttaa cttgttttatt gcagcttata atggttacaa  3480
ataaagcaat agcatcacaa atttcacaaa taaagcattt ttttcactgc attctagttg  3540
tggtttgtcc aaaactcatca atgtatctta agatatctag atctcgaggt aaccacgtgc  3600
ggaccgagcg gccgcaggaa ccctagtga tggagttggc cactccctct ctgcgcgctc  3660
gctcgctcac tgaggccggg cgaccaaagg tcgcccgacg cccgggcttt gcccgggcgg  3720
cctcagtgag cgagcgagcg cgcagctgcc tgcagg                           3756

SEQ ID NO: 130      moltype = DNA   length = 3699
FEATURE             Location/Qualifiers
source              1..3699
                    mol_type = other DNA
                    organism = synthetic construct
SEQUENCE: 130
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac gcgtcttcgc gatgtacggg ccagatatat actgccgaat   180
ccaggtctcc gggcttaaca caacgaagg ggctgtgact ggctgctttc tcaaccaatc   240
agcaccgaac tcatttgcat gggctgagaa caaatgttcg cgaactctag aaatgaatga   300
cttaagtaag ttccttagaa tattattttt cctactgaaa gttaccacat gcgtcgttgt   360
ttatacagta ataggaacaa gaaaaaagtc acctaagctc accctcatca attgtggagt   420
tcctttatat cccatcttct ctccaaacac atacgcagga gttcaccaga agcgtaccat   480
actcacgaaa tttttggagt aggctttctg gctccttaccg gaaagcccct tcttatgatg   540
tttgttgcca atgatagatt gttttcactg tgcaaaaatt atgggtagtt ttggtggtct   600
tgatgcagtt gtaagcttgg aggatccgag ctcggtacca agcaaactac agagccaagt   660
gctatccaca gagagctttc tgggttgcca tctcaagcag actacaaggc catcagctca   720
tactcacaat tgactttgag agcttcgcga tgtacgggcc agatatatac tgccgaatcc   780
aggtctccgg gcttaacaac aacgaagggg ctgtgactgg ctgctttctc aaccaatcag   840
```

```
caccgaactc atttgcatgg gctgagaaca aatgttcgcg aactctagaa atgaatgact    900
taagtaagtt ccttagaata ttattttcc tactgaaagt taccacatgc gtcgttgttt    960
atacagtaat aggaacaaga aaaaagtcac ctaagctcac cctcatcaat tgtggagttc   1020
ctttatatcc catcttctct ccaaacacat acgcaggagt tcaccagaag cgtaccatac   1080
tcacgaaatt tttggagtag gctttctggc tcctttaccgg aaagccctc ttatgatgtt   1140
tgttgccaat gatagattgt tttcactgtg caaaaattat gggtagtttt ggtggtcttg   1200
atgcagttgt aagcttggag gatccgagct cggtaccaag ttgaccacat acgtgctctt   1260
tcaaagttct gtgtttgaag ttatgttagt aacaactgat gcccatcctg caatgacaaa   1320
tccaattctc agtgcagctc cttcgcgatg tacgggcag atatatactg ccgaatccag    1380
gtctccgggc ttaacaacaa cgaagggct gtgactggct gctttctcaa ccaatcagca    1440
ccgaactcat ttgcatggc tgagaacaaa tgttcgcgaa ctctagaaat gaatgactta    1500
agtaagttcc ttagaatatt attttccta ctgaaagtta ccacatgcgt cgttgtttat    1560
acagtaatag gaacaagaaa aaagtcacct aagctcaccc tcatcaattg tggagttcct   1620
ttatatccca tcttctctcc aaacacatac gcaggagtc accagaagc taccatactc    1680
acgaaatttt tggagtaggc tttctggctc cttaccggaa agcccctctt atgatgttg    1740
ttgccaatga tagattgttt tcactgtgca aaaattatgg gtagttttgg tggtcttgat   1800
gcagttgtaa gcttggagga tccgagctcg gtaccaagac tagtcgcgtc gacggatccg   1860
aattcgatat cgctagcata atagtaatca attacggct cattagttca tagcccatat    1920
atggagttcc gcgttacata acttacggta aatggcccgc ctggctgacc gcccaacgac   1980
ccccgcccat tgacgtcaat aatgacgtat gttcccatag taacgccaat agggactttc   2040
cattgacgtc aatgggtgga gtatttacgg taaactgccc acttggcagt acatcaagtg   2100
tatcatatgc caagtacgcc ccctattgac gtcaatgacg gtaaatggcc cgcctggcat   2160
tatgcccagt acatgacctt atgggactt cctacttggc agtacatcta cgtattagtc    2220
atcgctatta ccatggtgat gcggttttgg cagtacatca atgggcgtgg atagcggttt   2280
gactcacggg gatttccaag tctccacccc attgacgtca atgggagttt gttttggcac   2340
caaaatcaac gggactttcc aaaatgtcgt aacaactccc ccattgac gcaaatgggc    2400
ggtaggcgtg tacggtggga ggtctatata agcagagctg gtttagtgaa ccgtcagatc   2460
cgctagcgct accggactca gatctcgagc tcaagcttcg aattctgcag tcgacggtac   2520
cgcgggcccg gatccaccg tcgccacca tggtgagcaa gggcgaggag ctgttcaccg    2580
gggtggtgcc catcctggtc gagctggacg gcgacgtaaa cggccacaag ttcagcgtgt   2640
ccggcgaggg cgagggcgat gccacctacg gcaagctgac cctgaagttc atctgcacca   2700
ccggcaagct gcccgtgccc tggcccaccc tcgtgaccac cctgacctac ggcgtgcagt   2760
gcttcagccg ctaccccgac cacatgaagc agcacgactt cttcaagtcc gccatgcccg   2820
aaggctacgt ccaggagcgc accatcttct tcaaggacga cggcaactac aagacccgcg   2880
ccgaggtgaa gttcgagggc gacaccctgg tgaaccgcat cgagctgaag ggcatcgact   2940
tcaaggagga cggcaacatc ctggggcaca agctggagta caactacaac agccacaacg   3000
tctatatcat ggccgacaag cagaagaacg gcatcaaggt gaacttcaag atccgccaca   3060
acatcgagga cggcagcgtg cagctcgccg accactacca gcagaacacc cccatcggcg   3120
acggccccgt gctgctgccc gacaaccact acctgagcac ccagtccgcc ctgagcaaag   3180
accccaacga gaagcgcgat cacatggtcc tgctggagtt cgtgaccgcc gccgggatca   3240
ctctcggcat ggacgagctg tacaagtaaa gcggccgcga ctctagatca taatcagcca   3300
taccacatt gtagaggttt tacttgcttt aaaaaacctc ccacacctcc cctgaacct    3360
gaaacataaa atgaatgcaa ttgttgttgt taacttgttt attgcagctt ataatggtta   3420
caaataaagc aatagcatca caaatttcac aaataaagca tttttttcac tgcattctag   3480
ttgtggtttg tccaaactca tcaatgtatc ttaagatatc tagatctcga ggtaaccacg   3540
tgcggaccga gcggccgcag gaacccctag tgatggagtt ggccactccc tctctgcgcg   3600
ctcgctcgct cactgaggcc gggcgaccaa aggtcgcccg acgcccgggc tttgcccggg   3660
cggcctcagt gagcgagcga gcgcgcagct gcctgcagg                         3699
```

SEQ ID NO: 131        moltype = DNA   length = 3756
FEATURE              Location/Qualifiers
source               1..3756
                      mol_type = other DNA
                      organism = synthetic construct
SEQUENCE: 131

```
cctgcaggca gctgcgcgct cgctcgctca ctgaggccgc ccgggcgtcg gcgaccttt      60
ggtcgcccgg cctcagtgag cgagcgagcg cgcagagagg gagtggccaa ctccatcact    120
aggggttcct gcggccgcac gcgtcttcgc gatgtacggg ccagatatat actgccgaat    180
ccaggtctcc gggcttaaca caacgaagg ggctgtgact ggctgctttc tcaaccaatc     240
agcaccgaac tcatttgcat gggctgagaa caaatgttcg cgaactctag aaatgaatga    300
cttaagtaag ttccttagaa tattattttt cctactgaaa gttaccacat gcgtcgttgt    360
ttatacagta ataggaacaa gaaaaaagtc acctaagctc accctcatca attgtggagt    420
tcctttatat cccatcttct ctccaaacac atacgcagga gtctgctgct gctgctgctg    480
ctgctgctgc tgctgctgct gctgctgaat ttttggagta gctttctggc ttcctttaccg   540
gaaagcccct cttatgatgt tgttgccaat gatagattgt ttttcactgt gcaaaaatta    600
tgggtagttt tggtggtctt gatgcagttg taagcttgga ggatccgagc tcggtaccaa    660
gcaaactaca gagccaagtg ctatccacag agagctttct gggttgccat ctcaagcaga    720
ctacaaggcc atcagctcat actcacaatt gactttgaga gcttcgcggt gtacgggcca    780
gatatatact gccgaatcca ggtctccggg cttaacaaca acgaaggggc tgtgactggc    840
tgctttctca accaatcagc accgaactca tttgcatggg ctgagaacaa atgttcgcga    900
actctagaaa tgaatgactt aagtaagttc cttagaatat tattttcct actgaaagtt    960
accacatgcg tcgttgttta tacagtaata ggaacaagaa aaaagtcacc taagctcacc   1020
ctcatcaatt gtggagttcc tttatatccc atcttctctc caaacacata cgcaggagtc   1080
tgctgctgct gctgctgctg ctgctgctgc tgctgctgct gctgaatttt tggagtaggc   1140
tttctggctc cttaccggaa agcccctctt atgatgtttg ttgccaatga tagattgttt   1200
tcactgtgca aaaattatgg gtagttttgg tggtcttgat gcagttgtaa gcttggagga   1260
tccgagctcg gtaccaagtt gaccacatac gtgctctttc aaagttctgt gtttgaagtt   1320
atgttagtaa caactgatgc ccatcctgca atgacaaatc aattctcagt gcagctcct   1380
tcgcgatgta cgggccagat atatactgcc gaatccaggt ctccgggctt aacaacaacg   1440
```

```
aaggggctgt gactggctgc tttctcaacc aatcagcacc gaactcattt gcatgggctg 1500
agaacaaatg ttcgcgaact ctagaaatga atgacttaag taagttcctt agaatattat 1560
ttttcctact gaaagttacc acatgcgtcg ttgtttatac agtaatagga acaagaaaaa 1620
agtcacctaa gctcaccctc atcaattgtg gagttccttt atatcccatc ttctctccaa 1680
acacatacgc aggagtctgc tgctgctgct gctgctgctg ctgctgctgc tgctgctgct 1740
gaattttttgg agtaggcttt ctggctcctt accggaaagc ccctcttatg atgtttgttg 1800
ccaatgatag attgttttca ctgtgcaaaa attatgggta gttttggtgg tcttgatgca 1860
gttgtaagct tggaggatcc gagctcggta ccaagactag tcgcgtcgac ggatccgaat 1920
tcgatatcgc tagcataata gtaatcaatt acggggtcat tagttcatag cccatatatg 1980
gagttccgcg ttacataact tacggtaaat ggcccgcctg gctgaccgcc caacgacccc 2040
cgcccattga cgtcaataat gacgtatgtt cccatagtaa cgccaatagg gactttccat 2100
tgacgtcaat gggtggagta tttacggtaa actgcccact tggcagtaca tcaagtgtat 2160
catatgccaa gtacgccccc tattgacgtc aatgacggta aatggcccgc ctggcattat 2220
gcccagtaca tgaccttatg gactttcct acttggcagt acatctacgt attagtcatc 2280
gctattacca tggtgatgcg gttttggcag tacatcaatg ggcgtggata gcggtttgac 2340
tcacggggat ttccaagtct ccaccccatt gacgtcaatg ggagtttgtt ttggcaccaa 2400
aatcaacggg actttccaaa atgtcgtaac aactccgccc cattgacgca aatgggcggt 2460
aggcgtgtac ggtgggaggt ctatataagc agagctggtt tagtgaaccg tcagatccgc 2520
tagcgctacc ggactcagat ctcgagctca agcttgaat tctgcagtcg acggtaccgc 2580
gggcccggga tccaccggtc gccaccatgg tgagcaaggg cgaggagctg ttcaccgggg 2640
tggtgcccat cctggtcgag ctggacggcg acgtaaacgg ccacaagttc agcgtgtccg 2700
gcgagggcga gggcgatgcc acctacggca agctgaccct gaagttcatc tgcaccaccg 2760
gcaagctgcc cgtgccctgg cccaccctcg tgaccaccct gacctacggc gtgcagtgct 2820
tcagccgcta ccccgaccac atgaagcagc acgacttctt caagtccgcc atgcccgaag 2880
gctacgtcca ggagcgcacc atcttcttca aggacgacgg caactacaag acccgcgccg 2940
aggtgaagtt cgagggcgac accctggtga accgcatcga gctgaagggc atcgacttca 3000
aggaggacgg caacatcctg gggcacaagc tggagtacaa ctacaacagc cacaacgtct 3060
atatcatggc cgacaagcag aagaacggca tcaaggtgaa cttcaagatc cgccacaaca 3120
tcgaggacgg cagcgtgcag ctcgccgacc actaccagca gaacaccccc atcggcgacg 3180
gccccgtgct gctgcccgac aaccactacc tgagcaccca gtccgccctg agcaaagacc 3240
ccaacgagaa gcgcgatcac atggtcctgc tggagttcgt gaccgccgcc gggatcactc 3300
tcggcatgga cgagctgtac aagtaaagcg gccgcgactc tagatcataa tcagccatac 3360
cacatttgta gaggttttac ttgctttaaa aaacctccca cacctccccc tgaacctgaa 3420
acataaaatg aatgcaattg ttgttgttaa cttgtttatt gcagcttata atggttacaa 3480
ataaagcaat agcatcacaa atttcacaaa taaagcattt ttttcactgc attctagttg 3540
tggtttgtcc aaactcatca atgtatctta agatatctag atctcgaggt aaccacgtgc 3600
ggaccgagcg gccgcaggaa cccctagtga tggagttggc cactccctct ctgcgcgctc 3660
gctcgctcac tgaggccggg cgaccaaagg tcgcccgacg cccgggcttt gcccgggcgg 3720
cctcagtgag cgagcgagcg cgcagctgcc tgcagg 3756
```

SEQ ID NO: 132          moltype = DNA   length = 4556
FEATURE                 Location/Qualifiers
source                  1..4556
                        mol_type = other DNA
                        organism = synthetic construct
SEQUENCE: 132
```
cctgcaggca gctgcgcgct cgctcgctca ctgaggccgc ccgggcgtcg ggcgaccttt 60
ggtcgcccgg cctcagtgag cgagcgagcg cgcagagagg gagtggccaa ctccatcact 120
aggggttcct gcggccgcac gcgtcttcgc gatgtacggg ccagatatat actgccgaat 180
ccaggtctcc gggcttaaca caacgaaggg gctgtgact ggctgctttc tcaaccaatc 240
agcaccgaac tcatttgcat gggctgagaa caaatgttcg cgaactctag aaatgaatga 300
cttaagtaag ttccttagaa tattatttt cctactgaaa gttaccacat gcgtcgttgt 360
ttatacagta ataggaacaa gaaaaagtc acctaagctc accctcatca attgtggagt 420
tcctttatat cccatcttct ctccaaacac atacgcagga gtcagcagca gcagcagcag 480
cagcagcagc agcagcagca gcagcagaat ttttggagta ggctttctgg ctccttaccg 540
gaaagccct cttatgatgt ttgttgccaa tgatagattg ttttcactgt gcaaaaatta 600
tgggtagttt tggtggtctt gatgcagttg taagcttgga ggatccgagc tcggtaccaa 660
gcaaactaca gagccaagtg ctatccacag agagctttct gggttgccat ctcaagcaga 720
ctacaaggcc atcagctcat actcacaatt gactttgaga gtcattttcc aatgctccta 780
cacacccctt cttcacaatc cccaacaaat ctgaggctgg aacttggtac cataacaatc 840
attacattat ttcaccagaa gtacaccttg cctggaagat tggcattata gcatcttcta 900
acattgtgaa agttagtgac caatgaggag atccaagtca gttccagttg gatttctcta 960
tactctataa taaatatata tggtgtcttc aacaatagga ctttgccatc cagtgatgct 1020
aaaaatcaat aacaatggca ataacctgcc ctgtttgaaa agcctctggc ttccatgact 1080
aacaattcaa ggcaggtctc ctatacctag tactgagatt tttatttgat aaactatatc 1140
ttctgggagg agaagcattg tcttcgcgat gtacgggcca gatatatact gccgaatcca 1200
ggtctccggg cttaacaaca acgaaggggc tgtgactggc tgctttctca accaatcagc 1260
accgaactca tttgcatggg ctgagaacaa atgttccgca actctagaaa tgaatgactt 1320
aagtaagttc cttagaatat tatttttcct actgaaagtt accacatgcg tcgttgttta 1380
tacagtaata ggaacaagaa aaagtcacc taagctcacc ctcatcaatt gtggagttcc 1440
tttatatccc atcttctctc caaacacata cgcaggagtc agcagcagca gcagcagcag 1500
cagcagcagc agcagcagca gcagaatttt tggagtaggc tttctggctc cttaccggaa 1560
agcccctctt atgatgtttg ttgccaatga tagattgttt tcactgtgca aaaattatgg 1620
gtagttttgg tggtcttgat gcagttgtaa gcttggaggat gcaagttt ctaagcgccgaccaaagt 1680
gaccacatac gtgctctttc aaagttctgt gtttgaagtt atgttagtaa caactgatgc 1740
ccatcctgca atgacaaatc caattctcag tgcagctctc tgaaatagtt ttgctttctc 1800
tctctaggtc tgttctatac tcctaactct ccaggagttt acaaggaata aaatctcttc 1860
caaatgcttt ctgttgcaac aactggacca tactgaaagc tgaggcccac aattgcaatc 1920
taggttagca ggtaatcatt gttggtgagg tcctcccttt ccccaggctc gtgtttgtat 1980
```

```
tggggagcag gaaattttg ctagagcagc actgccatct ctctacactc cacctgattg    2040
gtgggatgga ccagagaaat ggacattccc aacacagtcc ctcctttcac atctgctcac    2100
ctgcccacag gatactttcc accatgcata ctgggctctg caccaaccat tcagcagtga    2160
tgaagaggaa acttgaacct tcgcgatgta cgggccagat atatactgcc gaatccaggt    2220
ctccgggctt aacaacaacg aaggggctgt gactggctgc tttctcaacc aatcagcacc    2280
gaactcattt gcatgggctg agaacaaatg ttcgcgaact ctagaaatga atgacttaag    2340
taagttcctt agaatattat ttttcctact gaaagttacc acatgcgtcg ttgtttatac    2400
agtaatagga acaagaaaaa agtcacctaa gctcaccctc atcaattgtg gagttccttt    2460
atatcccatc ttctctccaa acacatacgc aggagtcagc agcagcagca gcagcagcag    2520
cagcagcagc agcagcagca gaattttttgg agtaggcttt ctggctcctt accggaaagc    2580
ccctcttatg atgtttgttg ccaatgatag attgttttca ctgtgcaaaa attatgggta    2640
gttttggtgg tcttgatgca gttgtaagct tggaggatcc gagctcggta ccaagactag    2700
tcgcgtcgac ggatccgaat tcgatatcgc tagcataata gtaatcaatt acgggtcat    2760
tagttcatag cccatatatg gagttccgcg ttacataact tacggtaaat ggcccgcctg    2820
gctgaccgcc caacgacccc cgcccattga cgtcaataat gacgtatgtt cccatagtaa    2880
cgccaatagg gactttccat tgacgtcaat gggtggagta tttacggtaa actgcccact    2940
tggcagtaca tcaagtgtat catatgccaa gtacgccccc tattgacgtc aatgacggta    3000
aatggcccgc ctggcattat gcccagtaca tgaccttatg ggactttcct acttggcagt    3060
acatctacgt attagtcatc gctattacca tggtgatgcg gttttggcag tacatcaatg    3120
ggcgtggata gcggtttgac tcacggggat ttccaagtct caccccatt gacgtcaatg    3180
ggagtttgtt ttggcaccaa aatcaacggg actttccaaa atgtcgtaac aactccgccc    3240
cattgacgca aatgggcggt aggcgtgtac ggtgggaggt ctatataagc agagctggtt    3300
tagtgaaccg tcagatccgc tagcgctacc ggactcagat ctcgagctca agcttcgaat    3360
tctgcagtcg acggtaccgc gggcccggga tccaccggtc gccaccatgg tgagcaaggg    3420
cgaggagctg ttcaccgggg tggtgcccat cctggtcgag ctggacggcg acgtaaacgg    3480
ccacaagttc agcgtgtccg gcgagggcga gggcgatgcc acctacggca agctgaccct    3540
gaagttcatc tgcaccaccg gcaagctgcc cgtgccctgg cccaccctcg tgaccaccct    3600
gacctacggc gtgcagtgct tcagccgcta ccccgaccac atgaagcagc acgacttctt    3660
caagtccgcc atgcccgaag gctacgtcca ggagcgcacc atcttcttca aggacgacgg    3720
caactacaag acccgcgccg aggtgaagtt cgagggcgac accctggtga accgcatcga    3780
gctgaagggc atcgacttca aggaggacgg caacatcctg gggcacaagc tggagtacaa    3840
ctacaacagc cacaacgtct atatcatggc cgacaagcag aagaacggca tcaaggtgaa    3900
cttcaagatc cgccacaaca tcgaggacgg cagcgtgcag ctcgccgacc actaccagca    3960
gaacaccccc atcggcgacg gccccgtgct gctgcccgac aaccactact tgagcaccca    4020
gtccgccctg agcaaagacc ccaacgagaa gcgcgatcac atggtcctgc tggagttcgt    4080
gaccgccgcc gggatcactc tcggcatgga cgagctgtac aagtaaagcg gccgcgactc    4140
tagatcataa tcagccatac cacatttgta gaggttttac ttgctttaaa aaacctccca    4200
cacctccccc tgaacctgaa acataaaatg aatgcaattg ttgttgttaa cttgtttatt    4260
gcagcttata atggttacaa ataaagcaat agcatcacaa atttcacaaa taaagcattt    4320
tttcactgc attctagttg tggtttgtcc aaactcatca atgtatctta agatatctag    4380
atctcgaggt aaccacgtgc ggaccgagcg gccgcaggaa ccctagtga tggagttggc    4440
cactccctct ctgcgcgctc gctcgctcac tgaggccggg cgaccaaagg tcgcccgacg    4500
cccgggcttt gcccggggcgg cctcagtgag cgagcgagcg cgcagctgcc tgcagg        4556
```

SEQ ID NO: 133        moltype = DNA  length = 4499
FEATURE              Location/Qualifiers
source               1..4499
                      mol_type = other DNA
                      organism = synthetic construct
SEQUENCE: 133

```
cctgcaggca gctgcgcgct cgctcgctca ctgaggccgc ccgggcgtcg ggcgaccttt      60
ggtcgcccgg cctcagtgag cgagcgagcc cgcagagagg gagtggccaa ctccatcact     120
aggggttcct gcggccgcac gcgtcttcgc gatgtacggg ccagatatat actgccgaat     180
ccaggtctcc gggcttaaca acaacgaagg ggctgtgact ggctgctttc tcaaccaatc     240
agcaccgaac tcatttgcat gggctgagaa caaatgttcg cgaactctag aaatgaatga     300
cttaagtaag ttccttagaa tattattttt cctactgaaa gttaccacat gcgtcgttgt     360
ttatacagta ataggaacaa gaaaaaagtc acctaagctc accctcatca attgtggagt     420
tcctttatat cccatcttct ctccaaacac atacgcagga gttcaccaga gcgtaccat     480
actcacgaca tttttggagt aggctttctg gctccttacc ggaaagcccc tcttatgatg     540
tttgttgcca atgatagatt gttttcactg tgcaaaaatt atgggtagtt ttggtggtct     600
tgatgcagtt gtaagcttgg aggatccgag ctcggtacca gcaaactac agagccaagt     660
gctatccaca gagagctttc tgggttgcca tctcaagcag actacaaggc catcagctca     720
tactcacaat tgactttgag agtcattttc caatgctcct acacacccct tcttcacaat     780
ccccaacaaa tctgaggctg gaacttggta ccataacaat cattacatta tttccaccaga     840
agtacacctt gctgaaga ttggcattat agcatcttct aacattgtga agttagtga     900
ccaatgagga gatccaagtc agttccagtt ggatttctct atactctata ataaatatat     960
atggtgtctt caacaatagg actttgccat ccagtgatgc taaaaatcaa taacaatggc    1020
aataacctgc cctgtttga aagcctctgg cttccatgac taacaattca aggcaggtct    1080
cctataccta gtactgagat tttttatttga taaactatat cttctgggag gagaagcatt    1140
gtcttcgcga tgtacgggcc agatatatac tgccgaatcc aggtctccgg gcttaacaac    1200
aacgaagggg ctgtgactgg ctgctttctc aaccaatcag caccgaactc atttgcatgg    1260
gctgagaaca aatgttcgcg aactctagaa atgaatgact taagtaagtt ccttagaata    1320
ttattttcc tactgaaagt taccacatgc gtcgttgttt atacagtaat aggaacaaga    1380
aaaaagtcac ctaagctcac cctcatcaat catcttctca catcttctca    1440
ccaaacacat acgcaggagt tcaccagaag cgtaccatc tcacgaaatt tttggagtag    1500
gctttctggc tccttaccgg aaagcccctc ttatgatgt tgttgccaat gatagattgt    1560
tttcactgtg caaaaattat gggtagtttt ggtggtcttg atgcagttgt aagcttggag    1620
gatccgagct cggtaccaag ttgaccacat acgtgctctt tcaagttct gtgtttgaag    1680
ttatgttagt aacaactgat gcccatcctg caatgacaaa tccaattctc agtgcagctc    1740
```

```
tctgaaatag ttttgctttc tctctctagg tctgttctat actcctaact ctccaggagt  1800
ttacaaggaa taaatctct tccaaatgct ttctgttgca acaactggac catactgaaa   1860
gctgaggccc acaattgcaa tctaggttag caggtaatca ttgttggtga ggtcctccct  1920
ttccccaggc tcgtgtttgt attggggagc aggaaatttt tgctagagca gcactgccat  1980
ctctctacac tccacctgat tggtgggatg gaccagagaa atggacattc ccaacacagt  2040
ccctcctttc acatctgctc acctgcccac aggatacttt ccaccatgca tactgggctc  2100
tgcaccaacc attcagcagt gatgaagagg aaacttgaac cttcgcgatg tacgggccag  2160
atatatactg ccgaatccag gtctccgggc ttaacaacaa cgaaggggct gtgactggct  2220
gctttctcaa ccaatcagca ccgaactcat ttgcatgggc tgagaacaaa tgttcgcgaa  2280
ctctagaaat gaatgactta agtaagttcc ttagaatatt attttcctaa ctgaaagtta  2340
ccacatgcgt cgttgtttat acagtaatag gaacaagaaa aaagtcacct aagctcaccc  2400
tcatcaattg tggagttcct ttatatccca tcttctctcc aaacacatac gcaggagttc  2460
accagaagcg taccatactc acgaaatttt tggagtaggc tttctggctc cttaccggaa  2520
agcccctctt atgatgtttg ttgccaatga tagattgttt tcactgtgca aaaattatgg  2580
gtagttttgg tggtcttgat gcagttgtaa gcttggagga tccgagctcg gtaccaagac  2640
tagtcgcgtc gacggatccg aattcgatat cgctagcata atagtaatca attacggggt  2700
cattagttca tagcccatat atggagttcc gcgttacata acttacggta aatggcccgc  2760
ctggctgacc gcccaacgac ccccgcccat tgacgtcaat aatgacgtat gttcccatag  2820
taacgccaat agggactttc cattgacgtc aatgggtgga gtatttacgg taaactgccc  2880
acttggcagt acatcaagtg tatcatatgc caagtacgcc ccctattgac gtcaatgacg  2940
gtaaatggcc cgcctggcat tatgcccagt acatgacctt atgggacttt cctacttggc  3000
agtacatcta cgtattagtc atcgctatta ccatggtgat gcggttttgg cagtacatca  3060
atgggcgtgg atagcggttt gactcacggg gatttccaag tctccacccc attgacgtca  3120
atgggagttt gttttggcac caaaatcaac gggactttcc aaaatgtcgt aacaactccg  3180
ccccattgac gcaaatgggc ggtaggcgtg tacggtggga ggtctatata agcagagctg  3240
gtttagtgaa ccgtcagatc cgctagcgct accggactca gatctcgagc tcaagcttcg  3300
aattctgcag tcgacggtac cgcgggcccg gatccaccg gtcgccacca tggtgagcaa   3360
gggcgaggag ctgttcaccg gggtggtgcc catcctggtc gagctggacg gcgacgtaaa  3420
cggccacaag ttcagcgtgt ccggcgaggg cgagggcgat gccacctacg gcaagctgac  3480
cctgaagttc atctgcacca ccggcaagct gcccgtgccc tggcccaccc tcgtgaccac  3540
cctgacctac ggcgtgcagt gcttcagccg ctaccccgac cacatgaagc agcacgactt  3600
cttcaagtcc gccatgcccg aaggctacgt ccaggagcgc accatcttct tcaaggacga  3660
cggcaactac aagacccgcg ccgaggtgaa gttcgagggc gacaccctgg tgaaccgcat  3720
cgagctgaag ggcatcgact tcaaggagga cggcaacatc ctggggcaca gctggagta   3780
caactacaac agccacaacg tctatatcat ggccgacaag cagaagaacg gcatcaaggt  3840
gaacttcaag atccgccaca acatcgagga cggcagcgtg cagctcgccg accactacca  3900
gcagaacacc cccatcggcg acggccccgt gctgctgccc gacaaccact acctgagcac  3960
ccagtccgcc ctgagcaaag accccaacga gaagcgcgat cacatggtcc tgctggagtt  4020
cgtgaccgcc gccgggatca ctctcggcat ggacgagctg tacaagtaaa gcggccgcga  4080
ctctagatca taatcagcca taccacattt gtagaggttt tacttgcttt aaaaaacctc  4140
ccacacctcc ccctgaacct gaaacataaa atgaatgcaa ttgttgttgt taacttgttt  4200
attgcagctt ataatggtta caaataaagc aatagcatca caaatttcac aaataaagca  4260
tttttttcac tgcattctag ttgtggtttg tccaaactca tcaatgtatc ttaagatatc  4320
tagatctcga ggtaaccacg tgcggaccga gcggccgcag gaaccctag tgatggagtt   4380
ggccactccc tctctgcgcg ctcgctcgct cactgaggcc gggcgaccaa aggtcgcccg  4440
acgcccgggc tttgcccggg cggcctcagt gagcgagcga gcgcgcagct gcctgcagg   4499
```

SEQ ID NO: 134        moltype = DNA  length = 4556
FEATURE             Location/Qualifiers
source              1..4556
                     mol_type = other DNA
                     organism = synthetic construct
SEQUENCE: 134

```
cctgcaggca gctgcgcgct cgctcgctca ctgaggccgc ccgggcgtcg ggcgaccttt   60
ggtcgccggg cctcagtgag cgagcgagcg cgcagagagg gagtggccaa ttccatcact  120
aggggttcct gcggccgcac gcgtcttcgc gatgtacggg ccagatatat actgccgaat  180
ccaggtctcc gggcttaaca acaacgaagg ggctgtgact ggctgctttc tcaaccaatc  240
agcaccgaac tcatttgcat gggctgagaa caaatgttcg cgaactctag aaatgaatga  300
cttaagtaag ttccttagaa tattattttt cctactgaaa gttaccacat gcgtcgttgt  360
ttatacagta ataggaacaa gaaaaagtc acctaagctc accctcatca attgtggagt   420
tcctttatat cccatcttct ctccaaacac atacgcagga gtctgctgct gctgctgctg  480
ctgctgctgc tgctgctgct gctgctgaat ttttggagta ggctttctgg ctccttaccg  540
gaaagcccct cttatgatgt ttgttgccaa tgatagatt ttttcactgt gcaaaaatta   600
tgggtagttt tggtggtctt gatgcagttg taagcttgga ggatccgagc tcggtaccaa  660
gcaaactaca gagccaagtg ctatccacag agagcttct gggttgccat ctcaagcaga   720
ctacaaggcc atcagctcat actcacaatt gactttgaga gtcattttcc aatgctccta  780
cacacccctt cttcacaatc cccaacaaat ctgaggctgg aacttggtac cataacaatc  840
attacattat ttcaccagaa gtacaccttg cctggaagat tggcattata gcatcttcta  900
acattgtgaa agttagtgac caatgaggag atccaagtca gttccagttg gatttctcta  960
tactctataa taaatatata tggtgtcttc aacaatagga ctttgccatc cagtgatgct  1020
aaaaatcaat aacaatggca ataacctgcc ctgtttggaa agcctctggc ttccatgact  1080
aacaattcaa ggcaggtctc ctatacctag tactgagatt tttatttgat aaactatatc  1140
ttctggggag agaagcattg tcttcgcgat gtacgggcca gatatatact gccgaatcca  1200
ggtctccggg cttaacaaca cgaaggggct gtgactggct gctttctcaa ccaatcagca  1260
accgaactca tttgcatggg ctgagaacaa atgttcgcga actctagaaa tgaatgactt  1320
aagtaagttc cttagaatat tatttttcct actgaaagtt accacatgcg tcgttgttta  1380
tacagtaata ggaacaagaa aaagtcacc taagctcacc ctcatcaatt gtggagttcc   1440
tttatatccc atcttctctc caaacacata cgcaggagtc tgctgctgct gctgctgctg  1500
ctgctgctgc tgctgctgct gctgaatttt tggagtaggc tttctggctc cttaccggaa  1560
```

```
agccctctt  atgatgtttg  ttgccaatga  tagattgttt  tcactgtgca  aaaattatgg  1620
gtagttttgg  tggtcttgat  gcagttgtaa  gcttggagga  tccgagctcg  gtaccaagtt  1680
gaccacatac  gtgctctttc  aaagttctgt  gtttgaagtt  atgttagtaa  caactgatgc  1740
ccatcctgca  atgacaaatc  caattctcag  tgcagctctc  tgaaatagtt  ttgctttctc  1800
tctctaggtc  tgttctatac  tcctaactct  ccaggagttt  acaaggaata  aaatctcttc  1860
caaatgcttt  ctgttgcaac  aactggacca  tactgaaagc  tgaggccac   aattgcaatc  1920
taggttagca  ggtaatcatt  gttggtgagg  tcctcccttt  ccccaggctc  gtgtttgtat  1980
tggggagcag  gaaatttttg  ctagagcagc  actgccatct  ctctacactc  cacctgattg  2040
gtgggatgga  ccagagaaat  ggacattccc  aacacagtcc  ctcctttcac  atctgctcac  2100
ctgcccacag  gatacttcc   accatgcata  ctgggctctg  caccaaccat  tcagcagtga  2160
tgaagaggaa  acttgaacct  tcgcgatgta  cgggccagat  atatactgcc  gaatccaggt  2220
ctccgggctt  aacaacaacg  aaggggctgt  gactggctgc  tttctcaacc  aatcagcacc  2280
gaactcattt  gcatgggctg  agaacaaatg  ttcgcgaact  ctagaaatga  atgacttaag  2340
taagttcctt  agaatattat  ttttcctact  gaaagttacc  acatgcgtcg  ttgtttatac  2400
agtaatagga  acaagaaaaa  agtcacctaa  gctcaccctc  atcaattgtg  gagttccttt  2460
atatcccatc  ttctctccaa  acacatacg   aggagtctgc  tgctgctgct  gctgctgctg  2520
ctgctgctgc  tgctgctgct  gaattttggg  agtaggcttt  ctggctcctt  accggaaagc  2580
ccctcttatg  atgttttg   ccaatgatag  attgttttcg  ctgtgcaaaa  attatgggta  2640
gttttggtgg  tcttgatgca  gttgtaagct  tggaggatcc  gagctcggta  ccaagactag  2700
tcgcgtcgac  ggatccgaat  tcgatatcgc  tagcataata  gtaatcaatt  acggggtcat  2760
tagttcatag  cccatatatg  gagttccgcg  ttacataact  tacggtaaat  ggcccgcctg  2820
gctgaccgcc  caacgacccc  cgcccattga  cgtcaataat  gacgtatgtt  cccatagtaa  2880
cgccaataggg  gactttccat  tgacgtcaat  gggtggagta  tttacggtaa  actgcccact  2940
tggcagtaca  tcaagtgtat  catatgccaa  gtacgccccc  tattgacgtc  aatgacggta  3000
aatgccccgc  tggcattat   gcccagtaca  tgaccttatg  ggactttcct  acttggcagt  3060
acatctacgt  attagtcatc  gctattacca  tggtgatgcg  gttttggcag  tacatcaatg  3120
ggcgtggata  gcggtttgac  tcacggggat  ttccaagtct  ccaccccatt  gacgtcaatg  3180
ggagtttgtt  ttggcaccaa  aatcaacggg  acttccaaaa  atgtcgtaac  aactccgccc  3240
cattgacgca  aatgggcggt  aggcgtgtac  ggtgggaggt  ctatataagc  agagctggtt  3300
tagtgaaccg  tcagatccgc  tagcgctacc  ggactcagat  ctcgagctca  agcttcgaat  3360
tctgcagtcg  acggtaccgc  gggcccggga  tccaccggtc  gccaccatgg  tgagcaaggg  3420
cgaggagctg  ttcaccgggg  tggtgcccat  cctggtcgag  ctggacggcg  acgtaaacgg  3480
ccacaagttc  agcgtgtccg  gcgagggcga  gggcgatgcc  acctacggca  agctgaccct  3540
gaagttcatc  tgcaccaccg  gcaagctgcc  cgtgccctgg  cccaccctcg  tgaccaccct  3600
gacctacggc  gtgcagtgct  tcagccgcta  ccccgaccac  atgaagcagc  acgacttctt  3660
caagtccgcc  atgcccgaag  gctacgtcca  ggagcgcacc  atcttcttca  aggacgacgg  3720
caactacaag  acccgcgccg  aggtgaagtt  cgagggcgac  accctggtga  accgcatcga  3780
gctgaagggc  atcgacttca  aggaggacgg  caacatcctg  gggcacaagc  tggagtacaa  3840
ctacaacagc  cacaacgtct  atatcatggc  cgacaagcag  aagaacggca  tcaaggtgaa  3900
cttcaagatc  cgccacaaca  tcgaggacgg  cagcgtgcag  ctcgccgacc  actaccagca  3960
gaacacccc   atcggcgacg  gccccgtgct  gctgcccgac  aaccactacc  tgagcaccca  4020
gtccgccctg  agcaaagacc  ccaacgagaa  gcgcgatcac  atggtcctgc  tggagttcgt  4080
gaccgcgcc  gggatcactc  tcggcatgga  cgagctgtac  aagtaaagcg  gccgcgactc  4140
tagatcataa  tcagccatac  cacatttgta  gaggttttac  ttgctttaaa  aaacctccca  4200
cacctccccc  tgaacctgaa  acataaaatg  aatgcaattg  ttgttgttaa  cttgtttatt  4260
gcagcttata  atggttacaa  ataaagcaat  agcatcacaa  atttcacaaa  taaagcattt  4320
ttttcactgc  attctagttg  tggtttgtcc  aaactcatca  atgtatctta  agatatctag  4380
atctcgaggt  aaccacgtgc  ggaccgagcg  gccgcaggaa  ccctagtga   tggagttggc  4440
cactccctct  ctgcgcgctc  gctcgctcac  tgaggccggg  cgaccaaagg  tcgcccgacg  4500
cccgggcttt  gcccggcgg   cctcagtgag  cgagcgagcg  cgcagctgcc  tgcagg      4556

SEQ ID NO: 135         moltype = DNA   length = 1424
FEATURE                Location/Qualifiers
source                 1..1424
                       mol_type = other DNA
                       organism = synthetic construct
SEQUENCE: 135
cctgcaggca  gctgcgcgct  cgctcgctca  ctgaggccgc  ccgggcgtcg  ggcgaccttt   60
ggtcgcccgg  cctcagtgag  cgagcgagcg  cgcagagagg  gagtggccaa  ctccatcact  120
aggggttcct  gcggccgcac  ttcgcgatgt  acgggccagga  tatatactgc  cgaatccagg  180
tctccgggct  taacaacaac  gaaggggctg  tgactggctg  cttttctcaac  caatcagcac  240
cgaactcatt  tgcatgggct  gagaacaaat  gttcgcgaac  tctagaaatg  aatgacttaa  300
gtaagttcct  tagaatatta  ttttttcctac  tgaaagttac  cacatgcgtc  gttgtttata  360
cagtaatagg  aacaagaaaa  agtcaccta   agctcccct   catcaattgt  ggagttcctt  420
tatatcccat  cttctctcca  aacacatacg  caggagttac  ctccaacatc  aaggaagatg  480
gcagtaacca  caggttgtgt  caccagagta  acaaattttt  ggagtaggct  ttctggctcc  540
ttaccggaaa  gcccctctta  tgatgttgt   tgccaatgat  agattgtttt  cactgtgcaa  600
aaattatggg  tagttttggt  ggtcttgatg  cagttgtaag  cttggaggat  ccgagctcgg  660
taccaagcta  tcgcgtaag   gaccagcttc  tttgggagag  aacagacgca  ggggcggaag  720
ggaaaaaggg  agaggcagac  gtcacttccc  cttggcggct  ctggcagcag  attggtcggt  780
tgagtggcag  aaaggcagac  ggggactggg  caaggcactg  tcgtgacat   cacggacagg  840
gcgacttcta  tgtagatgag  gcagcgcaga  ggctgacgtc  ttcgccactt  gctgcttcac  900
cacgaaggag  ttccgtgcc   ctgggagcgg  gttcaggacc  gctgatcgga  agtgagaatc  960
ccagctgtgt  gtcagggctg  gaaagggctc  gggagtgcca  gggcaagtg   accgtgtgtg  1020
taaagagtga  ggcgtatgag  gctgtgtcgg  ggcagaggca  caacgtttcg  gagttacctc  1080
caacatcaag  gaagatggca  gtaaccacag  gttgtgtcac  cagagtaaca  aattttttgga  1140
gtaggctttc  tggctcctta  ccggaaagcc  acttttctgga  gtttcaaaaa  cagactgtac  1200
gccaagggtc  atatctttt   cgtcgacgga  tccgaattcg  atatctagat  ctcgaggtaa  1260
ccacgtgcgg  accgagcggc  cgcaggaacc  cctagtgatg  gagttggcca  ctccctctct  1320
```

```
gcgcgctcgc tcgctcactg aggccgggcg accaaaggtc gcccgacgcc cgggctttgc   1380
ccgggcggcc tcagtgagcg agcgagcgcg cagctgcctg cagg                    1424

SEQ ID NO: 136          moltype = DNA   length = 1368
FEATURE                 Location/Qualifiers
source                  1..1368
                        mol_type = other DNA
                        organism = synthetic construct
SEQUENCE: 136
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg ctttctcaac caatcagcac   240
cgaactcatt tgcatgggct gagaacaaat gttcgcgaac tctagaaatg aatgacttaa   300
gtaagttcct tagaatatta ttttttcctac tgaaagttac cacatgcgtc gttgtttata   360
cagtaatagg aacaagaaaa aagtcaccta agctcaccct catcaattgt ggagttcctt   420
tatatcccat cttctctcca aacacatacg caggagtgta accacaggtt gtgtcaccag   480
agtaacaaat ttttggagta ggcttttctgg ctccttaccg gaaagcccct cttatgatgt   540
ttgttgccaa tgatagattg ttttcactgt gcaaaaatta tgggtagttt tggtggtctt   600
gatgcagttg taagcttgga ggatccgagc tcggtaccaa gctagtcgcg taaggaccag   660
cttctttggg agaaacagca cgcaggggcg ggagggaaaa agggagaggc agacgtcact   720
tcccccttggc ggctctggca gcagattggt cggttgagtg gcagaaaggc agacggggac   780
tgggcaaggc actgtcggtg acatcacgga cagggcgact tctatgtaga tgaggcagcg   840
cagaggctga cgtcttcgcc acttgctgct tcaccacgaa ggagttcccg tgccctggga   900
gcgggttcag gaccgctgat cggaagtgag aatcccagct gtgtgtcagg gctggaaagg   960
gctcgggagt gcgcgggggca agtgaccgtg tgtgtaaaga gtgaggcgta tgaggctgtg   1020
tcggggcaga ggcacaacgt ttcggagtta cctccaacat caaggaagat ggcaaattttt   1080
tggagtaggc tttctggctc cttaccggaa agccactttc tggagtttca aaaacagact   1140
gtacgccaag ggtcatatct ttttcgtcga cggatccgaa ttcgatatct agatctcgag   1200
gtaaccacgt gcggaccgag cggccgcagg aaccccctag gatggagttg gccactcct   1260
ctctgcgcgc tcgctcgctc actgaggccg ggcgaccaaa ggtcgcccga cgcccgggct   1320
ttgcccgggc ggcctcagtg agcgagcgag cgcgcagctg cctgcagg                1368

SEQ ID NO: 137          moltype = DNA   length = 1407
FEATURE                 Location/Qualifiers
source                  1..1407
                        mol_type = other DNA
                        organism = synthetic construct
SEQUENCE: 137
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccggtc gcgtctagta acttcgcgat gtacgggcca gatatatact   180
gccgaatcca ggtctccggg cttaacaaca acgaaggggc tgtgactggc tgctttctca   240
accaatcagc accgaactca tttgcatggg ctgagaacaa atgttcgcga actctagaaa   300
tgaatgactt aagtaagttc cttagaatat tatttttcct actgaaagtt accacatgcg   360
tcgttgttta tacagtaata ggaacaagaa aaaagtcacc taagctcacc ctcatcaatt   420
gtggagttcc tttatatccc atcttctctc caaacacata cgcaggagtt acctccaaca   480
tcaaggaaga tggcagtaac cacaggttgt gtcaccagag taacaaattt ttggagtagg   540
cttttctggct ccttaccgga aagcccctct tatgatgttt gttgccaatg atagattgtt   600
ttcactgtgc aaaaattatg ggtagttttg gtggtcttga tgcagttgta agcttggagg   660
atccgaagc ggtaccaagc tagtcgcgta aggaccagct tctttgggag agaacagacg   720
caggggcggg agggaaaaag gggagaggcag acgtcacttc cccttggcgg ctctggcagc   780
agattggtcg gttgagtggc agaaaggcag acggggactg gcaaggcac tgtcggtgac   840
atcacggaca gggcgacttc tatgtagatg aggcagcgca gaggctgacg tcttcgccac   900
ttgctgcttc accacgaagg agttcccgtg ccctgggagc gggttcagga ccgctgatcg   960
gaagtgagaa tcccagctgt gtgtcaggg tggaaagggc tcgggagtgc gcggggcaag   1020
tgaccgtgtg tgtaaagagt gaggcgtatg aggctgtgtc ggggcagagg cacaacgttt   1080
cggagttacc tccaacatca aggaagatgg cagtaaccac aggttgtgtc accagagtaa   1140
caaattttttg gagtaggctt tctggctcct taccggaaag ccactttctg gagtttcaaa   1200
aacagactg acgccaaggg tcatatcttt ttcgtcgacg gatccgaatt cgatatctag   1260
atctcgaggt aaccacgtgc ggaccgagcc tagtccactc cctctctgcg cgctcgctcg   1320
ctcactgagg ccgggcgacc aaaggtcgcc gacgcccgg ctttgcccg gcggcctca   1380
gtgagcgagc gagcgcgcag agaggga                                       1407

SEQ ID NO: 138          moltype = DNA   length = 3074
FEATURE                 Location/Qualifiers
source                  1..3074
                        mol_type = other DNA
                        organism = synthetic construct
SEQUENCE: 138
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg ctttctcaac caatcagcac   240
cgaactcatt tgcatgggct gagaacaaat gttcgcgaac tctagaaatg aatgacttaa   300
gtaagttcct tagaatatta ttttttcctac tgaaagttac cacatgcgtc gttgtttata   360
cagtaatagg aacaagaaaa aagtcaccta agctcaccct catcaattgt ggagttcctt   420
tatatcccat cttctctcca aacacatacg caggagttac ctccaacatc aaggaagatg   480
gcagtaacca caggttgtgt caccagagta acaaattttt ggagtaggct ttctggctcc   540
```

```
ttaccggaaa gccccctctta tgatgtttgt tgccaatgat agattgtttt cactgtgcaa   600
aaattatggg tagttttggt ggtcttgatg cagttgtaag cttggaggat ccgagctcgg   660
taccaagcta gtcgcgtaag gaccagcttc tttgggagag aacagacgca ggggcgggag   720
ggaaaaaggg agaggcagac gtcacttccc cttggcggct ctggcagcag attggtcggt   780
tgagtggcag aaaggcagac ggggactggg caaggcactg tcggtgacat cacggacagg   840
gcgacttcta tgtagatgag gcagcgcaga ggctgacgtc ttcgccactt gctgcttcac   900
cacgaaggag ttcccgtgcc ctgggagcgg gttcaggacc gctgatcgga agtgagaatc   960
ccagctgtgt gtcagggctg aaagggctc ggagtgcgc ggggcaagtg accgtgtgtg   1020
taaagagtga ggcgtatgag gctgtgtcgg ggcagaggca caacgtttcg gagttacctc   1080
caacatcaag gaagatggca gtaaccacag gttgtgtcac cagagtaaca aatttttgga   1140
gtaggctttc tggctcctta ccggaaagcc actttctgga gtttcaaaaa cagactgtac   1200
gccaagggtc atatctttt cgtcgacgga tccgcaaact acagagccaa gtgctatcca   1260
cagagagctt tctgggttgc catctcaagc agactacaag gccatcagct catactcaca   1320
attgactttg agagtcattt tccaatgctc ctacacaaca cttcttcaca atccccacaa   1380
aatctgaggc tggaacttgg taccataaca atcattacat tatttcacca gaagtacacc   1440
ttgcctggaa gattggcatt atagcatctt ctaacattgt gaaagttagt gaccaatgag   1500
gagatccaag tcagttccag ttggatttct ctatactcta aataaatat atatggtgtc   1560
ttcaacaata ggactttgcc atccatgat gctaaaaatc aataacaatg gcaataaacct   1620
gccctgtttg gaaagcctct ggcttccatg actaacaatt caaggcaggt ctcctatacc   1680
tagtactgag attttatt gataaactat atcttctggg aggagaagca ttgtttgacc   1740
acatacgtgc tcttcaaag ttctgtgttt gaagttatgt tagtaacaac tgatgcccat   1800
cctgcaatga caaatccaat tctcagtgca gctctctgaa atagttttgc tttctctctc   1860
taggtctgtt ctatactcct aactctccag gagtttacaa ggaataaaat ctcttccaaa   1920
tgctttctgt tgcaacaact ggaccatact gaaagctgag gcccacaatt gcaatctagg   1980
ttagcaggta atcattgttg gtgaggtcct ccctttcccc aggctcgtgt ttgtattggg   2040
gagcaggaaa ttttgctag agcagcactg ccatctctct acactccacc tgattgggtg   2100
gatggaccag agaaatggac attcccaaca cagtccctcc tttcacatct gctcacctgc   2160
ccacaggata ctttccacca tgcatactgg gctctgcacc aaccattcag cagtgatgaa   2220
gaggaaactt gaacccatgc agagtacctc tagagaaaag tttctaaagt tggttttgcc   2280
ttgcttagaa aggaggtcaa aggtgaagcc taggagaaac attcagcaat gttgcacaaa   2340
gacatgagaa taaatgattt tagcatcctg aaatgaagag catagtgatc tcaccatagc   2400
tacccaccta cccagagaac ttccaggctt tcactgtctc ttttctgaat cacccacatt   2460
acagaatatc agtcattgtg taattagata acagattgtg aggtgcccaa acagaaacaa   2520
acttacagg aggagagaga aaatcaaggt gatgactata gagaacaaaa tgagaaggag   2580
aggtggagtt cctgctgcat gaacacctat cctgctatag agcccatttc ttccataaat   2640
aatacaactc tgtaactcca taggtcagaa agaaacagtg ttctgtgtct tcccatctag   2700
caccacaaac ccccacaaga ttaatttgtt tctagggacc cttaaatctc tatcaaaatt   2760
ctggaaacct ctactttaga aaatcttata tttattattc aggctacttt ccagagtgat   2820
aagctactga gtctcctaag tgtcatctat ggtacacagg gataagatca ggaataaacc   2880
tgggaattcg atatctagat ctcgaggtaa ccacgtgcgg accgagcggc gcaggaacc   2940
cctagtgatg gagttggcca ctcccctctct gcgcgctcgc tcgctcactg aggcggggcg   3000
accaaaggtc gcccgacgcc cgggctttgc ccggcggcc tcagtgagcg agcgagcgcg   3060
cagctgcctg cagg                                                    3074
SEQ ID NO: 139          moltype = DNA   length = 3051
FEATURE                 Location/Qualifiers
source                  1..3051
                        mol_type = other DNA
                        organism = synthetic construct
SEQUENCE: 139
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg cttttctcaac caatcagcac   240
cgaactcatt tgcatgggct gagaacaaat gttcgcaaac tctagaaatg aatgacttaa   300
gtaagttcct tagaatatta ttttttcctac tgaaagttac cacatgcgtc gttgtttata   360
cagtaatagg aacaagaaaa aagtcaccta agctcaccct catcaattgt ggagttcctt   420
tatatcccat cttctctcca aacacatacg caggagtcag cagcagcagc agcagcagca   480
gcagcagcag cagcagcagc agaatttttg gagtaggctt tctggctcct taccggaaag   540
ccctctttat gatgtttgtt gccaatgata gattgttttc actgtgcaaa aattatgggg   600
agttttggtg gtcttgatgc agttgtaagc ttggaggatc cgagctcggt accaagctag   660
tcgcgtaagg accagcttct ttgggagaga acagacgcag gggcgggagg gaaaagggga   720
gaggcagacg tcacttcccc ttggcggctc tggcagcaga ttggtcggtt gagtggcaga   780
aaggcagacg gggactgggc aaggcactgt cggtgacatc acggacaggg cgacttctat   840
gtagatgagg cagcgcagag gctgacgtct tcgccacttg ctgcttcacc acgaaggagt   900
tcccgtgccc tgggagcggg ttcaggaccc tgatcggaa gtgagaatcc agctgtgtgt   960
tcagggctga aagggctcg ggagtgcgcg gggcaagtga ccgtgtgtgt aaagagtgag  1020
gcgtatgagg ctgtgtcggg gcagaggcac aacgtttcgg agtcagcagc agcagcagca  1080
gcagcagcag cagcagcagc agcagcagaa ttttggagtt aggcttctg gctccttacc  1140
ggaaagccac tttctggagt tcaaaaaca gactgtacgc caagggtcat atcttttcg  1200
tcgacggatc cgaattcgat atcgctagca taatagtaat caattacggg gtcattagtt  1260
catagcccat atatggagtt ccgcgttaca taacttacgg taaatggccc gcctggctga  1320
ccgcccaacg acccccgccc attgacgtca ataatgacgt atgttcccat agtaacgcca  1380
atagggactt tccatttacg tcaatgggtg gagtatttac ggtaaactgc ccacttggca  1440
gtacatcaag tgtatcatat gccaagtacg ccccctattg acgtcaatga cggtaaatgg  1500
cccgcctggc attatgccca gtacatgacc ttatgggact ttcctacttg gcagtacatc  1560
tacgtattag tcatcgctat taccatggtg atgcggtttt ggcagtacat caatgggcgt  1620
ggatagcggt ttgactcacg gggatttcca agtctccacc ccattgacgt caatgggagt  1680
ttgttttggc accaaaatca acgggacttt ccaaaatgtc gtaacaactc cgccccattg  1740
```

```
acgcaaatgg gcggtaggcg tgtacggtgg gaggtctata taagcagagc tggtttagtg   1800
aaccgtcaga tccgctagcg ctaccggact cagatctcga gctcaagctt cgaattctgc   1860
agtcgacggt accgcgggcc cgggatccac cggtcgccac catggtgagc aagggcgagg   1920
agctgttcac cggggtggtg cccatcctgg tcgagctgga cggcgacgta aacggccaca   1980
agttcagcgt gtccggcgag ggcgagggcg atgccaccta cggcaagctg accctgaagt   2040
tcatctgcac caccggcaag ctgcccgtgc cctggcccac cctcgtgacc accctgacct   2100
acggcgtgca gtgcttcagc cgctaccccg accacatgaa gcagcacgac ttcttcaagt   2160
ccgccatgcc cgaaggctac gtccaggagc gcaccatctt cttcaaggac gacggcaact   2220
acaagacccg cgccgaggtg aagttcgagg gcgacaccct ggtgaaccgc atcgagctga   2280
agggcatcga cttcaaggag gacggcaaca tcctgggcca caagctggag tacaactaca   2340
acagccacaa cgtctatatc atggccgaca agcagaagaa cggcatcaag gtgaacttca   2400
agatccgcca caacatcgag gacggcagcg tgcagctcgc cgaccactac cagcagaaca   2460
cccccatcgg cgacggcccc gtgctgctgc ccgacaacca ctacctgagc acccagtccg   2520
ccctgagcaa agaccccaac gagaagcgcg atcacatggt cctgctggag ttcgtgaccg   2580
ccgccgggat cactctcggc atggacgagc tgtacaagta aagcggccgc gactctagat   2640
cataatcagc cataccacat ttgtagaggt tttacttgct ttaaaaaacc tcccacacct   2700
ccccctgaac ctgaaacata aaatgaatgc aattgttgtt gttaacttgt ttattgcagc   2760
ttataatggt tacaaataaa gcaatagcat cacaaatttc acaaataaag catttttttc   2820
actgcattct agttgtggtt tgtccaaact catcaatgta tcttaagata tctagatctc   2880
gaggtaacca cgtgcggacc gagcggccgc aggaacccct agtgatggag ttggccactc   2940
cctctctgcg cgctcgctcg ctcactgagg ccgggcgacc aaaggtcgcc cgacgcccgg   3000
gctttgcccg ggcggcctca gtgagcgagc gagcgcgcag ctgcctgcag g            3051

SEQ ID NO: 140         moltype = DNA   length = 3055
FEATURE                Location/Qualifiers
source                 1..3055
                       mol_type = other DNA
                       organism = synthetic construct
SEQUENCE: 140
cctgcaggca gctgcgcgct cgctcgctca ctgaggccgc ccgggcgtcg ggcgacctttt   60
ggtcgcccgg cctcagtgag cgagcgagcg cgcagagagg gagtggccaa ctccatcact   120
aggggttcct gcggccgcac ttcgcgatgt acgggccaga tatatactgc cgactagtta   180
aggaccagct tctttgggag agaacagacg caggggcggg agggaaaaag ggagaggcag   240
acgtcacttc ccccttggcgg ctctggcagc agattggtcg gttgagtggc agaaaggcag   300
acggggactg ggcaaggcac tgtcggtgac atcacggaca gggcgacttc tatgtagatg   360
aggcagcgca gaggctgacg tcttcgccac ttgctgcttc accacgaagg agttcccgtg   420
ccctgggagc gggttcagga ccgctgatcg gaagtgagaa tccagctgt gtgtcagggc   480
tggaaagggc tcgggagtgc gcggggcaag tgaccgtgtg tgtaaagagt gaggcgtatg   540
aggctgtgtc ggggcagagg cacaacgttt cggagtcagc agcagcagca gcagcagcag   600
cagcagcagc agcagcagca gaattttttgg agtaggcttt ctggctcctt accggaaagc   660
cactttctgg agtttcaaaa acagactgta cgccaagggt catatctttt taatccaggt   720
ctccgggctt aacaacaacg aaggggctgt gactggctgc tttctcaacc aatcagcacc   780
gaactcattt gcatgggctg agaacaaatg ttcgcgaact ctagaaatga atgacttaag   840
taagttcctt agaatattat ttttcctact gaaagttacc acatgcgtcg ttgttatac    900
agtaatagga acaagaaaaa gtcacctaa gctcaccctc atcaattgtg gagttccttt   960
atatcccatc ttctctccaa acacatacg aggagtcagc agcagcagca gcagcagcag   1020
cagcagcagc agcagcagca gaattttttgg agtaggcttt ctggctcctt accggaaagc   1080
ccctcttatg atgtttgttg ccaatgatag attgttttca ctgtgcaaaa attatgggta   1140
gttttggtgg tcttgatgca gttgtaagct tggaggatcc gagctcggta ccaagctagt   1200
cgcgtcgacg gatccgaatt cgatatcgct agcataatag taatcaatta cggggtcatt   1260
agttcatagc ccatatatgg agttccgcgt tacataactt acggtaaatg gcccgcctgg   1320
ctgaccgccc aacgaccccc gcccattgac gtcaataatg acgtatgttc ccatagtaac   1380
gccaataggg actttccatt gacgtcaatg ggtggagtat ttacggtaaa ctgcccactt   1440
ggcagtacat caagtgtatc atatgccaag tacgccccct attgacgtca atgacggtaa   1500
atggcccgcc tggcattatg cccagtacat gaccttatgg gactttccta cttggcagta   1560
catctacgta ttagtcatcg ctattaccat ggtgatgcgg ttttggcagt acatcaatgg   1620
gcgtggatag cggtttgact cacggggatt tccaagtctc cacccatg acgtcaatgg   1680
gagtttgttt tggcaccaaa atcaacggga ctttccaaaa tgtcgtaaca actccgcccc   1740
attgacgcaa atgggcggta ggcgtgtacg gtgggaggtc tatataagca gagctggttt   1800
agtgaaccgt cagatccgct agcgctaccg gactcagatc tcgagcttcga attct       1860
ctgcagtcga cggtaccgcg ggcccgggat ccaccggtcg ccaccatggt gagcaagggc   1920
gaggagctgt tcaccggggt ggtgcccatc ctggtcgagc tggacggcga cgtaaacggc   1980
cacaagttca gcgtgtccgg cgagggcgag ggcgatgcca cctacggcaa gctgaccctg   2040
aagttcatct gcaccaccgg caagctgccc gtgccctggc ccaccctcgt gaccaccctg   2100
acctacggcg tgcagtgctt cagccgctac cccgaccaca tgaagcagca cgacttcttc   2160
aagtccgcca tgcccgaagg ctacgtccag gagcgcacca tcttcttcaa ggacgacggc   2220
aactacaaga cccgcgccga ggtgaagttc gagggcgaca ccctggtgaa ccgcatcgag   2280
ctgaagggca tcgacttcaa ggaggacggc aacatcctgg gcacaagct ggagtacaac   2340
tacaacagcc acaacgtcta tatcatggcc gacaagcagg agaacggcat caaggtgaac   2400
ttcaagatcc gccacaacat cgaggacggc agcgtgcagc tcgccgacca ctaccagcag   2460
aacacccccca tcggcgacgg ccccgtgctg ctgcccgaca accactacct gagcacccag   2520
tccgccctga gcaagacccc aacgagaagc gcgatcaca tggtcctgct ggagttcgtg   2580
accgccgccg ggatcactct cggcatggac gagctgtaca gtaaagcgg ccgcgactct   2640
agatcataat cagccatacc acatttgtag aggttttact tgctttaaaa aacctcccac   2700
acctcccccct gaacctgaaa cataaaatga atgcaattgt tgttgttaac ttgtttattg   2760
cagcttataa tggttacaaa taaagcaata gcatcacaaa tttcacaaat aaagcatttt   2820
tttcactgca ttctagttgt ggtttgtcca aactcatcaa tgtatcttaa gatatctaga   2880
tctcgaggta accacgtgcg gaccgagcgg ccgcaggaac ccctagtgat ggagttggcc   2940
actccctctc tgcgcgctcg ctcgctcact gaggccgggc gaccaaaggt cgcccgacgc   3000
```

```
ccgggctttg cccgggcggc ctcagtgagc gagcgagcgc gcagctgcct gcagg        3055

SEQ ID NO: 141          moltype = DNA   length = 3013
FEATURE                 Location/Qualifiers
source                  1..3013
                        mol_type = other DNA
                        organism = synthetic construct
SEQUENCE: 141
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg ctttctcaac caatcagcac   240
cgaactcatt tgcatgggct gagaacaaat gttcgcgaac tctagaaatg aatgacttaa   300
gtaagttcct tagaatatta ttttttccta ctgaaagttac cacatgcgtc gttgtttata   360
cagtaatagg aacaagaaaa aagtcaccta agctcaccct catcaattgt ggagttcctt   420
tatatcccat cttctctcca aacacatacg caggagttca ccagaagcgt accatactca   480
cgaaattttt ggagtaggct ttctggctcc ttaccggaaa gcccctctta tgatgtttgt   540
tgccaatgat agattgtttt cactgtgcaa aaattatggg tagtttttggt ggtcttgatg   600
cagttgtaag cttggaggat ccgagctcgg taccaagcta gtcgcgtaag gaccagcttc   660
tttgggagaa acagacgca ggggcgggag ggaaaaaggg agaggcagac gtcacttccc    720
cttggcggct ctggcagcag attggtcggt tgagtggcag aaaggcagac ggggactggg   780
caaggcactg tcggtgacat cacggacagg gcgacttcta tgtagatgag gcagcgcaga   840
ggctgacgtc ttcgccactt gctgcttcac cacgaaggaa ttcccgtgcc ctgggagcgg   900
gttcaggacc gctgatcgga agtgagaatc ccagctgtgt gtcagggctg aaagggctc    960
gggagtgcgc ggggcaagtg accgtgtgtg taaagagtga ggcgtatgag gctgtgtcgg   1020
ggcagaggca caacgtttcg gagttcacca gaagcgtacc atactcacga aattttttgga  1080
gtaggctttc tggctcctta ccggaaagcc actttctgga gtttcaaaaa cagactgtac   1140
gccaagggtc atatctttttt cgtcgacgga tccgaattcg atatcgctag cataatagta  1200
atcaattacg gggtcattag ttcatagccc atatatggag ttccgcgtta cataacttac   1260
ggtaaatgcc ccgcctggct gaccgcccaa cgacccccgc ccattgacgt caataatgac   1320
gtatgttccc atagtaacgc caatagggac tttccattga cgtcaatggg tggagtattt   1380
acggtaaact gcccacttgg cagtacatca agtgtatcat atgccaagta cgccccctat   1440
tgacgtcaat gacggtaaat ggcccgcctg gcattatgcc cagtacatga ccttatggga   1500
ctttcctact tggcagtaca tctacgtatt agtcatcgct attaccatg tgatgcggtt    1560
ttggcagtac atcaatgggc gtggatagcg gtttgactca cggggatttc caagtctcca   1620
ccccattgac gtcaatggga gtttgttttg gcaccaaaat caacgggact ttccaaaatg   1680
tcgtaacaac tccgccccat tgacgcaaat gggcggtagg cgtgtacggt gggaggtcta   1740
tataagcaga gctggtttag tgaaccgtca gatccgctag cgctcaccgga ctcagatctc   1800
gagctcaagc ttcgaattct gcagtcgacg gtaccgcgg ccccgggatcc accggtcgcc   1860
accatggtga gcaagggcga ggagctgttc accggggtgg tgcccatcct ggtcgagctg   1920
gacggcgacg taaacggcca caagttcagc gtgtccggcg agggcgaggg cgatgccacc   1980
tacggcaagc tgaccctgaa gttcatctgc accaccggca agctgcccgt gccctggccc   2040
accctcgtga ccacccctgac ctacggcgtg cagtgcttca gccgctaccc cgaccacatg   2100
aagcagcacg acttcttcaa gtccgccatg cccgaaggct acgtccagga gcgcaccatc   2160
ttcttcaagg acgacggcaa ctacaagacc cgcgccgagg tgaagttcga gggcgacacc   2220
ctggtgaacc gcatcgagct gaagggcatc gacttcaagg aggacggcaa catcctgggg   2280
cacaagctgg agtacaacta caacagccac aacgtctata tcatggccga caagcagaag   2340
aacggcatca aggtgaactt caagatccgc cacaacatcg aggacggcag cgtgcagctc   2400
gccgaccact accagcagaa cacccccatc ggcgacggcc ccgtgctgct gcccgacaac   2460
cactacctga gcacccagtc cgccctgagc aaagacccca acgagaagcg cgatcacatg   2520
gtcctgctgg agttcgtgac cgccgccggg atcactctcg gcatggacga gctgtacaag   2580
taaagcggcc gcgactctag atcataatca gccataccac atttgtagag gttttacttg   2640
ctttaaaaaa cctcccacac ctccccctga acctgaaaca taaaatgaat gcaattgttg   2700
ttgttaactt gtttattgca gcttataatg gttacaaata aagcaatagc atcacaaatt   2760
tcacaaataa agcattttttt tcactgcatt ctagttgtgg tttgtccaaa ctcatcaatg   2820
tatcttaaga tatctagatc tcgaggtaac cacgtcggaa ccgagcggcc gcaggaaccc   2880
ctagtgatgg agttggccac tccctctctg cgcgctcgct cgctcactga ggccgggcga   2940
ccaaaggtcg cccgacgccc gggctttgcc cggcggcct cagtgagcga gcgagcgcgc    3000
agctgcctgc agg                                                      3013

SEQ ID NO: 142          moltype = DNA   length = 1402
FEATURE                 Location/Qualifiers
source                  1..1402
                        mol_type = other DNA
                        organism = synthetic construct
SEQUENCE: 142
cctgcaggca gctgcgcgct cgctcgctca ctgaggccgc ccgggcgtcg ggcgaccttt   60
ggtcgcccgg cctcagtgag cgagcgagcg cgcagagagg gagtggccaa ctccatcact   120
aggggttcct gcggccgcac ttcgcgatgt acgggccaga tatatactgc cgaatccagg   180
tctccgggct taacaacaac gaaggggctg tgactggctg ctttctcaac caatcagcac   240
cgaactcatt tgcatgggct gagaacaaat gttcgcgaac tctagaaatg aatgacttaa   300
gtaagttcct tagaatatta ttttttccta ctgaaagttac cacatgcgtc gttgtttata   360
cagtaatagg aacaagaaaa aagtcaccta agctcaccct catcaattgt ggagttcctt   420
tatatcccat cttctctcca aacacatacg caggagtcag cagcagcag agcagcagca   480
gcagcagcag cagcagcagc agaattttg gagtaggctt tctggctcct taccggaaag   540
cccctcttat gatgtttgtt gccaatgata gattgttttc actgtgcaaa aattatgggt   600
agttttggtg gtcttgatgc agttgtaagc ttggaggatc cgagctcggt accaagctag   660
tcgcgtaagg accagcttct ttgggagaga acagacgcag gggcgggagg gaaaaaggga   720
gaggcagacg tcacttcccc ttggcggctc tggcagcaga ttggtcggtt gagtggcaga   780
```

```
aaggcagacg gggactgggc aaggcactgt cggtgacatc acggacaggg cgacttctat    840
gtagatgagg cagcgcagag gctgacgtct tcgccacttg ctgcttcacc acgaaggagt    900
tcccgtgccc tgggagcggg ttcaggaccg ctgatcggaa gtgagaatcc cagctgtgtg    960
tcagggctga aaagggctcg ggagtgcgcg gggcaagtga ccgtgtgtgt aaagagtgag   1020
gcgtatgagg ctgtgtcggg gcagaggcac aacgtttcgg agtcagcagc agcagcagca   1080
gcagcagcag cagcagcagc agcagcagaa ttttggagt aggctttctg gctccttacc    1140
ggaaagccac tttctggagt ttcaaaaaca gactgtacgc caagggtcat atcttttcg    1200
tcgacggatc cgaattcgat atctagatct cgaggtaacc acgtgcggac cgagcggccg   1260
caggaacccc tagtgatgga gttggccact ccctctctgc gcgctcgctc gctcactgag   1320
gccgggcgac caaaggtcgc ccgacgcccg ggctttgccc gggcggcctc agtgagcgag   1380
cgagcgcgca gctgcctgca gg                                             1402

SEQ ID NO: 143          moltype = DNA   length = 1385
FEATURE                 Location/Qualifiers
source                  1..1385
                        mol_type = other DNA
                        organism = synthetic construct
SEQUENCE: 143
cctgcaggca gctgcgcgct cgctcgctca ctgaggccgc ccgggcgtcg ggcgacctt     60
ggtcgcccgg cctcagtgag cgagcgagcg cgcagagagg gagtggccaa ctccatcact   120
aggggttcct gcggccggtc gcgtctagta acttcgcgat gtacgggcca gatatatact   180
gccgaatcca ggtctccggg cttaacaaca acgaaggagc tgtgactggc tgctttctca   240
accaatcagc accgaactca tttgcatggg ctgagaacaa atgttcgcga actctagaaa   300
tgaatgactt aagtaagttc cttagaatat tattttcct actgaaagtt accacatgcg    360
tcgttgttta tacagtaata ggaacaagaa aaaagtcacc taagctcacc ctcatcaatt   420
gtggagttcc tttatatccc atcttctctc caaacacata cgcaggagtc agcagcagca   480
gcagcagcag cagcagcagc agcagcagca gcagaatttt tggagtaggc tttctggctc   540
cttaccggaa agcccctctt atgatgtttg ttgccaatga tagattgttt tcactgtgca   600
aaaattatgg gtagttttgg tggtcttgat gcagttgtaa gcttggagga tccgagctcg   660
gtaccaagct agtcgcgtaa ggaccagctt ctttgggaga gaacagacgc aggggcggga   720
gggaaaaagg gagaggcaga cgtcacttcc ccttggcggc tctggcagca gattggtcgg   780
ttgagtggca gaaaggcaga cggggactgg gcaaggcact gtcggtgaca tcacggacag   840
ggcgacttct atgtagatga ggcagcgcag aggctgacgt cttcgccact tgctgcttca   900
ccacgaagga gttcccgtgc cctgggagcg ggttcaggac cgctgatcgg aagtgagaat   960
cccagctgtg tgtcagggct ggaaagggct cgggagtgcg cggggcaagt gaccgtgtgt  1020
gtaaagagtg aggcgtatga ggctgtgtcg ggcagaggc acaacgtttc ggagtcagca   1080
gcagcagcag cagcagcagc agcagcagca gcagcagcag aattttgga gtaggctttc   1140
tggctcctta ccggaaagcc actttctgga gtttcaaaaa cagactgtac gccaagggtc   1200
atatcttttt cgtcgacgga tccgaattcg atatctagat ctcgaggtaa ccacgtgcgg   1260
accgagccta gtccactccc tctctgcgcg ctcgctcgct cactgaggcc gggcgaccaa   1320
aggtcgcccg acgcccgggc tttgcccggg cggcctcagt gagcgagcga gcgcgcagag   1380
aggga                                                                1385

SEQ ID NO: 144          moltype = DNA   length = 1650
FEATURE                 Location/Qualifiers
source                  1..1650
                        mol_type = other DNA
                        organism = synthetic construct
SEQUENCE: 144
caaactacag agccaagtgc tatccacaga gagcttctg ggttgccatc tcaagcagac      60
tacaaggcca tcagctcata ctcacaattg actttgagag tcatttttca atgctcctac    120
acacccttc ttcacaatcc ccaacaaatc tgaggctgga acttggtacc ataacaatca    180
ttacattatt tcaccagaag tacaccttgc ctggaagatt ggcattatag catcttctaa    240
cattgtgaaa gttagtgacc aatgaggaga tccaagtcag ttccagttgg atttctctat    300
actctataat aaatatatat ggtgtcttca acaataggac tttgccatcc agtgatgcta    360
aaaatcaata acaatggcaa taacctgccc tgtttggaaa gcctctggct tccatgacta    420
acaattcaag gcaggtctcc tatacctagt actgagattt ttatttgata aactatatct    480
tctgggagga gaagcattgt ttgaccacat acgtgctctt tcaaagttct gtgtttgaag    540
ttatgttagt aacaactgat gcccatcctg caatgacaaa tccaattctc agtgcagctc    600
tctgaaatag ttttgctttc tctctctagg tctgttctat actcctaact ctccaggagt    660
ttacaaggaa taaaatctct tccaaatgct ttctgttgca acaactggac catactgaaa    720
gctgaggccc acaattgcaa tctaggttag caggtaatca ttgttggtga ggtcctccct    780
ttccccaggc tcgtgtttgt attggggagc aggaaatttt tgctagagca gcactgccat    840
ctctctacac tccacctgat tggtgggatg gaccagagat atggacattc ccaacacagt    900
ccctcctttc acatctgctc acctgcccac aggatacttt ccaccatgca tactgggctc    960
tgcaccaacc attcagcagt gatgaagagg aaacttgaac ccatgcagag tacctctaga   1020
gaaaagtttc taaagttggt tttgccttgc ttagaaagga ggtcaaaggt gaagcctagg   1080
agaacattc agcaatgttg cacaaagaca tgaagataaa tgattttagc atcctgaaat   1140
gaagagcata gtgatctcac catgctacc cacctaccca gagaacttcc aggctttcac   1200
tgtctctttt ctgaatcacc cacattacag aatatcagtc attgtgtaat tagataacag   1260
attgtgaggt gcccaaacag aaacaaactt tacaggagga gagagaaaat caaggtgatg   1320
actatgagag acaaaatgag aaggagaggt ggagttcctg ctgcatgaac acctatcctg   1380
ctatagagcc cattcttcc ataataata caactctgta actccatagg tcagaaagaa    1440
acagtgttct gtgtcttccc actagcacc acaaacccc acaagattaa tttgttttca   1500
gggacccctta aatctctatc aaaattctgg aaacctctac tttagaaaat cttatatta   1560
ttattcaggc tactttccag agtgataagc tactgagtct cctaagtgtc atctatgta   1620
cacagggata agatcaggaa taaacctggg                                    1650

SEQ ID NO: 145          moltype = DNA   length = 29
```

```
FEATURE                 Location/Qualifiers
source                  1..29
                        mol_type = other DNA
                        organism = synthetic construct
SEQUENCE: 145
ggttttctga cttcggtcgg aaaacccct                                           29

SEQ ID NO: 146          moltype = DNA   length = 29
FEATURE                 Location/Qualifiers
source                  1..29
                        mol_type = other DNA
                        organism = synthetic construct
SEQUENCE: 146
ggttttctga cctccgtcgg aaaacccct                                           29

SEQ ID NO: 147          moltype = DNA   length = 33
FEATURE                 Location/Qualifiers
source                  1..33
                        mol_type = other DNA
                        organism = synthetic construct
SEQUENCE: 147
ggttttctga cctccttcgg tcggaaaacc cct                                      33

SEQ ID NO: 148          moltype = DNA   length = 26
FEATURE                 Location/Qualifiers
source                  1..26
                        mol_type = other DNA
                        organism = synthetic construct
SEQUENCE: 148
ggttttctga cctccgtcgg aaaacc                                              26

SEQ ID NO: 149          moltype = DNA   length = 56
FEATURE                 Location/Qualifiers
source                  1..56
                        mol_type = other DNA
                        organism = synthetic construct
SEQUENCE: 149
gtaaccacag gttgtgtcac cagagtaaca tacctccaac atcaaggaag atggca            56

SEQ ID NO: 150          moltype = DNA   length = 56
FEATURE                 Location/Qualifiers
source                  1..56
                        mol_type = other DNA
                        organism = synthetic construct
SEQUENCE: 150
tacctccaac atcaaggaag atggcagtaa ccacaggttg tgtcaccaga gtaaca            56

SEQ ID NO: 151          moltype = DNA   length = 256
FEATURE                 Location/Qualifiers
source                  1..256
                        mol_type = other DNA
                        organism = synthetic construct
SEQUENCE: 151
taacaacata ggagctgtga ttggctgttt tcagccaatc agcactgact catttgcata        60
gcctttacaa gcggtcacaa actcaagaaa cgagcgtctt taatagtctt ttagaatatt       120
gtttatcgaa ccgaataagg aactgtgctt tgtgattcac atatcagtgg aggggtgtgg       180
aaatggcacc ttgatctcac cctcatcgaa agtggagttg atgtccttcc ctggctcgct       240
acagacgcac ttccgc                                                        256

SEQ ID NO: 152          moltype = DNA   length = 440
FEATURE                 Location/Qualifiers
source                  1..440
                        mol_type = other DNA
                        organism = synthetic construct
SEQUENCE: 152
tgccaacagc tttgaaatcc tctgtgctct tgtgccaatc ccaccctcag aacagggagt        60
ctgtcggtta tgttttcgtc ctttacagtt cttcgccgtc taatccattg gaaacctcct       120
ttatttaaag gaaaccgtgt ccaaattcag tgtacagagg tgcaaacctc cgccccgctc       180
cttgtaggaa gcccacggga actgggccaa tcggacgggc cttactcggc tcatttacat       240
acccataaca caccgcggct aatgcaaata ttttcgtgaa aagatcttcc attactcgaa       300
gttttaaaac taaaaacaaa atattatttc aaaagatcat gaagaaattt ctgtcggtaa       360
cagcagtttc aattgataaa tcaccatcac ttatctagga ggttctgtta ctctagaagt       420
gaattaagca ggacagctgt                                                    440

SEQ ID NO: 153          moltype = DNA   length = 231
FEATURE                 Location/Qualifiers
source                  1..231
                        mol_type = other DNA
                        organism = synthetic construct
```

```
SEQUENCE: 153
gggcggggca tgcaaataac tgctctgtgg aactctggga gcaaaaacaa aaaactgcaa        60
ccaaaacttc tcggcctcct tgaatcttac aggcttttcg tggcgtaaag gtggtgtact       120
caatgaagag gagagtctgt gttggctgca tgtttgagtc ggttggttgg tgactgtgaa       180
ttaaaggtgt ggtcggtgtt gagtgtatgg ggcgtgtggg cgtagttcgg t                231

SEQ ID NO: 154          moltype = DNA  length = 311
FEATURE                 Location/Qualifiers
source                  1..311
                        mol_type = other DNA
                        organism = synthetic construct
SEQUENCE: 154
cgacgccgcc atctctaggc ccgcgccggc cccctcgcac agacttgtgg gagaagctcg        60
gctactcccc tgccccggtt aatttgcata taatatttcc tagtaactat agaggcttaa       120
tgtgcgataa aagacagata atctgttctt tttaatacta gctacatttt acatgatagg       180
cttggatttc tataagagat acaaatacta aattattatt ttaaaaaaca gcacaaaagg       240
aaactcaccc taactgtaaa gtaattgtgt gttttgagac tataaatatc ccttggagaa       300
aagccttgtt t                                                             311

SEQ ID NO: 155          moltype = DNA  length = 97
FEATURE                 Location/Qualifiers
source                  1..97
                        mol_type = other DNA
                        organism = synthetic construct
SEQUENCE: 155
catgcaaatt acgcgctgtg ctttgtggga aatcacccta aacgtaaaat ttattcctct        60
ttcgagcctt atagtggcgg ccggtctaca ccctaaa                                 97

SEQ ID NO: 156          moltype = DNA  length = 107
FEATURE                 Location/Qualifiers
source                  1..107
                        mol_type = other DNA
                        organism = synthetic construct
SEQUENCE: 156
cccaatttca ctggtctaca atgaaagcaa aacagttctc ttccccgctc ccggtgtgt         60
gagaggggct tgatccttc tctggtttcc taggaaacgc gtatgtg                      107

SEQ ID NO: 157          moltype = DNA  length = 200
FEATURE                 Location/Qualifiers
source                  1..200
                        mol_type = other DNA
                        organism = synthetic construct
SEQUENCE: 157
ccacattttg tgtttaaaaa tagaaatatt taagtgagat cagtttaaat ctgctttatc        60
tagggtgtct aactgcttgc atcttttaa cttttcctta tttgtgagaa ggtctgtaaa       120
acttattata tgttagtaca ctgtagctgt cttcagacac tccagaagag ggattcagat       180
caccttacag atggttttga                                                    200

SEQ ID NO: 158          moltype = DNA  length = 78
FEATURE                 Location/Qualifiers
source                  1..78
                        mol_type = other DNA
                        organism = synthetic construct
SEQUENCE: 158
ccctctgggg agtaaagttg gttttaaagt cagagcatgg tgattgtagg gcagtccaac        60
ttttttaaat atgctgtg                                                      78

SEQ ID NO: 159          moltype =       length =
SEQUENCE: 159
000

SEQ ID NO: 160          moltype =       length =
SEQUENCE: 160
000

SEQ ID NO: 161          moltype = DNA  length = 13
FEATURE                 Location/Qualifiers
source                  1..13
                        mol_type = other DNA
                        organism = synthetic construct
SEQUENCE: 161
aatttttgga gca                                                           13

SEQ ID NO: 162          moltype = DNA  length = 110
FEATURE                 Location/Qualifiers
source                  1..110
                        mol_type = other DNA
                        organism = synthetic construct
SEQUENCE: 162
```

```
ctgcgcgctc gctcgctcac tgaggccgcc cgggcaaagc ccgggcgtcg ggcgaccttt    60
ggtcgcccgg cctcagtgag cgagcgagcg cgcagagagg gagtgggtt              110

SEQ ID NO: 163           moltype = DNA  length = 30
FEATURE                  Location/Qualifiers
source                   1..30
                         mol_type = other DNA
                         organism = synthetic construct
SEQUENCE: 163
ggctttctgg ctccttaccg gaaagcccct                                    30

SEQ ID NO: 164           moltype = DNA  length = 13
FEATURE                  Location/Qualifiers
source                   1..13
                         mol_type = other DNA
                         organism = synthetic construct
SEQUENCE: 164
aatttttgga gta                                                      13

SEQ ID NO: 165           moltype = DNA  length = 45
FEATURE                  Location/Qualifiers
source                   1..45
                         mol_type = other DNA
                         organism = synthetic construct
SEQUENCE: 165
cagcagcagc agcagcagca gcagcagcag cagcagcagc agcag                   45

SEQ ID NO: 166           moltype = DNA  length = 133
FEATURE                  Location/Qualifiers
source                   1..133
                         mol_type = other DNA
                         organism = synthetic construct
SEQUENCE: 166
aaggaacccc tagtgatgga gttggccact ccctctctgc gcgctcgctc gctcactgag    60
gccgggcgac caaaggtcgc ccgacgcccg ggctttgccc gggcggcctc agtgagcgag   120
cgagcgcgcc agc                                                     133

SEQ ID NO: 167           moltype = DNA  length = 45
FEATURE                  Location/Qualifiers
source                   1..45
                         mol_type = other DNA
                         organism = synthetic construct
SEQUENCE: 167
ctgctgctgc tgctgctgct gctgctgctg ctgctgctgc tgctg                   45

SEQ ID NO: 168           moltype = DNA  length = 1532
FEATURE                  Location/Qualifiers
source                   1..1532
                         mol_type = other DNA
                         organism = synthetic construct
SEQUENCE: 168
ctgcgcgctc gctcgctcac tgaggccgcc cgggcaaagc ccgggcgtcg ggcgaccttt    60
ggtcgcccgg cctcagtgag cgagcgagcg cgcagagagg gagtgggtt cttcgaaaca   120
ccggttaaca acataggagc tgtgattggc tgttttcagc caatcagcac tgactcattt   180
gcatagcctt tacaagcggt cacaaactca agaaacggac ggttttaata gtcttttaga   240
atattgttta tcgaaccgaa taaggaactg tgctttgtga ttcacatatc agtggagggg   300
tgtggaaatg gcaccttgat ctcaccctca tcgaaagtgg agttgatgtc cttccctggc   360
tcgctacaga cgcacttccg caaggagtgt aaccacaggt tgtgtcacca gagtaacata   420
cctccaacat caaggaagat ggcaaatttt tggagcaggt tttctgacct ccgtcggaaa   480
accccctccca atttcactgg tctacaatga aagcaaaaca gttctcttcc ccgctccccg   540
gtgtgtgaga ggggctttga tccttctctg gtttcctagg aaacgcgtat gtgttgttcc   600
tcttagtgtt aattcacact aaagactgtg catccgactc ctacatttat gaaagtaaat   660
gcctgttgtt agaacaaaaa aggctacaga acaaaaaaca aagcgaaata ccatctgctt   720
taggttcagt gtggtatttt cccgctgaca gggaggcggg ttttttgggta caggaaacga   780
gtcactatgg aggcggtact atgtagatga gaattcaggt gcaaactggg aaaagcaact   840
gcttccaaat atttgtgatt tttacagtgt agttttggaa aaactcttag cctaccaatt   900
cttctaagtg ttttaaaatg tgggagccag tacacatgaa gttatagagt gttttaatga   960
ggcttaaata tttaccgtaa ctatgaaatg ctacgcatat catgctgttc aggctccgtg   1020
gccacgcaac tcggagtgta accacaggtt gtgtcaccag agtaacatac ctccaacatc   1080
aaggaagatg gcaaattttt ggagcaggtt ttctgacctc cgtcggaaaa cccctgttta   1140
cttggttta aaaatagctt gcactagcga tacggaatat ggttattagg tttgttaggc   1200
atcatgtcgt gtcttactat agaaaaataa cgtagtgttc attttagcct gcctgtatgt   1260
gttaatttgt ccttattgcg cattgttctt gttaagtctt ctgctaaggag ttgcgggttt   1320
caaactgtca gtctgagagc agaattcgat atctagatct cgaggtaacc acgtgcggac   1380
ccaacggccg caggaacccc tagtgatgga gttggccact ccctctctgc gcgctcgctc   1440
gctcactgag gccgggcgac caaaggtcgc ccgacgcccg ggctttgccc gggcggcctc   1500
agtgagcgag cgagcgcgca gctgcctgca gg                                1532

SEQ ID NO: 169           moltype = DNA  length = 1532
```

```
FEATURE              Location/Qualifiers
source               1..1532
                     mol_type = other DNA
                     organism = synthetic construct
SEQUENCE: 169
ctgcgcgctc gctcgctcac tgaggccgcc cgggcaaagc ccgggcgtcg ggcgaccttt   60
ggtcgcccgg cctcagtgag cgagcgagcg cgcagagagg gagtgggggtt cttcgaaaca  120
ccggttaaca acataggagc tgtgattggc tgttttcagc caatcagcac tgactcattt  180
gcatagcctt tacaagcggt cacaaactca agaaacgagc ggttttaata gtcttttaga  240
atattgttta tcgaaccgaa taaggaactg tgctttgtga ttcacatatc agtggagggg  300
tgtggaaatg gcaccttgat ctcaccctca tcgaaagtgg agttgatgtc cttccctggc  360
tcgctacaga cgcacttccg caaggagtta cctccaacat caaggaagat ggcagtaacc  420
acaggttgtg tcaccagagt aacaaatttt tggagcaggt tttctgacct ccgtcggaaa  480
accccctccca atttcactgg tctacaatga aagcaaaaca gttctcttcc ccgctccccg  540
gtgtgtgaga ggggctttga tccttctctg gtttcctagg aaacgcgtat gtgttgttcc  600
tcttagtgtt aattcacact aaagactgtg catccgactc ctacatttat gaaagtaaat  660
gcctgttgtt agaacaaaaa aggctacaga acaaaaaaca aagcgaaata ccatctgctt  720
taggttcagt gtggtatttt cccgctgaca gggaggcggg tttttgggta caggaaacga  780
gtcactatgg aggcggtact atgtagatga gaattcaggt gcaaactggg aaaagcaact  840
gcttccaaat atttgtgatt tttacagtgt agttttggaa aaactcttag cctaccaatt  900
cttctaagtg tttttaaaatg tgggagccag tacacatgaa gttatagagt gttttaatga  960
ggcttaaata tttaccgtaa ctatgaaatg ctacgcatat catgctgttc aggctccgtg 1020
gccacgcaac tcggagttac ctccaacatc aaggaagatg gcagtaacca caggttgtgt 1080
caccagagta acaaattttt ggagcaggtt ttctgacctc cgtcggaaaa ccctgtttaa 1140
cttggttta aaaatagctt gcactagcga tacgaatat ggttattagg tttgttaggc 1200
atcatgtcgt gtcttactat agaaaaataa cgtagtgttc attttagcct gctgtatgt 1260
gttaatttgt ccttattgcg cattgttctt gttaagtctt ctgtaaggag ttgcgggttt 1320
caaactgtca gtctgagagc agaattcgat atctagatct cgaggtaacc acgtgcggac 1380
ccaacggccg caggaacccc tagtgatgga gttggccact ccctctctgc gcgctcgctc 1440
gctcactgag gccgggcgac caaaggtcgc ccgacgcccg ggctttgccc gggcggcctc 1500
agtgagcgag cgagcgcgca gctgcctgca gg                               1532

SEQ ID NO: 170       moltype = DNA  length = 1526
FEATURE              Location/Qualifiers
source               1..1526
                     mol_type = other DNA
                     organism = synthetic construct
SEQUENCE: 170
ctgcgcgctc gctcgctcac tgaggccgcc cgggcaaagc ccgggcgtcg ggcgaccttt   60
ggtcgcccgg cctcagtgag cgagcgagcg cgcagagagg gagtgggggtt cttcgaaaca  120
ccggttaaca acataggagc tgtgattggc tgttttcagc caatcagcac tgactcattt  180
gcatagcctt tacaagcggt cacaaactca agaaacgagc ggttttaata gtcttttaga  240
atattgttta tcgaaccgaa taaggaactg tgctttgtga ttcacatatc agtggagggg  300
tgtggaaatg gcaccttgat ctcaccctca tcgaaagtgg agttgatgtc cttccctggc  360
tcgctacaga cgcacttccg caaggagtgt aaccacaggt tgtgtcacca gagtaacata  420
cctccaacat caaggaagat ggcaaatttt tggagcaggt tttctgacct ccgtcggaaa  480
accccaatt tcactggtct acaatgaaag caaaacagt ctctccccg ctcccccggtg  540
tgtgagaggg gctttgatcc ttctctggtt tcctaggaaa cgcgtatgtg ttgttcctct  600
tagtgttaat tcacactaaa gactgtgcat ccgactccta catttatgaa agtaaatgcc  660
tgttgttaga acaaaaaagg ctacagaaca aaaacaaag cgaaataccA tctgctttag  720
gttcagtgt gtattttccc gctgacaggg aggcgggtt tgggtacag gaaacgagtc  780
actatggagg cggtactatg tagatgagaa ttcaggtgca aactgggaaa agcaactgct  840
tccaaatatt tgtgattttt acagtgtagt tttggaaaaa ctcttagcct accaattctt  900
ctaagtgttt aaaatgtgg gagccagtac acatgaagtt atagagtgtt ttaatgaggc  960
ttaaatattt accgtaacta tgaaatgcta cgcatatgct gttcaggctc cgtggcc 1020
acgcaactcg gagtgtaacc acaggttgtg tcaccagagt aacatacctc caacatcaag 1080
gaagatggca atttttgga gcaggttttc tgacctccgt cggaaaaccg tttacttggt 1140
tttaaaaata gcttgcacta gcgatacgga atatggttat tagggtttgtt aggcatcatg 1200
tcgtgtctta ctatagaaaa ataacgtagt gttcattta gcctgccgct atgtgttaat 1260
ttgtccttat tgcgcattgt tcttgttaag tcttctgta ggagttgcgg gtttcaaact 1320
gtcagtctga gagcagaatt cgatatctag atctcgaggt aaccacgtgc ggacccaacg 1380
gccgcaggaa ccctagtga tggagttggc cactccctct ctgcgcgctc gctcgctcac 1440
tgaggccggg cgaccaaagg tcgccccgacg cccgggcttt gccgggcggg cctcagtgag 1500
cgagcgagcg cgcagctgcc tgcagg                                      1526

SEQ ID NO: 171       moltype = DNA  length = 1242
FEATURE              Location/Qualifiers
source               1..1242
                     mol_type = other DNA
                     organism = synthetic construct
SEQUENCE: 171
ctgcgcgctc gctcgctcac tgaggccgcc cgggcaaagc ccgggcgtcg ggcgaccttt   60
ggtcgcccgg cctcagtgag cgagcgagcg cgcagagagg gagtgggggtt cttcgaaaca  120
ccggttaaca acataggagc tgtgattggc tgttttcagc caatcagcac tgactcattt  180
gcatagcctt tacaagcggt cacaaactca agaaacgagc ggttttaata gtcttttaga  240
atattgttta tcgaaccgaa taaggaactg tgctttgtga ttcacatatc agtggagggg  300
tgtggaaatg gcaccttgat ctcaccctca tcgaaagtgg agttgatgtc cttccctggc  360
tcgctacaga cgcacttccg caatacctcc aacatcaagg aagatggcag taaccacagg  420
ttgtgtcacc agagtaacaa attttgggag caggttttct gacttcggtc ggaaaacccc  480
```

```
tcccaattto actggtctac aatgaaagca aaacagttct cttccccgct ccccggtgtg    540
tgagagggc tttgatcctt ctctggtttc ctaggaaacg cgtatgtgta acaacatagg    600
agctgtgatt ggctgttttc agccaatcag cactgactca tttgcatagc ctttacaagc    660
ggtcacaaac tcaagaaacg agcggtttta atagtctttt agaatattgt ttatcgaacc    720
gaataaggaa ctgtgctttg tgattcacat atcagtggag gggtgtggaa atggcacctt    780
gatctcaccc tcatcgaaag tggagttgat gtccttccct ggctcgctac agacgcactt    840
ccgcaatacc tccaacatca aggaagatgg cagtaaccac aggttgtgtc accagagtaa    900
caaattttg gagcaggttt tctgacttcg gtcggaaaac ccctcccaat ttcactggtc    960
tacaatgaaa gcaaaacagt tctcttcccc gctcccggt gtgtgagagg ggctttgatc   1020
cttctctggt ttcctaggaa acgcgtatgt ggaattcgat atctagatct cgaggtaacc   1080
acgtgcggac ccaacggccg caggaacccc tagtgatgga gttggccact ccctctctgc   1140
gcgctcgctc gctcactgag gccgggcgac caaaggtcgc ccgacgcccg ggctttgccc   1200
gggcggcctc agtgagcgag cgagcgcgca gctgcctgca gg                     1242

SEQ ID NO: 172           moltype = DNA   length = 1522
FEATURE                  Location/Qualifiers
source                   1..1522
                         mol_type = other DNA
                         organism = synthetic construct
SEQUENCE: 172
ctgcgcgctc gctcgctcac tgaggccgcc cgggcaaagc ccgggcgtcg ggcgaccttt     60
ggtcgcccgg cctcagtgag cgagcgagcg cgcagagagg gagtggggtt cttcgaaaca    120
ccggttaaca acataggagc tgtgattggc tgttttcagc caatcagcac tgactcattt    180
gcatagcctt tacaagcggt cacaaactca agaaacgagc ggttttaata gtctttaga    240
atattgttta tcgaaccgaa taaggaactg tgctttgtga ttcacatatc agtggagggg    300
tgtggaaatg gcaccttgat ctcaccctca tcgaaagtgg agttgatgtc cttccctggc    360
tcgctacaga cgcacttccg caatacctcc aacatcaagg aagatggcag taaccacagg    420
ttgtgtcacc agagtaacaa atttttggag caggttttct gacttcgtc ggaaaacccc    480
tcccaatttc actggtctac aatgaaagca aaacagttct cttccccgct ccccggtgtg    540
tgagagggc tttgatcctt ctctggtttc ctaggaaacg cgtatgtgtt gttcctctta    600
gtgttaattc acactaaaga ctgtgcatcc gactcctaca tttatgaaag taaatgcctg    660
ttgttagaac aaaaaaggct acagaacaaa aacaaagcg aaataccatc tgctttaggt    720
tcagtgtggt attttcccgc tgacaggag gcgggttttt gggtacagga aacgagtcac    780
tatggagcg gtactatgta gatgagaatt caggtgcaaa ctggggaaag caactgcttc    840
caaatatttg tgatttttac agtgtagttt tggaaaaact cttagcctac caattcttct    900
aagtgtttta aatgtgggga gccagtacac atgaagttat agagtgtttt aatgaggctt    960
aaatatttac cgtaactatg aaatgctacg catatcatgc tgttcaggct ccgtggccac   1020
gcaactctac ctccaacatc aaggaagatg gcagtaacca caggttgtgt caccagagta   1080
acaaattttt ggagcaggtt ttctgacttc gtcggaaaaa cccctgttta cttggttta    1140
aaaatagctt gcactagcga tacgaatat ggttattagg tttgttaggc atcatgtcgt    1200
gtcttactat agaaaaataa cgtagtgttc atttagcct gcctgtatgt gttaatttgt   1260
ccttattgcg cattgttctt gttaagtctt ctgtaaggag ttgcgggttt caaactgtca   1320
gtctgagagc agaattcgat atctagatct cgaggtaacc acgtgcggac ccaacggccg   1380
caggaacccc tagtgatgga gttggccact ccctctctgc gcgctcgctc gctcactgag   1440
gccgggcgac caaaggtcgc ccgacgcccg ggctttgccc gggcggcctc agtgagcgag   1500
cgagcgcgca gctgcctgca gg                                          1522

SEQ ID NO: 173           moltype = DNA   length = 1528
FEATURE                  Location/Qualifiers
source                   1..1528
                         mol_type = other DNA
                         organism = synthetic construct
SEQUENCE: 173
ctgcgcgctc gctcgctcac tgaggccgcc cgggcaaagc ccgggcgtcg ggcgaccttt     60
ggtcgcccgg cctcagtgag cgagcgagcg cgcagagagg gagtggggtt cttcgaaaca    120
ccggttaaca acataggagc tgtgattggc tgttttcagc caatcagcac tgactcattt    180
gcatagcctt tacaagcggt cacaaactca agaaacgagc ggttttaata gtctttaga    240
atattgttta tcgaaccgaa taaggaactg tgctttgtga ttcacatatc agtggagggg    300
tgtggaaatg gcaccttgat ctcaccctca tcgaaagtgg agttgatgtc cttccctggc    360
tcgctacaga cgcacttccg caaggagtta cctccaacat caaggaagat ggcagtaacc    420
acaggttgtg tcaccagagt aacaaatttt tggagtaggc tttctggctc cttaccggaa    480
agcccccaat ttcactggtc tacaatgaaa gcaaaacagt tctcttcccc gctcccggt    540
gtgtgagagg ggctttgatc cttctctggt ttcctaggaa acgcgtatgt gttgttcctc    600
ttagtgttaa ttcacactaa agactgtgca tccgactcct acatttatga agtaaatgct    660
ctgttgttag aacaaaaaag gctacagaac aaaaaacaaa gcgaaatacc atctgcttta    720
ggttcagtgt ggtattttcc cgctgacagg aggcgggtt tttgggtaca ggaaacgagt    780
cactatggag cggtactata gtagatgaga attcaggtgc aaactgggaa aagcaactgc    840
ttccaaatat ttgtgatttt tacagtgtag ttttggaaaa actcttagcc taccaattct    900
tctaagtgtt ttaaaatgtg ggagccagta cacatgaagt tatagagtgt tttaatgagg    960
cttaaatatt taccgtaact atgaaatgct acgcatatca tgctgttcag gctccgtggc   1020
cacgcaactc tacctccaac atcaaggaag atggcagtaa ccacaggttg tgtca        1080
ccagagtaac aaatttttgg agtaggcttt ctggctcctt accggaaagc cgtttacttg   1140
gttttaaaaa tagcttgcac tagcgatacg gaatatggtt attaggtttg ttaggcatca   1200
tgtcgtgtct tactatagaa aataacgta gtgttctatt tagccttgcc tgtatgtgtta   1260
atttgtcctt attgcgcatt gttcttgtta agtcttctgt aaggagttgc gggtttcaaa   1320
ctgtcagtct gagagcagaa ttcgatatct agatctcgag gtaaccacgt gcggacccaa   1380
cggccgcagg aaccctagt gatggagttg gccactccct ctgcgcgc tcgctcgctc    1440
actgaggccg ggcgaccaaa ggtcgcccga cgcccgggct ttgcccggc ggcctcagtg    1500
agcgagcgag cgcgcagctg cctgcagg                                    1528
```

SEQ ID NO: 174         moltype = DNA   length = 1534
FEATURE                Location/Qualifiers
source                 1..1534
                       mol_type = other DNA
                       organism = synthetic construct
SEQUENCE: 174
ctgcgcgctc gctcgctcac tgaggccgcc cgggcaaagc ccgggcgtcg ggcgaccttt    60
ggtcgcccgg cctcagtgag cgagcgagcg cgcagagagg gagtgggggt cttcgaaaca   120
ccggttaaca acataggagc tgtgattggc tgttttcagc caatcagcac tgactcattt   180
gcatagcctt tacaagcggt cacaaaactca agaaacgagc ggttttaata gtcttttaga   240
atattgttta tcgaaccgaa taaggaactg tgctttgtga ttcacatatc agtggagggg   300
tgtggaaatg gcaccttgat ctcaccctca tcgaaagtgg agttgatgtc cttccctggc   360
tcgctacaga cgcacttccg caaggagtta cctccaacat caaggaagat ggcagtaacc   420
acaggttgtg tcaccagagt aacaaatttt tggagtaggc tttctggctc cttaccggaa   480
agcccctccc aatttcactg gtctacaatg aaagcaaaac agttctcttc cccgctcccc   540
ggtgtgtgag aggggctttg atccttctct ggtttcctag gaaacgcgta tgtgttgttc   600
ctcttagtgt taattcacac taaagactgt gcatccgact cctacattta tgaaagtaaa   660
tgcctgttgt tagaacaaaa aaggctacag aacaaaaaac aaagcgaaat accatctgct   720
ttaggttcag tgtggtattt tcccgctgac agggaggcgg gttttgggt acaggaaacg    780
agtcactatg gaggcggtac tatgtagatg agaattcagg tgcaaactgg gaaaagcaac   840
tgcttccaaa tatttgtgat ttttacagtg tagttttgga aaaactctta gcctaccaat   900
tcttctaagt gttttaaaat gtgggagcca gtacacatga agttatagag tgttttaatg   960
aggcttaaat atttaccgta actatgaaat gctacgcata tcatgctgtt caggctccgt  1020
ggccacgcaa ctcggagtta cctccaacat caaggaagat ggcagtaacc acaggttgtg  1080
tcaccagagt aacaaatttt tggagtaggc tttctggctc cttaccggaa agcccctgtt  1140
tacttggttt taaaaatagc ttgcactagc gatacgaat atggttatta ggtttgttag    1200
gcatcatgtc gtgtcttact atagaaaaat aacgtagtgt tcattttagc ctgcctgtat  1260
gtgttaattt gtccttattg cgcattgttc ttgttaagtc ttctgtaagg agttgcgggt  1320
ttcaaactgt cagtctgaga gcagaattcg atatctagat ctcgaggtaa ccacgtgcgg  1380
acccaacggc cgcaggaacc cctagtgatg gagttggcca ctccctctct gcgcgctcgc  1440
tcgctcactg aggccgggcg accaaaggtc gcccgacgcc cgggctttgc ccgggcggcc  1500
tcagtgagcg agcgagcgcg cagctgcctg cagg                              1534

SEQ ID NO: 175         moltype = DNA   length = 1540
FEATURE                Location/Qualifiers
source                 1..1540
                       mol_type = other DNA
                       organism = synthetic construct
SEQUENCE: 175
ctgcgcgctc gctcgctcac tgaggccgcc cgggcaaagc ccgggcgtcg ggcgaccttt    60
ggtcgcccgg cctcagtgag cgagcgagcg cgcagagagg gagtggggtt cttcgaaaca   120
ccggttaaca acataggagc tgtgattggc tgttttcagc caatcagcac tgactcattt   180
gcatagcctt tacaagcggt cacaaaactca agaaacgagc ggttttaata gtcttttaga   240
atattgttta tcgaaccgaa taaggaactg tgctttgtga ttcacatatc agtggagggg   300
tgtggaaatg gcaccttgat ctcaccctca tcgaaagtgg agttgatgtc cttccctggc   360
tcgctacaga cgcacttccg caaggagtta cctccaacat caaggaagat ggcagtaacc   420
acaggttgtg tcaccagagt aacaaatttt tggagcaggt tttctgacct ccttcggtcg   480
gaaaacccct cccaatttca ctggtctaca atgaaagcaa aacagttctc ttccccgctc   540
cccggtgtgt gagaggggct tgatccttc tctggttttcc taggaaacgc gtatgtgttg    600
ttcctcttag tgttaattca cactaaagac tgtgcatccg actcctacat ttatgaaagt   660
aaatgcctgt tgttagaaca aaaaaggcta cagaacaaaa acaaagcgaa ataccatctc   720
gctttaggtt cagtgtggta ttttcccgct gacaggagg cggttttttg gtacaggaa     780
acgagtcact atgaggcgg tactatgtag atgagaattc aggtgcaaac tgggaaaagc    840
aactgcttcc aaatatttgt gattttaca gtgtagtttt ggaaaaactct tagcctacc    900
aattcttcta agtgttttaa aatgtgggag ccagtacaca tgaagttata gagtgtttta   960
atgaggctta aatatttacc gtaactatga aatgctacgc atatcatgct gttcaggctc  1020
cgtgccacg caactcggag ttacctccaa catcaaggaa gatggcagta accacaggtt    1080
gtgtcaccag agtaacaaat ttttggagca ggttttctga cctccttcgg tcgaaaaacc  1140
cctgtttact tggttttaaa atagcttgc actagcgata cggaatatgg ttattaggtt    1200
tgttaggcat catgtcgtgt cttactatag aaaataacg tagtgttcat tttagcctgc    1260
ctgtatgtgt taatttgtcc ttattgcgca ttgttcttgt taagtcttct gtaaggagtt  1320
gcgggtttca aactgtcagt ctgagagcag aattcgatat ctagatctcg aggtaaccac  1380
gtgcggaccc aacggccgca ggaacccta gtgatggagt tggccactcc ctctctgcgc    1440
gctcgctcgc tcactgaggc cgggcgacca aaggtcgccc gacgcccggg ctttgcccgg  1500
gcggcctcag tgagcgagcg agcgcgcagc tgcctgcagg                        1540

SEQ ID NO: 176         moltype = DNA   length = 1385
FEATURE                Location/Qualifiers
source                 1..1385
                       mol_type = other DNA
                       organism = synthetic construct
SEQUENCE: 176
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccggtc gcgtctagta acttcgcgat gtacgggcca gatatatact   180
gccgaatcca ggtctccggg cttaacaaca acgaaggggc tgtgactggc tgcttttctca   240
accaatcagc accgaactca tttgcatggg ctgagaacaa atgttcgcga actctagaaa   300
tgaatgactt aagtaagttc cttagaatat tatttttcct actgaaagtt accacatgcg   360

```
tcgttgttta tacagtaata ggaacaagaa aaaagtcacc taagctcacc ctcatcaatt    420
gtggagttcc tttatatccc atcttctctc caaacacata cgcaggagtc agcagcagca    480
gcagcagcag cagcagcagc agcagcagca gcagaatttt tggagtaggc tttctggctc    540
cttaccggaa agcccctctt atgatgtttg ttgccaatga tagattgttt tcactgtgca    600
aaaattatgg gtagttttgg tggtcttgat gcagttgtaa gcttggagga tccgagctcg    660
gtaccaagct agtcgcgtaa ggaccagctt ctttgggaga aacagacgc agggggcggga    720
gggaaaaagg gagaggcaga cgtcacttcc ccttggcggc tctggcagca gattggtcgg    780
ttgagtggca gaaaggcaga cggggactgg gcaaggcact gtcggtgaca tcacggacag    840
ggcgacttct atgtagatga ggcagcgcag aggctgacgt cttcgccact tgctgcttca    900
ccacgaagga gttcccgtgc cctgggagcg ggttcaggac cgctgatcgg aagtgagaat    960
cccagctgtg tgtcagggct ggaaagggct cgggagtgcg cggggcaagt gaccgtgtgt   1020
gtaaagagtg aggcgtatga ggctgtgtcg gggcagaggc acaacgtttc ggagtcagca   1080
gcagcagcag cagcagcagc agcagcagca gcagcagcag aattttggaa gtaggctttc   1140
tggctcctta ccggaaaagcc actttctgga gtttcaaaaac cagactgtac gccaagggtc   1200
atatctttttt cgtcgacgga tccgaattcg atatctagat ctcgaggtaa ccacgtgcgg   1260
accgagccta gtccactccc tctctgcgcg ctcgctcgct cactgaggcc gggcgaccaa   1320
aggtcgcccg acgcccgggc tttgcccggg cggcctcagt gagcgagcga gcgcgcagag   1380
aggga                                                              1385

SEQ ID NO: 177       moltype = DNA  length = 1393
FEATURE              Location/Qualifiers
source               1..1393
                     mol_type = other DNA
                     organism = synthetic construct
SEQUENCE: 177
ctgcgcgctc gctcgctcac tgaggccgcc cggcaaagc ccgggcgtcg ggcgaccttt     60
ggtcgcccgg cctcagtgag cgagcgagcg cgcagagagg gagtgggggtt cttcgcgatg    120
tacgggccag atatatactg ccgaatccag gtctccgggc ttaacaacaa cgaaggggct    180
gtgactggct gctttctcaa ccaatcagca ccgaactcat ttgcatgggc tgagaacaaa    240
tgttcgcgaa ctctagaaat gaatgactta agtaagttcc ttagaatatt attttttccta    300
ctgaaagtta ccacatgcgt cgttgtttat acagtaatag gaacaagaaa aaagtcacct    360
aagctcaccc tcatcaattg tggagttcct ttatatccca tcttctctcc aaacacatac    420
gcaggagtca gcagcagcag cagcagcagc agcagcagca gcagcagcag cagaatttttt    480
ggagtaggct ttctggctcc ttaccggaaa gcccctctta tgatgtttgt tgccaatgat    540
agattgtttt cactgtgcaa aaattatggg tagttttggt ggtcttgatg cagttgtaag    600
cttggaggat ccgagctcgg taccaagcta gtcgcgtaag gaccagcttc tttgggagag    660
aacagacgca ggggcgggag ggaaaaaggg agaggcagac gtcacttccc cttggcggct    720
ctggcagcag attggtcggt tgagtggcag aaaggcagac ggggactggg caaggcactg    780
tcggtgacat cacggacagg gcgacttcta tgtagatgag gcagcgcaga ggctgacgtc    840
ttcgccactt gctgcttcac cacgaaggag ttcccgtgcc ctgggagcgg gttcaggacc    900
gctgatcgga agtgagaatc cagctgtgt gtcagggctg gaaagggctc gggagtgcgc    960
ggggcaagtg accgtgtgtg taaagagtga ggcgtatgag gctgtgtcgg ggcagaggca   1020
caacgtttcg gagtcagcag cagcagcagc agcagcagca gcagcagcag cagcagcaga   1080
atttttggag taggctttct ggctccttac cggaaagcca cttttctggag tttcaaaaac   1140
agactgtacg ccaagggtca tatcttttttc gtcgacggat ccgaattcga tatctagatc   1200
tcgaggtaac cacgtgcgga ccgagtagat aagtagcatg cgggttaat cattaactac   1260
aaggaacccc tagtgatgga gttggccact ccctctctgc gcgctcgctc gctcactgag   1320
gccgggcgac caaaggtcgc ccgacgcccg ggctttgccc gggcggcctc agtgagcgag   1380
cgagcgcgcc agc                                                      1393

SEQ ID NO: 178       moltype = DNA  length = 1390
FEATURE              Location/Qualifiers
source               1..1390
                     mol_type = other DNA
                     organism = synthetic construct
SEQUENCE: 178
ctgcgcgctc gctcgctcac tgaggccgcc cggcaaagc ccgggcgtcg ggcgaccttt     60
ggtcgcccgg cctcagtgag cgagcgagcg cgcagagagg gagtgggggtt gtacagtgag    120
gatctatttc aattcctcga gtactgccga atccaggtcc cgggcttaa caacaacga    180
ggggctgtga ctggctgctt tctcaaccaa tcagcaccga actcattgc atgggctgag    240
aacaaatgtt cgcgaactct agaaatgaat gacttaagta agttccttag aatattattt    300
ttcctactga aagttaccac atgcgtcgtt gtttatacag taataggaac aagaaaaaag    360
tcacctaagc tcaccctcat caattgtgga gttcctttat atccatctt ctctccaaac    420
acatacgcag gagtcgtcg ctgctgctgc tgctgctgct gctgctgctg ctgctgctga    480
atttttggag taggctttct ggctccttac cggaaagccc ctcttatgat gtttgttgcc    540
aatgatagat tgtttttcact gtgcaaaaat tatgggtagt tttggtggtc ttgatgcagt    600
tgtaagcttg gaggatccga gctcggtacc aagctagtcg cgtaaggacc agcttctttg    660
ggagagaaca gacgcagggg cgggagggaa aagggagag gcagacgtca cttcccccttg    720
gcggctctgg cagcagattg gtcggttgag tggcagaaag gcagacggga actgggcaag    780
gcactgtcgg tgacatcacg gacagggcga cttctatgta gatgaggcag cgcagaggct    840
gacgtcttcg ccacttgctg cttcaccacg aaggagttcc cgtgccctgg gagcgggttc    900
aggaccgctg atcggaagtg agaatcccag ctgtgtgtca gggctggaaa gggctcggga    960
gtgcgcgggg caagtgaccg tgtgtgtaaa gagtgaggcg tatgaggctg tgtcggggca   1020
gaggcacaac gtttcggagt ctgctgctgc tgctgctgct gctgctgctg ctgctgctga   1080
tgctgaattt tggagtaggc tttctggctc cttaccggaa agccactttc tggagtttc   1140
aaaacagact gtacgccaa gggtcatatc ttttcgtcg acggatccga attcgatatc   1200
gctagcctgc agtcgagata cgtagataag tagcatggcg ggttaatcat taactacaag   1260
gaaccctag tgatggagtt ggccactccc tctctgcgcg ctcgctcgct cactgaggcc   1320
gggcgaccaa aggtcgcccg acgcccgggc tttgcccggg cggcctcagt gagcgagcga   1380
```

```
                                                   -continued
gcgcgccagc                                                              1390

SEQ ID NO: 179          moltype = DNA   length = 103
FEATURE                 Location/Qualifiers
source                  1..103
                        mol_type = other DNA
                        organism = synthetic construct
SEQUENCE: 179
ggagtgtaac cacaggttgt gtcaccagag taacatacct ccaacatcaa ggaagatggc         60
aaattttttgg agcaggtttt ctgacctccg tcggaaaacc cct                         103

SEQ ID NO: 180          moltype = DNA   length = 103
FEATURE                 Location/Qualifiers
source                  1..103
                        mol_type = other DNA
                        organism = synthetic construct
SEQUENCE: 180
ggagttacct ccaacatcaa ggaagatggc agtaaccaca ggttgtgtca ccagagtaac         60
aaattttttgg agcaggtttt ctgacctccg tcggaaaacc cct                         103

SEQ ID NO: 181          moltype = DNA   length = 100
FEATURE                 Location/Qualifiers
source                  1..100
                        mol_type = other DNA
                        organism = synthetic construct
SEQUENCE: 181
ggagtgtaac cacaggttgt gtcaccagag taacatacct ccaacatcaa ggaagatggc         60
aaattttttgg agcaggtttt ctgacctccg tcggaaaacc                             100

SEQ ID NO: 182          moltype = DNA   length = 98
FEATURE                 Location/Qualifiers
source                  1..98
                        mol_type = other DNA
                        organism = synthetic construct
SEQUENCE: 182
tacctccaac atcaaggaag atggcagtaa ccacaggttg tgtcaccaga gtaacaaatt         60
tttggagcag gttttctgac ttcggtcgga aaacccct                                98

SEQ ID NO: 183          moltype = DNA   length = 101
FEATURE                 Location/Qualifiers
source                  1..101
                        mol_type = other DNA
                        organism = synthetic construct
SEQUENCE: 183
ggagttacct ccaacatcaa ggaagatggc agtaaccaca ggttgtgtca ccagagtaac         60
aaattttttgg agtaggcttt ctggctcctt accggaaagc c                           101

SEQ ID NO: 184          moltype = DNA   length = 104
FEATURE                 Location/Qualifiers
source                  1..104
                        mol_type = other DNA
                        organism = synthetic construct
SEQUENCE: 184
ggagttacct ccaacatcaa ggaagatggc agtaaccaca ggttgtgtca ccagagtaac         60
aaattttttgg agtaggcttt ctggctcctt accggaaagc ccct                        104

SEQ ID NO: 185          moltype = DNA   length = 107
FEATURE                 Location/Qualifiers
source                  1..107
                        mol_type = other DNA
                        organism = synthetic construct
SEQUENCE: 185
ggagttacct ccaacatcaa ggaagatggc agtaaccaca ggttgtgtca ccagagtaac         60
aaattttttgg agcaggtttt ctgacctcct tcggtcggaa aacccct                     107

SEQ ID NO: 186          moltype = DNA   length = 29
FEATURE                 Location/Qualifiers
source                  1..29
                        mol_type = other DNA
                        organism = synthetic construct
SEQUENCE: 186
ggctttctgg cctccgccgg aaagcccct                                          29

SEQ ID NO: 187          moltype = DNA   length = 30
FEATURE                 Location/Qualifiers
source                  1..30
                        mol_type = other DNA
                        organism = synthetic construct
SEQUENCE: 187
```

```
ggttttctga cactccgtcg gaaaacccct                                   30

SEQ ID NO: 188         moltype = DNA  length = 29
FEATURE                Location/Qualifiers
source                 1..29
                       mol_type = other DNA
                       organism = synthetic construct
SEQUENCE: 188
ggttttctga tctccatcgg aaaacccct                                    29

SEQ ID NO: 189         moltype = DNA  length = 29
FEATURE                Location/Qualifiers
source                 1..29
                       mol_type = other DNA
                       organism = synthetic construct
SEQUENCE: 189
ggttttccga cctccgtcgg aaaacccct                                    29

SEQ ID NO: 190         moltype = DNA  length = 30
FEATURE                Location/Qualifiers
source                 1..30
                       mol_type = other DNA
                       organism = synthetic construct
SEQUENCE: 190
ggctttctgg cactccaccg gaaagcccct                                   30

SEQ ID NO: 191         moltype = DNA  length = 30
FEATURE                Location/Qualifiers
source                 1..30
                       mol_type = other DNA
                       organism = synthetic construct
SEQUENCE: 191
ggctttctgg cactccgccg gaaagcccct                                   30

SEQ ID NO: 192         moltype = DNA  length = 29
FEATURE                Location/Qualifiers
source                 1..29
                       mol_type = other DNA
                       organism = synthetic construct
SEQUENCE: 192
ggctttctgg cctccaccgg aaagcccct                                    29

SEQ ID NO: 193         moltype = DNA  length = 29
FEATURE                Location/Qualifiers
source                 1..29
                       mol_type = other DNA
                       organism = synthetic construct
SEQUENCE: 193
ggttttccgg tctccaccgg aaagccccc                                    29

SEQ ID NO: 194         moltype = DNA  length = 29
FEATURE                Location/Qualifiers
source                 1..29
                       mol_type = other DNA
                       organism = synthetic construct
SEQUENCE: 194
ggctttccgg tctccaccgg aaagcccct                                    29

SEQ ID NO: 195         moltype = DNA  length = 29
FEATURE                Location/Qualifiers
source                 1..29
                       mol_type = other DNA
                       organism = synthetic construct
SEQUENCE: 195
ggctttccgg cctccgccgg aaagcccct                                    29

SEQ ID NO: 196         moltype = DNA  length = 29
FEATURE                Location/Qualifiers
source                 1..29
                       mol_type = other DNA
                       organism = synthetic construct
SEQUENCE: 196
ggttttccgg tctccaccgg aaaaccctt                                    29

SEQ ID NO: 197         moltype = DNA  length = 29
FEATURE                Location/Qualifiers
source                 1..29
                       mol_type = other DNA
                       organism = synthetic construct
```

```
SEQUENCE: 197
ggttttccgt gctcccacgg aaaacccctt                                            29

SEQ ID NO: 198          moltype = DNA   length = 29
FEATURE                 Location/Qualifiers
source                  1..29
                        mol_type = other DNA
                        organism = synthetic construct
SEQUENCE: 198
ggttttccgg cctccgccgg aaaacccctt                                            29

SEQ ID NO: 199          moltype = DNA   length = 30
FEATURE                 Location/Qualifiers
source                  1..30
                        mol_type = other DNA
                        organism = synthetic construct
SEQUENCE: 199
ggttttccgt gactcccacg gaaaacccctt                                           30

SEQ ID NO: 200          moltype = DNA   length = 30
FEATURE                 Location/Qualifiers
source                  1..30
                        mol_type = other DNA
                        organism = synthetic construct
SEQUENCE: 200
ggttttccgg cactccgccg gaaaacccctt                                           30

SEQ ID NO: 201          moltype = DNA   length = 29
FEATURE                 Location/Qualifiers
source                  1..29
                        mol_type = other DNA
                        organism = synthetic construct
SEQUENCE: 201
ggtcttccgg tctcctccgg aaggcccccc                                            29

SEQ ID NO: 202          moltype = DNA   length = 27
FEATURE                 Location/Qualifiers
source                  1..27
                        mol_type = other DNA
                        organism = synthetic construct
SEQUENCE: 202
ggtcttccgg ctccccggaa ggccccc                                               27

SEQ ID NO: 203          moltype = DNA   length = 29
FEATURE                 Location/Qualifiers
source                  1..29
                        mol_type = other DNA
                        organism = synthetic construct
SEQUENCE: 203
ggctttccgt gctcccacgg aaagcccct                                             29

SEQ ID NO: 204          moltype = DNA   length = 30
FEATURE                 Location/Qualifiers
source                  1..30
                        mol_type = other DNA
                        organism = synthetic construct
SEQUENCE: 204
ggctttccgt gactcccacg gaaagcccct                                            30

SEQ ID NO: 205          moltype = DNA   length = 30
FEATURE                 Location/Qualifiers
source                  1..30
                        mol_type = other DNA
                        organism = synthetic construct
SEQUENCE: 205
ggctttccgg cactccgccg gaaagcccct                                            30

SEQ ID NO: 206          moltype = DNA   length = 26
FEATURE                 Location/Qualifiers
source                  1..26
                        mol_type = other DNA
                        organism = synthetic construct
SEQUENCE: 206
tacctccaac atcaaggaag atggca                                                26

SEQ ID NO: 207          moltype = DNA   length = 30
FEATURE                 Location/Qualifiers
source                  1..30
                        mol_type = other DNA
```

```
                         organism = synthetic construct
SEQUENCE: 207
gtaaccacag gttgtgtcac cagagtaaca                                              30

SEQ ID NO: 208           moltype = DNA  length = 58
FEATURE                  Location/Qualifiers
source                   1..58
                         mol_type = other DNA
                         organism = synthetic construct
SEQUENCE: 208
cataccttct gcttgatgat catctcgcac cagagtaaca gtctgagtag gagctaaa              58

SEQ ID NO: 209           moltype = DNA  length = 53
FEATURE                  Location/Qualifiers
source                   1..53
                         mol_type = other DNA
                         organism = synthetic construct
SEQUENCE: 209
cataccttct gcttgatgat catctcgtgc cgctgcccaa tgccatcctg gag                    53

SEQ ID NO: 210           moltype = DNA  length = 52
FEATURE                  Location/Qualifiers
source                   1..52
                         mol_type = other DNA
                         organism = synthetic construct
SEQUENCE: 210
cataccttct gcttgatgat catctcggcc caatgccatc ctggagttcc tg                     52

SEQ ID NO: 211           moltype = DNA  length = 56
FEATURE                  Location/Qualifiers
source                   1..56
                         mol_type = other DNA
                         organism = synthetic construct
SEQUENCE: 211
tacctccaac atcaaggaag atggcagtaa ccacaggttg tgtcaccaga gtaaca               56

SEQ ID NO: 212           moltype = DNA  length = 56
FEATURE                  Location/Qualifiers
source                   1..56
                         mol_type = other DNA
                         organism = synthetic construct
SEQUENCE: 212
aacatcaagg aagatggcat ttctaggtaa ccacaggttg tgtcaccaga gtaaca               56

SEQ ID NO: 213           moltype = DNA  length = 52
FEATURE                  Location/Qualifiers
source                   1..52
                         mol_type = other DNA
                         organism = synthetic construct
SEQUENCE: 213
aacatcaagg aagatggcat ttctagtgcc gctgcccaat gccatcctgg ag                     52

SEQ ID NO: 214           moltype = DNA  length = 52
FEATURE                  Location/Qualifiers
source                   1..52
                         mol_type = other DNA
                         organism = synthetic construct
SEQUENCE: 214
tttttctcat accttctgct tgatgtctga gtaggagcta aaatattttg gg                     52

SEQ ID NO: 215           moltype = DNA  length = 56
FEATURE                  Location/Qualifiers
source                   1..56
                         mol_type = other DNA
                         organism = synthetic construct
SEQUENCE: 215
gtaaccacag gttgtgtcac cagagtaaca tacctccaac atcaaggaag atggca               56

SEQ ID NO: 216           moltype = DNA  length = 58
FEATURE                  Location/Qualifiers
source                   1..58
                         mol_type = other DNA
                         organism = synthetic construct
SEQUENCE: 216
cgagatgatc atcaagcaga aggtatgcac cagagtaaca gtctgagtag gagctaaa              58

SEQ ID NO: 217           moltype = DNA  length = 57
FEATURE                  Location/Qualifiers
source                   1..57
```

```
                        mol_type = other DNA
                        organism = synthetic construct
SEQUENCE: 217
caccagagta acagtctgag taggagctaa atacctccaa catcaaggaa gatggca         57

SEQ ID NO: 218          moltype = DNA   length = 57
FEATURE                 Location/Qualifiers
source                  1..57
                        mol_type = other DNA
                        organism = synthetic construct
SEQUENCE: 218
tacctccaac atcaaggaag atggcacacc agagtaacag tctgagtagg agctaaa         57

SEQ ID NO: 219          moltype = DNA   length = 54
FEATURE                 Location/Qualifiers
source                  1..54
                        mol_type = other DNA
                        organism = synthetic construct
SEQUENCE: 219
gtctgagtag gagctaaaat attttgggta cctccaacat caaggaagat ggca            54

SEQ ID NO: 220          moltype = DNA   length = 54
FEATURE                 Location/Qualifiers
source                  1..54
                        mol_type = other DNA
                        organism = synthetic construct
SEQUENCE: 220
tacctccaac atcaaggaag atggcagtct gagtaggagc taaaatattt tggg            54

SEQ ID NO: 221          moltype = DNA   length = 52
FEATURE                 Location/Qualifiers
source                  1..52
                        mol_type = other DNA
                        organism = synthetic construct
SEQUENCE: 221
gtctgagtag gagctaaaat attttgggtt tttctcatac cttctgcttg at              52

SEQ ID NO: 222          moltype = DNA   length = 45
FEATURE                 Location/Qualifiers
source                  1..45
                        mol_type = other DNA
                        organism = synthetic construct
SEQUENCE: 222
ccttctgctt gatgatcatc tcggagtaac agtctgagta ggagc                      45

SEQ ID NO: 223          moltype = DNA   length = 48
FEATURE                 Location/Qualifiers
source                  1..48
                        mol_type = other DNA
                        organism = synthetic construct
SEQUENCE: 223
ccttctgctt gatgatcatc tcgccagagt aacagtctga gtaggagc                   48

SEQ ID NO: 224          moltype = DNA   length = 43
FEATURE                 Location/Qualifiers
source                  1..43
                        mol_type = other DNA
                        organism = synthetic construct
SEQUENCE: 224
ccttctgctt gatgatcatc tcgcagtctg agtaggagct aaa                        43

SEQ ID NO: 225          moltype = DNA   length = 42
FEATURE                 Location/Qualifiers
source                  1..42
                        mol_type = other DNA
                        organism = synthetic construct
SEQUENCE: 225
ctcatacctt ctgcttgatg gagtaacagt ctgagtagga gc                         42

SEQ ID NO: 226          moltype = DNA   length = 45
FEATURE                 Location/Qualifiers
source                  1..45
                        mol_type = other DNA
                        organism = synthetic construct
SEQUENCE: 226
ctcatacctt ctgcttgatg ccagagtaac agtctgagta ggagc                      45

SEQ ID NO: 227          moltype = DNA   length = 40
FEATURE                 Location/Qualifiers
```

```
source                      1..40
                            mol_type = other DNA
                            organism = synthetic construct
SEQUENCE: 227
ctcatacctt ctgcttgatg cagtctgagt aggagctaaa                          40

SEQ ID NO: 228              moltype = DNA   length = 30
FEATURE                     Location/Qualifiers
source                      1..30
                            mol_type = other DNA
                            organism = synthetic construct
SEQUENCE: 228
ggttttctga cactccgtcg gaaaaccect                                     30

SEQ ID NO: 229              moltype = DNA   length = 29
FEATURE                     Location/Qualifiers
source                      1..29
                            mol_type = other DNA
                            organism = synthetic construct
SEQUENCE: 229
ggttttctga tctccatcgg aaaacccct                                      29

SEQ ID NO: 230              moltype = DNA   length = 29
FEATURE                     Location/Qualifiers
source                      1..29
                            mol_type = other DNA
                            organism = synthetic construct
SEQUENCE: 230
ggttttccga cctccgtcgg aaaacccct                                      29

SEQ ID NO: 231              moltype = DNA   length = 1510
FEATURE                     Location/Qualifiers
source                      1..1510
                            mol_type = other DNA
                            organism = synthetic construct
SEQUENCE: 231
ctgcgcgctc gctcgctcac tgaggccgcc cgggcaaagc ccgggcgtcg ggcgaccttt    60
ggtcgcccgg cctcagtgag cgagcgagcg cgcagagagg gagtgggggtt cttcgaaaaca 120
ccggttaaca acataggagc tgtgattggc tgttttcagc caatcagcac tgactcattt   180
gcatagcctt tacaagcggt cacaaactca agaaacgagc ggttttaata gtcttttaga   240
atattgttta tcgaaccgaa taaggaactg tgctttgtga ttcacatatc agtggagggg   300
tgtggaaatg gcaccttgat ctcaccctca tcgaaagtgg agttgatgtc cttccctggc   360
tcgctacaga cgcacttccg caaggagtca gcagcagcag cagcagcagc agcagcagaa   420
gcagcagcag cagaattttt ggagcaggtt ttctgacctc cgtcggaaaa cccctcccaa   480
tttcactggt ctacaatgaa agcaaaacag ttctcttccc cgctcccggg tgtgtgagag   540
gggctttgat ccttctctgg tttcctagga acgcgtatg tgttgttcct cttagtgtta    600
attcacacta aagactgtgc atccgactcc tacatttatg aaagtaaatg cctgttgtta   660
gaacaaaaaa ggctacagaa caaaaaacaa agcgaaatac catctgcttt aggttcagtg   720
tggtattttc ccgctgacag ggaggcgggt ttttgggtac aggaaacgag tcactatgga   780
ggcggtacta tgtagatgag aattcaggtg caaactggga aaagcaactg cttccaaata   840
tttgtgattt ttacagtgta gttttggaaa aactcttagc ctaccaattc ttctaagtgg   900
tttaaaatgt gggagccagt acacatgaag ttatagagtg ttttaatgag gcttaaaatat  960
ttaccgtaac tatgaaatgc tacgcatatc atgctgttca ggctccgtgg ccacgcaact  1020
cggagtcagc agcagcagca gcagcagcag cagcagcagc agcagcagca gaattttggg  1080
agcaggtttt ctgacctccg tcggaaaacc cctgttact tggttttaaa aatagcttgc    1140
actagcgata cggaatatgg ttattaggtt tgttaggcat catgtcgtgt cttactatag  1200
aaaaataacg tagtgttcat tttagcctgc ctgtatgtgt taatttgtcc ttattgcgca  1260
ttgttcttgt taagtcttct gtaaggagtt gcgggtttca aactgtcagt ctgagagcag  1320
aattcgatat ctagatctcg aggtaaccac gtgcggaccc aacggccgca ggaacccta   1380
gtgatggagt tggccactcc ctctctgcgc gctcgctcgc tcactgaggc cgggcgacca  1440
aaggtcgccc gacgcccggg ctttgcccgg gcggcctcag tgagcgagcg agcgcgcagc  1500
tgcctgcagg                                                        1510

SEQ ID NO: 232              moltype = DNA   length = 1474
FEATURE                     Location/Qualifiers
source                      1..1474
                            mol_type = other DNA
                            organism = synthetic construct
SEQUENCE: 232
ctgcgcgctc gctcgctcac tgaggccgcc cgggcaaagc ccgggcgtcg ggcgaccttt    60
ggtcgcccgg cctcagtgag cgagcgagcg cgcagagagg gagtgggggtt cttcgaaaaca 120
ccggttaaca acataggagc tgtgattggc tgttttcagc caatcagcac tgactcattt   180
gcatagcctt tacaagcggt cacaaactca agaaacgagc ggttttaata gtcttttaga   240
atattgttta tcgaaccgaa taaggaactg tgctttgtga ttcacatatc agtggagggg   300
tgtggaaatg gcaccttgat ctcaccctca tcgaaagtgg agttgatgtc cttccctggc   360
tcgctacaga cgcacttccg caaggagtca gcagcagcag cagcagcagc agcagcagaa   420
ttttggagc aggttttctg acctccgtcg gaaaaccccc aatttcactg gtctacaatg    480
aaagcaaaac agttctcttc cccgctcccc ggtgtgtgag aggggctttg atccttctct   540
ggtttcctag gaacgcgta tgtgttgttc ctcttagtgt taattcacac taaagactgt    600
```

```
gcatccgact cctacattta tgaaagtaaa tgcctgttgt tagaacaaaa aaggctacag    660
aacaaaaaac aaagcgaaat accatctgct ttaggttcag tgtggtattt tcccgctgac    720
agggaggcgg gttttgggt acaggaaacg agtcactatg gaggcggtac tatgtagatg    780
agaattcagg tgcaaactgg gaaaagcaac tgcttccaaa tatttgtgat ttttacagtg    840
tagttttgga aaaactctta gcctaccaat tcttctaagt gtttaaaat gtgggagcca    900
gtacacatga agttatagag tgttttaatg aggcttaaat atttaccgta actatgaaat    960
gctacgcata tcatgctgtt caggctccgt ggccacgcaa ctcggagtca gcagcagcag   1020
cagcagcagc agcagcagaa tttttggagc aggttttctg acctccgtcg gaaaaccgtt   1080
tacttggttt taaaaatagc ttgcactagc gatacggaat atggttatta ggtttgttag   1140
gcatcatgtc gtgtcttact atagaaaaat aacgtagtgt tcattttagc ctgcctgtat   1200
gtgttaattt gtccttattg cgcattgttc ttgttaagtc ttctgtaagg agttgcgggt   1260
ttcaaactgt cagtctgaga gcagaattcg atatctagat ctcgaggtaa ccacgtgcgg   1320
acccaacggc cgcaggaacc cctagtgatg gagttggcca ctccctctct gcgcgctcgc   1380
tcgctcactg aggccgggcg accaaaggtc gcccgacgcc cgggctttgc ccgggcggcc   1440
tcagtgagcg agcgagcgcg cagctgcctg cagg                              1474

SEQ ID NO: 233              moltype = DNA   length = 1510
FEATURE                     Location/Qualifiers
source                      1..1510
                            mol_type = other DNA
                            organism = synthetic construct
SEQUENCE: 233
ctgcgcgctc gctcgctcac tgaggccgcc cgggcaaagc ccgggcgtcg ggcgaccttt     60
ggtcgcccgg cctcagtgag cgagcgagcg cgcagagagg gagtgggtt cttcgaaaca    120
ccggttaaca acataggagc tgtgattggc tgttttcagc caatcagcac tgactcattt    180
gcatagcctt tacaagcggt cacaaactca agaaacggac ggttttaata gtcttttaga    240
atattgttta tcgaaccgaa taaggaactg tgctttgtga ttcacatatc agtggagggg    300
tgtggaaatg gcaccttgat ctcaccctca tcgaaagtgg agttgatgtc cttccctggc    360
tcgctacaga cgcacttccg caaggagtct gctgctgctg ctgctgctgc tgctgctgct    420
gctgctgctg ctgaattttt ggagcaggtt ttctgacctc cgtcggaaaa cccctcccaa    480
tttcactggt ctacaatgaa agcaaaacag ttctcttccc cgctcccgg tgtgtgagag    540
gggctttgat ccttctctgg tttcctagga aacgcgtatg tgttgttcct cttagtgtta    600
attcacacta aagactgtgc atccgactcc tacatttatg aaagtaaatg cctgttgtta    660
gaacaaaaaa ggctacagaa caaaaacaa agcgaaatac catctgcttt aggttcagtg    720
tggtattttc ccgctgacag ggaggcgggt ttttgggtac aggaaacgag tcactatga    780
ggcggtacta tgtagatgag aattcaggtg caaactggga aaagcaactg cttccaaata    840
tttgtgattt ttacagtgta gttttggaaa aactcttagc ctaccaattc ttctaagtgt    900
tttaaaatgt gggagccagt acacatgaag ttatagagtg ttttaatgag gcttaaatat    960
ttaccgtaac tatgaaatgc tacgcatatc atgctgttca ggctccgtgg ccacgcaact   1020
cggagtctgc tgctgctgct gctgctgctg ctgctgctgc tgctgctgct gaattttgg   1080
agcaggtttt ctgacctccg tcggaaaacc cctgtttact tggttttaaa aatagcttgc   1140
actagcgata cggaatatgg ttattaggtt tgttaggcat catgtcgtgt cttactatag   1200
aaaaataacg tagtgttcat tttagcctgc ctgtatgtgt taatttgtcc ttattgcgc   1260
ttgttcttgt taagtcttct gtaaggagtt gcgggtttca aactgtcagt ctgagagcag   1320
aattcgatat ctagatctcg aggtaaccac gtgcggaccc aacggccgca ggaacccta    1380
gtgatggagt tggccactcc ctctctgcgc gctcgctcgc tcactgaggc cgggcgacca   1440
aaggtcgccc gacgcccggg ctttgcccgg gcggcctcag tgagcgagcg agcgcgcagc   1500
tgcctgcagg                                                         1510
```